US012655415B2

(12) United States Patent (10) Patent No.: US 12,655,415 B2
Fu et al. (45) **Date of Patent: \*Jun. 16, 2026**

(54) NANOCAGED ENZYMES WITH ENHANCED CATALYTIC ACTIVITY AND INCREASED STABILITY

(71) Applicant: ARIZONA BOARD OF REGENTS ON BEHALF OF ARIZONA STATE UNIVERSITY, Scottsdale, AZ (US)

(72) Inventors: Jinglin Fu, Tempe, AZ (US); Zhao Zhao, Boston, MA (US); Neal Woodbury, Tempe, AZ (US); Hao Yan, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 318 days.

This patent is subject to a terminal disclaimer.

(21) Appl. No.: 18/481,955

(22) Filed: Oct. 5, 2023

(65) Prior Publication Data

US 2024/0158776 A1 May 16, 2024

Related U.S. Application Data

(63) Continuation of application No. 16/812,225, filed on Mar. 6, 2020, now Pat. No. 12,077,750, which is a continuation of application No. 15/649,351, filed on Jul. 13, 2017, now Pat. No. 10,669,534.

(60) Provisional application No. 62/361,884, filed on Jul. 13, 2016.

(51) Int. Cl.
| | |
|---|---|
| *C12N 11/04* | (2006.01) |
| *C12N 11/06* | (2006.01) |
| *C12N 11/10* | (2006.01) |
| *C12N 15/11* | (2006.01) |
| *B82Y 5/00* | (2011.01) |

(52) U.S. Cl.
CPC .............. *C12N 11/04* (2013.01); *C12N 11/06* (2013.01); *C12N 11/10* (2013.01); *C12N 15/11* (2013.01); *B82Y 5/00* (2013.01); *C12N 2310/532* (2013.01)

(58) Field of Classification Search
None
See application file for complete search history.

(56) References Cited

U.S. PATENT DOCUMENTS

| | | |
|---|---|---|
| 10,669,534 B2 | 6/2020 | Fu et al. |
| 2012/0094271 A1 | 4/2012 | Fu et al. |
| 2014/0341975 A1 | 11/2014 | Livneh |
| 2015/0218204 A1 | 8/2015 | Yin et al. |

FOREIGN PATENT DOCUMENTS

| | | |
|---|---|---|
| WO | WO-2010027642 A2 | 3/2010 |
| WO | WO-2010028214 A2 | 3/2010 |

OTHER PUBLICATIONS

Abelson, J. et al. Conformational dynamics of single pre-mRNA molecules during in vitro splicing Nat. Struct. Mal. Biol. 17, 504-512 (2010).
Andersen. E. S. et al. Self-assembly of a nanoscale DNA box with a controllable lid. Nature 459, 73-76 (2009).
Bellot, G., McClintock, M. A, Lin, C. X., Shih, W. M. Recovery of intact DNA nanostructures after agarose gel-based separation. Nat. Methods. 8, 192-194 (2011).
Bellot et al. Nat. Methods. 8, 192-194 (2011 ). Supplementary Material (Year: 2011).
Betancor , L., and Luckarift, H. R. Bioinspired enzyme encapsulation for biocatalysis. Trends. Biotechnol. 26, 566-572 (2008).
Blanco, M. & Walter, N. G. Analysis of Complex Single-Molecule FRET Time Trajectories. Method. Enzymol. 472, 153-178 (2010).
Bruns, N. & Tiller, J. C. Amphiphilic network as nanoreactor for enzymes in organic solvents. Nano Lett. 5, 45-48 (2005).
Castello, A et al. Insights into RNA Biology from an Atlas of Mammalian mRNABinding Proteins. Cell 149, 1393-1406 (2012).
Chapman, AD., Cortes, A, Dafforn, T. R., Clarke, AR. & Brady, R. L. Structural basis of substrate specificity in malate dehydrogenases: crystal structure of a ternary complex of porcine cytoplasmic malate dehydrogenase, alpha-ketomalonate and tetrahydoNAD. J Mal Biol. 285, 703-712 (1999).
Chen, A. H. & Silver, P. A. Designing biological compartmentalization. Trends. Cell.Biol. 12, 662-670 (2012).
Chuprina, V. P., Heinemann, U., Nurislamov, A A, Zielenkiewicz, P., Dickerson, R. E. & Saenger W. Molecular dynamics simulation ofthe hydration shell ofa B-DNA decamer reveals two main types of minor-groove hydration depending on groove width. Proc. Nati. Acad Sci. USA 88, 593-597 (1991).
Ciesla, J. Metabolic enzymes that bind RNA: yet another level of cellular regulatory network? Acta Biochim Pol. 53, 11-32 (2006).
Comellas-Aragones, M. et al. A virus-based single-enzyme nanoreactor. Nature Nanotech. 2, 635-639 (2007).
Douglas, S. M., Bachelet, I., Church, G. M. A logic-gated nanorobot for targeted transport of molecular payloads. Science 335, 831-834 (2012).
Douglas, S. M., Dietz, H., Liedl, T., Hogberg, B., Graf, F. & Shih, W. M. Self-assembly of DNA into nanoscale three-dimensional shapes. Nature 459, 414-418 (2009).

(Continued)

*Primary Examiner* — Michael D Burkhart

(74) *Attorney, Agent, or Firm* — Michael Best & Friedrich LLP

(57) ABSTRACT

The present disclosure describes a nanoparticle comprising a three dimensional DNA nanocage and a payload biological macromolecule, and methods of assembly thereof.

15 Claims, 67 Drawing Sheets
(57 of 67 Drawing Sheet(s) Filed in Color)
Specification includes a Sequence Listing.

(56)          References Cited

OTHER PUBLICATIONS

Eanes, R.Z., and Kun, E. Separation and characterization of aconitate hydratase isoenzymes from pig tissues. Biochim. Biophys. Acta 227, 204-210 (1971).

English, B. P., et al. Ever-fluctuating single enzyme molecules: Michaelis-Menten equation revisited. Nat. Chem. Bio. 2, 87-94 (2006).

Erkelenz, M., Kuo, C. H. & Niemeyer, C. M. DNA-Mediated Assembly of Cytochrome P450 BM3 Subdomains, J Am. Chem. Soc. 133, 16111-16118 (2011).

Fiedler, J. D., Brown. S. D., Lau. J. & Finn. M. G. RNA-directed packaging of enzymes within virus-like particles. Angew. Chem. Int. Ed 49, 9648-9651 (2010).

Fu, J., Liu, M., Liu, Y. & Yan, H. Spatially-Interactive Biomolecular Networks Organized by Nucleic Acid Nanostructures, Acc. Chem. Res. 45, 1215-1226 (2012).

Fu, J., Liu, M., Liu, Y., Woodbury, N. W. & Yan, H. Interenzyme Substrate Diffusion for an Enzyme Cascade Organized on Spatially Addressable DNA Nanostructures. J. Am. Chem. Soc. 134, 5516-5519 (2012).

Fu, J., Yang, Y. R., Johnson-Buck, A, Liu, Y., Walter, N. G., Woodbury, N. W., and Yan, H. Multi-enzyme complexes on DNA scaffolds capable of substrate channeling with an artificial swinging arm, Nature Nanotechnol. 9, 531-536 (2014).

Fu, Y., et al. Single-Step Rapid Assembly of DNA Origami Nanostructures for Addressable Nanoscale Bioreactors. J Am. Chem. Soc. 135, 696-702 (2013).

Gao, Y., Roberts, C. C., Zhu, J., Lin, J., Chang, C. A & Wheeldon, I. Tuning Enzyme Kinetics through Designed Intermolecular Interactions Far from the Active Site. ACS Catal. 5, 2149-2153 (2015).

Gourevitch, B. & Eggermont, J. J. A nonparametric approach for detection of bursts in spike trains. Journal of Neuroscience Methods 160, 349-358 (2007).

Graff, A., Winterhalter, M. & Meier, W. Nanoreactors from polymer-stabilized liposomes. Langmuir 17, 919-923 (2001).

Gray M. J., et al. Polyphosphate is a primordial chaperone. Mol. Cell. 53, 689-699 (2014).

Guo, S., Cao, R., Lu, A, Zhou, Q., Lu, T., Ding, X., Li, C. and Huang, X. One of the possible mechanisms for the inhibition effect of Tb(III) on peroxidase activity in horseradish (*Armoracia rusticana*) treated with Tb(III). J. Biol. Inorg. Chem. 13, 587-597 (2008).

Hammes, G. G., Benkovic, S. J. & Hammes-Schiffer, S. Flexibility, Diversity, and Cooperativity: Pillars of Enzyme Catalysis. Biochemistry 50, 10422-10430 (2011).

Han, D., Pal, S., Nangreave, J., Deng, Z., Liu, Y. & Yan, H. DNA origami with complex curvatures in three-dimensional space. Science 332, 342-346 (2011).

Hartl, F. U. Molecular chaperones m cellular protein folding Nature 381, 571-580 (1996).

Hecht, H. J., Kalisz, H. M., Rendle, J., Schmid, R. D. & Schomburg D. Crystal structure of glucose oxidase from Aspergillus niger refined at 2.3 A resolution. J Mol Biol. 229, 153-172 (1993).

Henriksen, A, Schuller, D. J., Gajhede, M. Structural interactions between horseradish peroxidase C and the substrate benzhydroxamic acid determined by X-ray crystallography. Biochemistry 37, 8054-8060 (1998).

Horikiri, S., Aizawa, Y., Kai, T., Amachi, S., Shinoyama, H. and Fujii, T. Electron acquisition system constructed from an NAD-independent D-lactate dehydrogenase and cytochrome c2 in Rhodopseudomonas palustris No. 7. Biosci. Biotechnol. Biochem. 68, 516-522 (2004).

Hurtley, S. Location, Location, Location. Science 326, 1205 (2009).

Jacobson, R. H., Zhang, X. J., DuBose, R. F. & Matthews, B. W. Three-dimensional structure of beta-galactosidase from *E.coli.* Nature 369, 761-766 (1994).

Jana, B., Pal, S., Maiti. P. K., Lin. S., Hynes, J. T. & Bagchi, B. Entropy of Water in the Hydration Layer of Major and Minor Grooves of DNA J Phys. Chem. B 110, 19611-19618 (2006).

Jiang, Q., Song, C., Nangreave, J., Liu, X., Lin, L., Qiu, Z., Wang, Z., Zou, G., Liang, X., Yan, H., Ding, B. DNA origami as a carrier for circumvention of drug resistance. J Am. Chem. Soc. 134, 13396-13403 (2012).

Juul, S., et al. Temperature-Controlled Encapsulation and Release of an Active Enzyme in the Cavity of a Self-Assembled DNA Nanocage. ACS Nano 7, 9724-9734 (2013).

Ke, Y., Ong, L. L., Shih, W. M. & Yin, P. Three-dimensional structures self-assembled from DNA bricks. Science, 338, 1177-1183 (2012).

Kerfeld, C. A., Sawaya, M. R., Tanaka, S., Nguyen, C. V., Phillips, M., Beeby, M. & Yeates, T. 0. Protein structures forming the shell of primitive bacterial organelles. Science 309, 936-938 (2005).

Kerfeld, C. A., Heinhorst, S. & Cannon, G. C. Bacterial microcompartments. Annu. Rev.Microbial. 64, 391-408 (2010).

Kuzyk, A et al. DNA-based self-assembly of chiral plasmonic nanostructures with tailored optical response. Nature 483, 311-314 (2012).

Langecker, M., Arnaut, V., Martin, T., List, J., Renner, S., Mayer, M., Dietz, H., & Simmel, F. Synthetic lipid membrane channels by designed DNA nanostructures. Science 338, 932-936 (2012).

Leberman, R. & Soper, A K. Effect of high salt concentrations on water structure. Nature 378, 364-366 (1995).

Levy, Y. & Onuchic, J. N. Water and proteins: A love-hate relationship. Proc. Natl. Acad Sci. USA 101, 3325-3326 (2004).

Lin, J. & Wheeldon, I. Kinetic Enhancements in DNA-Enzyme Nanostructures Mimic the Sabatier Principle ACS Cata !. 3, 560-564 (2013).

Linko, V., Eerikainen, M. & Kostiainen, M. A modular DNA origamibased enzyme cascade nanoreactor. Chem. Commun. 51, 5351-5354 (2015).

Liu, B., Baskin, R. J. & Kowalczykowski, S. C. NA unwinding heterogeneity by RecBCD results from static molecules able to equilibrate. Nature 500, 482-485 (2013).

Liu, M., Fu, J., Hejesen, C., Yang, Y., Woodbury, N. W., Gothelf, K., Liu, Y. & Yan, H. A DNA Tweezer-Actuated Enzyme Nanoreactor. Nature Commun. 4, 1-5 (2013).

Liu, Y. et al. Biomimetic enzyme nanocomplexes and their use as antidotes and preventive measures for alcohol intoxication. Nature Nanotech. 8, 187-192 (2013).

Lovell, S. L. & Winzor, D. J. Effects of phosphate on the dissociation and enzymic stability of rabbit muscle lactate dehydrogenase. Biochemistry 13, 3527-3531 (1974).

Marcus, Y. Effects of ions on the structure of water: structure making and breaking. Chem. Rev. 109, 1346-1370 (2009).

Mei, Q., Wei, X., Su, F., Liu, Y., Yongbull, C., Johnson, R., Lindsay, S., Yan, H., Meidrum, D. Stability of DNA origami nanoarrays in cell lysate. Nano Lett. 11, 1477-1482 (2011).

Mei, Q., Johnson, R.H., X. Wei, F. Su, Y. Liu, L. Kelbauskas, S. Lindsay, D. R. Meldrum, and H. Yan, On-chip Isotachophoresis Separation of Functional DNA Origami Capture Nanoarrays from Cell Lysate, Nano Research, 6, 712-719 (2013).

Michelotti, N. et al. A bird's eye view tracking slow nanometer-scale movements of single molecular nano-assemblies. Methods Enzymol. 475, 121-148 (2010).

Moelberta, S., Normandb, B. & Rios, P. D. L. Kosmotropes and chaotropes: modelling preferential exclusion, binding and aggregate stability. Biophys. Chem. 112, 45-57 (2004).

New England Biolabs, "M13mp18 Single-stranded DNA" [online], New England Biolabs, retrieved on Aug. 27, 2019 from archive.org, as it appeared on Mar. 16, 2016, retrieved from the internet: <URL:https://web.archive.org/web/20160316090101/neb.com/products/n4040-m13mp18-single-stranded-dna#tabselect0>.

Ramanathan, A & Agarwal P. K. Evolutionarily Conserved Linkage between Enzyme Fold, Flexibility, and Catalysis. PLoS Biol. 9, 1-17 (2011).

Ramanathan, A, Savol, A, Burger, V., Chennubhotla, C. S. & Agarwal, P. K. Protein Conformational Populations and Functionally Relevant Substates. Acc. Chem. Res. 47, 149-156 (2014).

Rinaldi, A J., Lund, P. E., Blanco, M. R. & Walter, N. G. The Shine-Dalgamo sequence of riboswitch-regulated single mRNAs shows ligand-dependent accessibility bursts. Nat. Commun., 8976 (2015), 10 pages.

(56)                    References Cited

OTHER PUBLICATIONS

Rowland, P., Basak, AK., Gover, S., Levy, H. R. & Adams, M. J. The three-dimensional structure of glucose 6-phosphate dehydrogenase from Leuconostoc mesenteroides refined at 2.0 A resolution. Structure 2(11), 1073-1087 (1994).

Rudiuk, S., Venancio-Marques, A & Baigl, D. Enhancement and modulation of enzymatic activity through higher-order structural changes of giant DNA-protein multibranch conjugates. Angew. Chem. Int. Ed 51, 12694-12698 (2012).

Sang, L. & Coppens, M. Effects of surface curvature and surface chemistry on the structure and activity of protein adsorbed in nanopores. Phys. Chem. Chem. Phys.13, 6689-6698 (2011).

Sung, J. Y. & Lee, Y. N. Isoforms of glucose 6-phosphate dehydrogenase in *Deinococcus radiophilus*. J Microbial. 45, 318-325 (2007).

Timasheff, S. N. Protein-solvent preferential interactions, protein hydration, and the modulation of biochemical reactions by solvent components. Proc. Natl. Acad Sci. 99, 9721-9726 (2002).

Timm, C. & Niemeyer, C. M. Assembly and Purification of Enzyme-Functionalized DNA Origami Structures. Angew. Chem. Int. Ed 54, 6745-6750 (2015).

Veitch, N. C. Horseradish peroxidase: a modern view of a classic enzyme. Phytochemistry 65, 249-259 (2004).

Vriezema, D. M., Aragones, M. C., Elemans, J., Cornelissen, J., Rowan, A E. & Nolte, R. J. M. Self-assembled nanoreactors. Chem. Rev. 105, 1445-1490 (2005).

Widom, J. R., Dhakal, S., Heinicke, L. A & Walter, N. G. Single-molecule tools for enzymology, structural biology, systems biology and nanotechnology: an update. Arch. Toxicol. 88, 1965-1985 (2014).

Wilner, 0. I., Weizmann, Y., Gill, R., Lioubashevski, 0., Freeman, R. & Willner, I. Enzyme cascades activated on topologically programmed DNA scaffolds. Nature Nanotechnol. 4, 249-254 (2009).

Wong, C. M., Wong, K. H. and Chen, X. D. Glucose oxidase: natural occurrence, function, properties and industrial application. Appl. Microbial. Biotechnol. 78, 927-938 (2008).

Zhao, H. Effects of ions and other compatible solutes on enzyme activity, and its implication for biocatalysis using ionic liquids. J Mal. Cata!. B-Enzym. 37, 16-25 (2005).

Zhao, H., Olubajo, 0., Song, Z., Sims, AL., Person, T. E., Lawal, R. A & Holley, L. A Effect of kosmotropicity of ionic liquids on the enzyme stability in aqueous solutions. Bioorg. Chem. 34, 15-25 (2006).

Zhao et al. Nature Communications, Feb. 10, 2016, pp. 1-9. http://www.nature.com/naturecommunications. (Year: 2016).

Zhao, Z. et al., "Nanocaged enzymes with enhanced catalytic activity and increased stability against protease digestion", Nature Communications, Feb. 2016, vol. 7, article 10619 and supl. S1-S106 <DOI:10.1038/ncomms10619>.

(A)

(B)

(A)

(B)

(C)

(A)

(B)

(C)

Cross-sectional view

3D View

| 0 | 1 | 2 | 3 | 4 | 5 | 6 | 7 | 8 | 9 | 10 | 11 |
|---|---|---|---|---|---|---|---|---|---|---|---|
| 143 | 122 | 121 | 100 | 99 | 78 | 77 | 56 | 55 | 34 | 33 | 12 |
| 142 | 123 | 120 | 101 | 98 | 79 | 76 | 57 | 54 | 35 | 32 | 13 |
| 141 | 124 | 119 | 102 | 97 | 80 | 75 | 58 | 53 | 36 | 31 | 14 |
| 140 | 125 | 118 | 103 | 96 | 81 | 74 | 59 | 52 | 37 | 30 | 15 |
| 139 | 126 | 117 | 104 | 95 | 82 | 73 | 60 | 51 | 38 | 29 | 16 |
| 138 | 127 | 116 | 105 | 94 | 83 | 72 | 61 | 50 | 39 | 28 | 17 |
| 137 | 128 | 115 | 106 | 93 | 84 | 71 | 62 | 49 | 40 | 27 | 18 |
| 136 | 129 | 114 | 107 | 92 | 85 | 70 | 63 | 48 | 41 | 26 | 19 |
| 135 | 130 | 113 | 108 | 91 | 86 | 69 | 64 | 47 | 42 | 25 | 20 |
| 134 | 131 | 112 | 109 | 90 | 87 | 68 | 65 | 46 | 43 | 24 | 21 |
| 133 | 132 | 111 | 110 | 89 | 88 | 67 | 66 | 45 | 44 | 23 | 22 |

| | $K_M$ (μM) | $k_{cat}$ (s⁻¹) |
|---|---|---|
| Full Cage[HRP] | 4.3±0.6 | 290±5 |
| Free HRP | 2.3±0.5 | 32±1 |

| | $K_M$ (µM) | $k_{cat}$ (s$^{-1}$) |
|---|---|---|
| AB-HRP | 2500±200 | 560±20 |
| HRP control | 2600±400 | 59±5 |

| | $K_M$ (µM) | $K_{cat}$ (s⁻¹) |
|---|---|---|
| AB-GOx | 3000±600 | 1300±50 |
| GOx control | 6200±900 | 240±10 |

| | $K_M$ (µM) | $k_{cat}$ (s$^{-1}$) |
|---|---|---|
| Full[G6pDH] | 590±40 | 480±10 |
| G6pDH control | 510±50 | 100±3 |

| | $K_M$ (µM) | $k_{cat}$ (s$^{-1}$) |
|---|---|---|
| Full[G6pDH] | 310±30 | 460±10 |
| G6pDH control | 220±20 | 130±3 |

Determination of the Michaelis-Menten constants for enzymes-MDH

| | $K_M$ (µM) | $k_{cat}$ (s$^{-1}$) |
|---|---|---|
| Full[MDH] | 270±50 | 460±30 |
| MDH control | 180±50 | 51±5 |

| | $K_M$ (µM) | $k_{cat}$ (s$^{-1}$) |
|---|---|---|
| Full[LDH] | 17.0±1.5 | 190±5 |
| LDH control | 7.2±1.3 | 46±2 |

| | $K_M$ (µM) | $k_{cat}$ (s⁻¹) |
|---|---|---|
| Full[β-Gal] | 95.5±18.9 | 1.6±0.1 |
| β-Gal control | 58.7±16.0 | 8.5±0.6 |

FIGS. 61A-61D
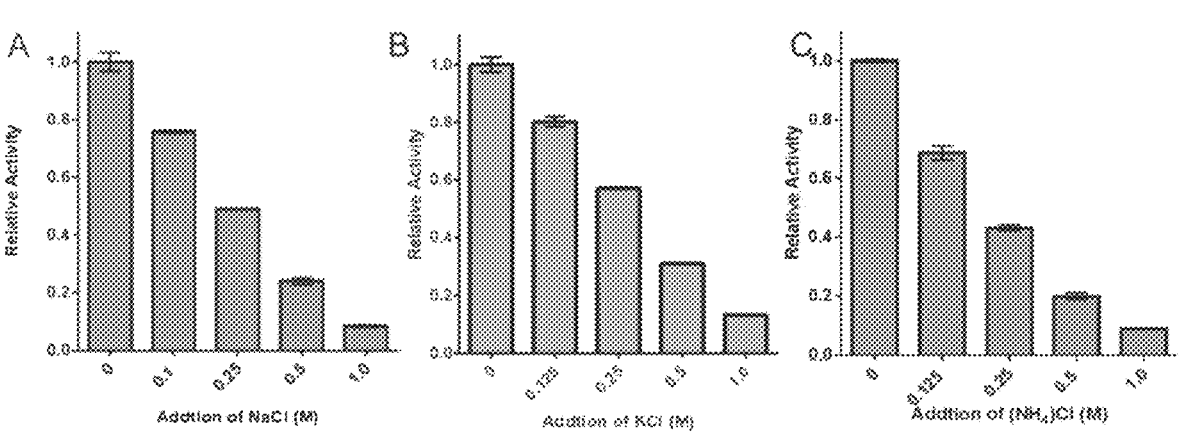
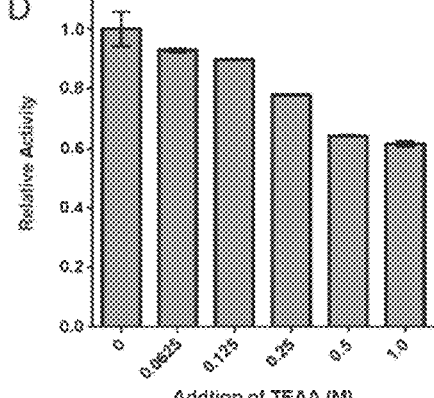

| | $K_M$ (µM) | $k_{cat}$ (s$^{-1}$) |
|---|---|---|
| SH-G6pDH | 411±32 | 520±10 |
| SS-G6pDH | 436±26 | 620±10 |
| DS-G6pDH | 527±37 | 900±20 |
| G6pDH control | 340±47 | 100±10 |

1

NANOCAGED ENZYMES WITH ENHANCED CATALYTIC ACTIVITY AND INCREASED STABILITY

CROSS-REFERENCE TO RELATED APPLICATIONS

This application is a Continuation of U.S. application Ser. No. 16/812,225 filed Mar. 6, 2020, which is a Continuation of U.S. application Ser. No. 15/649,351 filed Jul. 13, 2017, which claims the benefit of U.S. Provisional Application No. 62/361,884, filed Jul. 13, 2016, which are both hereby incorporated by reference in its entirety for all purposes.

STATEMENT REGARDING FEDERALLY SPONSORED RESEARCH

This invention was made with government support under W911NF-11-1-0137 and W911NF-12-1-0420 awarded by the Army Research Office. The government has certain rights in the invention.

SEQUENCE LISTING

The instant application contains a Sequence Listing which has been filed electronically in XML format and is hereby incorporated by reference in its entirety. Said XML copy, created on Mar. 6, 2020, is named G8118-00403.xml and is 1,250,732 bytes in size.

BACKGROUND

Common micro- and nanoscale subcellular compartments are formed from either lipids or proteins and include mitochondria, lysosomes, peroxisomes, carboxysomes and other metabolosomes, as well as multi-enzyme complexes. Compartments increase the overall activity and specificity of the encapsulated enzyme pathways by maintaining a high local concentration of enzymes and substrates, promoting substrate channeling and protecting their content from damage, as well as by segregating potentially damaging reactions from the cytosol. Spatial confinement is also an important aspect for chaperone-assisted folding of linear polypeptides into active tertiary and quaternary conformations, as well as for preventing proteins from aggregating under cellular stress conditions. A better understanding of the effects of spatial confinement on protein function will not only enhance the fundamental knowledge of cellular organization and metabolism but also increase the ability to translate biochemical pathways into a variety of noncellular applications, ranging from diagnostics and drug delivery to the production of high-value chemicals and smart materials. Over the past few decades, artificial enzymatic particles have been created using compartmentalization by virus-like protein particles, liposomes or polymersomes and chemical crosslinking. However, severe obstacles to a broader application remain, including low encapsulation yield of large proteins because of steric hindrance, insufficient access of substrates to the encapsulated enzymes, aggregation of vesicle shells and limited control over the spatial arrangement of proteins within the compartments.

SUMMARY

In a first aspect, provided herein is a nanocage, where the nanocage comprises a three dimensional body comprising a plurality of structural members comprising DNA, wherein internal surfaces of the plurality of structural members form an inner cavity. The DNA can be M13 viral DNA. Architectural arrangement of the structural members in the three dimensional body can form a honeycomb lattice. Architectural arrangement of the structural members in the three dimensional body can form a square lattice. In some cases, the architectural arrangement of the structural members in the three dimensional body can form a single-walled square lattice. In other cases, the architectural arrangement of the structural members in the three dimensional body can form a double-walled square lattice. The three dimensional body can be smaller than 100 nm×100 nm×100 nm. The three dimensional body can be smaller than 75 nm×50 nm×50 nm. The inner cavity of the three dimensional body can measure less than 50 nm×50 nm×50 nm. The three dimensional body can further comprise at least one nanopore. The at least one nanopore can have a diameter of about 1 nm to about 5 nm. The at least one nanopore has a diameter of about 1.5 nm to about 3 nm. The three dimensional body can comprise between 0.10 to 0.30 DNA helices per $nm^2$. The three dimensional body can comprise between 0.11 to 0.17 DNA helices per $nm^2$.

In another aspect, provided herein is a nanoparticle comprising a nanocage comprising a plurality of structural members comprising DNA in a three-dimensional lattice, wherein internal surfaces of the plurality of structural members form an inner cavity; and one or more payload molecules bound to internal surfaces of the inner cavity. The payload molecules can comprise enzymes, nucleic acids, polypeptides, antibodies, phospholipids, or any combination thereof. The inner cavity can encapsulate two payload molecules. The one or more payload molecules can be covalently linked to internal surfaces of the inner cavity. The nanocage can be configured to prevent proteolytic degradation of the trapped payload molecule. The nanocage can be configured to enhance the activity of the trapped payload molecule.

In another aspect, provided herein is a method of making a nanoparticle, where the method comprises trapping a payload macromolecule in an open half cage; and assembling two half cages into a closed nanocage; wherein the closed nanocage has an inner cavity; wherein the closed nanocage has nanopores; and wherein the resulting nanoparticle comprises a closed nanocage comprising nanopores and an inner cavity comprising one or more biological macromolecules. The half cage can comprise DNA. The DNA can be M13 viral DNA. The half cage comprising DNA can be constructed by folding full-length M13 viral DNA. The half cage can comprise a base and two adjoined side walls protruding from the base. The biological macromolecule can be covalently linked to the half cage. Two half cages can be assembled into a closed nanocage by adding short bridge DNA strands.

BRIEF DESCRIPTION OF DRAWINGS

The patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein.

US 12,655,415 B2

5

FIGS. 14A-14F show quantification of fluorescent dye-labeled enzyme-DNA conjugates using UV-Vis absorbance spectroscopy. (A) Cy3-labeled HRP-TTTTTCCCTCCCTCC (SEQ ID NO:1393) with an average dye-to-protein ratio of 1.8; (B) Cy3-labeled GOx-TTTTTCCCTCCCTCC (SEQ ID NO:1393) with an average dye-to-protein ratio of 1.5; (C) Cy3-labeled G6pDH-TTTTTCCCTCCCTCC (SEQ ID NO:1393) with an average dye-to-protein ratio of 1.6; (D) Alexa Fluor 647-labeled MDH-TTTTTGGCTGGCTGG (SEQ ID NO:1394) with an average dye-to-protein ratio of 1.2; (E) Alexa Fluor 647-labeled LDH-TTTTTGGCTGGCTGG (SEQ ID NO:1394) with an average dye-to-protein ratio of 1.7; (F) Cy3-labeled (β-Gal)-TTTTTCCCTCCCTCC (SEQ ID NO:1393) with an average dye-to-protein ratio of 0.6.

Figures 15A, 15B:
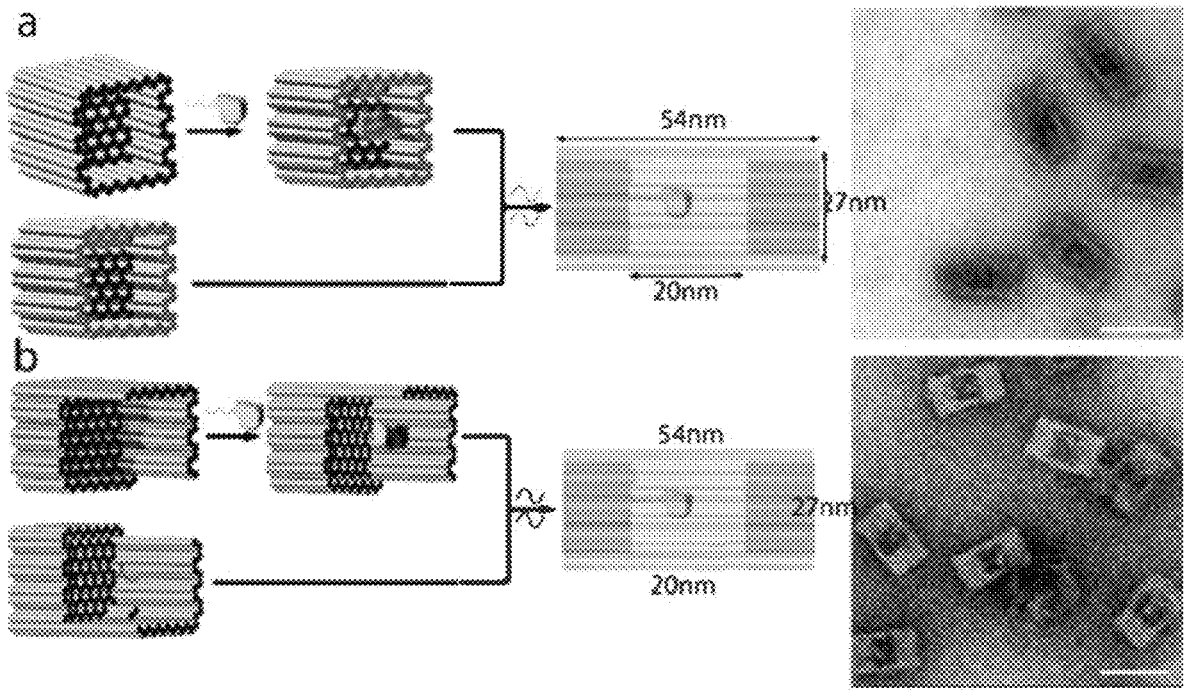

FIGS. 15A-15B shows two different designs for the cage structure with different encapsulation yields (see FIG. 16 and FIG. 17), assembled with GOx. (A) Cage with closed-wall design. (B) Cage with open-wall design.

Figure 16:
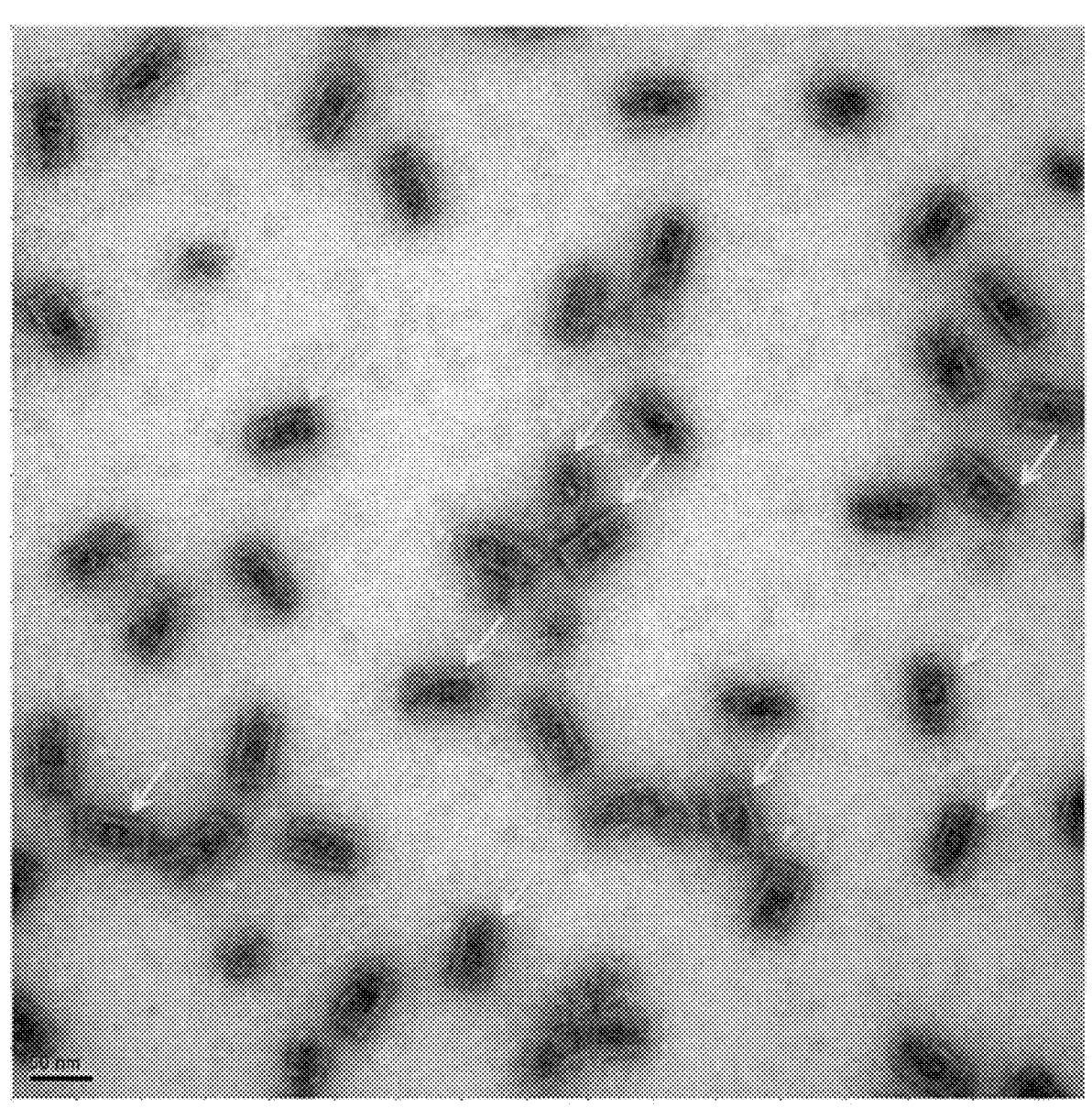

FIG. 16 shows TEM image of full-cages with closed-wall design (FIG. 15A) encapsulating GOx. An encapsulation yield of 38% was estimated from similar images containing about 230 DNA cages by dividing the number of cages with a discernible protein inside by the total number of the cages counted (yellow arrow indicates DNA cage with enzyme inside).

Figure 17:
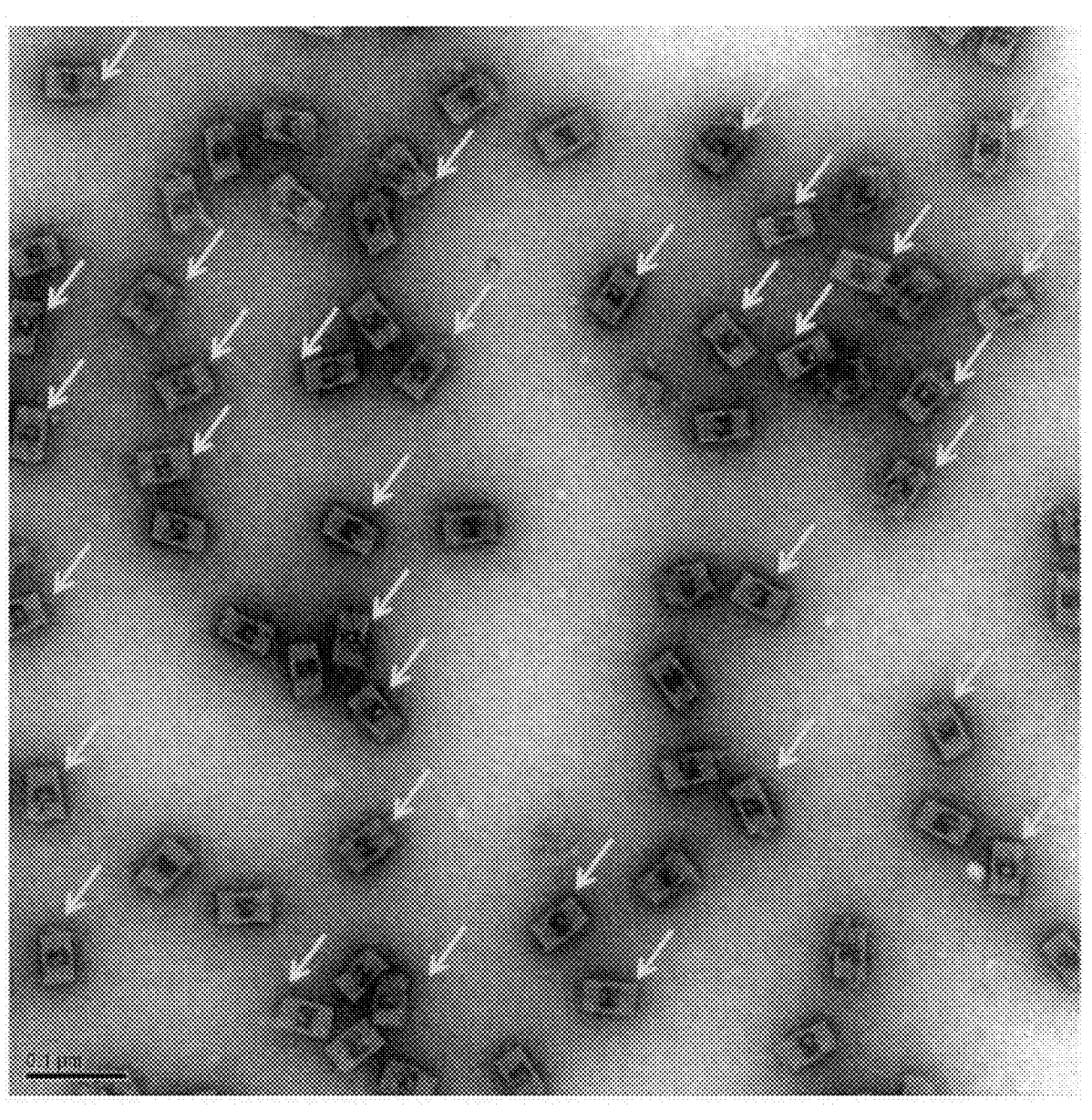

FIG. 17 shows TEM image of full-cage with open-wall design (FIG. 15B) encapsulating GOx. An encapsulation yield of 77% was estimated from similar images containing about 300 DNA cages by dividing the number of cages with a discernible protein inside by the total number of cages counted (yellow arrow indicates DNA cage with enzyme inside).

Figure 18:
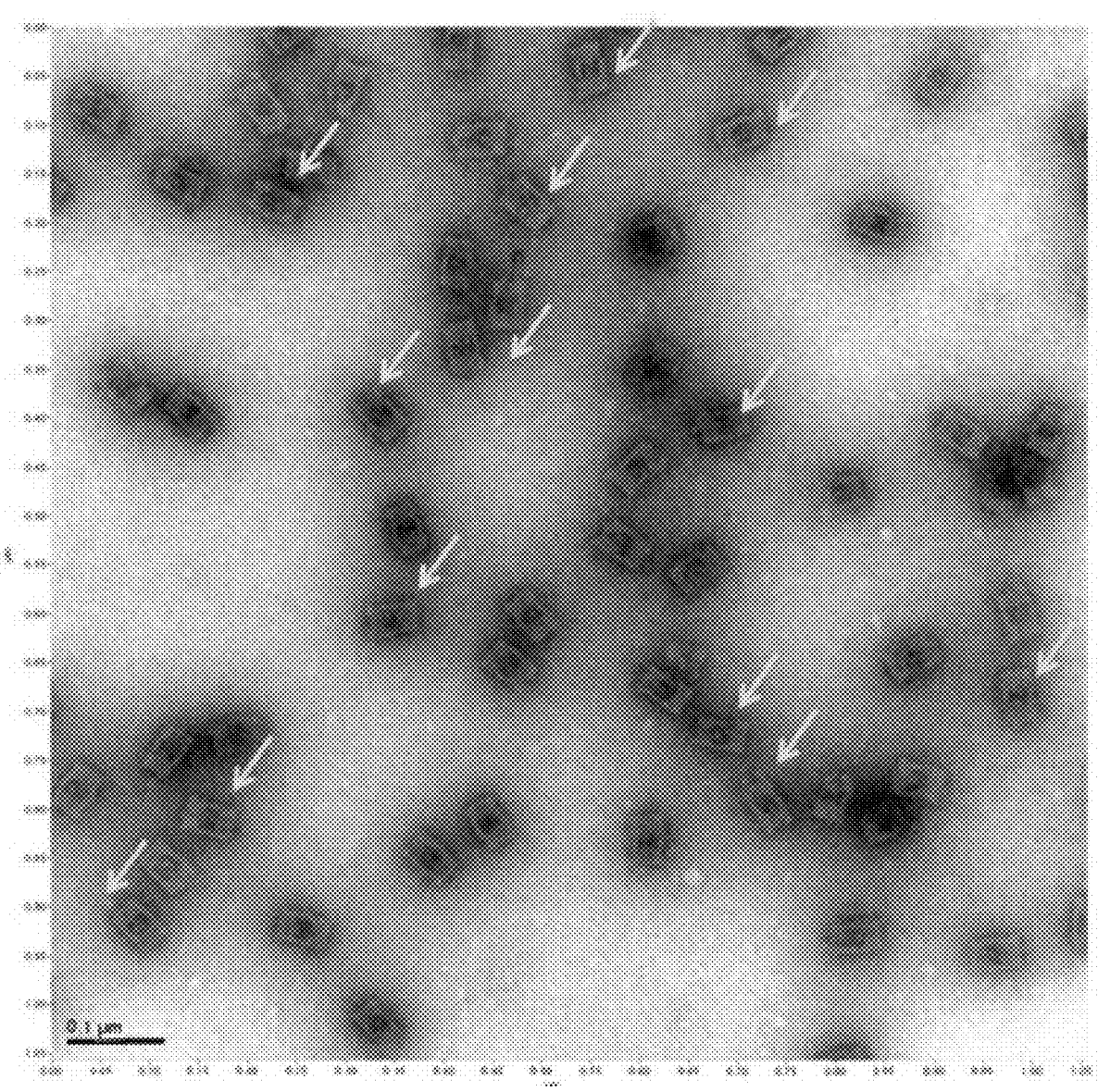

FIG. 18 shows TEM image for HRP-GOx enzyme pairs encapsulated in DNA full-cage. Despite variable quality of staining across the field of view, the inner cavity of many nanocages appeared to contain two bright spots, which we interpreted as intact HRP-GOx enzyme pairs (yellow arrow indicates DNA cage with enzyme pair inside).

Figure 19:
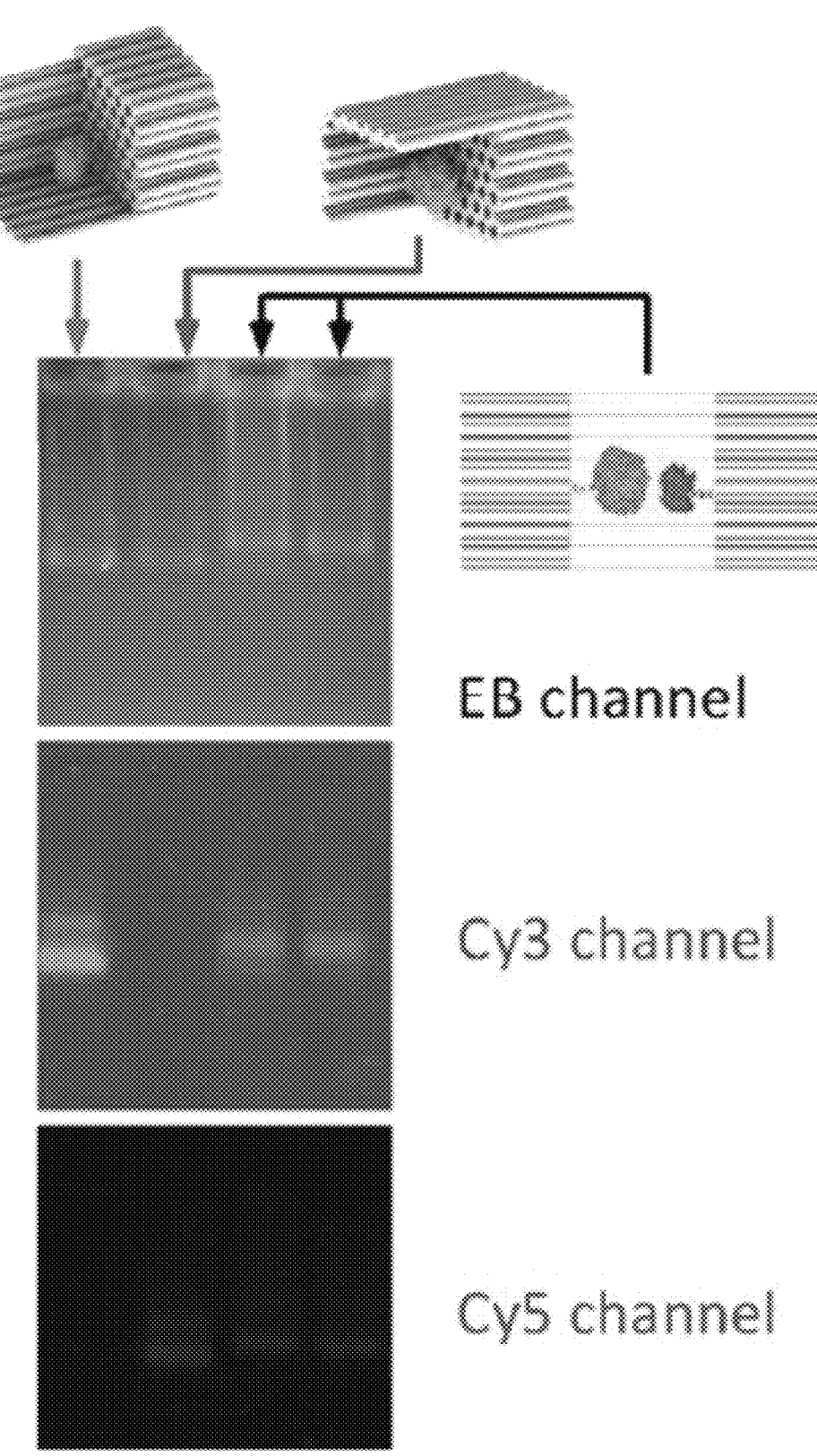

FIG. 19 shows native AGE characterization of a DNA nanocage encapsulating a GOx/HRP pair. GOx and HRP were conjugated with Cy3 and Cy5, respectively. Lane 1 (from left): half-cage assembled with GOx-Cy3, lane 2: half-cage assembled with HRP-Cy5, lanes 3 and 4: full-cage with GOx/HRP. "EB" indicates ethidium bromide staining of the gel to visualize all DNA bands.

Figure 20:
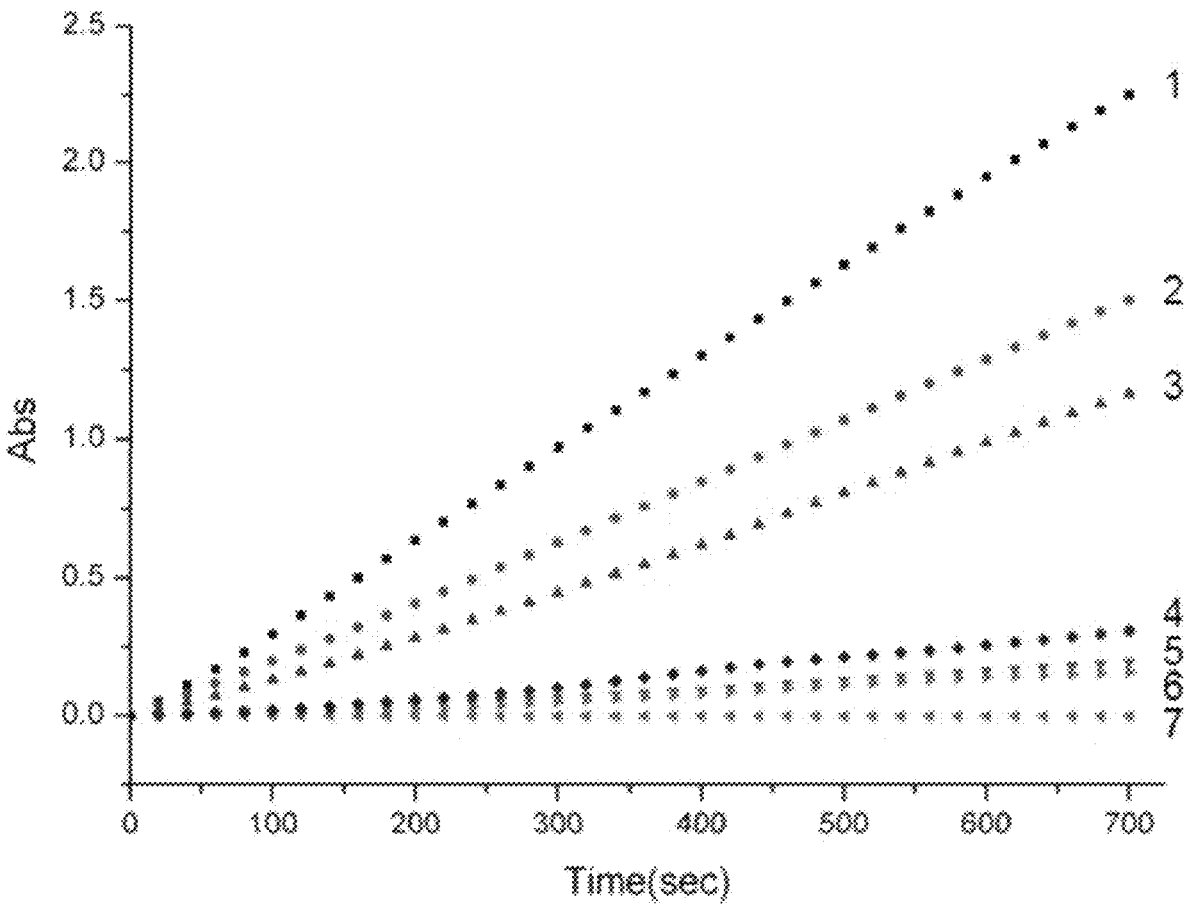

FIG. 20 shows raw activity data for a set of DNA cage-encapsulated enzymes. 1: Full[H+G], a full cage-encapsulated GOx and HRP; 2: Full[H]+Full[G], a full cage-encapsulated HRP and a full cage-encapsulated GOx; 3: half[H]+half[G], a half cage-encapsulated HRP and a half-cage encapsulated GOx; 4: Full+H+G, a full cage incubated with a pair of free HRP and GOx; 5: H+G fresh control, a fresh solution of free HRP and GOx; 6: H+G annealing control, a solution of free HRP and GOx that is incubated using the same thermal program as the DNA cage-encapsulated enzymes; 7: substrate background control. Assay conditions: 1 nM enzyme or enzyme-encapsulating DNA cage, with 1 mM Glucose, 2 mM ABTS in pH 7.5, lx TBS buffer. Absorbance is monitored at 410 nm.

Figure 21:
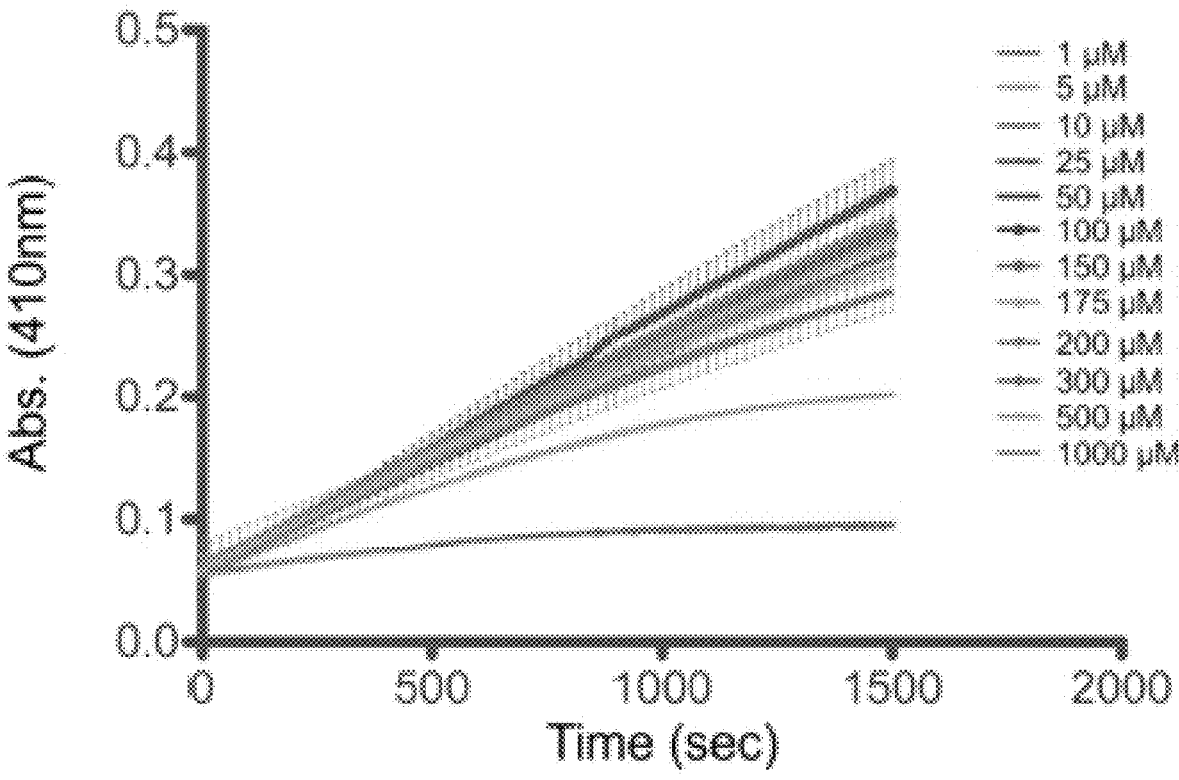

FIG. 21 shows determination of the Michaelis-Menten constants for enzymes-HRP. Raw activity data for free enzyme solution of DNA-conjugated HRP (0.5 nM) with $H_2O_2$ concentration varied from 1 μM to 1000 μM, and 2 mM ABTS, monitoring absorbance at 410 nm. Error bars were calculated from the standard deviation of at least three replicates.

6

Figure 22:
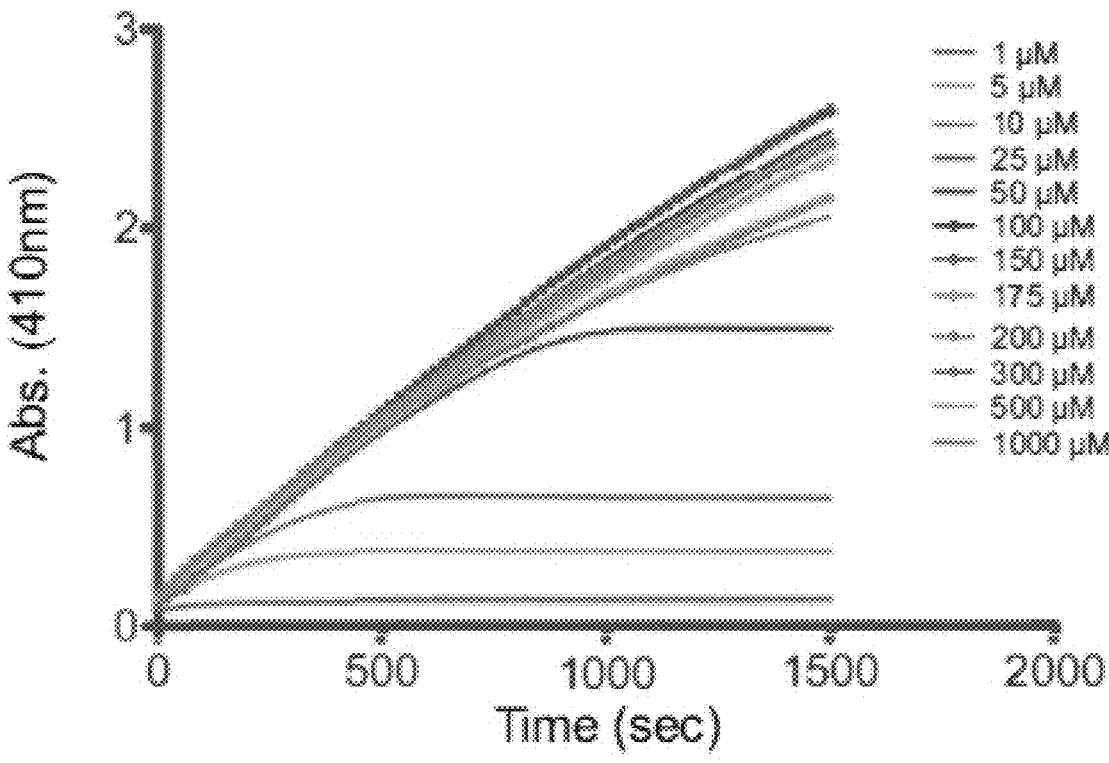

FIG. 22 shows determination of the Michaelis-Menten constants for enzymes-HRP. Raw activity data for DNA cage-encapsulating HRP (0.5 nM) with $H_2O_2$ varied from 1 μM to 1000 μM and 2 mM ABTS, monitoring absorbance at 410 nm. Error bars were calculated from the standard deviation of at least three replicates.

Figure 23:
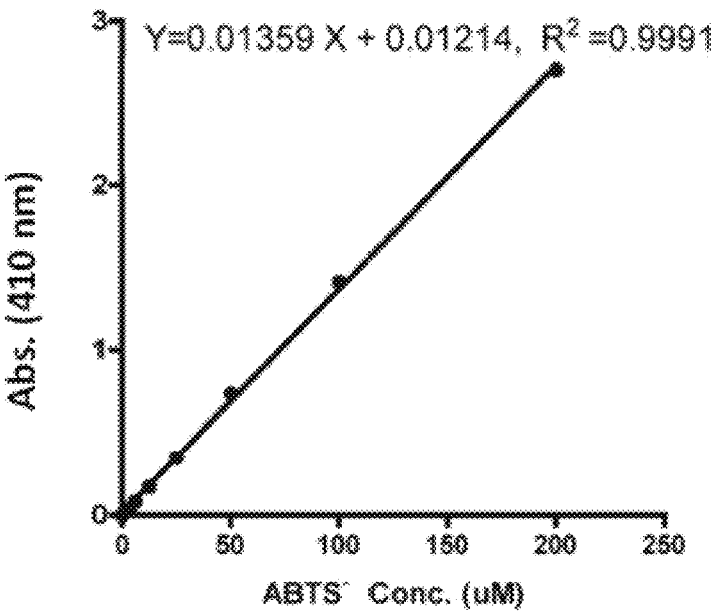

FIG. 23 shows ABTS standard curve to calculate $k_{cat}$ value (Y=0.01359x+0.01214).

Figure 24:
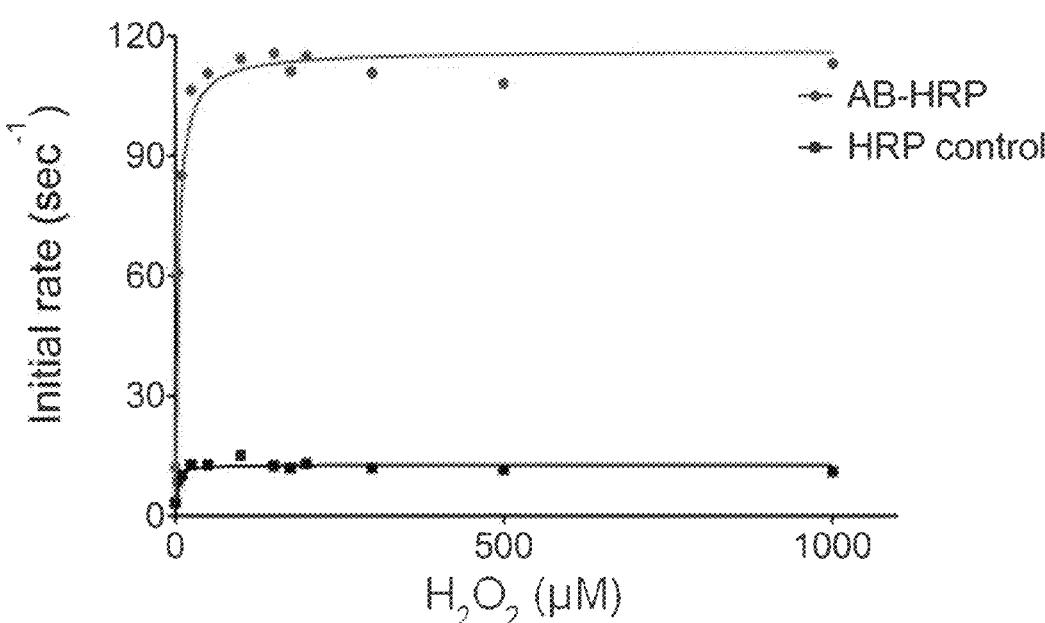

FIG. 24 shows a Michaelis-Menten plot of HRP encapsulated within a full-cage (Full-Cage[HRP], red circles), compared with that of free HRP (HRP control, black squares) using $H_2O_2$ as the substrate. The solid lines represent fits of the Michaelis-Menten model to the data. Enzyme assay conditions: 0.5 nM enzyme or DNA-cage-encapsulated enzyme, 2 mM ABTS with different concentrations of $H_2O_2$ ranging from 1 μM to 1000 μM, in 1×TBS buffer (pH 7.5, 1 mM $MgCl_2$), absorbance monitored at 410 nm. The table lists the fit parameters. Full-cage encapsulation of the enzyme caused a 2-fold increase in $K_M$ and an about 9-fold increase in $k_{cat}$.

Figure 25:
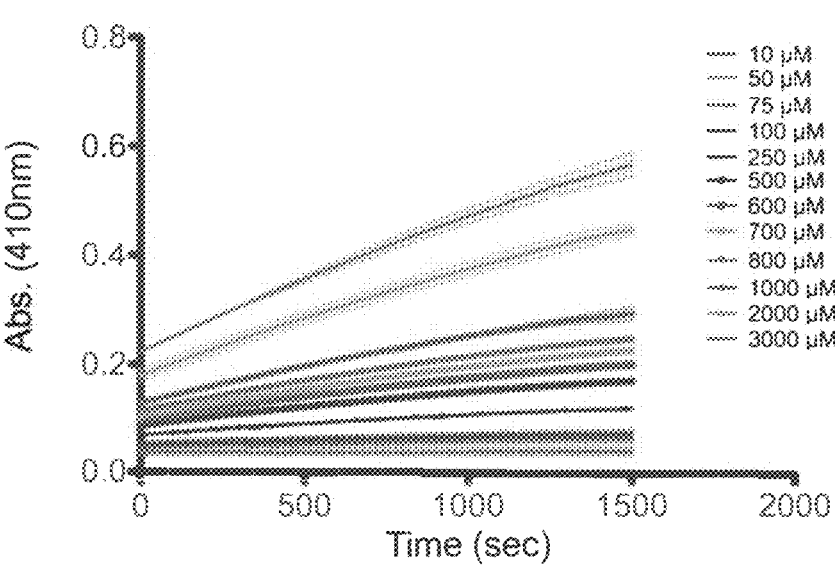

FIG. 25 shows raw activity data measurement of Full-Cage [HRP] (0.5 nM) with ABTS concentration varied from 10 μM to 3000 μM and 2000 μM $H_2O_2$, monitoring absorbance at 410 nm. Error bars were calculated from the standard deviation of at least three replicates.

Figure 26:
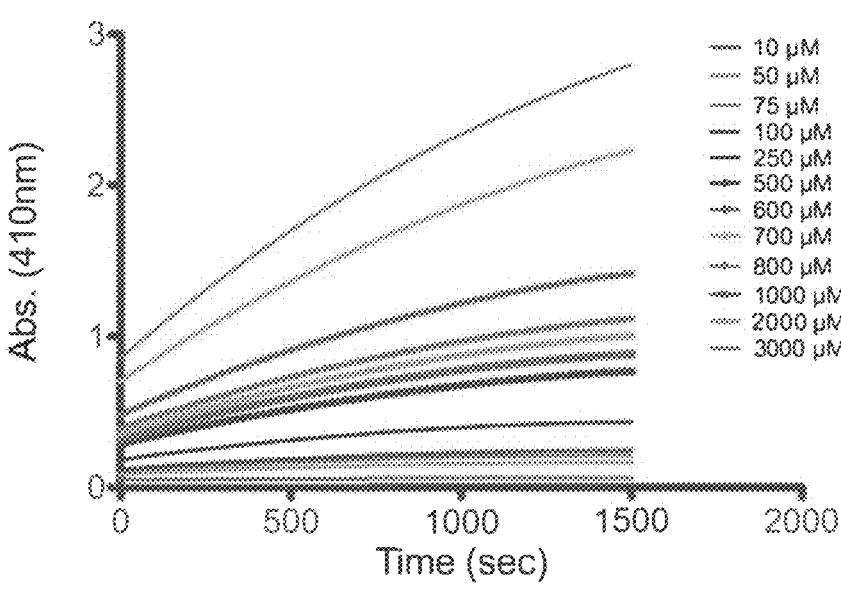

FIG. 26 shows raw activity data measurement of free DNA-conjugated HRP (0.5 nM) with ABTS concentration varied from 10 μM to 3000 μM, and 2000 μM $H_2O_2$, monitoring absorbance at 410 nm. Error bars were calculated from the standard deviation of at least three replicates.

Figure 27:
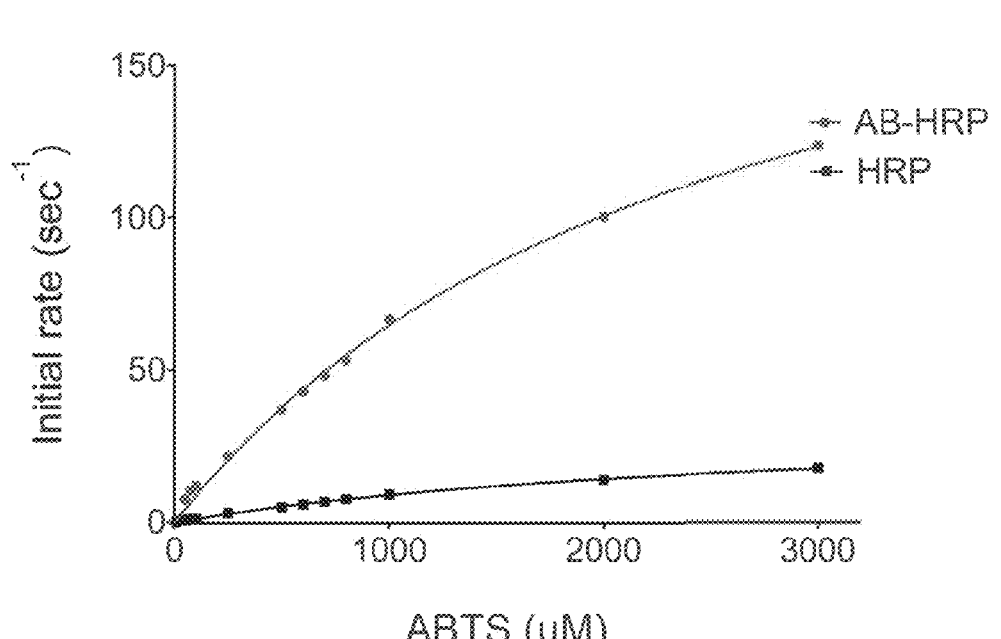

FIG. 27 shows a Michaelis-Menten plot for HRP encapsulated within a full-cage (AB-HRP, red circles), compared with that of free HRP enzyme (HRP control, black squares) using ABTS as the substrate. The solid lines represent fits of the Michaelis-Menten model to the data. Enzyme assay conditions: 0.5 nM enzyme or full-cage-encapsulated enzyme, 2000 μM $H_2O_2$ with different concentrations of ABTS, ranging from 10 μM to 3000 μM, in 1×TBS buffer (pH 7.5, 1 mM $MgCl_2$), monitoring absorbance at 410 nm. The table lists the fit parameters. DNA encapsulation of the enzyme caused no change in $K_M$ and a −9-fold increase in $k_{cat}$.

Figure 28:
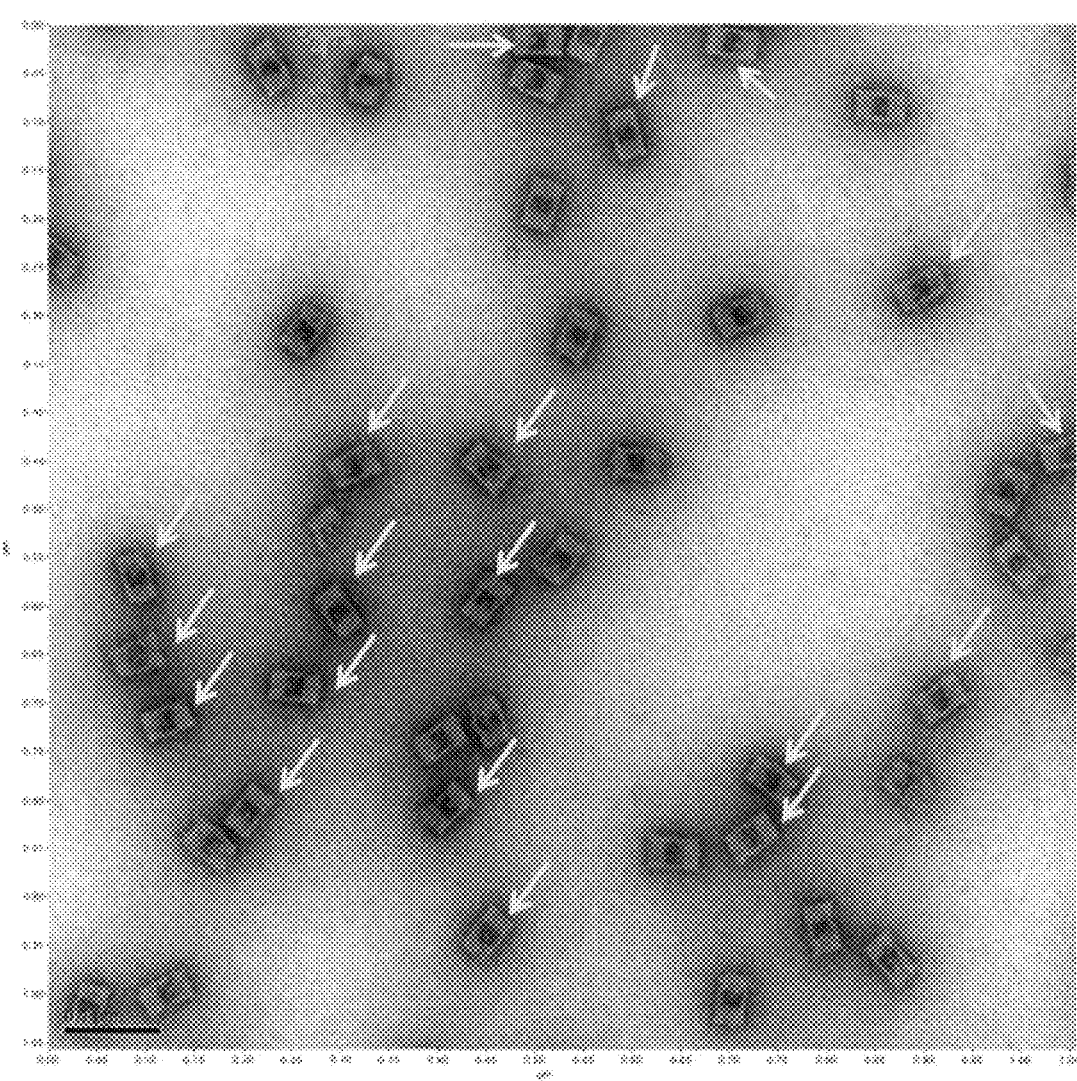

FIG. 28 shows a TEM image for the purified DNA full-cage with only HRP enzyme inside. Scale bar: 100 nm. The majority of cages showed one lighter spot inside the cavity, representing the enzyme. Despite variable quality of staining across the field of view, the inner cavity of many nanocages appeared to contain one bright spot, which we interpreted as intact one HRP enzyme (yellow arrow indicates DNA cage with enzyme inside).

Figure 29:
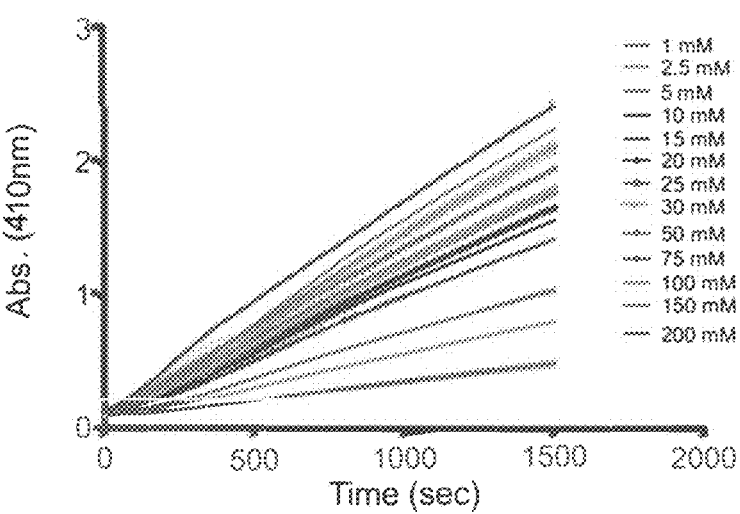

FIG. 29 shows raw activity date for free DNA-conjugated GOx (0.5 nM) with different concentrations of glucose ranging from 1 mM to 200 mM. 2 mM ABTS and 100 nM HRP were used to quickly convert $H_2O_2$ to detectable signal that was monitored at 410 nm. Error bars were calculated from the standard deviation of at least three replicates.

Figure 30:
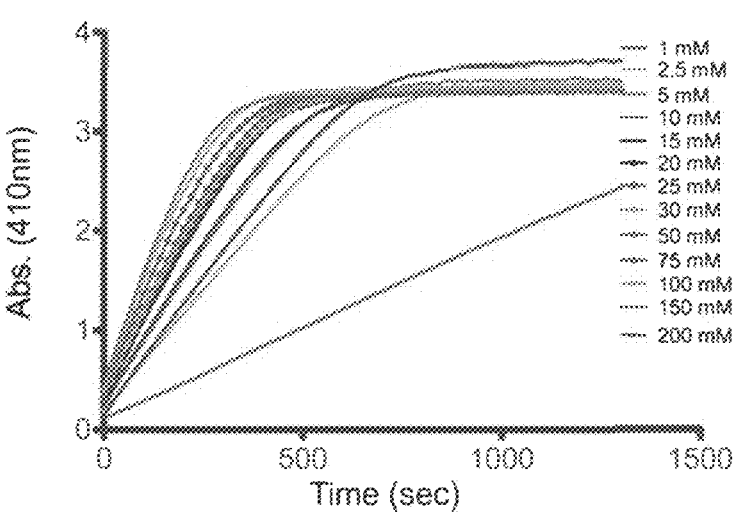

FIG. 30 shows raw activity data for DNA cage-encapsulating GOx (0.5 nM) with different concentrations of glucose ranging from 1 mM to 200 mM. 2 mM ABTS and 100 nM HRP were used to quickly convert $H_2O_2$ to detectable signal that was monitored at 410 nm. Error bars were calculated from the standard deviation of at least three replicates.

Figure 31:
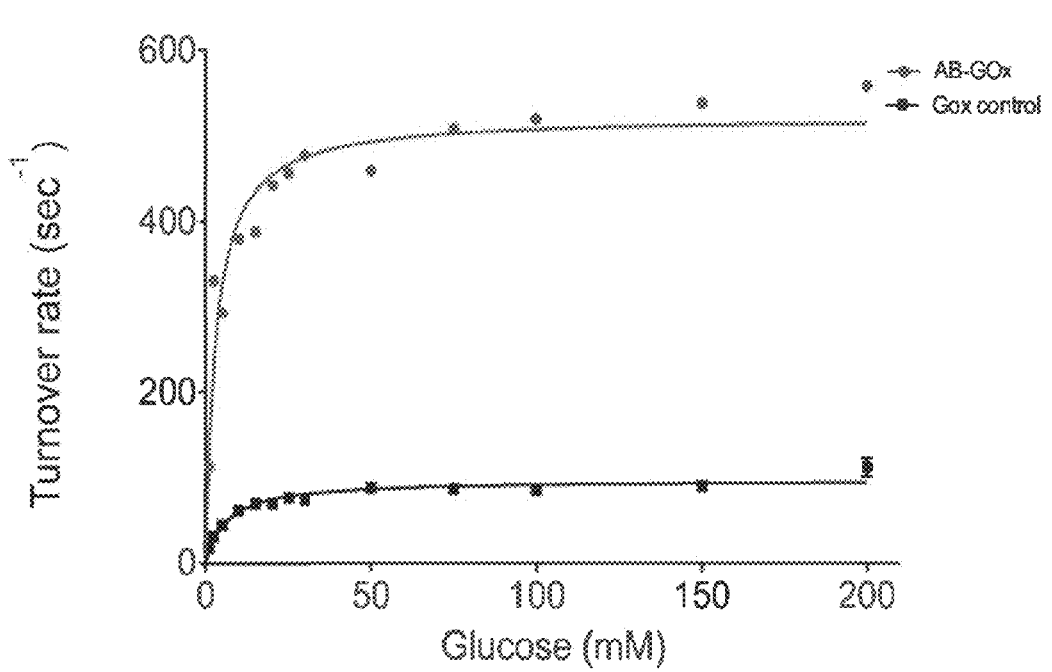

FIG. 31 shows a Michaelis-Menten plot of GOx inside the full-cage (AB-GOx, red circles), compared with that of free GOx enzyme (GOx control, black squares) using glucose as the substrate. The solid lines represent fits of the Michaelis-Menten model to the data. Enzyme assay conditions: 0.5 nM enzyme or DNA cage encapsulated enzyme, 2 mM ABTS, 100 nM HRP with different concentrations of glucose ranging from 1 mM to 200 mM, in 1×TBS buffer (pH 7.5, 1 mM $MgCl_2$) monitoring absorbance at 410 nm. The table lists the fit parameters. DNA encapsulation of the enzyme caused a 2-fold decrease in $K_M$ and a 5-fold increase in $k_{cat}$.

Figure 32:
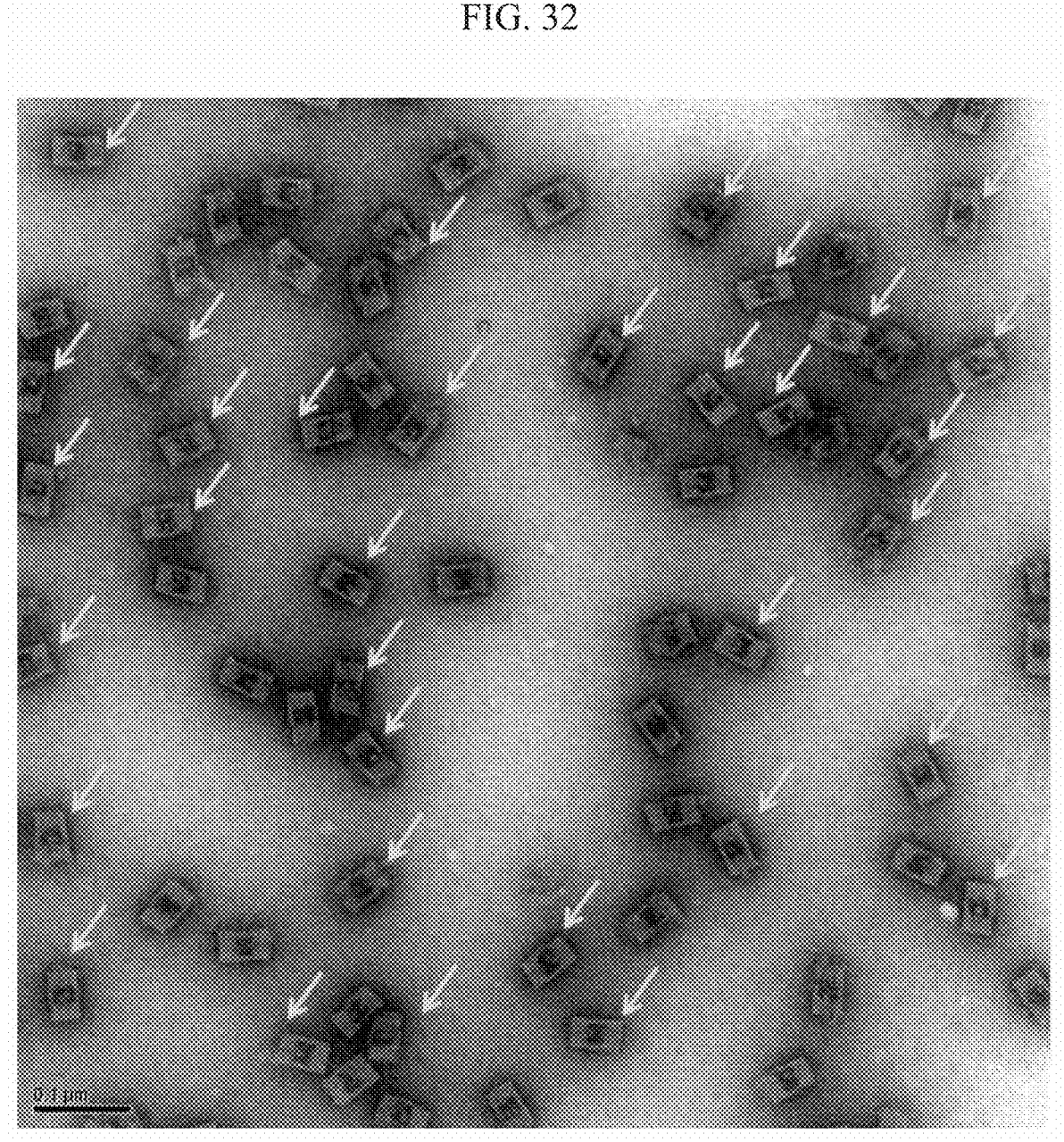

FIG. 32 shows a TEM image of the purified DNA full-cage with only GOx inside (yellow arrow indicates DNA cage with enzyme inside).

Figure 33:
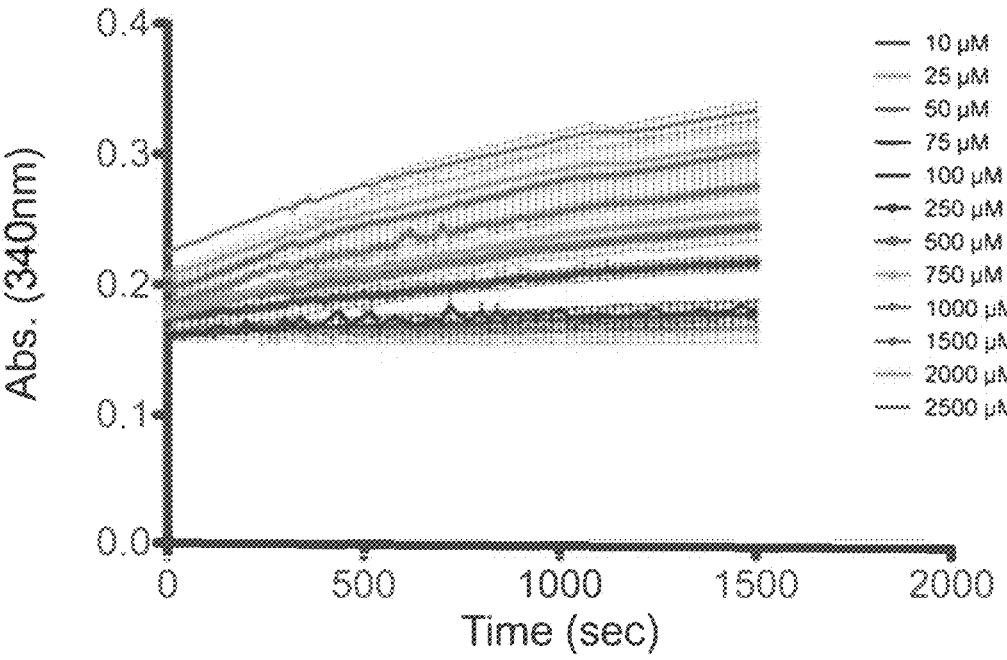

FIG. 33 determination of the Michaelis-Menten constants for enzymes-G6pDH. Raw activity data for free DNA-modified G6pDH (0.5 nM) with 10-2500 μM NAD+ and 1 mM glucose 6-phosphate, monitoring absorbance at 340 nm. Error bars were calculated from the standard deviation of at least three replicates.

Figure 34:
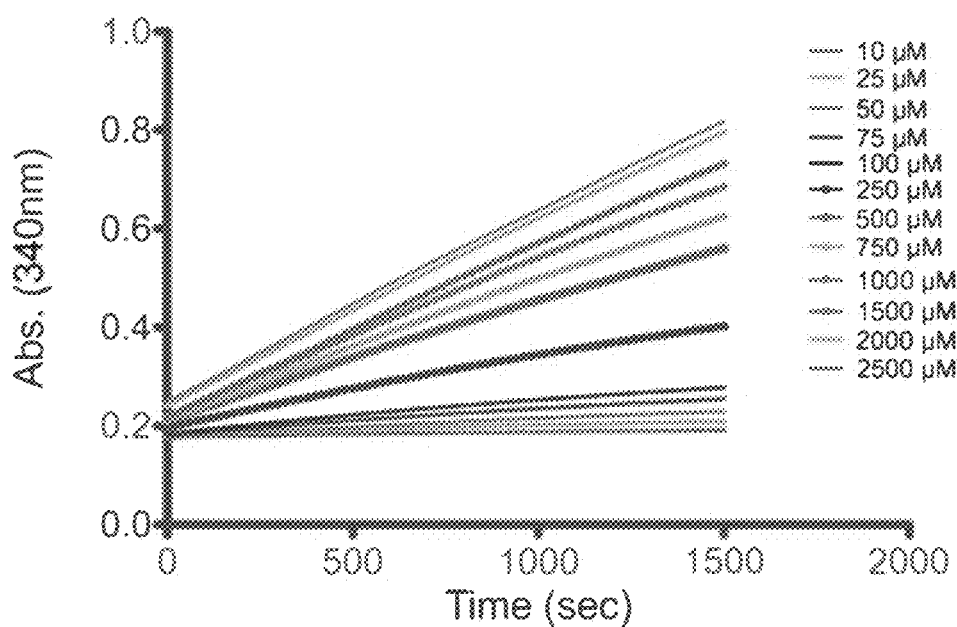

FIG. 34 shows raw activity data for Full-Cage [G6pDH] (0.5 nM) with 10-2500 μM NAD+ and 1 mM glucose 6-phosphate, monitoring absorbance at 340 nm. Error bars were calculated from the standard deviation of at least three replicates.

Figure 35:
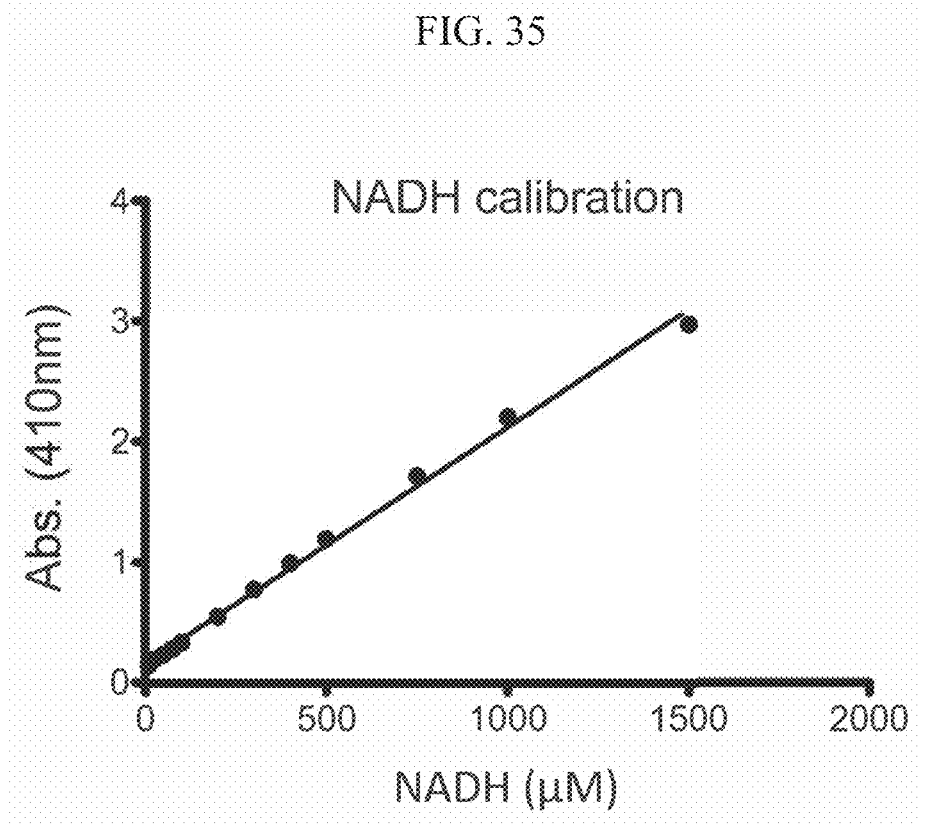

FIG. 35 shows NADH absorbance standard curve to calculate $k_{cat}$ (Y=0.001951X+0.1694).

Figure 36:
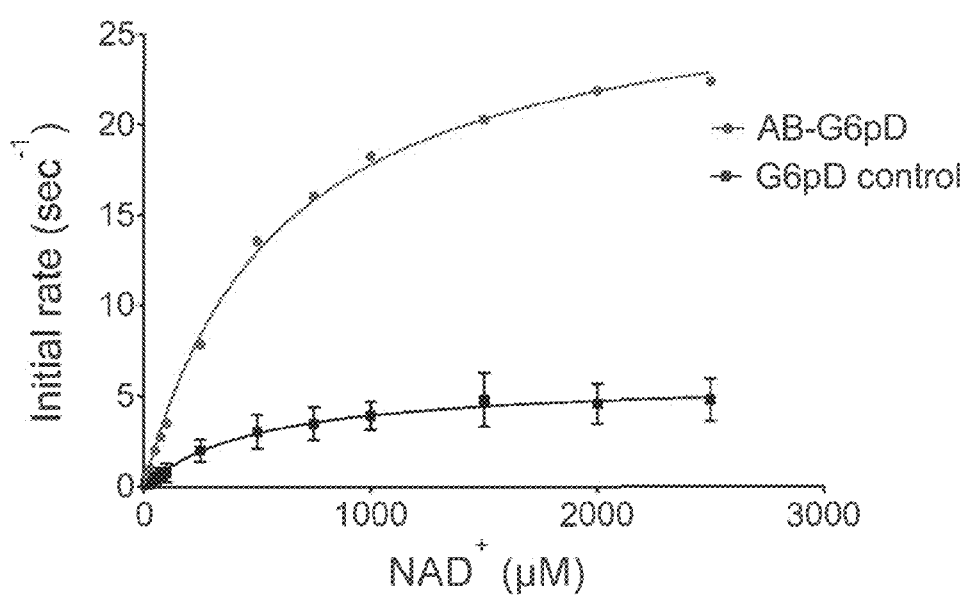

FIG. 36 shows a Michaelis-Menten plot of Full-Cage [G6pDH] (red circles) compared with that of free G6pDH (black square), using NAD+ as the varying substrate. The solid lines represent fits of the Michaelis-Menten model to the data. Enzyme assay conditions: 0.5 nM enzyme or DNA cage-encapsulated enzyme, 1 mM glucose 6-phosphate, with different concentrations of NAD+ ranging from 10 μM to 2500 μM, in 1×TBS buffer (pH 7.5, 1 mM $MgCl_2$), monitoring absorbance at 340 nm. The table lists the fit parameters. Full-cage encapsulation of the enzyme caused little change in $K_M$ and a 5-fold increase in $k_{cat}$. Error bars were calculated from the standard deviation of at least three replicates.

Figure 37:
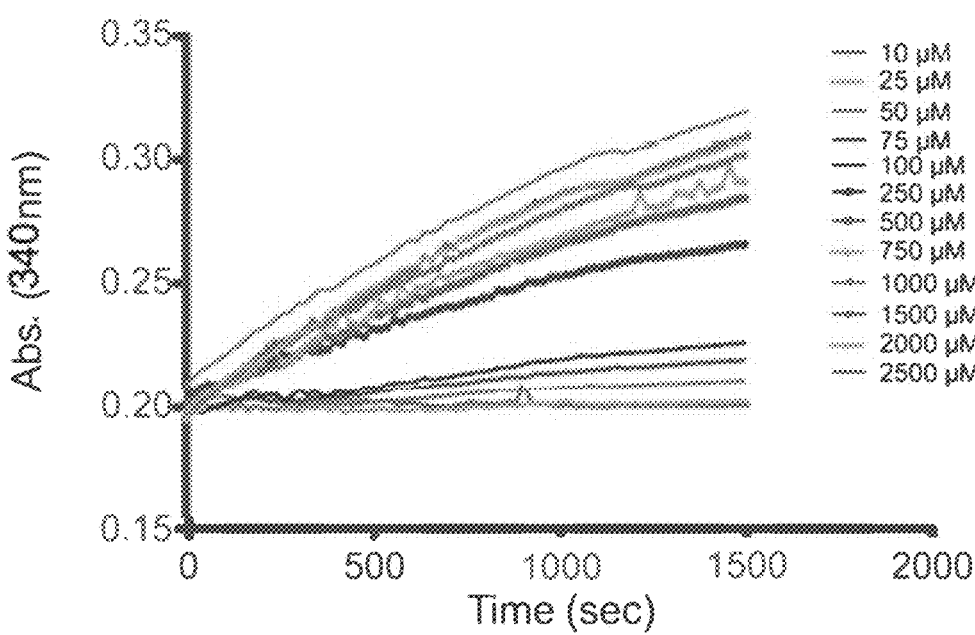

FIG. 37 shows raw activity data for free DNA-modified G6pDH (0.5 nM) with glucose 6-phosphate varied from 10 μM to 2500 μM, and 1 mM NAD+, monitoring at 340 nm. Error bars were calculated from the standard deviation of at least three replicates.

Figure 38:
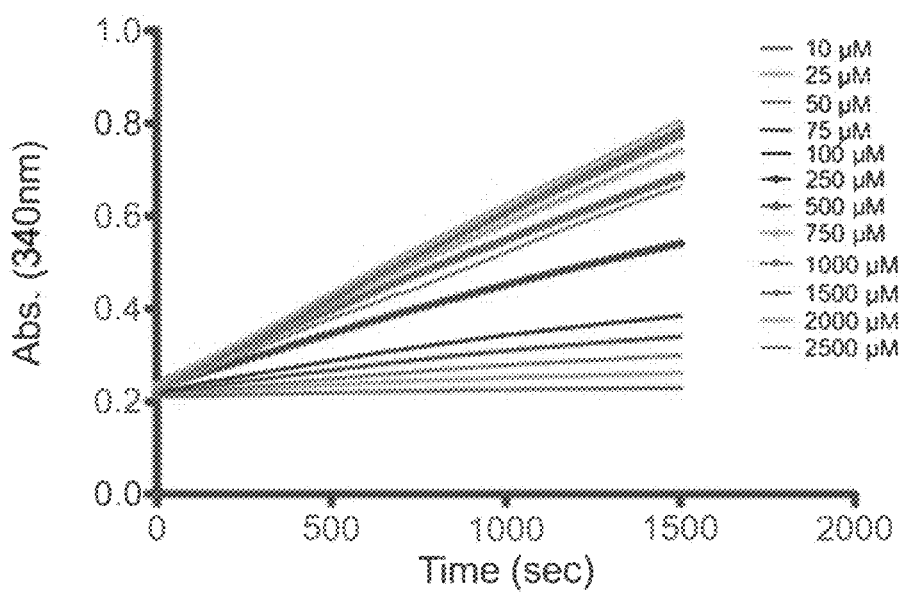

FIG. 38 shows raw activity data for Full-Cage [G6pDH] (0.5 nM) with glucose 6-phosphate varied from 10 μM to 2500 μM, and 1 mM NAD+, monitoring absorbance at 340 nm. Error bars were calculated from the standard deviation of at least three replicates.

Figure 39:
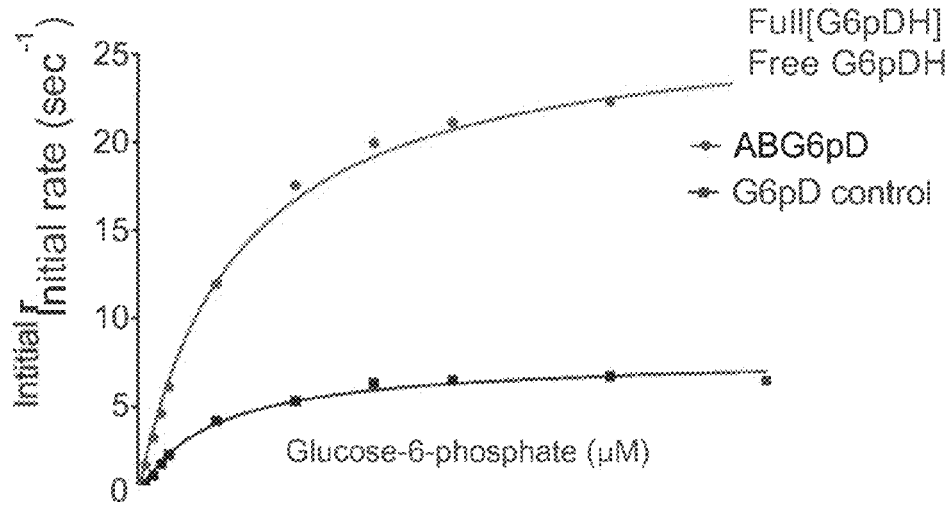

FIG. 39 shows a Michaelis-Menten plot of Full-Cage [G6pDH] (red circles), compared with that of the free G6pDH enzyme (black squares), using glucose 6-phosphate as the substrate. The solid lines represent fits of the Michaelis-Menten model to the data. Enzyme assay conditions: 0.5 nM enzyme or DNA cage-encapsulated enzyme, 1 mM NAO+, with different concentration of glucose-6-phosphate ranging from 10 μM to 2000 μM, in 1×TBS buffer (pH 7.5, 1 mM $MgCl_2$) monitoring absorbance at 340 nm. The table lists the fitting parameters. DNA encapsulation of the enzyme caused a 1.4-fold increase in $K_M$ and a 4-fold increase in $k_{cat}$.

Figure 40:
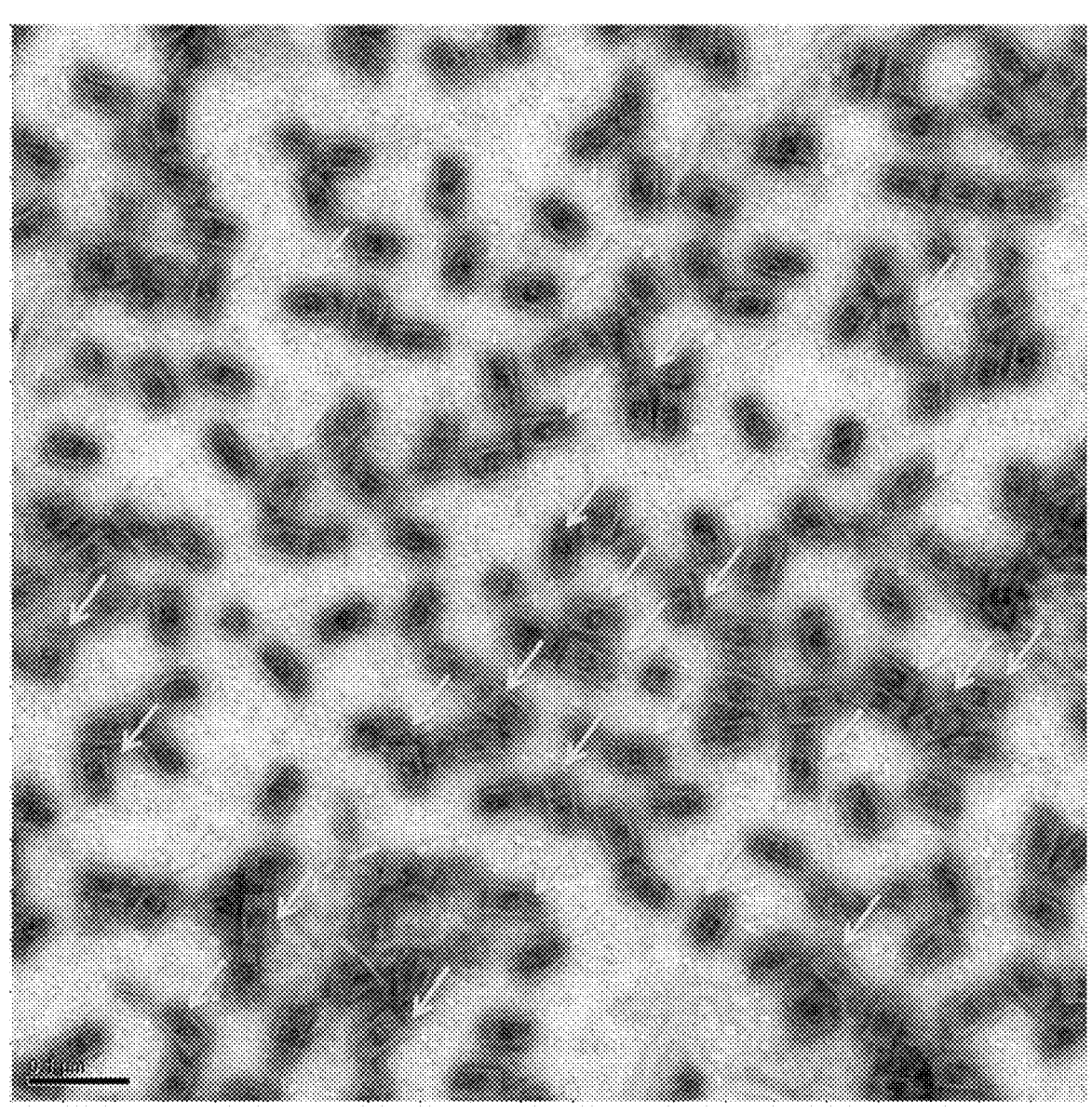

FIG. 40 shows a TEM image of AGE-purified DNA full-cages with G6pDH inside (yellow arrow indicates DNA cage with enzyme inside).

Figure 41:
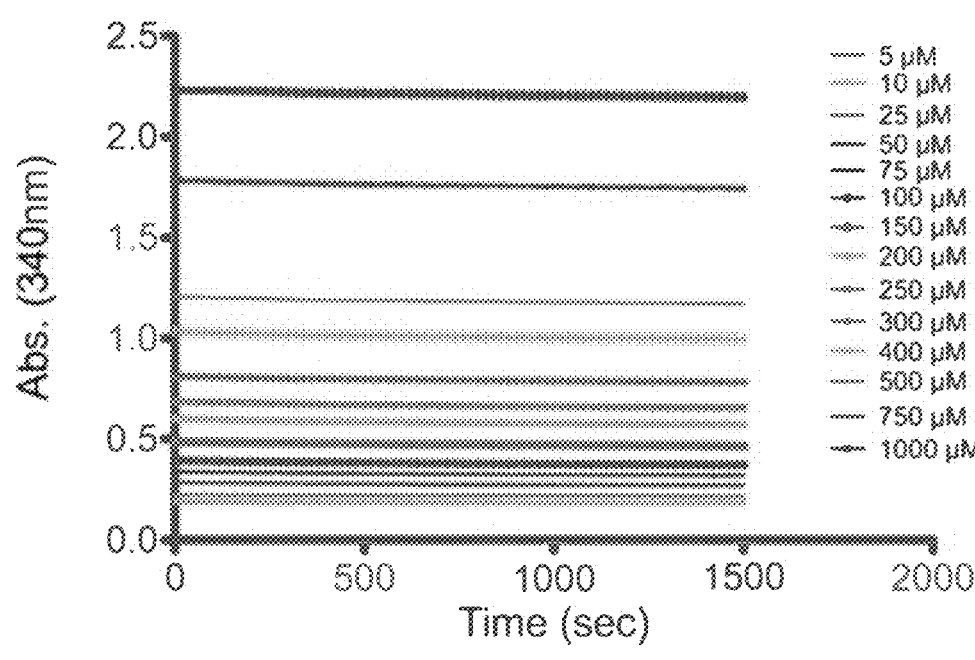

FIG. 41 shows raw activity data for free DNA-modified MDH (0.5 nM) with 5-1000 μM NADH and 2 mM OAA, monitoring absorbance at 340 nm. Error bars were calculated from the standard deviation of at least three replicates.

Figure 42:
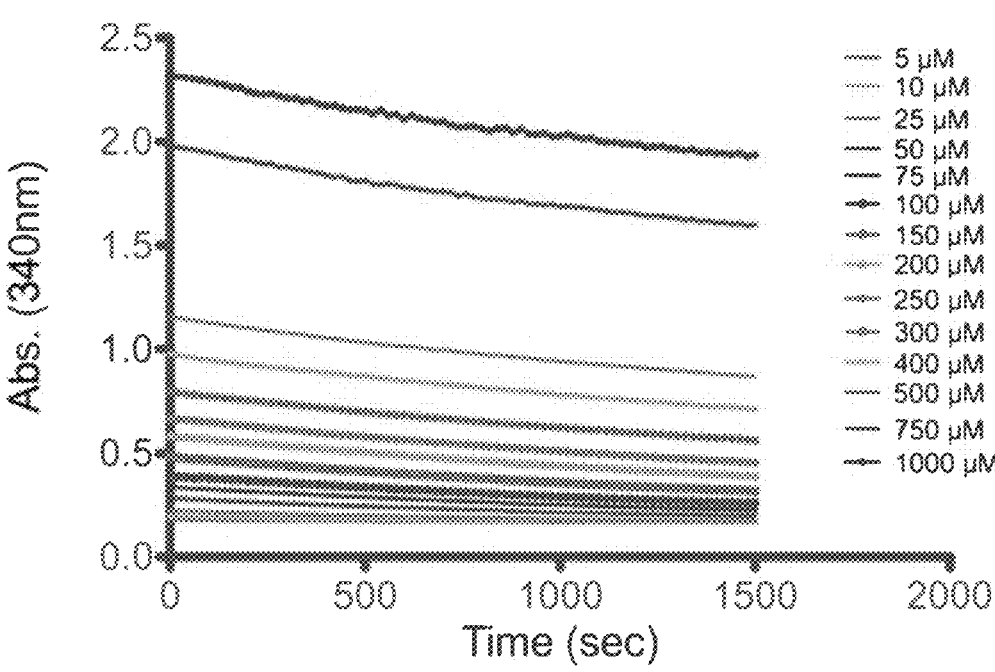

FIG. 42 shows raw activity data for Full-Cage [MDH] (0.5 nM) with 5-1000 μM NADH and 2 mM OAA, monitoring absorbance at 340 nm. Error bars were calculated from the standard deviation of at least three replicates.

Figure 43:
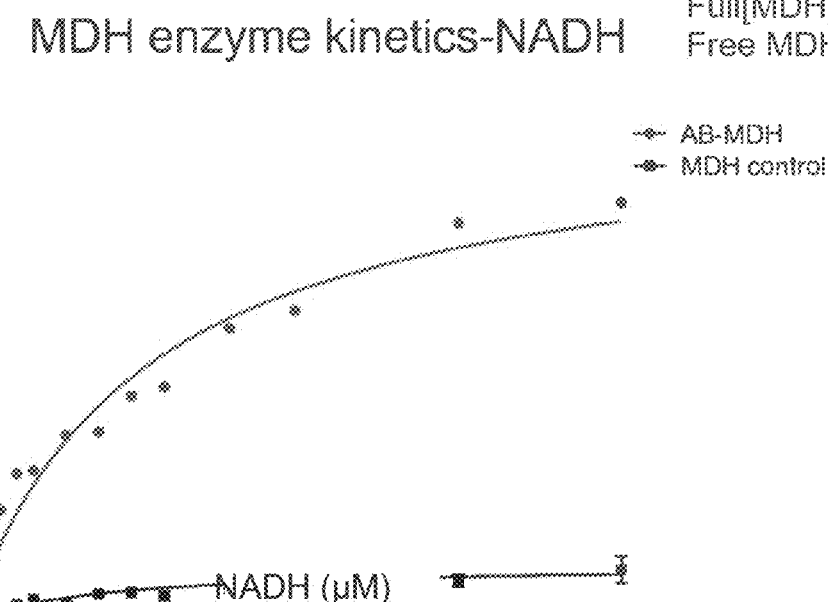

FIG. 43 shows a Michaelis-Menten plot of Full-Cage [MDH] (red circles), compared with that of free MOH (black squares) using NADH as the varying substrate. The solid lines represent fits of the Michaelis-Menten model to the data. Enzyme assay conditions: 0.5 nM enzyme or DNA cage-encapsulated enzyme, 2 mM OAA, with different concentration of NADH ranging from 5 μM to 1000 μM, in HEPES buffer (pH 7.5, 1 mM $MgCl_2$) monitoring absorbance at 340 nm. The table lists the fit parameters. DNA encapsulation of the enzyme caused a 1.5-fold increase in $K_M$ and a 9-fold increase in $k_{cat}$.

Figure 44:
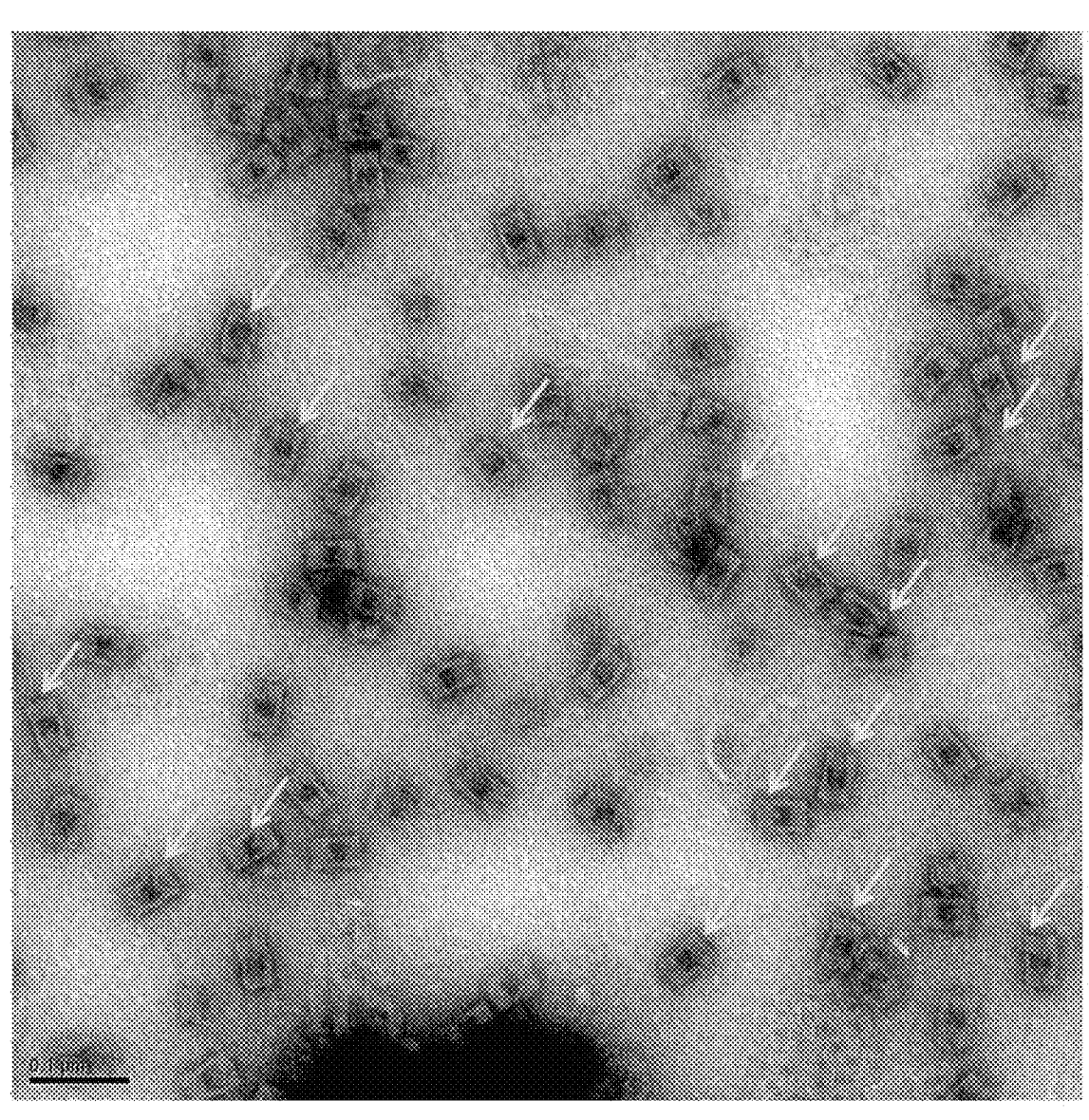

FIG. 44 shows a TEM image for DNA full-cages with MDH inside (yellow arrow indicates DNA cage with enzyme inside).

Figure 45:
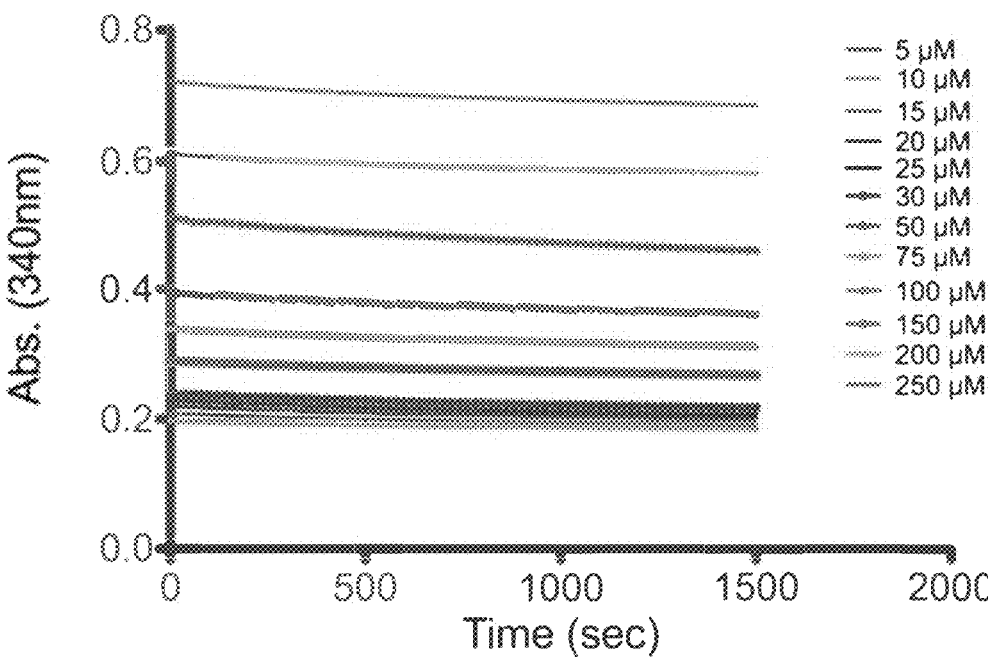

FIG. 45 shows determination of the Michaelis-Menten constants for enzymes-LDH. Raw activity for free DNA-modified LDH (0.5 nM) with 5-250 μM NADH and 2 mM pyruvate, monitoring absorbance at 340 nm. (Error bars were calculated from the standard deviation of at least three replicates)

Figure 46:
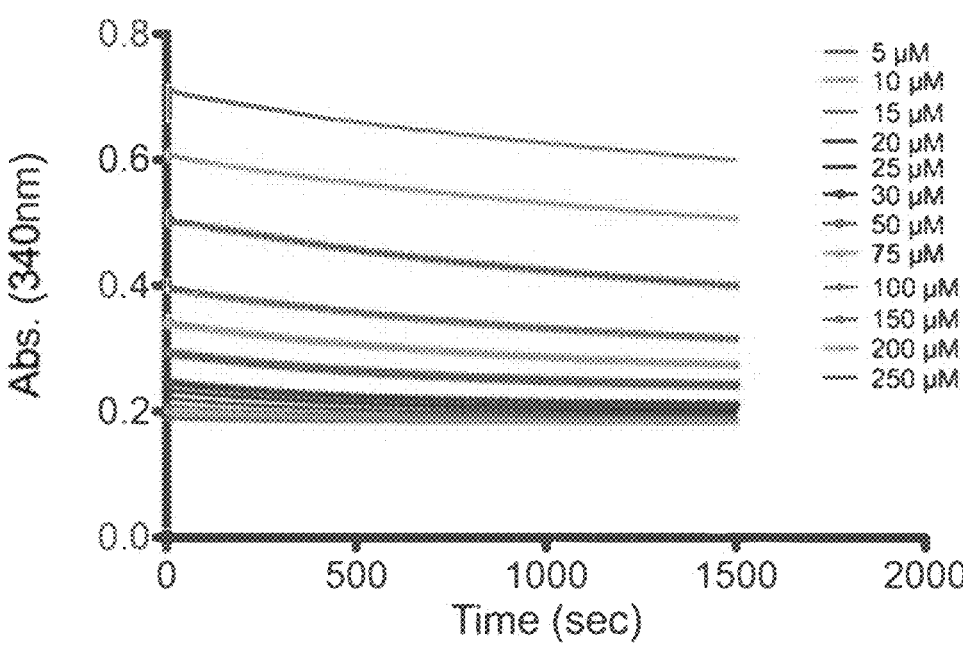

FIG. 46 shows raw activity data for full-cage [LDH] (0.5 nM) with 5-250 μM NADH and 2 mM pyruvate, monitoring absorbance at 340 nm. (Error bars were calculated from the standard deviation of at least three replicates)

Figure 47:
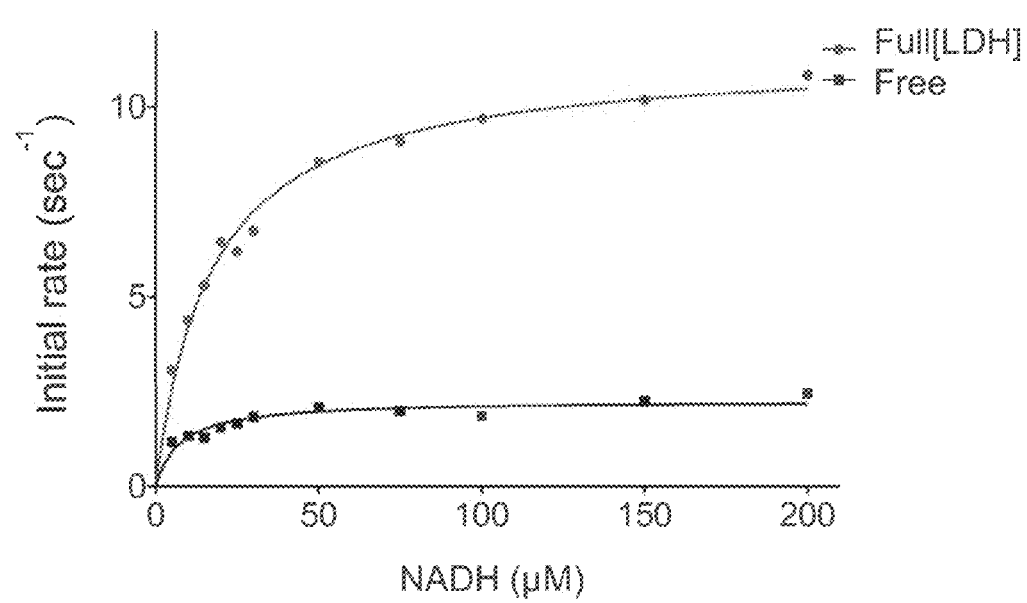

FIG. 47 shows a Michaelis-Menten plot of Full-Cage [LDH] (red circles), compared with that of free LDH (black squares), using NADH as the varying substrate. The solid lines represent fits of the Michaelis-Menten model to the data. Enzyme assay condition: 0.5 nM enzyme or DNA cage encapsulated enzyme, 2 mM pyruvate, with different concentration of NADH ranging from 5 μM to 200 μM, in HEPES buffer (pH 7.5, 1 mM $MgCl_2$) monitoring absorbance at 340 nm. The table lists the fit parameters. DNA encapsulation of the enzyme caused a 2.4-fold increase in $K_M$ and a 4-fold increase in $k_{cat}$.

Figure 48:
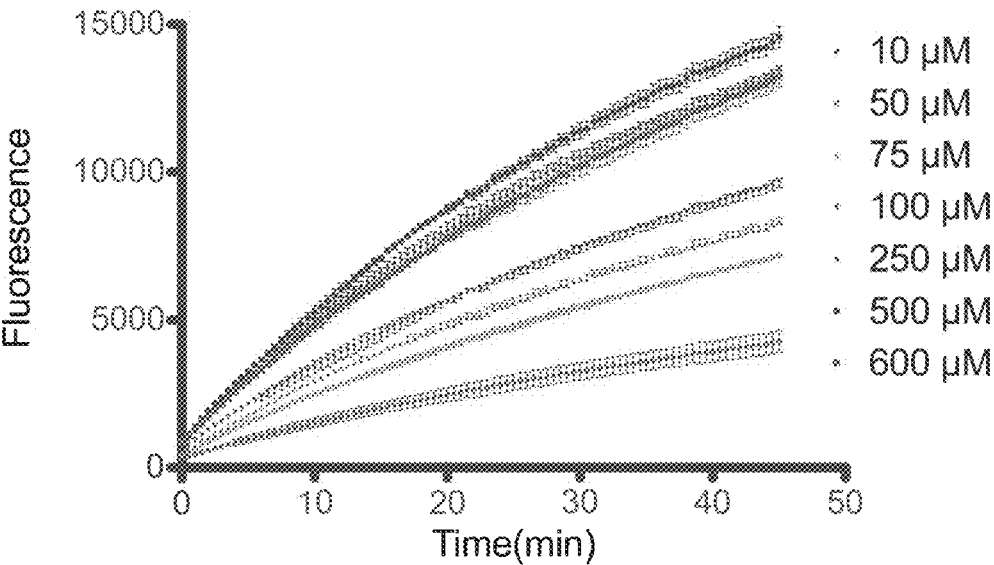

FIG. 48 shows determination of the Michaelis-Menten constants for enzymes-β-Gal. Raw activity data for free DNA-modified β-Gal (0.5 nM) with different concentration of, ranging from 10 μM to 600 μM RBG, monitoring fluorescence at 590 nm (excitation 532 nm). Error bars were calculated from the standard deviation of at least three replicates.

Figure 49:
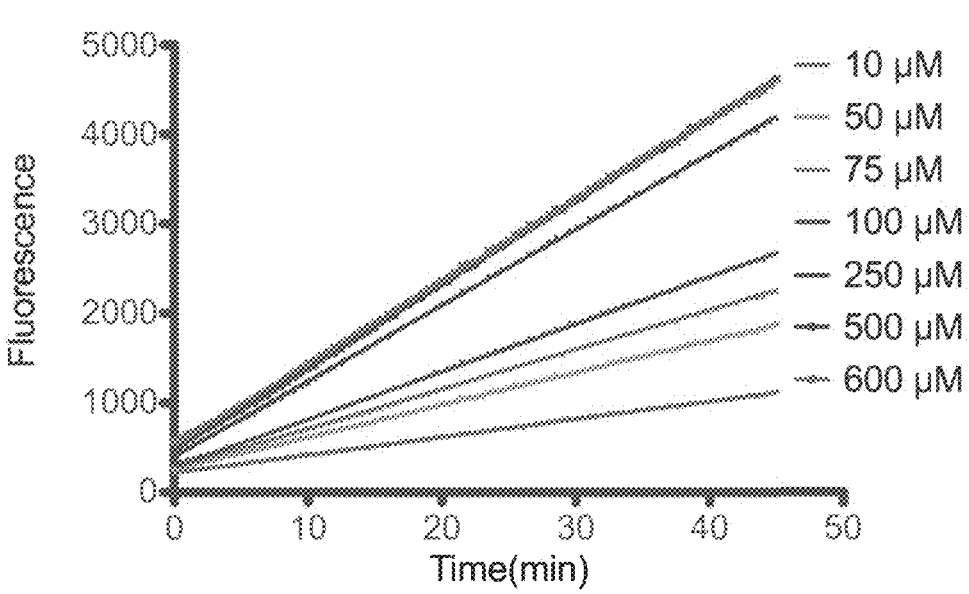

FIG. 49 shows raw activity for full-cage β-Gal (0.5 nM) with different concentration of, ranging from 10 μM to 600 μM RBG, monitoring fluorescence at 590 nm (excitation 532 nm). Error bars were calculated from the standard deviation of at least three replicates.

Figure 50:
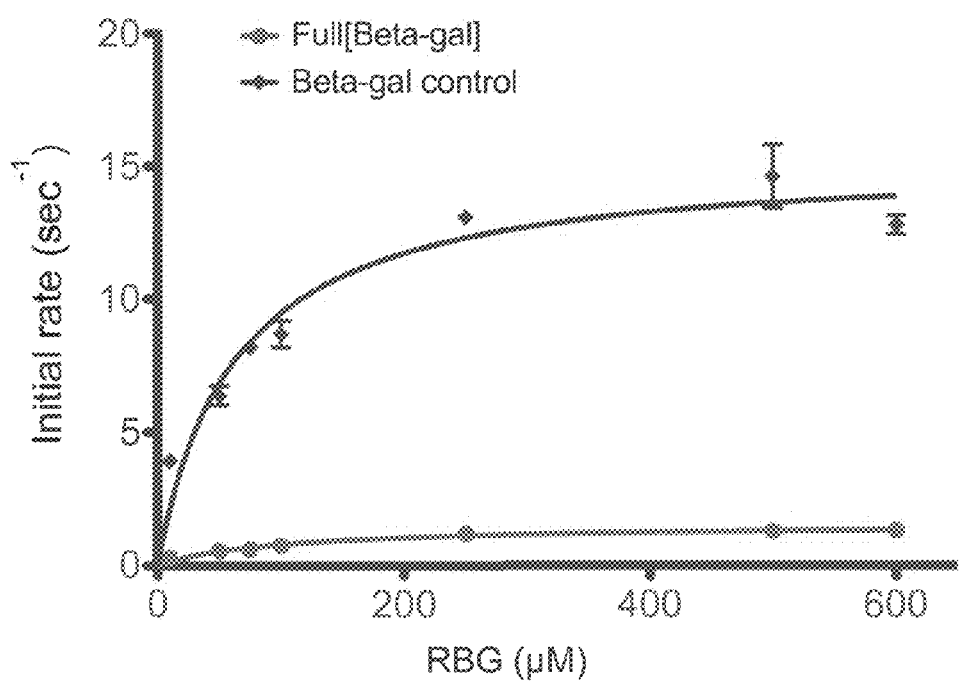

FIG. 50 shows a Michaelis-Menten plot of full-cage β-Gal (red circle), compared with that of the fresh free MDH enzyme (blue square) using RBG as the substrate. The solid line is the fitting curve using the Michaelis-Menten model. Enzyme assay condition: 0.5 nM enzyme or DNA cage encapsulated enzyme, with different concentration of RBG, ranging from 10 μM to 600 μM, in TBS buffer (pH 7.5, 1 mM $MgCl_2$) monitoring fluorescence at 532/590 nm. The table lists the fitting parameters. DNA encapsulation of the enzyme caused a −1.6-fold increase in $K_M$ and a −81% decrease in $k_{cat}$ Error bars were calculated from the standard deviation of at least three replicates.

Figure 51:
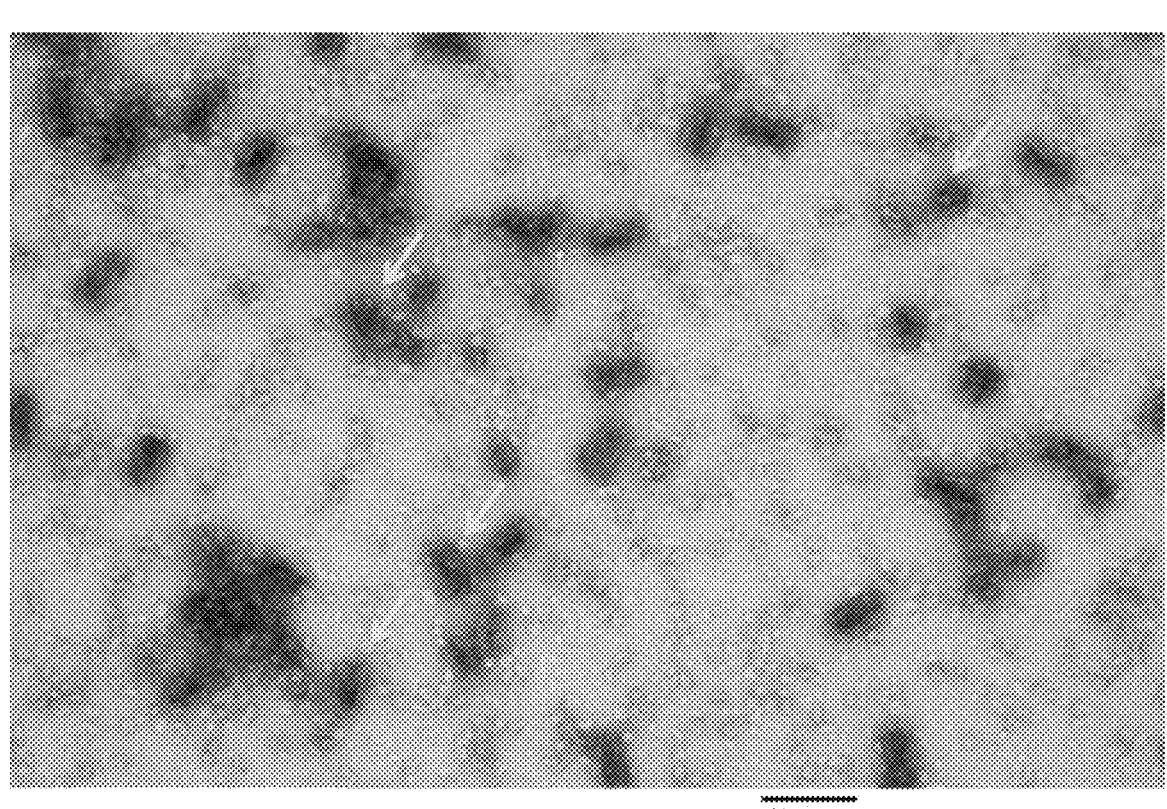
Figures 52A, 52B, 52C, 52D, 52E:
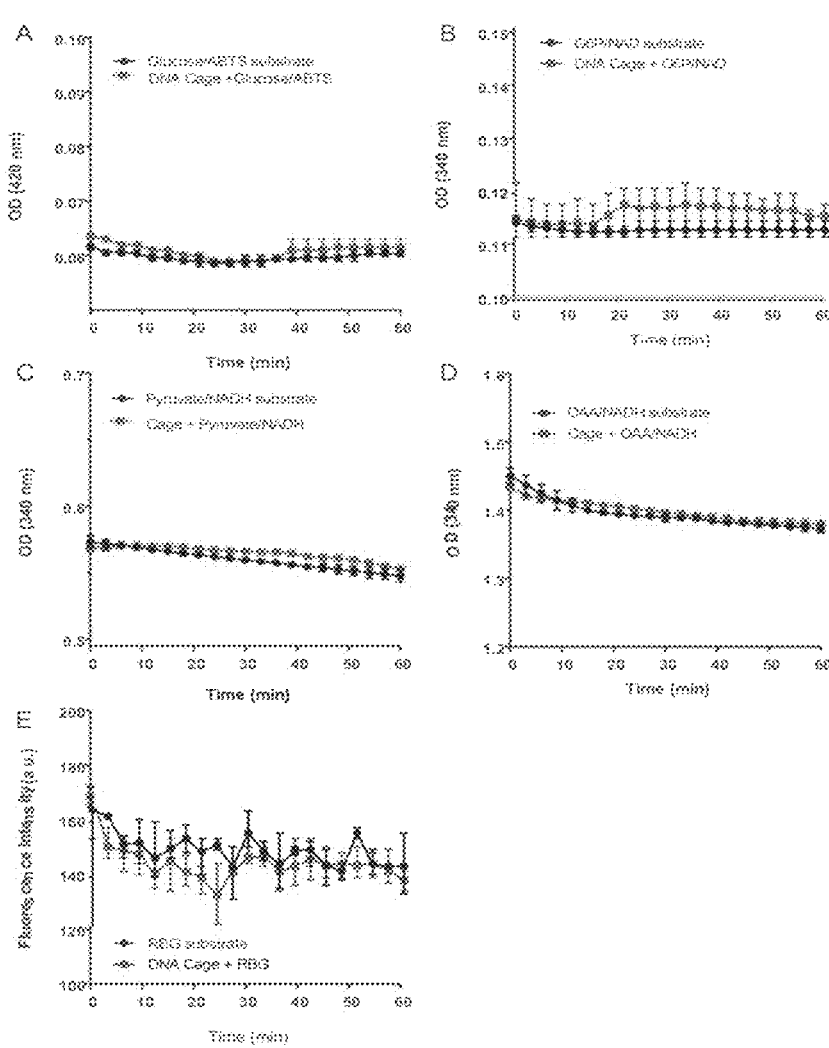

FIG. 51 shows a TEM image for the DNA full-cages with β-Gal inside (yellow arrow indicates DNA cage with enzyme inside).

FIGS. 52A-52E show control experiments in which DNA cages were incubated with enzyme substrates. (A) Red curve: 1 nM Cage was incubated with 1 mM glucose and 2 mM ABTS (GOx/HRP substrates) in 1×TBS, pH 7.5; Black: Autocatalysis of 1 mM glucose and 2 mM ABTS (GOx/HRP substrates) in 1×TBS, pH 7.5. (B) Red: 0.5 nM Cage was incubated with 1 mM glucose-6-phosphate and 1 mM NAO+ (G6pDH substrates) in 1×TBS, pH 7.5; Black: Autocatalysis of 1 mM glucose-6-phosphate and 1 mM NAO+ in 1×TBS, pH 7.5. (C) Red: 0.5 nM Cage was incubated with 2 mM pyruvate and 0.25 mM NAOH (LOH substrates) in 1×TBS, pH 7.5; Black: Autocatalysis of 2 mM pyruvate and 0.25 mM NAOH in 1×TBS, pH 7.5. (D) Red: 0.5 nM Cage was incubated with 2 mM oxaloacetate (OAA) and 1 mM NAOH (MOH substrates) in 1×TBS, pH 7.5; Black: Autocatalysis of 2 mM OAA and 1 mM NAOH in 1×TBS, pH 7.5. (E) Red: 0.5 nM Cage was incubated with 100 μM resorufin beta-D-galactopyranoside (RBG, β-Gal substrate) in 1×TBS, pH 7.5; Black: Autocatalysis of 100 μM RBG in 1×TBS, pH 7.5, 532 nm (excitation)/590 nm (emission). Error bars were calculated from the standard deviation of at least three replicates. All above results indicate that DNA cages at our experimental concentrations do not significantly catalyze substrate conversion.

Figure 53:
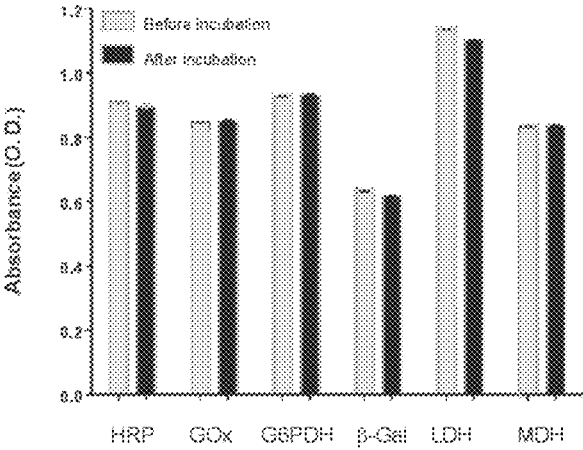

FIG. 53 shows a test of the nonspecific adsorption of enzymes onto a plastic 96-well plate. Enzyme concentrations are quantified by UV-VIS spectrometer using the following extinction coefficients: HRP ($E_{405nm}$—100,000 M-1 cm-1), GOx ($E_{280nm}$—267,200 M-1 cm-1), G6pDH ($E_{280nm}$—118,450 M-1 cm-1), β-Gal ($E_{280nm}$—972,093 M-1 cm-1), LDH ($E_{280nm}$—202,640 M-1 cm-1), MDH ($E_{280nm}$—19,600 M-1 cm-1). The UV-Vis absorbance of 100 μL of each enzyme solution was measured before adding to the plates, as well as after one hour incubation within the plates in the dark. These conditions are the same as those of the enzyme activity assay. As shown in the Figure, all enzyme solutions showed only a very slight decrease in absorbance after incubation in the plates, suggesting very weak nonspecific adsorption of enzymes onto the plastic plates. Error bars were calculated from the standard deviation of at least three replicates.

Figure 54:
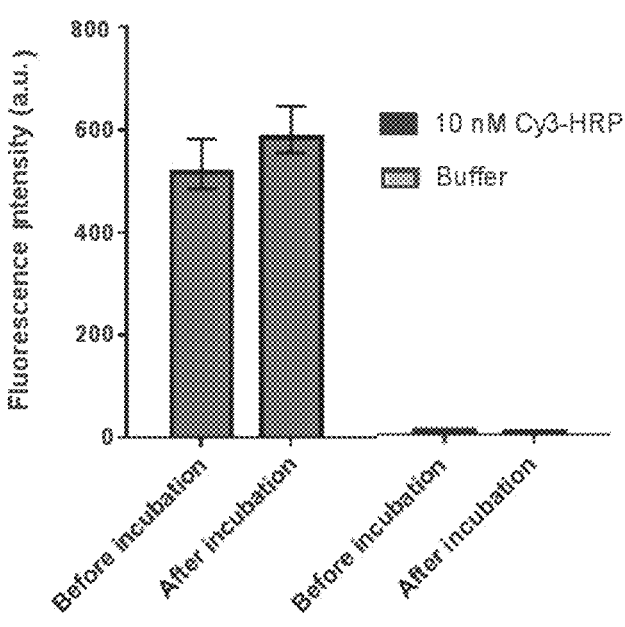

FIG. 54 shows testing for nonspecific adsorption of low nanomolar concentrations of enzymes onto plastic 96-well plates was tested using Cy3-labeled HRP. 100 μL of 10 nM Cy3-labeled HRP was assayed for fluorescence intensity, and then the plate was incubated inside a plate reader for one hour. The remaining fluorescence intensity was tested again. A slight increase of fluorescence intensity was observed, possibly due to the buffer evaporation during the incubation. This result suggests that there is very little nonspecific adsorption of Cy3-HRP onto the 96-well plate. Error bars were calculated from the standard deviation of at least three replicates.

Figure 55:
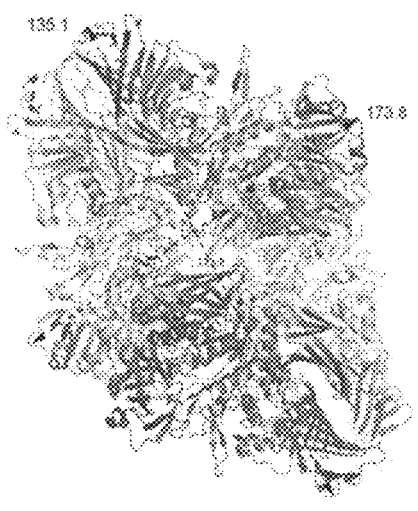
Figure 55:
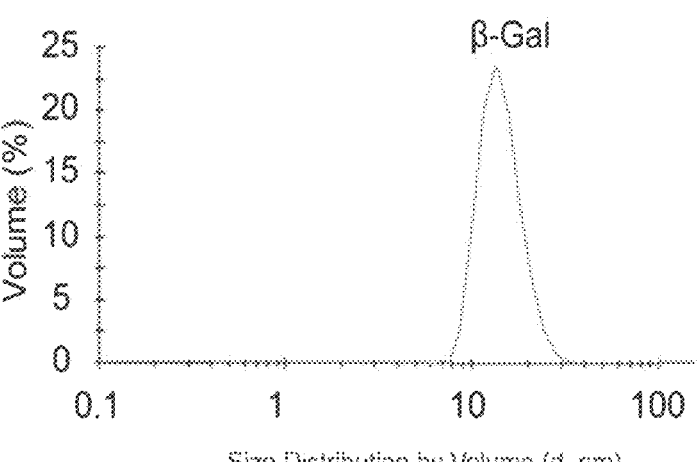

FIG. 55 shows the crystal structure of β-Gal which shows its dimensions to be 17 nm×14 nm (left) (Jacobson, R. H. et al. Nature 369, 761-766 (1994)). Dynamic Light Scattering measures a hydrodynamic diameter of 14-18 nm.

Figure 56:
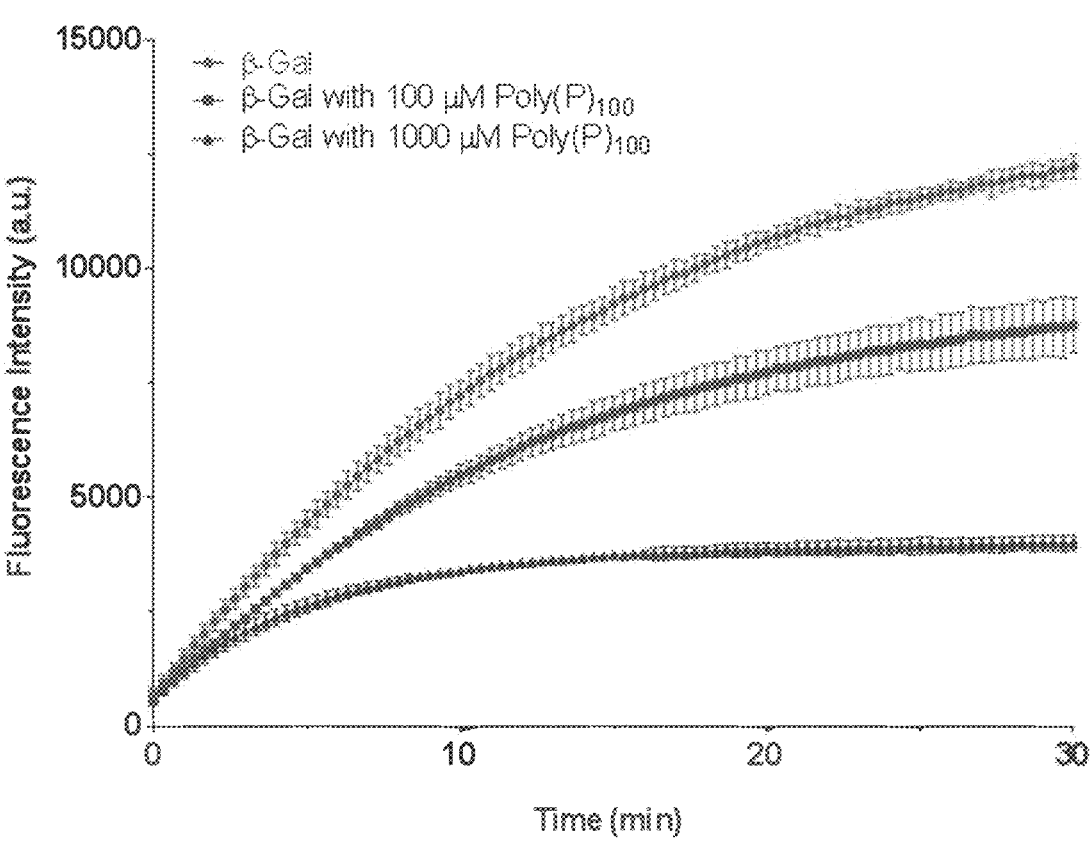
Figures 57A, 57B, 57C, 57D, 57E:
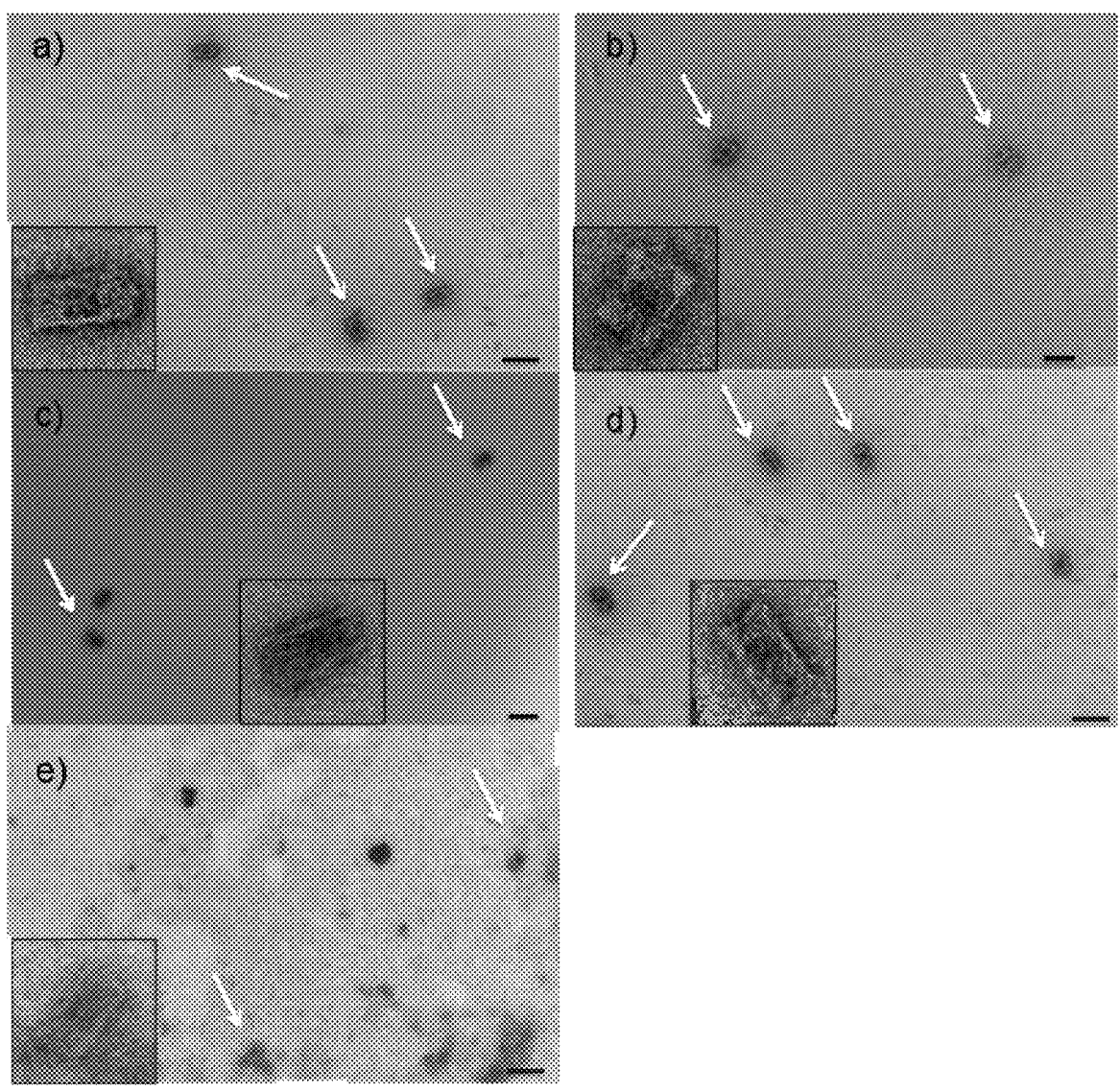

FIG. 56 shows inhibition of β-Gal activity by 100-mer polyphosphate (Poly(P)100) in solution. Assay condition: 0.25 nM β-Gal and 100 μM RBG in pH 7.4, 50 mM HEPES buffer. For inhibition assay, β-Gal was first incubated with Poly(P)100 for half an hour, then RBG substrate was added before measuring the activity. The control β-Gal was run at the same condition except for the incubation with buffer for half an hour. The activity of β-Gal was significantly inhibited by 1000 μM Poly(P)100. Error bars were calculated from the standard deviation of at least three replicates.

FIGS. 57A-57E show TEM images of DNA cages after 1 h incubation with a) GOx-HRP enzymatic reaction (conditions: 50 mM HEPES, pH 7.5, 1 mM MgCl₂, 1 mM glucose, 2 mM ABTS, 1 nM GOx-HRP, 0.5 nM DNA cage), b) G6pDH enzyme reaction (conditions: 50 mM HEPES, pH 7.5, 1 mM MgCl₂, 1 mM glucose-6-phosphate, 1 mM NAD\ 1 nM G6pDH, 0.5 nM DNA cage), c) MDH enzyme reaction (conditions: 50 mM HEPES, pH 7.5, 1 mM MgCl₂, 2 mM OAA, 1 mM NADH, 1 nM MDH, 0.5 nM DNA cage), d) LDH enzyme reaction (conditions: 50 mM HEPES, pH 7.5, 1 mM MgCl₂, 2 mM pyruvate, 1 mM NADH, 1 nM LDH, 0.5 nM DNA cage), e) (3-gal enzyme reaction (conditions: 50 mM HEPES, pH 7.5, 1 mM MgCl₂, 1 mM RBG 1 nM Beta-gal, 0.5 nM DNA cage). (Scale bars: 50 nm)

Figure 58:
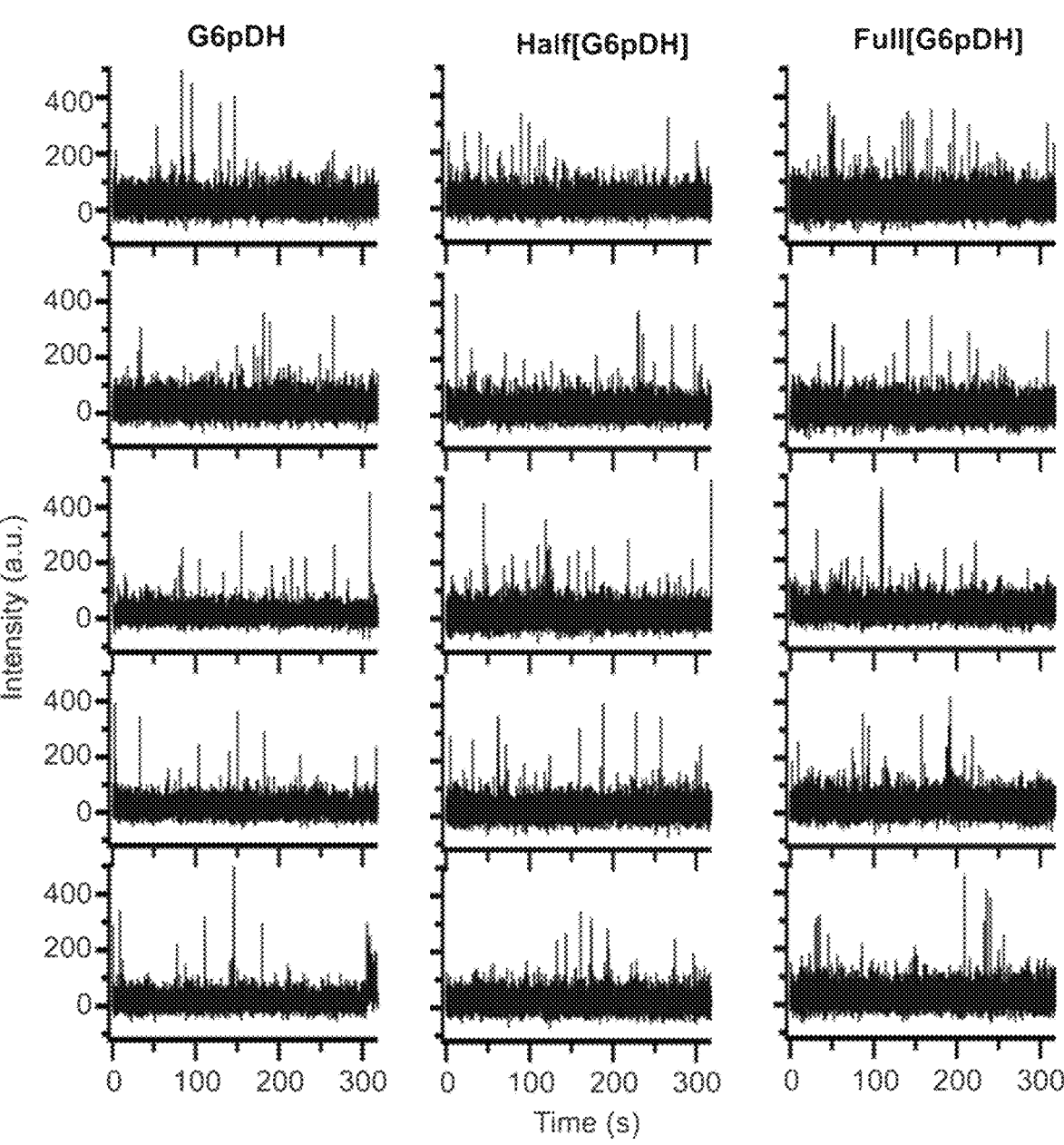
Figures 59A, 59B, 59C, 59D:
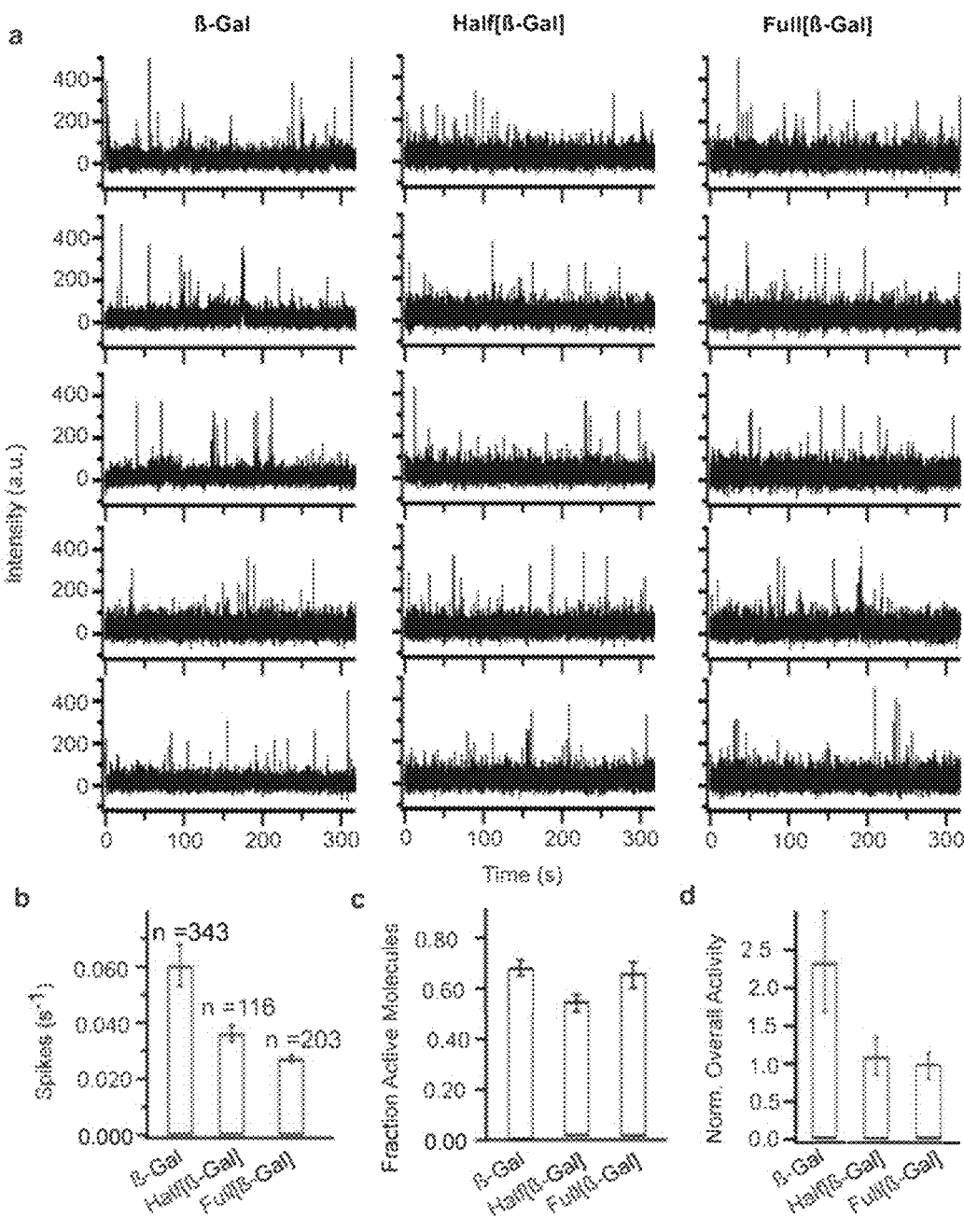

FIG. 58 shows raw enzyme activity data of single G6pDH molecules. Representative fluorescence-time traces of free-, half-cage and full-cage G6pDH. Five representative molecules are shown for each sample. The fluorescence intensity of enzyme reaction on the microscope slide was recorded for 5 min at 35 ms time resolution. The average spikes per molecule for different samples are compared in FIG. 5. All experiments were carried out at room temperature in 1×TBS buffer in presence of 1 mM Mg2+, pH 7.5 (Table 5).

FIGS. 59A-59D show enzyme activity data of single β-Gal molecules. (A) Representative raw fluorescence-time traces of free-, half-cage and full-cage β-Gal. Five representative molecules are shown for each sample. The fluorescence intensity of enzyme reaction on the microscope slide was recorded for 5 min at 35 ms time resolution. (B, C, D) Statistics of spike frequency, fraction of active molecules, and overall observed enzyme activity. The number of active molecules analyzed is denoted by 'n' in (B). The standard deviations for spike frequency and fraction of active molecules were calculated after randomly assigning the active molecules into three groups. The standard deviation for the normalized overall activity was estimated from the propagation of errors. All experiments were carried out at room temperature in Ix TBS buffer, pH 7.5 in presence of 1 mM $Mg^{2+}$ and 10% (w/v) PEG 8000.

Figure 60:
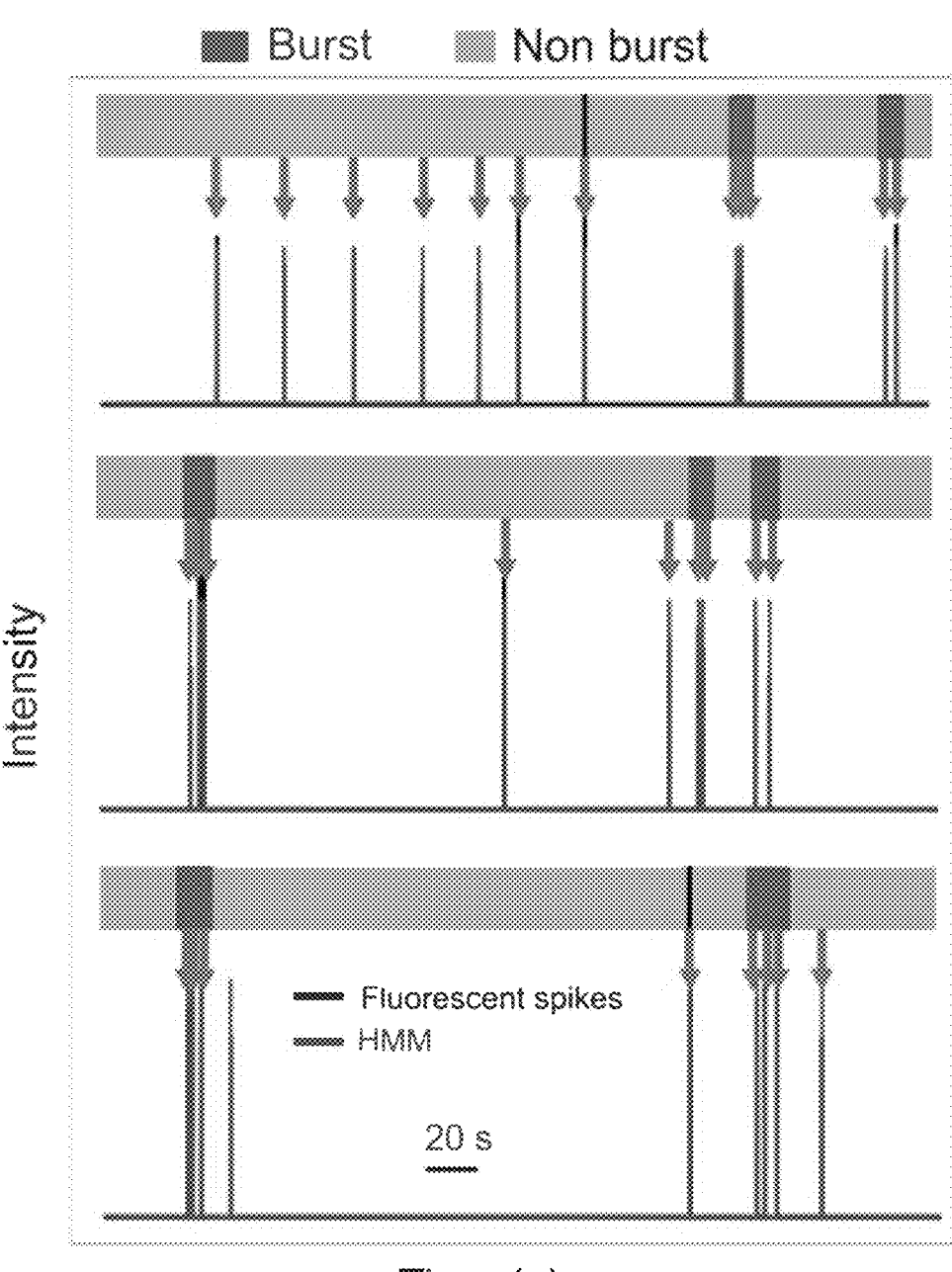

FIG. 60 shows representative intensity-time traces (black) of full-cage enzyme after background correction and Hidden Markov Model (HMM) idealization to a two-state model (red). The fluorescence-time traces of the enzyme reaction on the microscope slide were recorded at 35 ms time resolution over 5 min.

FIGS. 61A-61D show titrations showing the effects of (A) NaCl, (B) KCl, (C) NH4Cl and (D) Triethylammonium acetate (TEAA) on the activity of free G6pDH. Assay conditions: 0.5 nM enzyme was incubated with a series of ion concentrations from low to high. Enzyme activity was monitored by absorbance at 340 nm with the addition of 1 mM Glucose-6-phosphate and 1 mM NAO+ in 1×TBS buffer (pH 7.5). The results show that high concentration of salts containing small cations such as Na+, K+ and NH4+ significantly reduce the activity of G6pDH, possibly due to the chaotropic ion effect that disrupts hydrogen-bonded water structures as reported in the previous studies (Zhao, H. Journal of Molecular Catalysis B: Enzymatic 2005, 37, 16; Leberman, R. and Soper, A. K. Nature 1995, 378, 364.). Conversely, the salt containing a bulky organic cation (kosmotropic), triethylammonium, does not strongly inhibit enzyme activity, even at high concentrations. Error bars were calculated from the standard deviation of at least three replicates.

Figure 62:
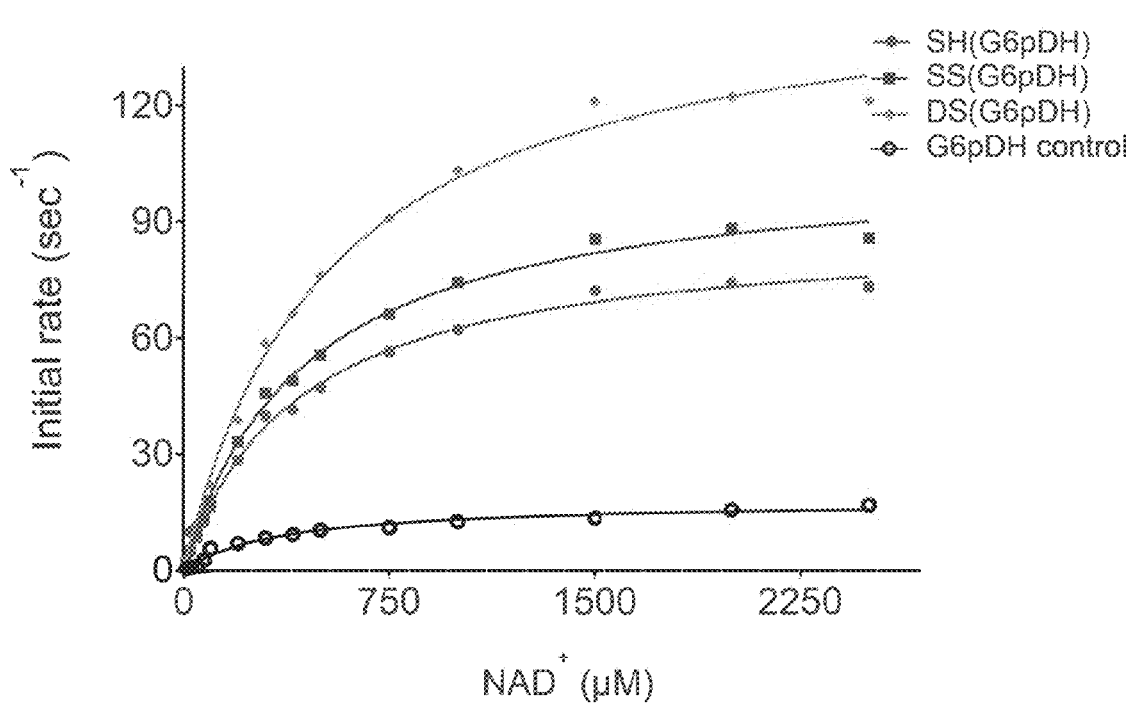

FIG. 62 shows comparison of G6pDH activity inside three different DNA full-cages, compared with that of free G6pDH, using NAO+ as the varying substrate. The SH, SS and DS cages are described in the main text. Enzyme assay conditions: 0.5 nM enzyme or DNA-cage-encapsulated enzyme, 1 mM glucose 6-phosphate, with different concentration of NAO+ ranging from 10 µM to 2500 µM, in 1×TBS buffer (pH 7.5, 1 mM MgCl$_2$) monitoring absorbance at 340 nm. The table lists the fit parameters. Encapsulation of the enzyme in different DNA full-cages caused a 1.2- to 1.5-fold increase in K$_M$ and a 5- to 9-fold increase in k$_{cat}$.

Figure 63:
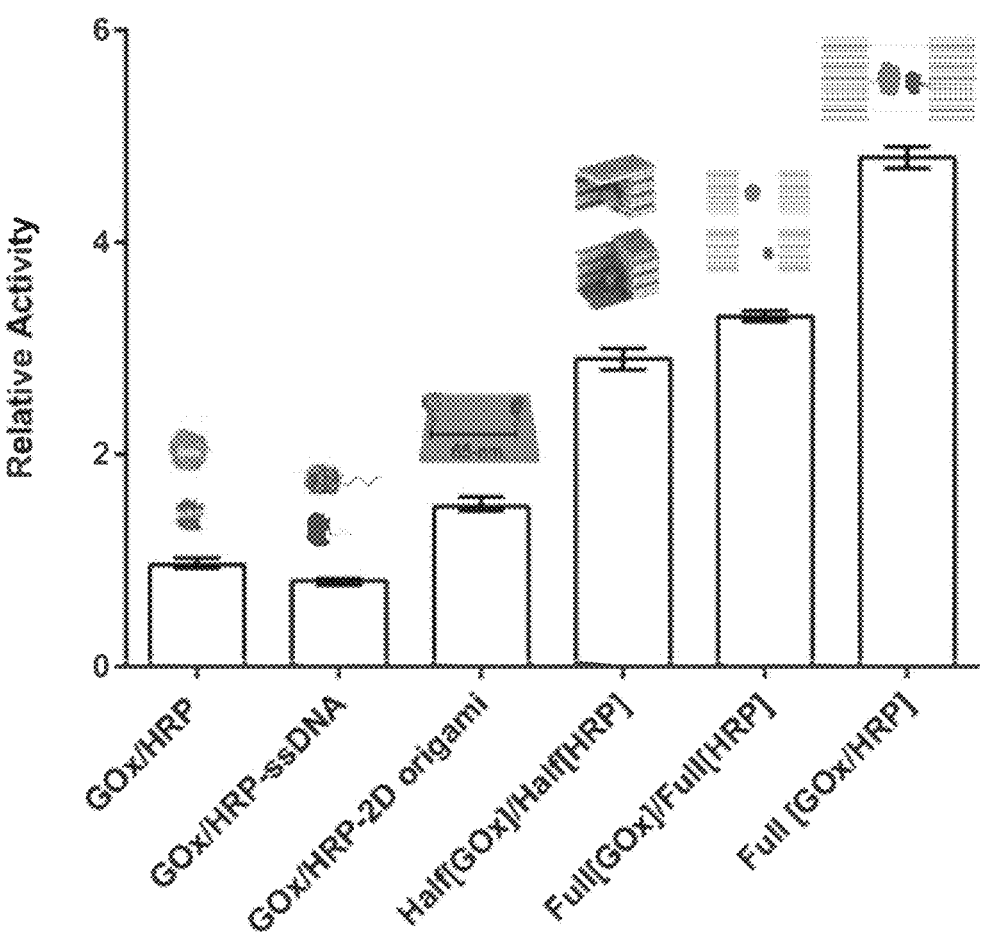

FIG. 63 The relative activity of a GOx/HRP pair when attached to a variety of DNA scaffolds: enzyme wildtypes (GOx/HRP), ssDNA (GOx/HRP-ssDNA), 2D rectangular DNA origami (GOx/HRP-2D origami), separate 3D half cages (Half[GOx]/Half1HRPD, separate full cages (Full [GOx]/Full[HRPD]) and the same full cage (Full [GOx/ HRP]). Enzyme activity is positively correlated to the density of DNA helices within the scaffolds, and partially or fully caged enzymes exhibit activity several-fold higher than that of free and unconjugated enzymes. Error bars were calculated from the standard deviation of at least three replicates. The value for GOx/HRP-2D origami is extracted from our previously published article (Fu, J. et al. JACS 2012, 134, 5516-5519). We concluded that the boosted activities of Full[GOx/HRP] cannot be simply attributed to a single factor of DNA density or close proximity, but may be induced by both of the high DNA density and close proximity within a DNA cage.

Figure 64:
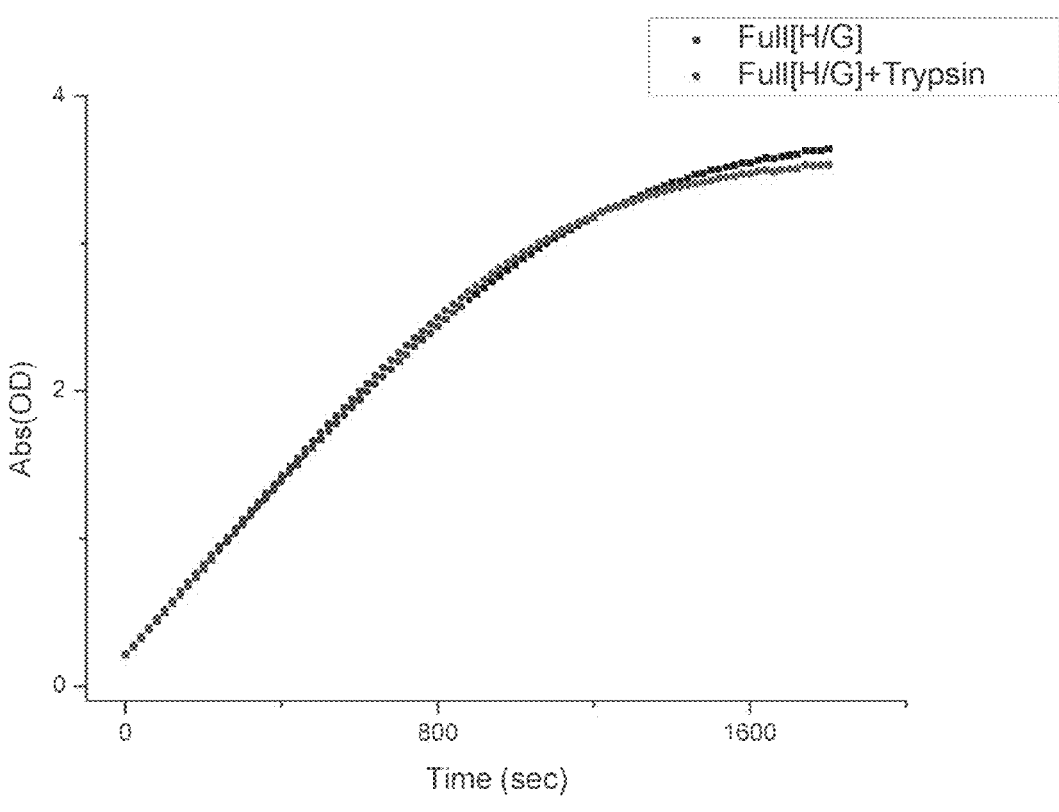

FIG. 64 shows raw activity data for full-cage [HRP/GOx] (0.5 nM) before and after trypsin digestion for 24 hours at 37° C. in 1×TBS buffer (pH 7.5).

Figure 65:
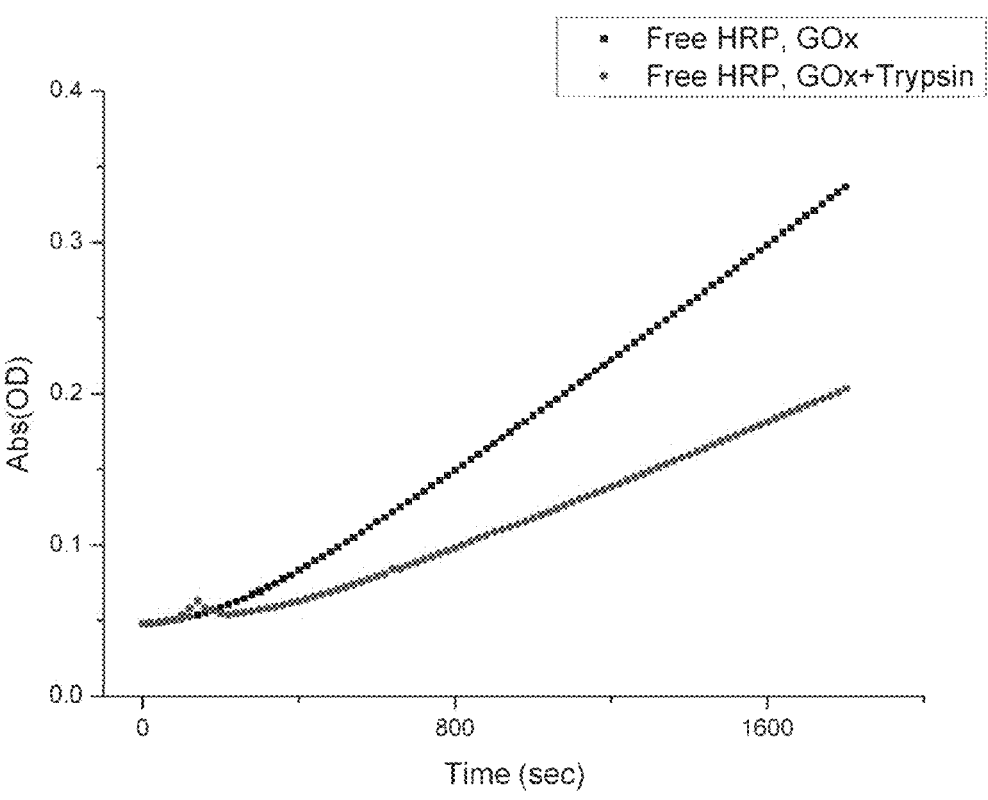

FIG. 65 shows raw activity data of a free pair of HRP and GOx (0.5 nM) before and after trypsin digestion for 24 hours at 37° C. in 1×TBS buffer (pH 7.5).

Figure 66:
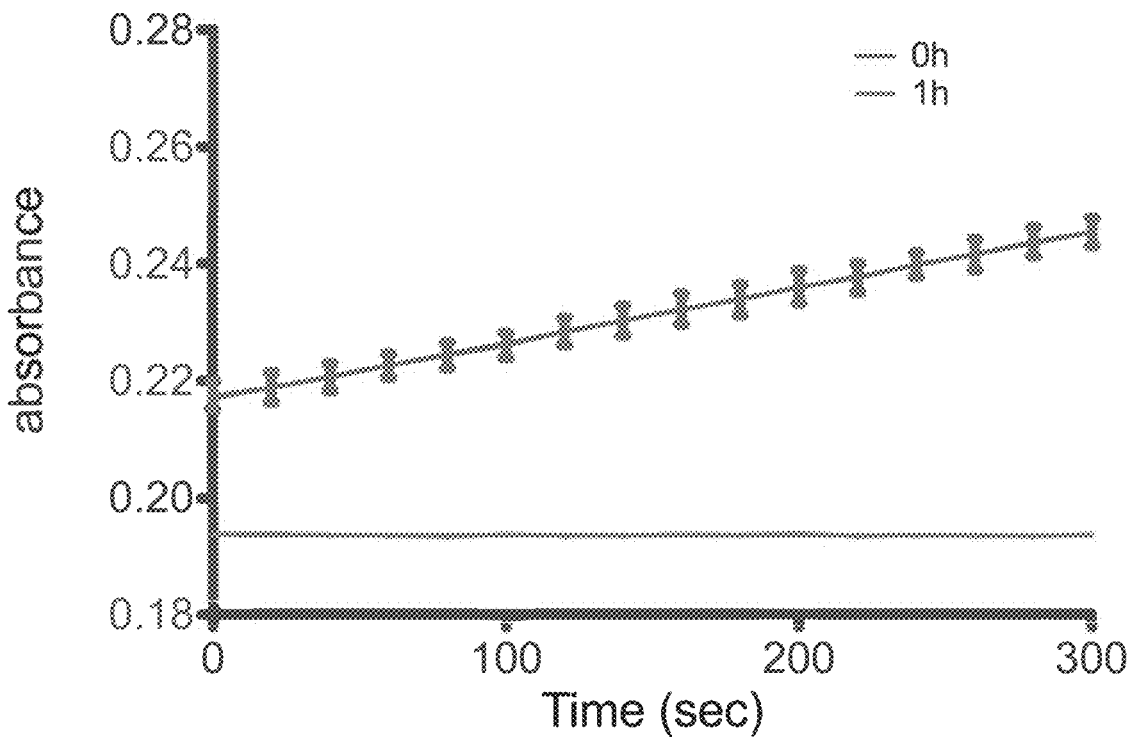

FIG. 66 shows raw activity data for free G6pDH (0.5 nM) before and after trypsin digestion for 1 h at 37° C. in 1×TBS buffer (pH 7.5). Error bars were calculated from the standard deviation of at least three replicates.

Figure 67:
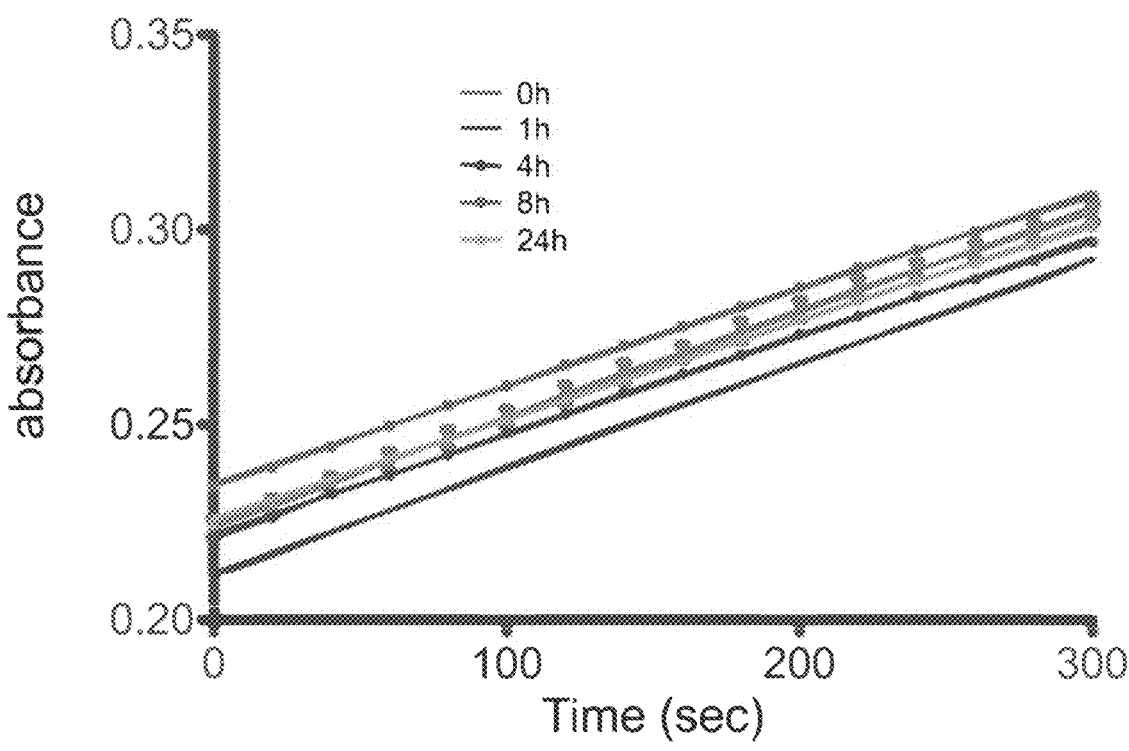

FIG. 67 shows raw activity data for Full[G6pDH] (0.5 nM) time course trypsin digestion from 0 h to 24 h at 3 7° C. Error bars were calculated from the standard deviation of at least three replicates.

DETAILED DESCRIPTION

The present disclosure describes a three dimensional nanocage assembly to encapsulate a biological macromolecule and methods of nanocage assembly. DNA nanostructures have emerged as promising molecular scaffolds to organize biomolecules at the nanoscale based on their programmable, sequence-driven self-assembly. For example, multi-enzyme cascades have been assembled on DNA nanostructures with precise control over the spatial arrangement to enhance catalytic activity by substrate channeling. Conversely, self-assembling DNA nanoboxes and -cages have shown promise in the delivery of macromolecular payloads such as antibodies and enzymes. Tubular DNA nanostructures have also been used to construct efficient enzyme cascade nanoreactors. The present invention is based at least in part on the inventors' development of a simple and robust strategy for encapsulating metabolic enzymes in DNA-templated nanocages, where nanoparticles comprising the nanocaged enzymes are obtained with high assembly yield and controlled packaging stoichiometry.

Accordingly, in a first aspect, provided herein is a nanoparticle useful for the transport and administration of therapeutic agents, bioactive compounds, biomolecular reagents, biocatalysts, and other molecular compounds of interest, referred to generally herein as payload molecules (e.g., nucleic acids, polypeptides, enzymes, antibodies, or phospholipids). As used herein, the term "nanoparticle" refers to a structural composition comprising a full closed nanocage and at least one payload biological macromolecule tapped within the inner cavity of the nanocage. As used herein, "nanocage" may refer to a three dimensional body comprising an inner cavity. The three dimensional body of the nanocage is an assembly of a plurality of structural members. The internal surfaces of the structural members form the edges of the inner cavity. In one embodiment, these structural members are, tubular, rod like or linear, and may be constructed using nucleic acids. In another embodiment, the structural members are assemblies of double stranded DNA. A full closed nanocage may be formed by the assembly of two half cages.

The nanocage may be assembled using any means known in the art in which a nano-scale structure if formed. Assembly methods include, but are not limited to, DNA origami, or assembly using liposomes, polymersomes, or virus-like particles. For example, nanocages can be assembled by genetic fusion, chemical crosslinking, surface co-immobilization, and encapsulation within polymer vesicles, or virus-like particles. As used herein, "DNA origami" may refer to an assembly technique that folds a single-stranded DNA template into a 2 or 3 dimensional target structure by annealing it with short staple strands. In one embodiment, the body of the nanocage comprises between 0.10 to 0.30 DNA helices per nm$^2$. In another embodiment, the body of the nanocage comprises between 0.11 to 0.17 DNA helices per nm$^2$.

In one embodiment, the DNA used to assembly the body of the nanocage is M13mp18 single-stranded DNA. M13mp18 DNA is a circular, single-stranded virus DNA of approximately 7249 nucleotides in length and was isolated from M13mp18, a M13 lac phage vector comprising single HindIII, SphI, SbfI, PstI, SalI (AccI/HincII), XbaI, BamHI, SmaI (XmaI), KpnI (Acc65I), Sad and EcoRI sites within the gene encoding β-Galactosidase. Generally, M13mp18 DNA is useful as a standard and has been tested as a template in the dideoxy-nucleotide termination method of sequencing DNA. Detailed sequences are available at neb.com/products/n4040-ml3mp18-single-stranded-dna#pd-description on the World Wide Web.

Other single-stranded circular DNA that can be used to fold a DNA nanocage include, without limitation, p'7308, p'7560, p7704, p8064, p8634, and pEGFP.

Figure 7:
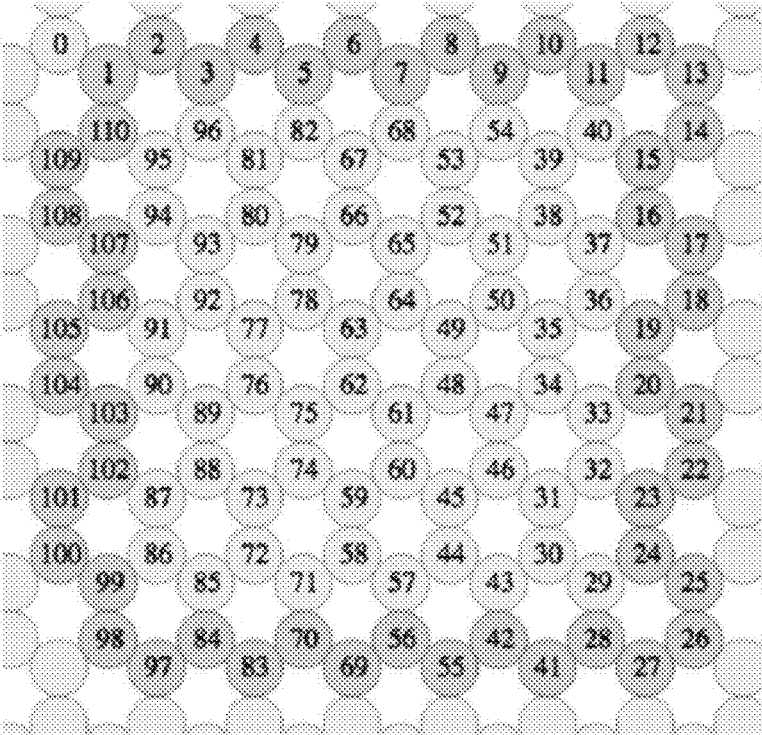
FIG. 7 illustrates an exemplary SH full-cage having a honeycomb lattice arrangement, presented in cross-sectional view and 3D view.
Figure 7:
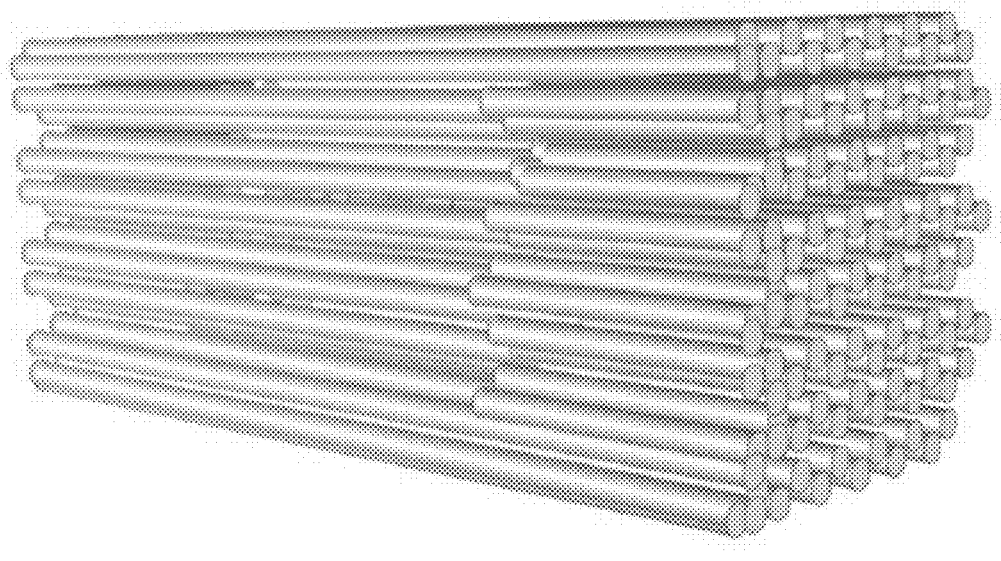
Figure 8:
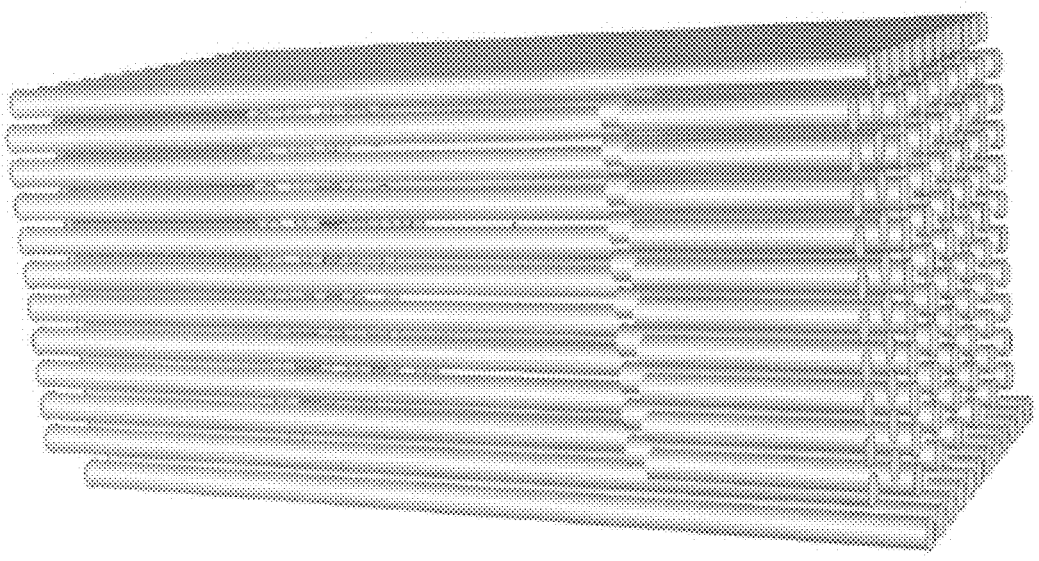
FIG. 8 illustrates an exemplary SS cage having a square lattice arrangement, presented in cross-sectional view and 3D view.
Figure 9:
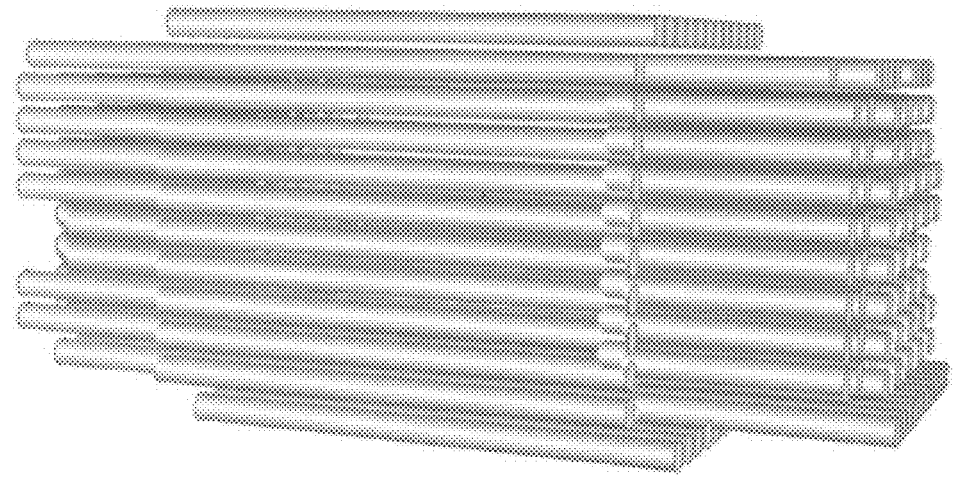
FIG. 9 illustrates an exemplary DS cage having a square lattice arrangement, presented in cross-sectional view and 3D view.

The nanocage may be formed in any architecture compatible with the chosen method of assembly. In one embodiment, the architecture of the structural members forms a square lattice, wherein the structural members and arranged in columns and rows. In another embodiment, the architecture of the structural members forms a honeycomb lattice (see FIG. 7). The architecture, assembly and three dimensional lattice of the nanocage may also accommodate variations in the number of and thickness of the walls of the nanocage. In one embodiment, the nanocage has a single walled square lattice arrangement as shown in FIG. 8, where there is a single layer of structural element between the inner cavity and the exterior of the nanocage. In one embodiment, the nanocage has a double walled square lattice arrangement as shown in FIG. 9, where there is a double layer of structural element between the inner cavity and the exterior of the nanocage. In another embodiment, the nanocage is multi-walled with several layers of structural elements between the inner cavity and the exterior of the nanocage.

The nanocage may be any size to accommodate the encapsulation of the enzyme or macromolecule of interest. In one embodiment, the dimensions of the nanocage are less than 100 nm×100 nm×100 nm. In another embodiment, the dimensions of the nanocage are less than 75 nm×50 nm×50 nm. In another embodiment, the dimensions of the nanocage are about 40-70 nm×15-40 nm×15-40 nm.

The inner cavity of the nanocage is a hollow, open space enclosed within the nanocage to contain the macromolecule or enzyme of interest. The inner cavity will have dimensions smaller than those of the nanocage. In one embodiment, the dimensions of the inner cavity are less than 50 nm×50 nm×50 nm. In one embodiment, the dimensions of the inner cavity are less than 30 nm×30 nm×20 nm.

In some cases, a nanoparticle as provided herein encapsulates a biological macromolecule within the inner cavity of the nanocage. Any biological macromolecule having any purpose or function can be encapsulated as payload within a nanocage thereby forming a nanoparticle. Exemplary biological macromolecules include, without limitation, proteins, enzymes, antibodies, protein complexes, phospholipids, nucleic acids, and combinations thereof. In one embodiment, the biological macromolecule is an enzyme. The design and structure of the nanocage may be changed and adjusted to accommodate a variety of enzymes with any size, shape, morphology or function. In one embodiment the enzyme has a molecular weight between 10-600 kilodaltons (kDa). Preferably, the nanocage accommodates enzymes having a molecular weight equal to or less than about 600 kDa.

Without being limited to one particular theory or practice, the nanocage structure may be configured for a variety of functions in regards to the encapsulated enzyme or macromolecule. In embodiments in which the macromolecule is an enzyme, the nanocage may be configured such that the catalytic activity of the enzyme may be tested while the enzyme is encapsulated within the nanocage. The nanocage may also be configured such that the catalytic activity of the enzyme is enhanced when encapsulated within the inner cavity. The nanocage may also be configured such that the enzyme is stabilized against protease digestion or proteolytic degradation when encapsulated within the inner cavity.

The nanocage structure and assembly may be designed and assembled into a nanoparticle to accommodate a variety of macromolecular configurations within the inner cavity. For example, a single nanocage may encapsulate a payload including but not limited to, a single biological macromolecule, a pair of biological macromolecules, a plurality of biological macromolecule, assemblies of biological macromolecules, multi-component complexes of biological macromolecules, or combinations thereof. When the nanoparticle comprises a payload of multiple biological macromolecules, the macromolecules may be the same, or they may be an assembly of two or more different macromolecules.

A nanocage may comprise one or more nanopores. As used herein, "nanopore" may refer to a nano-scale passage, pore or opening in the nanocage. The nanopore may be configured to allow the passage of small molecule substrates, solvents, enzyme substrates and products and the like into and out of the nanocage. The nanopores are sized such that the enzyme encapsulated within the nanocage cannot escape. In one embodiment, the nanocage comprises at least one nanopore. In another embodiment, the nanocage comprises 1-200 nanopores. In another embodiment, the nanocage comprises 10-75 nanopores. The size of the nanopores is determined by the interaction, arrangement and architecture of the structural members of the body of the nanocage, such that nanopores may be formed in the gaps between the structural members. In one embodiment, the nanopores are between 1 and 5 nm in diameter. In another embodiment, the nanopores are between 1.5 and 3 nm in diameter.

In some embodiments, the enzyme may be non-covalently linked to the internal surface of the nanocage. In another embodiment, the enzyme may be covalently connected to the internal surfaces of the nanocage. In one non-limiting, exemplary embodiment, succinimidyl 3-(2-pyridyldithio) propionate (SPDP) chemistry may be used to crosslink a surface lysine residue on the biological macromolecule to a thiol-modified oligonucleotide. Other useful methods include, without limitation, aptamer-protein noncovalent interactions, NTA-hexahistidine interactions, click chemistry, disulfide and maleimide coupling, and SPDP and SMCC (N-Succinimidyl 3-(2-pyridyldithio)-propionate) cross-linking.

A half-cage of the body of the nanocage may be assembled utilizing DNA origami. DNA structures can be designed with caDNAno and single strand DNA may be used as the scaffold. To form the half-cage, single strand DNA may be mixed with corresponding staple strands and annealed. Excess staple strands may be removed by filtration.

An enzyme molecule may be attached to the open half-cage by any appropriate covalent or non-covalent chemistry such as, for example, include, without limitation, aptamer-protein noncovalent interactions, NTA—hexahistidine interactions, click chemistry, disulfide and maleimide coupling, and SPDP and SMCC (N-Succinimidyl 3-(2-pyridyldithio)-propionate) cross-linking.

In some cases, two half-cages of the body of the nanocage are assembled by linking together half-cages. Linking may occur by incubating half-cages with DNA linkers. For example, DNA linkers may hybridize with sticky ends extending from the edge of "DNA half-cages." Preferably, DNA linkers are complimentary to these sticky ends, and can be varied for different DNA cage sequences.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates a simple and robust strategy for the DNA nanocage-templated encapsulation of metabolic enzymes with high assembly yield and controlled packaging stoichiometry. With such an approach in hand, the hypothesis that the recently described, chaperone-like stabilizing impact of polyphosphate on metabolic protein enzymes together with the cryptic RNA binding properties of many enzymes may lead to beneficial effects when enzymes are surrounded by DNA nanocages, is tested.

Methods

The design and characterization of DNA half-cages and full-cages.

DNA origami half-cage and structures were designed with caDNAno, each used one M13mp18 ssDNA as the scaffold. Detailed design schemes are shown in FIGS. 7-9. One or both of the half-cages contained single-stranded probe strands (4 in each half-cage) extended toward the inside of the cage for binding with the DNA conjugated enzymes. Two of the half-cages can be linked together to form a fully enclosed full-cage though 24 linker strands. To form each of the half-cages, the M13mp18 ssDNA was mixed with the corresponding staples at a 1:10 molar ratio in 1×TAE-Mg2+ buffer (40 mM Tris, 20 mM acetic acid, 2 mM EDTA and 12.5 mM magnesium acetate, pH 8.0), annealed from 80° C. to 4° C. for 37 h. The excess staple strands were removed by the filtration of the DNA cages solution using 100-kD Amicon filter with 1×TAE-Mg2+ buffer for three times. To form a full-cage, 24 single-stranded DNA linkers were incubated with the two purified half-cages at a molar ratio of 5:1 for three hours at room temperature, in order to connect the two half-cages together.

Enzyme-DNA Cage Assembly.

A 15-fold molar excess of oligonucleotide-conjugated enzyme was incubated with the DNA half-cage containing capture strands. Protein assembly was performed using an annealing protocol in which the temperature was gradually decreased from 37° C. to 4° C. over 2 h and then held constant at 4° C. using an established procedure. Two Enzyme-attached half cages were then assembled into a full cage by adding DNA linkers as described above. The DNA caged-enzymes were further purified by agarose gel electrophoresis to remove excess free enzymes.

Preparation, Purification, and Characterization of Protein-DNA Conjugates.

Figure 13:
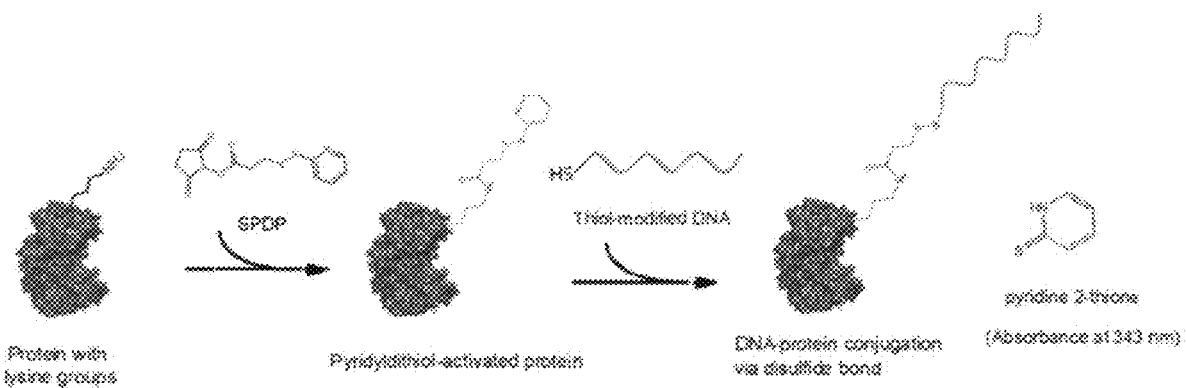
FIG. 13 shows a schematic illustration of the SPDP conjugation chemistry used for protein-DNA conjugation.
Figures 14A, 14B, 14C, 14D, 14E, 14F:
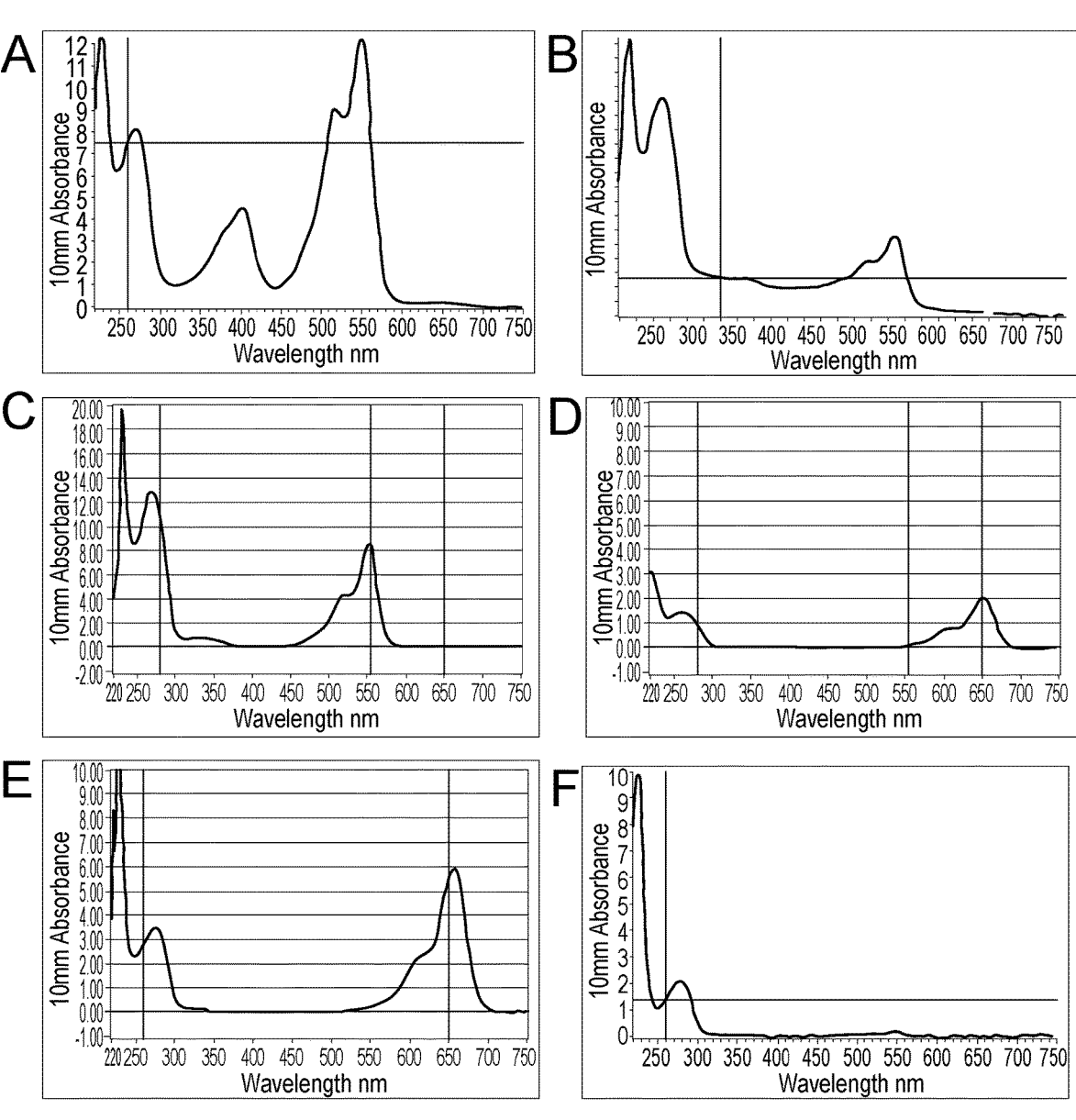

Protein-DNA conjugation—as shown in FIG. 13, SPDP conjugation chemistry was used to couple enzymes to oligonucleotides as reported previously. Enzymes (GOx, HRP, G6pDH, LDH, MDH and β-Gal) were first conjugated with SPDP at enzyme-to-SPDP ratios of 1:5, 1:20, 1:3, 1:5, 1:5, and 1:5, respectively, in HEPES buffer (50 mM HEPES, pH 8.5) for 1 h at room temperature. Different values of SPDP-to-Protein ratio were used due to the varied number of accessible surface lysine residues for each protein. Excess SPDP was removed by washing with 50 mM HEPES buffer using Amicon centrifugal filters (30 kD cutoff). The SPDP coupling efficiency was evaluated by monitoring the increase in absorbance at 343 nm due to the release of pyridine-2-thione (extinction coefficient: 8080 $M^{-1}$ $cm^{-1}$).

TCEP-treated thiolated DNA (/5ThioC6–/–TTTTTCCCTCCCTCC (SEQ ID NO:1393) (P1), or /5ThioC6-D/-TTTTTGGCTGGCTGG (SEQ ID NO:1394) (P2) was incubated with the SPDP-modified enzymes at an enzyme-to-DNA ratio of 1:10 in 50 mM HEPES buffer (pH 7.4) for 1 h in the dark. Excess unreacted oligonucleotide was removed by ultrafiltration using Amicon 30 kD cutoff filters: washing one time with 50 mM HEPES (pH 7.4) containing 1 M NaCl and three times with 50 mM HEPES (pH 7.4). The high salt concentration in the first washing buffer helps remove DNA nonspecifically bound to the surface of the protein due to electrostatic interactions.

The absorbance values at 260 nm and 280 nm ($A_{260}$ and $A_{280}$) were recorded to quantify the enzyme-DNA complex concentrations and the labeling ratios using a Nanodrop spectrophotometer (Thermo Scientific) (FIGS. 14A-14F and Table 2). Extinction coefficients of DNA oligonucleotides were received from IDT-DNA, and extinction coefficients of enzymes were obtained from published data.

Dye labeling of DNA-conjugated proteins: The DNA-conjugated proteins were further labeled with spectrally distinct fluorescent dyes, which allow us to use native gel electrophoresis and single-molecule fluorescence to confirm the encapsulation of proteins within DNA nanocages. NHS-ester-modified dyes were reacted with the purified DNA-conjugated proteins from the above steps at a 20:1 ratio in 50 mM HEPES buffer, pH 8.5. Cy3 was directly labeled to the lysine residues on the protein surface. Excess dyes were then removed using 3-kD cutoff Amicon filters. The UV-Vis absorbance spectra of the purified dye-labeled proteins are shown in FIGS. 14A-14F and were used together with the extinction coefficients of the dye (150,000 $M^{-1}$ $cm^{-1}$ for Cy3 at 546 nm; 250,000 $M^{-1}$ $cm^{-1}$ for Alexa647 at 647 nm) and of the protein-DNA conjugates to quantify the concentration and labeling ratio of the dye-labeled proteins.

Conjugate proteins to Cy3-labeled DNA: In order to perform the single-molecule enzyme activity assay, selected enzymes (G6pDH and β-Gal) were conjugated to a Cy3-labeled DNA. First, NHS-ester-modified dyes were reacted with the 3'-amine of oligonucleotides at a 20:1 ratio in 50 mM HEPES buffer, pH 8.5. Excess dyes were then removed using 3-kD cutoff Amicon filters. Dye-modified oligonucleotides were then conjugated to proteins via the 5'-thiol using the SPDP chemistry described above. Fast Protein Liquid Chromatography (FPLC) was used to purify the protein-DNA-Cy3 conjugates for removing excess DNA-Cy3, and characterized with the UV-Vis absorbance spectra.

Enzyme-DNA Cage Assembly, Purification, and Characterization

The purified DNA half-cage containing capture strands was mixed with one of several enzyme-DNA conjugates at a 1:15 cage:enzyme ratio and annealed from 37° C. to 4° C. over 2 h in 1×TAE-Mg$^{2+}$ buffer (containing 12.5 mM Mg(OAc)$_2$). Twenty-four single-stranded DNA linkers were mixed with the two purified half-cages at a 5:1 linker: cage ratio to connect the two half-cages together by incubating at room temperature for 3 h. Agarose gel electrophoresis (2%, 1×TAE-Mg21 was employed to remove excess free enzymes (70V, 2 h). The band of the DNA cage containing the enzyme was cut from the gel and extracted using a Freeze 'N Squeeze column (Bio-Rad). The DNA origami concentration was quantified by measuring the absorbance at 260 nm ($A_{260}$) using an extinction coefficient of 0.109 $nM^{-1}cm^{-1}$.

DNA Sequences of the Designed Nanocages

Sequences of staple strands in the SH Full-Cage-Left cage are listed in SEQ ID NOs: 1-210.

Sequences of staple strands in the SH-right cage are listed in SEQ ID NOs:211-420.

AB-Linker strands are listed in SEQ ID NOs:421-444.

SH-probe strands are listed in SEQ ID NOs:445-450. The BOLD portions of the sequences are complementary to the ssDNA conjugated to the enzymes, and are located in the Left (SEQ ID NOs:445-447, top) and Right (SEQ ID NOs: 448-450, bottom) half-cages.

34[53]
ATGACCATAAATCGCCTGATAAAT GGAGGGAGGG

48[53]
TGTGTCGAAATCCCTCAGAACCGC GGAGGGAGGG

62[53]
CACCCTCAGAGCGCAGCACCGTAA GGAGGGAGGG

51[117]
TTTAGGCAGAGGCATTCAACGCCAACATGTAA CCAGCCAGCC

61[117]
CGAACAAAGTTACCAGAAAGTAAGCAGATAGC CCAGCCAGCC

75[117]
GTAAGCGTCATACATGTGAATTTACCGTTCCA CCAGCCAGCC

Sequences of staple strands in the SS-left half-cage are listed in SEQ ID NOs:451-669.

Sequences of staple strands in the SS-right half-cage are listed in SEQ ID NOs:670-890.

SS-linker strands are listed in SEQ ID NOs:891-908.

SS-probes are listed in SEQ ID NOs:909-914. The BOLD portions of the sequences are complementary to the ssDNA conjugated to the enzymes, and are located in the Left (SEQ ID NOs:909-911, top) and Right (SEQ ID NOs:912-914, bottom) half-cages.

94[44]
GATATAAGTATAGTGACACAGACAGCCCTCATGGAGGGAGGG

104[50]
CTTTTGATGATGTCAGTGCCTTGGAGGGAGGG

110[44]
CATTGACAGGAGGATTTAAGCGTCATACATGGGAGGGAGGG

87[115]
GCAAGCAAATCAGGCTTATTTTGCACCCAGCTCCAGCCAGCC

93[109]
ACAATTTTATCCAGAGCCTAATCCAGCCAGCC

103[115]
GTAAGCAGATAGCTATAATAGAAAATTCATATCCAGCCAGCC

DNA Sequences for DS Full-Cage Design, Cross Sectional View

Sequences of staple strands in the DS-left half-cage are listed in SEQ ID NOs:915-1134.

Sequences of staple strands in the DS-right half-cage are listed in SEQ ID NOs:1135-1362.

DS-linker strands are listed in SEQ ID NOs:1363-1386.

DS-probes are listed in SEQ ID NOs:1387-1392. The BOLD portions of the sequences are complementary to the ssDNA conjugated to the enzymes, and are located in the Left (SEQ ID NOs:1387-1389, top) and Right (SEQ ID NOs:1390-1392, bottom) half-cages.

64[71]
ATTCATTTCAATTACCCGCGCAGAGGCGAATTTTTTGGAGGGAGGG

74[76]
TCAGATGATGGCAACAATAACTTTTGGAGGGAGGG

76[66]
ATTATCATTTTTTATCATCATATTCCTGATTATTTTGGAGGGAGGG

34[149]
TTCTGTGCAAAAGAAGGCACCAGGCTGACCGTAATCTTGACAAGAACCGGA

TTTTC CAGCCAGCC

67[136]
GCAAAAGACGGTGTACAGACCTTTTCCAGCCAGCC

73[131]
GCATCAAAAAGATTAAGAGGAACTTCAAATATCGCGTTTTAATTTTCCAGC

CAGCC

Single-Molecule Fluorescence Microscopy.

All single-molecule measurements were performed at room temperature using a total internal reflection fluorescence (TIRF) microscope on PEGylated fused silica microscope slides. To passivate the microscope slides and functionalize the surface with biotin for selective immobilization of nanocages, a biotin- and PEG-coated surface was prepared by silylation with APTES, followed by incubation with a 1:10 mixture of biotin-PEG-SVA 5 k:mPEG-SVA 5 k as described previously. A flow channel was constructed as described elsewhere. To prepare the surface for enzyme or nanocage binding, a solution of 0.2 mg/mL streptavidin in T50 buffer (50 mM Tris-HCl, pH 8.0, 50 mM NaCl, 1 mM EDTA) was injected in to the flow channel, incubated for 10 min, and the excess streptavidin was flushed out thoroughly first with T50, then with 1×TAE-Mg2+.

Yield estimation by TIRF colocalization: All single-molecule measurements were performed at room temperature using a total internal reflection fluorescence (TIRF) microscope on PEGylated fused silica microscope slides. To passivate the microscope slides and functionalize the surface with biotin for selective immobilization of nanocages, a biotin- and PEG-coated surface was prepared by silylation with APTES, followed by incubation with a 1:10 mixture of biotin-PEG-SVA 5 k:mPEG-SVA 5 k as described previously[3]. A flow channel was constructed as described elsewhere 3. To prepare the surface for enzyme or nanocage binding, a solution of 0.2 mg/mL streptavidin in TSO buffer (50 mM Tris-HCl, pH 8.0, 50 mM NaCl, 1 mM EDTA) was injected in to the flow channel, incubated for 10 min, and the excess streptavidin was flushed out thoroughly first with TSO, then with 1×TAE-Mg.

The right half of the DNA origami cage was labeled with Cy5 dye inside the cavity, via hybridization of Cy5-labeled DNA to complementary handles incorporated into the structure. Each of the ssDNA conjugated enzymes (HRP, GOx, G6pD, LDH, MDH and β-Gal) was covalently labeled with Cy3 as described in section 3 (Cy3-Enzyme-5'-TTTTTCCCTCCCTCC, SEQ ID NO:1393), and then linked to the left half of the DNA origami cage via hybridization with complementary handles. Because Cy3 was directly labeled onto the enzyme surface, any observed Cy3 signal of the immobilized DNA nanocages came from the encapsulated enzymes. Linker strands were added to a 1:1 mixture of the two half-cages to encapsulate the enzymes in a full-cage. To capture DNA-modified enzymes in the absence of nanocage (as control) the microscope slide was incubated with 10-20 nM biotin-modified complementary DNA oligonucleotide (5'-biotin-TTTTTGGAGGGAGGG, SEQ ID NO:1395) for 3 min, followed by 10 min incubation with 20-50 pM enzyme sample in 1×TAE-Mg buffer. Excess enzyme was flushed out with 400 uL buffer (channel volume 30 μL). For the nanocage experiments, the samples were diluted to 20-50 pM in 1×TAE-Mg and immobilized on the streptavidin-coated PEG surface for 1 min, and the excess sample was flushed out with 400 (IL of 1×TAE-Mg. The DNA-modified enzymes were imaged with illumination at 532 nm (15 W/cm2), and the nanocage-encapsulated enzymes were imaged with simultaneous illumination at both 532 nm (15 W/cm2) and 640 nm (40 W/cm2) as described. Particle-finding and colocalization analysis were performed using custom-written scripts in IDL and MATLAB, using a threshold of 150 counts per frame for particle identification (typical particles showed 500-1,000 counts per frame in each detection channel). The enzyme encapsulation yield, defined as the fraction of assembled nanocages containing enzyme(s), was estimated by dividing $N_{caloc}$ by the total number of particles containing a right half-cage, $N_{right}$ (Table 3).

Figures 2A, 2B, 2C, 2D, 2E:
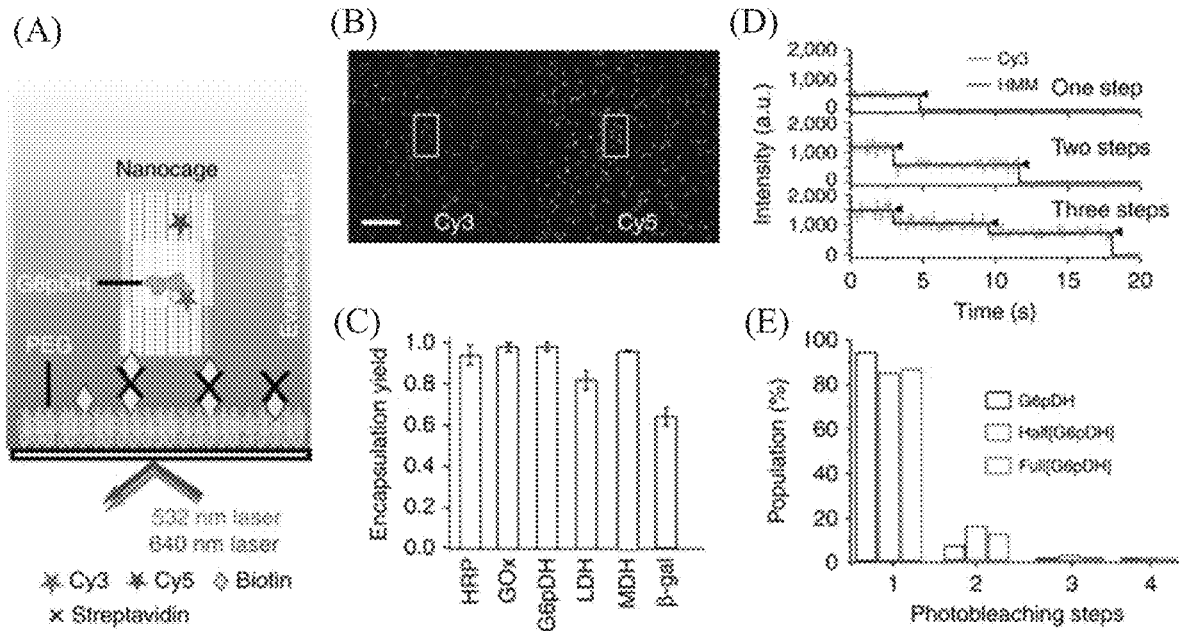
FIGS. 2A-2E show single-molecule fluorescence characterization of enzyme encapsulation. (A) Schematic illustration of single-molecule fluorescence co-localization of Cy3-labelled protein with Cy5-labelled cage using TIRF microscopy. DNA cages were captured on the surface by biotin-streptavidin interaction. (B) Representative field of view of enzyme-encapsulating cages under TIRF microscope. Examples of Cy3-Cy5 co-localization are highlighted using a pair of rectangles. Scale bar, 10 μm. (C) Quantified encapsulation yield for six different enzymes. The total number of molecules analyzed for each protein is shown in Table 3. The error bars represent the standard deviation obtained from the analysis of two to four movies of the sample from the same batch. (D) Fluorophore photobleaching trajectories with one, two, and three photobleaching steps. Photobleaching steps were quantitatively analyzed by fitting the trajectories by HMM in QUB program. (E) Photobleaching statistics for Cy3-labelled proteins encapsulated within half-cages (Half[G6pDH]) or full-cages (Full [G6pDH]), as well as for an unencapsulated protein control (G6pDH). HMM, hidden-Markov modelling.

Estimation of enzyme copy number per nanocage: The number of enzyme copies per nanocage ($N_{enz}$) was determined by single-molecule photobleaching (SMPB). First, the number of Cy3 photobleaching steps was determined separately for unencapsulated as well as half-cage and full-cage-encapsulated enzymes. For this, the donor channel data of all single molecules were idealized in QuB (http://www.qub.buffalo.edu) using a six-state model. The histogram of the photobleaching steps was then acquired using a custom-written MATLAB script. Representative intensity traces exhibiting one, two, and three photobleaching steps are shown in FIG. 2D (more than three photobleaching steps were rarely seen). Finally, the number of enzyme molecules per cage was estimated by dividing the mean number of Cy3 photobleaching steps of the full-cage ($\mu_{cy3\_Encap}$) by the mean number of Cy3 photobleaching steps for the unencapsulated enzyme ($\mu_{cy3\_Unencap}$). Results are summarized in Table 4.

Single-Molecule Enzymology

Figures 5A, 5B, 5C, 5D, 5E, 5F, 5G:
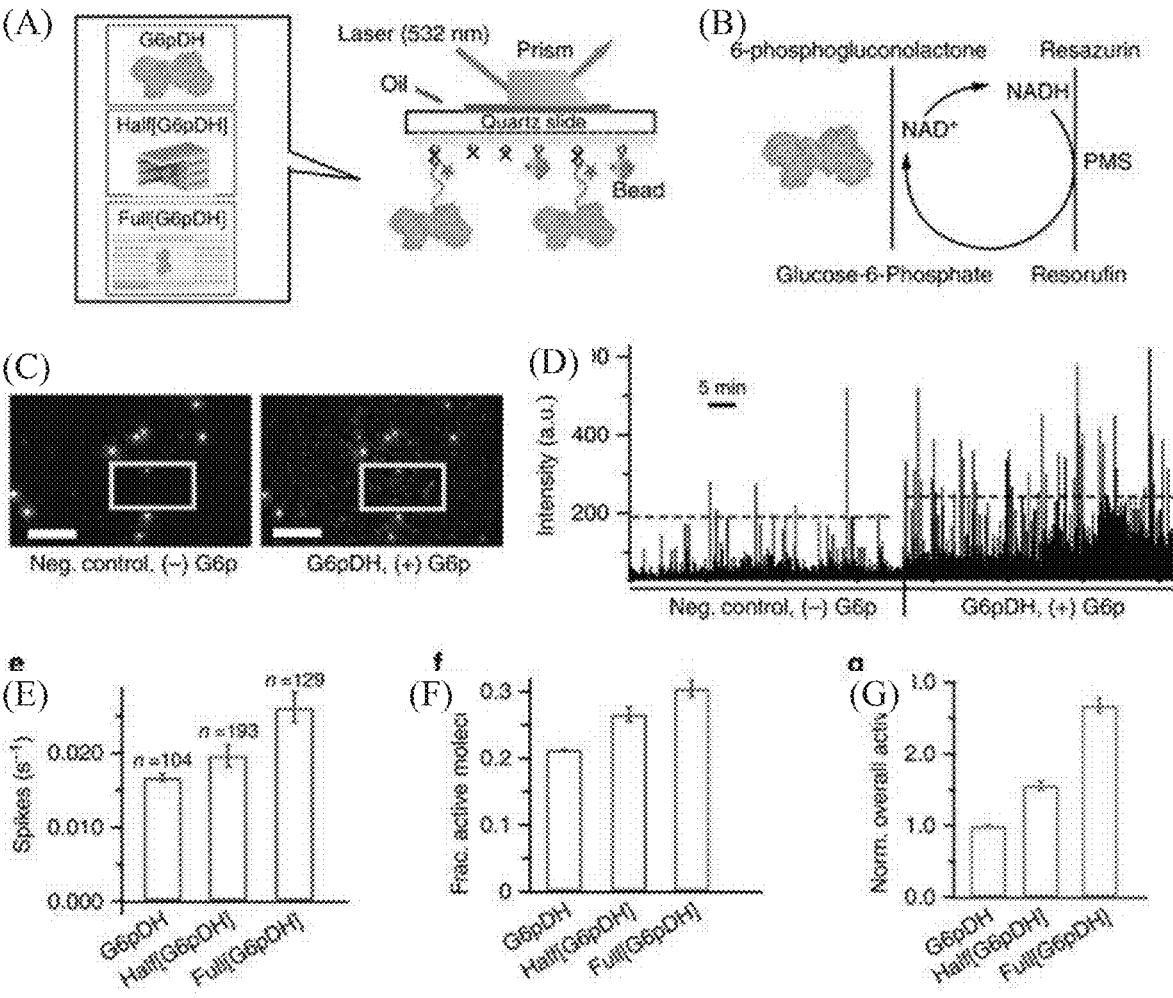
FIGS. 5A-5G show single-molecule kinetics of nanocage-encapsulated enzymes. (A) Schematic of the experimental TIRF set up for characterizing G6pDH encapsulated within a full-cage (Full[G6pDH]) and a half-cage (Half[G6pDH]), as well as an unencapsulated control. (B) A PMS/resazurin-coupled fluorescence assay used to characterize the activity of G6pDH. NAD+ is first reduced to NADH by G6pDH, followed by PMS-catalyzed electron transfer from NADH to resazurin, producing a strongly fluorescent resorufin, which has an excitation/emission maximum at 544/590 nm. (C) TIRFM snapshots captured before and after the injection of substrate G6p. In presence of G6p, the field of view showed increased fluorescence due to the formation of resorufin (compare the boxed regions). Fluorescent beads (very bright spots present in both +G6p and −G6p images) were used as reference markers to correct for the drift. Scale bars, 10 μm. (D) Real-time traces of fluorescence spikes (resorufin production) for enzymes without and with the addition of G6p substrate. Ten single-molecule traces for each condition were concatenated. (E) Statistics of spike frequency, (F) fraction of active molecules, and (G) overall observed enzyme activity for G6pDH. The number of active molecules analyzed is denoted by 'n' in (E). The standard deviations for the spike frequency were calculated after randomly assigning the active molecules into three groups; those for the fractions of active molecules were calculated from three to four independent movies, and those for the normalized overall activity were estimated from the propagation of errors. All experiments were carried out at room temperature in 1×TBS buffer, pH 7.5, in the presence of 1 mM Mg2+ and 10% (w/v) PEG 8000.

Single-molecule enzyme activity assay: Prior to single-molecule activity measurement, streptavidin-modified slides were incubated for 2 min with neutravidin-coated fluorescent beads (Invitrogen, 0.04 μm diameter, excitation/emission; 550/605 nm) at 106-fold dilution and the excess flushed out with 1×TBS buffer. These beads (5-8 per field of view) were used as fiducial markers to correct for drift of the microscope stage and/or slide (FIGS. 5A and 5C). Following complete photobleaching of Cy3 in a field of view, the activity of single unencapsulated or nanocage-encapsulated enzyme molecules was imaged on the same field of view. During analysis of the movies, the coordinates of the initial photobleaching movie were registered with those of subsequent movies using the fiducial markers (visible throughout all sequential movies) in a custom-written MATLAB script. This approach allowed us to infer the locations (x- and y-coordinates) of all individual enzymes/nanocages in the field of view even after bleaching Cy3, and to monitor enzyme turnovers (resorufin formation) at these specific coordinates.

To image enzyme activity, 300 μL of substrate solution in 1×TBS buffer (pH 7.5, 1 mM Mg$^{2+}$, and 10% (w/v) PEG8000) (Table 5) was injected into the flow channel. Movies were recorded for 5 min (9,091 frames) at 35 ms frame exposure time immediately after injecting the substrate solution. In case of G6pDH, the activity was measured in the same field of view under identical laser illumination and microscope settings, with or without glucose-6-phosphate (G6p) (FIG. 5c). Enzyme activity for β-Gal was measured similarly using a 500 nM solution of resorufin β-D-galactopyranoside (RBG) as substrate, which is hydrolyzed by β-Gal into fluorescent resorufin. Fluorescence fluctuations over time were measured for unencapsulated enzyme as well as half- and full-cage-encapsulated enzyme (FIG. 65 and FIG. 66), and the fluorescence time traces were analyzed for intensity spikes using custom-written MATLAB script. The script allowed us to measure the background intensity of single-molecule traces and set a threshold (mean+8 standard deviations) to subtract from the raw intensity. Since we often observed one or two spikes above this intensity threshold in the control experiments, only those molecules with 2:4 spikes were counted as active molecules (FIG. 67) and considered for burst analysis. Due to the low concentration of resazurin (Table 5), the criteria we used to determine the fraction of active molecules might have excluded some molecules that are not highly active.

Burst analysis: Burst analysis was carried out using a modified Rank Surprise (RS) method6 recently utilized to analyze the binding of fluorescent DNA probes to a riboswitch. Briefly, Interspike Intervals (ISIs) were determined by calculating the time in between individual fluorescent spikes for each molecule (FIG. 67). The RS method was used to demarcate the start and end points of bursts after collecting ISIs for all molecules. Only intensity spikes characterized by an ISIs of greater than 3 seconds were considered part of a burst; any other intensity spikes are counted as non-bursts.

Comparing bulk and single-molecule enzyme activity: Unlike our single-molecule assay, the bulk measurement of enzyme activity cannot explicitly determine the fraction of active enzyme molecules present in the solution (it is well known that a fraction of enzyme molecules loses their activity during oligonucleotide conjugation, buffer exchange and the purification process). However, the observed bulk activity is contributed not only by enzyme turnover rate but also by the fraction of enzyme molecules that are still active. Both of these contributing factors need to be accounted for to directly compare the single-molecule enzyme activity with the bulk measurements. Therefore, in the single-molecule experiment, the overall activity of free, half-cage and full-cage enzymes were calculated by multiplying the turnover rate with the fraction of active molecules for the given sample.

Bulk Solution Enzyme Assay.

A 96-well-plate reader was used to monitor enzyme activity through absorbance changes of the samples. The enzyme samples and substrates were loaded in the wells of the 96-well plate with a final concentration of caged enzymes 0.5 nM in 1×TBS (Tris buffered saline with 1 mM MgCl2, pH 7.5) for most assays.

Enzymes and Substrates:

Glucose-6-phosphate dehydrogenase (G6pDH, *Leuconostoc mesenteroides*), malic dehydrogenase (MDH, porcine heart), lactate dehydrogenase (LDH, rabbit muscle), glucose oxidase (GOx, *Aspergillus niger*), horseradish peroxidase (HRP) and β-galactosidase (β-Gal, *E. coli*) were purchased from Sigma (St. Louis, MO). Pyruvate, oxaloacetate (OAA), glucose 6-phosphate (G6P), glucose, resorufin β-D-glucopyranoside (RBG), β-nicotinamide adenine dinucleotide (NAD), resazurin (RESA) and phenazine methosulfate (PMS) were obtained from Sigma-Aldrich. ABTS (2,2'-Azino-bis[3-ethylbenzothiazoline-6-sulfonic acid] diammonium salt) was purchased from Pierce (Rockford, IL), polyphosphate (100) is ordered from Kerafast.

DNA Strands:

Single-stranded MI3mp18 DNA was purchased from New England Biolabs. Staple strand oligonucleotides were obtained from Integrated DNA Technologies (IDT) on 96-well plates and used without further purification. Thiol-modified DNA oligonucleotides were also purchased from IDT, and were purified by denaturing PAGE before use.

Crosslinking Reagents:

N-Succinimidyl 3-(2-pyridyldithio)propionate (SPDP) and tris(2-carboxyethyl)phosphine (TCEP) were obtained from Pierce. Dimethyl sulfoxide (DMSO) was purchased from Sigma.

Buffers:

Phosphate buffered saline (PBS), HEPES sodium salt, Tris buffered saline (TBS), Tris base, acetic acid, EDTA, and magnesium acetate were purchased from Sigma. 1×TAE/Mg$^{2+}$ buffer (pH 8.0) is prepared by 40 mM Tris, 20 mM acetic acid, 2 mM EDTA and 12.5 mM magnesium acetate.

Dye-Labeling Reagents:

NHS-Cy3, Cy5 amine reactive dyes were purchased from GE Healthcare Life Sciences. NHS-AlexaFluor®555 and AlexaFluor®647 amine reactive dyes were obtained from Life Technologies.

Amicon centrifugal filters were purchased from Millipore.

PEG 8000 was purchased from Promega.

Surface PEGylating Reagents:

APTES (3-Aminopropyl)triethoxysilane was purchased from Sigma-Aldrich. mPEG-SV A 5 k and biotin-PEG-SY A 5 k were obtained from Laysan Bio, Inc.

TEM Imaging:

TEM grids (400 mesh, copper grid coated with ultrathin carbon, Ted Pella) were glow discharged (Emitech K1 OOX). 2 μl concentrated samples were deposited onto the grids for 1 min, washed with 10 (11 DI water for 5 sec, stained with 10 μl 1% uranyl formate twice (2 sec for the first time and 15 sec for the second time), and imaged using Philips CM12 transmission electron microscope.

Enzyme Activity Assay:

A 96-well-plate reader was used to monitor enzyme activity through absorbance changes of the samples. The enzyme samples and substrates were loaded in the wells of the 96-well plate with a final concentration of caged enzymes of 0.5 nM in 1×TBS (Tris buffered saline with 1 mM MgCl$_2$, pH 7.5) for most assays. The DNA cage concentration was determined by the A$_{260}$ value as described above. For a typical GOx and HRP assay, 1 mM Glucose and 2 mM ABTS was used as substrate and enzyme activity was measured by monitoring the increase in absorbance at 410 nm (ABTs-1). For a typical G6pDH assay, 1 mM G6P and 1 mM NAD+ were used as substrates, and enzyme activity was measured by monitoring the increased absorbance at 340 nm due to the reduction of NAD+ to NADH. For a typical LDH assay, 2 mM pyruvate and 1 mM NADH were used as substrates, and enzyme activity was measured by monitoring the decreased absorbance at 340 nm due to the oxidation of NADH to NAD+. For a typical MDH assay, 2 mM OAA and 1 mM NADH were used as substrates, and enzyme activity was measured by monitoring the decrease in absorbance at 340 nm. For a typical β-Gal assay, 100 μM RBG was used as substrate and enzyme activity was measured by monitoring fluorescence intensity, with excitation at 532 nm and emission at 590 nm.

Trypsin Assay:

Enzyme activity was measured after incubation with or without trypsin (1 μM) at 37° C. for 24 h in 1×TAE-10 mM Mg buffer (pH 8.0). Activity assay conditions: 1 mM Glucose, 1 mM ABTS, 1 nM of free GOx and HRP in pH 7.5, 1×TBS buffer containing 1 mM MgCl$_2$, and monitoring absorbance at 410 nm. In the DNA cage experiment, all conditions were the same except for incubating 1 nM DNA cage-encapsulated GOx and HRP with trypsin.

Results

Enzyme Encapsulation Strategy.

Figures 1A, 1B, 1C:
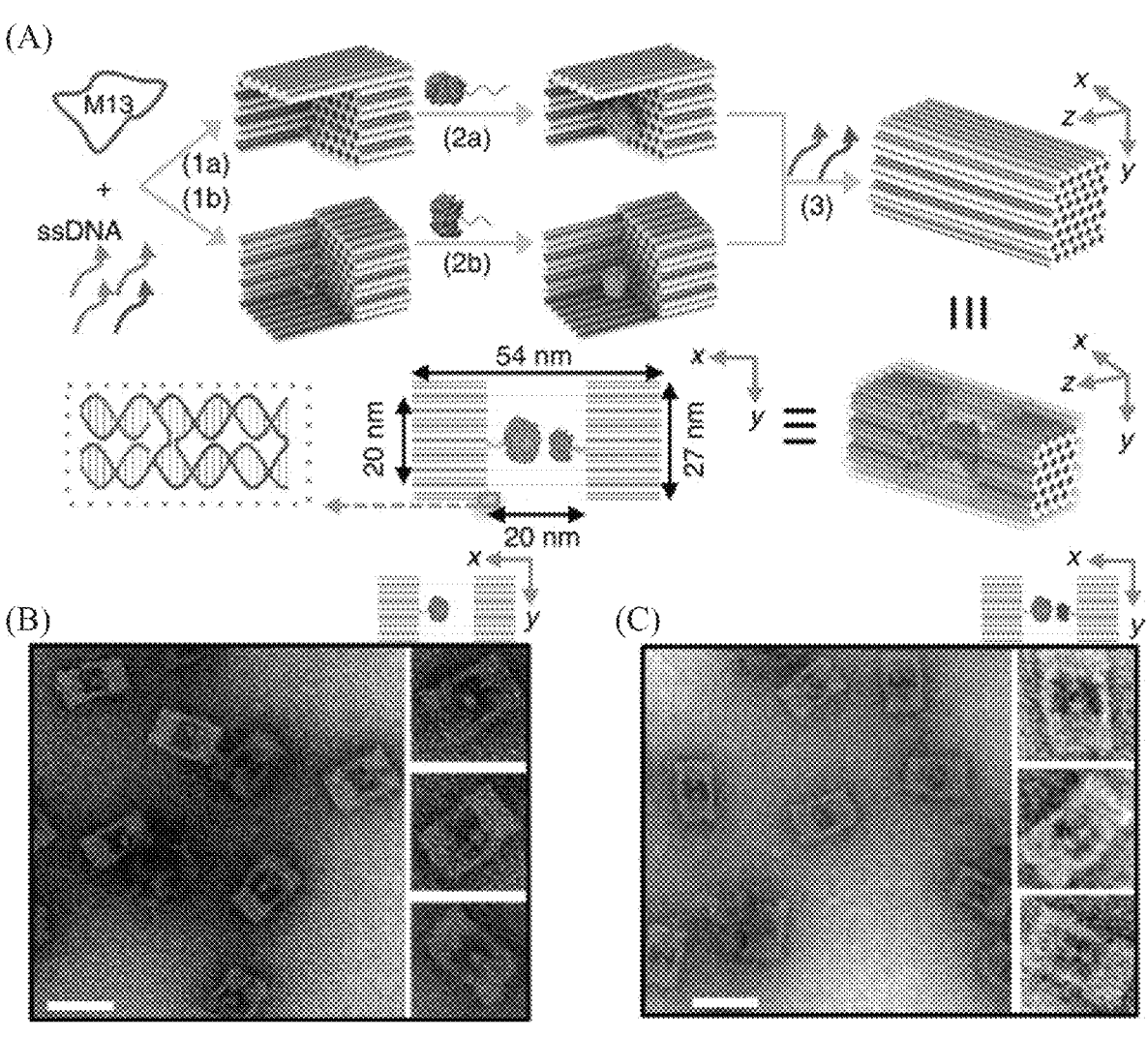
FIGS. 1A-1C show design and characterization of DNA nanocage-encapsulated enzymes with controlled stoichiometry. (A) Schematic representations of the assembly of a DNA nanocage encapsulating a pair of GOx (orange) and HRP (green) enzymes. Individual enzymes were first attached to half-cages, followed by the addition of linker strands (red) to combine the two halves into a full-cage. Small pores of honeycomb shape (~2.5 nm d.i.) were designed on the bottom of cages to facilitate the diffusion of substrate molecules in an out of the cage. (B) Negatively stained TEM images of DNA cages containing a single GOx (shown as less stained dots) and (C) a pair of GOx and HRP (shown as less stained dots). Scale bar, 50 nm.

As shown in FIG. 1A, the current embodiment of the approach for enzyme encapsulation within DNA nanocages involves two steps: 1) the attachment of an individual enzyme into an open half-cage and 2) the assembly of two half-cages into a full (closed) nanocage. DNA half-cages were constructed by folding a full-length M13 viral DNA29 into the indicated shape based on a honeycomb lattice using the DNA origami technique; a shape with two open sides was chosen to improve accessibility of the internal cavity to large proteins. Two half-cages were then linked into a full-cage by adding 24 short bridge DNA strands that hybridize with the complementary ssDNA sequences extending from the edges of either half-cage. The DNA full-cage is 54 nm×27 nm×26 nm with designed inner cavity dimensions of 20 nm×20 nm×17 nm. By design, 42 small nanopores (each 2.5 nm in diameter) were introduced on each of the top and bottom surfaces of the DNA nanocage to permit the diffusion of small molecules (e.g., enzyme substrates) across the DNA walls (FIG. 7).

Figure 10:
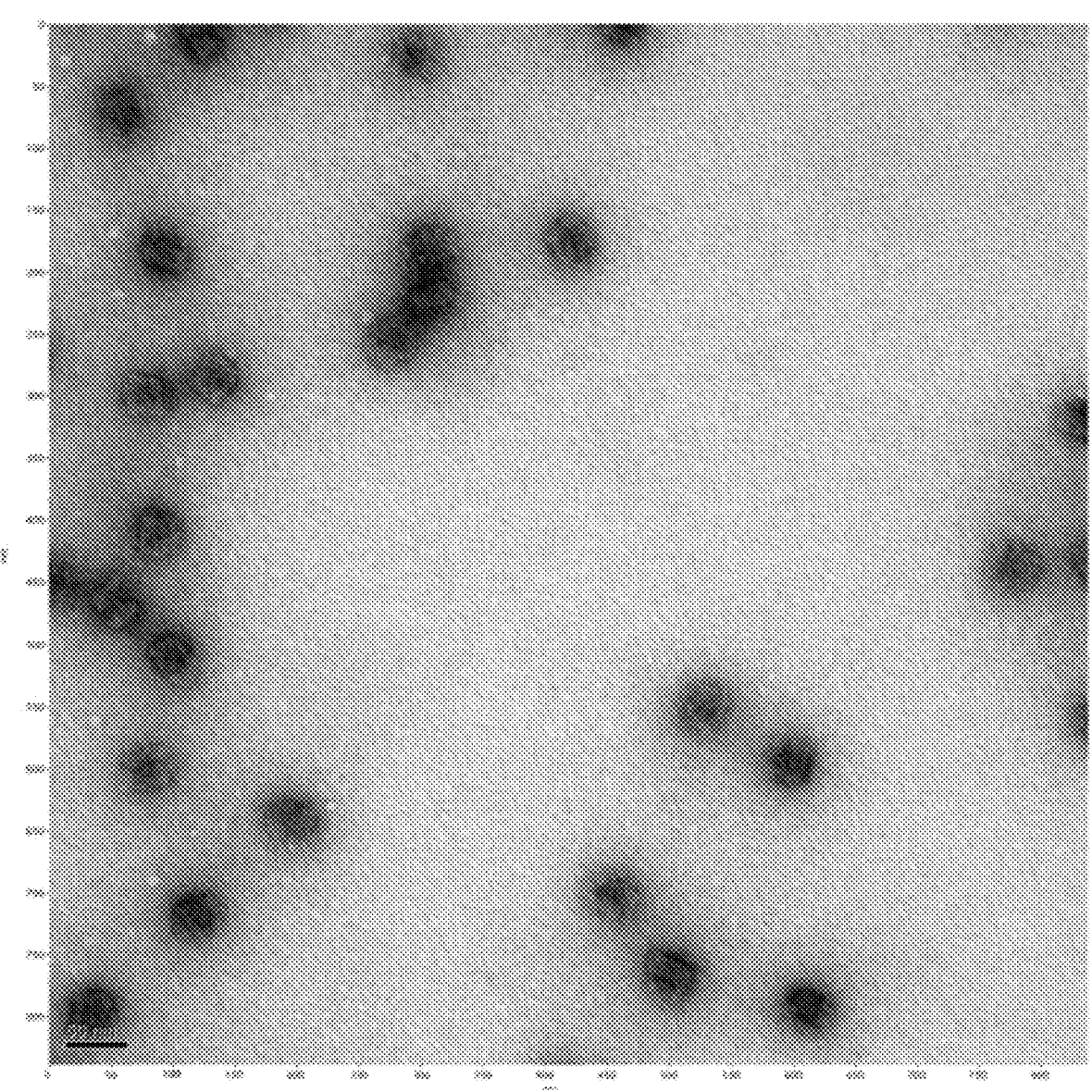
FIG. 10 shows a representative TEM image of the half-cage structure (scale bar: 50 nm).
Figure 11:
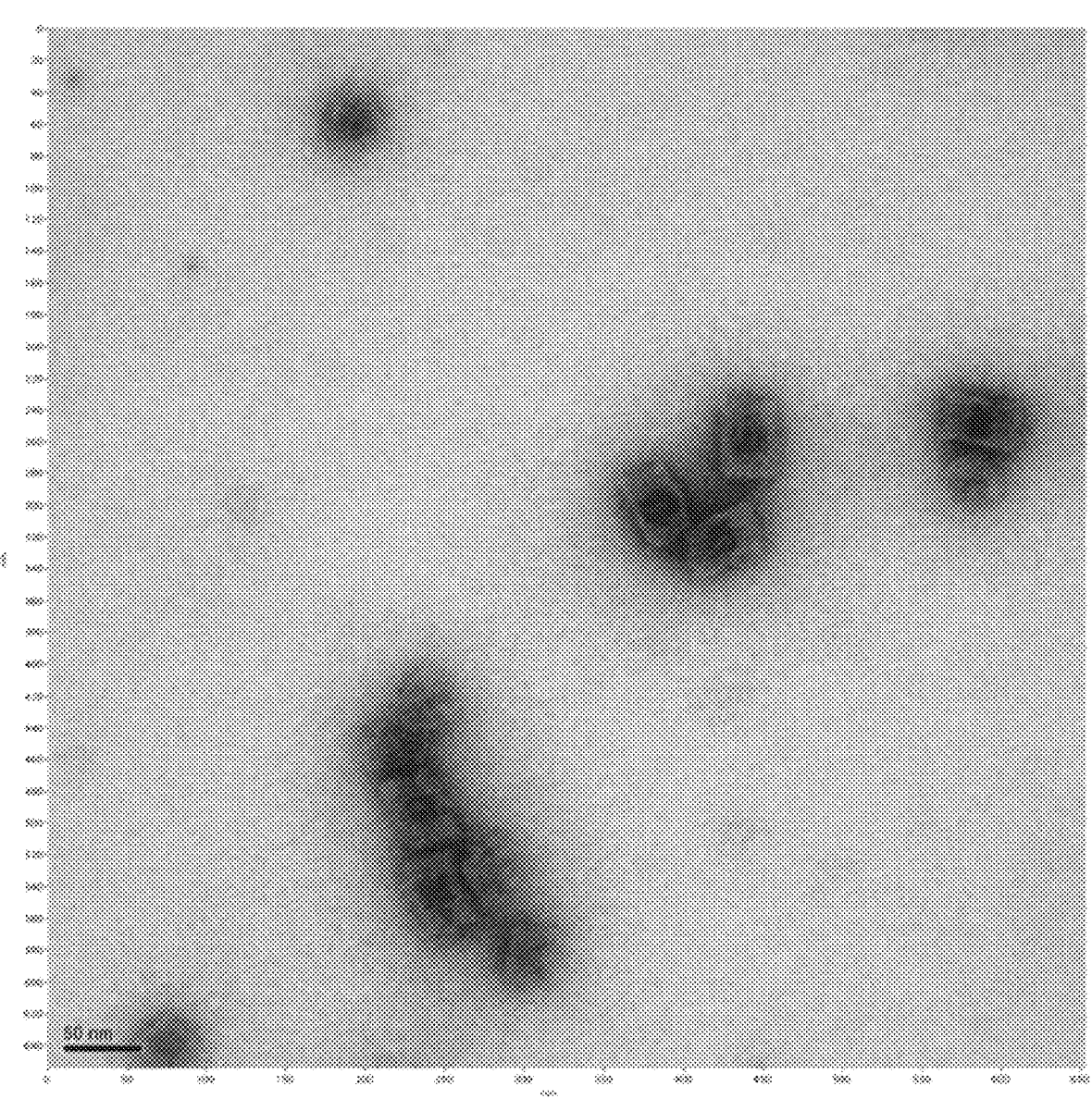
FIG. 11 shows a representative TEM image of the full-cage structure (scale bar: 50 nm).
Figure 12:
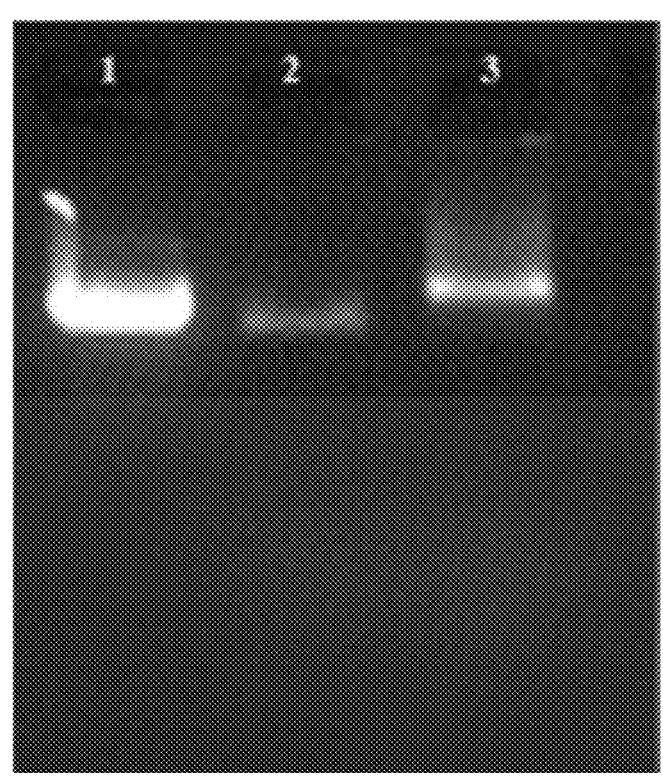
FIG. 12 shows an agarose gel electrophoresis (AGE) to characterize the full-cage structure (lane 1: MI3 DNA, lane 2: half-cage; lane 3: full-cage). According to the gel band intensity, the assembly yield of the full-cage was higher than 90%.

The formation of half and full DNA nanocages was first characterized using transmission electron microscopy (TEM) (FIG. 10 and FIG. 11) and gel electrophoresis (FIG. 12), which indicate a nearly 100% yield for half-cages and a more than 90% yield for full-cages. To capture target enzymes into a half-cage, a previously reported succinimidyl 3-(2-pyridyldithio) propionate (SPDP) chemistry was used to crosslink a lysine residue on the protein surface to a thiol-modified oligonucleotide. Two anchor probes of complementary sequence were displayed on the bottom of the half-cage cavity to capture a DNA-modified enzyme via sequence-specific DNA hybridization.

As a demonstration of an enzyme cascade, a glucose oxidase (GOx)-attached half-cage was incubated with a horseradish peroxidase (HRP)-attached half-cage at a stoichiometric ratio of 1:1, followed by the addition of bridge strands into solution to assemble a full DNA nanocage containing a GOx/HRP pair. The inner cavity of a full nanocage is of sufficient size to encapsulate this enzyme pair (GOx is 10 nm32 and HRP 5 nm in diameter33). Unencapsulated enzyme and excess short DNA strands were removed using agarose gel electrophoresis (AGE). Details of the enzyme-DNA conjugation and optimization of the assembly are shown in FIGS. 13, 14A-14F, 15A-15B, 16, 17, 18, Table 2.

Characterization of Enzyme Encapsulation.

To verify the presence of both enzymes within a DNA nanocage, the co-localization of a Cy3-labeled GOx (green emission) and a Cy5-labeled HRP (red emission) was quantified by dual-color fluorescence gel electrophoresis where a gel band with overlapped green and red color was identified (FIG. 18). By comparison, the GOx-containing half-cage (Half[GOx]) shows the presence of only Cy3 (green), whereas a HRP-half-cage (Half[HRP]) shows the presence of only Cy5 (red). In addition, negatively-stained TEM images were used to visualize DNA cages upon stoichiometrically controlled encapsulation of a single GOx (FIG. 1B) or a single GOx/HRP pair (FIG. 1C), where GOx and HRP were visible as brighter spots within the cage. To quantitatively analyze the yield of DNA nanocage encapsulation, two-color total internal reflection fluorescence (TIRF) microscopy34 (FIG. 2A) was used to characterize the fluorescence co-localization of a Cy3-labeled enzyme and a Cy5-labeled nanocage (FIG. 2B). Six different enzymes were tested and characterized for encapsulation, ranging from the smallest HRP (44 kD)35, malic dehydrogenase (MDH, 70 kD)36, glucose-6-phosphate dehydrogenase (G6pDH, 100 kD)37, lactic dehydrogenase (LDH, 140 kD)38 and GOx (160 kD)39 to the largest β-galactosidase (β-Gal, 450 kD)40. All six enzymes were successfully encapsulated within full DNA nanocages with high yields, ranging from 64-98% (FIG. 2C and Table 3). The relatively low yield of β-Gal (64%) may be due to its large size (16 nm in diameter), which is comparable to the inner diameter of the nanocage (20 nm), likely resulting in steric hindrance for encapsulation. To evaluate how many copies of the same enzyme were encapsulated per DNA nanocage, single-molecule fluorescence photobleaching (SMPB) was used to count the number of photobleaching of Cy3 fluorophores per cage (FIG. 2D). The number of copies of each enzyme per cage was estimated by normalizing the number of Cy3 fluorophores per DNA nanocage with the average number of Cy3 labels per free enzyme. A majority of nanocage-encapsulated enzymes showed only one- or two-step photobleaching of Cy3, similar to the photobleaching of single free enzymes (FIG. 2E). These results suggest that most nanocages (90%) contain exactly one enzyme per cage, as expected (FIG. 2E and Table 4).

Activity Characterization of Nano-Caged Enzymes.

Figure 3A:
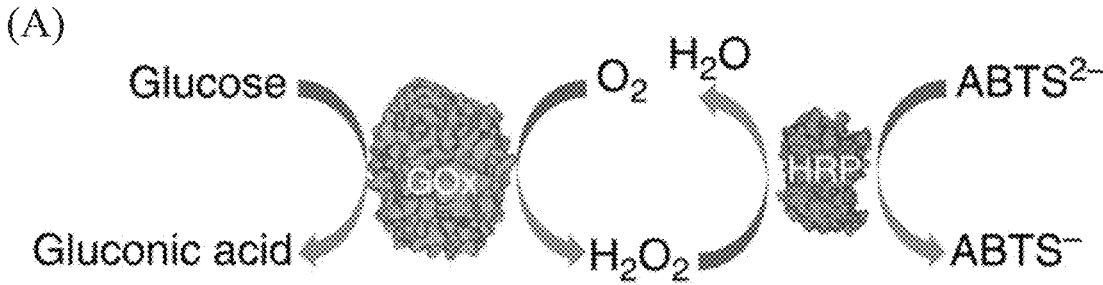
FIGS. 3A-3B show activity characterization of encapsulated GOx/HRP pairs. (A) Schematic representation of the GOx/HRP cascade. (B) Normalized cascade activities for a GOx/HRP pair encapsulated within a full-cage (Full[GOx/HRP]), two individual full-cages (Full[GOx]+Full[HRP]) and two individual half-cages (Half[GOx]+Half[HRP]), as well as unencapsulated enzyme pairs with and without the presence of DNA cages. Assay conditions: 1 nM enzyme or 1 nM enzyme-DNA cage, 1 mM glucose and 2 mM ABTS in TBS buffer (pH 7.5), and monitoring absorbance at 410 nm. Error bars were generated as the standard deviation of at least three replicates.
Figure 3B:
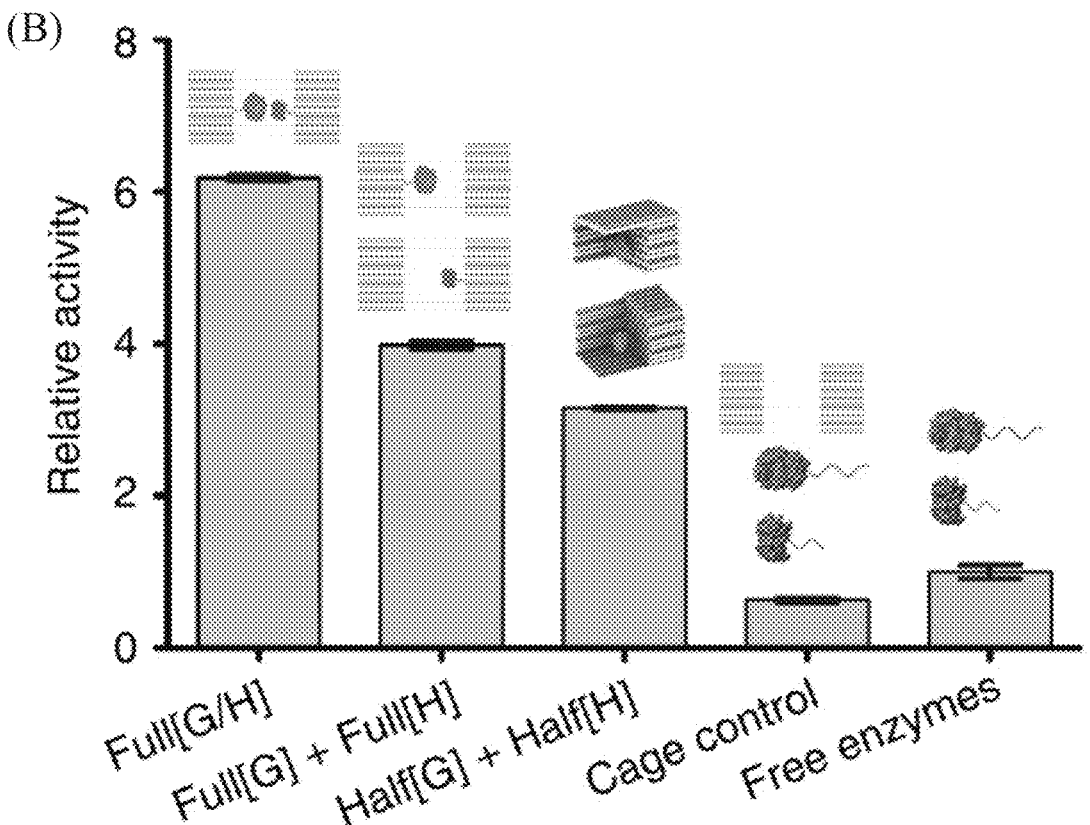

To evaluate the effect of DNA nanocages on enzyme activity, an encapsulated GOx/HRP pair was tested (FIG. 3A). This pair of enzymes catalyzes a reaction cascade beginning with the oxidation of glucose by GOx to generate hydrogen peroxide ($H_2O_2$). $H_2O_2$ is subsequently used by HRP to oxidize ABTS, producing a strong colorimetric signal. As shown in FIG. 3B, the overall activity of a co-assembled GOx/HRP cage (Full[GOx/HRP]) is 8-fold higher than that of a control enzyme pair incubated with the same cage but without encapsulation. Two plausible effects are hypothesized which could contribute to such a significant activity enhancement: 1) The proximity effect that brings the two enzymes close together and facilitates their substrate transfer, as described previously; and/or 2) the unique environment provided by the high charge density of DNA helices within a nanocage.

To separate the proximity effect from the charge density effect, control experiments of DNA nanocages encapsulating only a single GOx or HRP enzyme are designed, which clearly do not allow for substrate channeling between two proximal enzymes. For example, an equimolar mixture of two separate nanocages encapsulating either a single GOx or a single HRP (Full[GOx]+Full[HRP]) exhibited an 4-fold increase in overall activity compared to the unencapsulated control enzymes. Similarly, an equimolar mixture of two half-cages encapsulating either a single GOx or a single HRP already showed an increase in overall activity by 3-fold. Since there was no proximity effect in the case of two enzymes encapsulated into two different nanocages, the local environment modified by a DNA nanocage appears to be more important for the observed activity enhancement. Similarly, a half-cage was almost as effective in activity enhancement (3-fold) as a full-cage, suggesting that enzyme access to substrate does not play a role in this enhancement. Interestingly, a similar enhancement was reported previously upon conjugation of enzymes to a giant multi-branched DNA scaffold, without further explanation.

To test the generality of nanocage activity observations, the activity of six different enzymes upon encapsulation within DNA nanocages are evaluated. As shown in Table 1, five of them (GOx, HRP, G6pDH, MDH, and LDH) exhibited higher activity in nanocages than the free enzyme, with enhancements ranging from 3- to 10-fold.

Figure 4A:
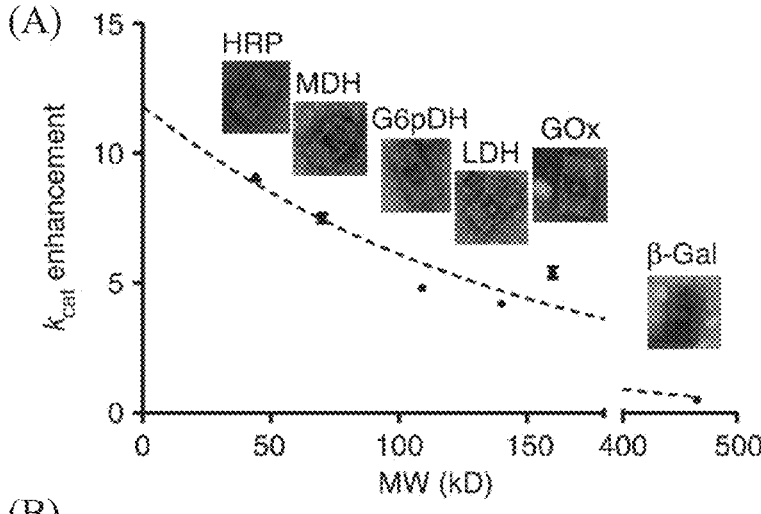
FIGS. 4A-4C show mechanistic study of the activity enhancement of DNA nanocage-encapsulated enzymes. (A) Relationship between turnover rate enhancement factor after encapsulation against enzyme molecular weight (fitted using one-phase decay function). (B) Nanocage-encapsulated G6pDH activity change after incubation with different amount of NaCl. Assay conditions: 0.5 nM enzyme-DNA cage, incubation with 1 mM glucose-6-phosphate and 1 mM NAD+ in TBS buffer (pH 7.5), and monitoring absorbance at 340 nm. (C) Normalized $k_{cat}$ and $K_M$ values of free G6pDH and G6pDH that is encapsulated within different DNA cage: SH(G6pDH), a honeycomb lattice origami with a single layer; SS(G6pDH), a square-lattice origami with a single layer; and DS(G6pDH), a square-lattice origami with two layers. $k_{cat}$ and $K_M$ values of caged enzymes are normalized to that of free enzymes. Error bars were generated as the standard deviation of at least three replicates.

Detailed kinetic analyses show that the $K_M$ (the Michaelis-Menten constant) varies little between encapsulated and free enzyme for most substrates (ranging from 0.5 to 2.4-fold of the free enzyme), suggesting that the porous DNA cages do not substantially hinder diffusion of small-molecule substrates. In contrast, a large increase in turnover number ($k_{cat}$) was observed for these five enzymes (ranging from 3.5- to 9.6-fold of the free enzyme), suggesting an inherently higher catalytic activity of the proteins. For all the raw kinetics data, please see FIGS. 20-54. An inverse correlation was observed between enhanced turnover and size of the encapsulated enzyme (FIG. 4A). That is, the smaller HRP (44 kD) and MDH (70 kD) exhibited relatively large increases in turnover number of 9.6±0.4 and 9.0±0.7 fold, respectively, whereas the larger enzymes G6pDH, LDH, and GOx exhibited smaller enhancements of 4.7±0.1 fold, 4.1±0.1 fold, and 5.4±0.2 fold, respectively. No correlation was observed between enhancement and isoelectric point (pI), despite the wide range of pI values for these enzymes (ranging from 4.2 to 10.0).

In contrast to these five enzymes, β-Gal is strongly inhibited upon encapsulation, possibly due to its large size (16 nm in diameter, FIG. 55) that is comparable to the inner cavity diameter (20 nm) of the DNA nanocage. Alternatively, the β-Gal orientation may be unfavorable and block binding of substrate to the active site. Notably, in a control experiment polyphosphate inhibited the activity of β-Gal (FIG. 56), suggesting that the local high density of backbone phosphates of the DNA nanocage might be responsible for the decrease in activity of β-Gal. The DNA cages retained their structural integrity during the enzymatic reactions (FIGS. 57A-57E).

To gain more detailed mechanistic insight into the enhancement of catalytic turnover, a novel single-molecule fluorescence assay to characterize the activity of individual enzymes with and without encapsulation was applied (FIG. 5). As shown in FIGS. 5A and 5B, TIRF microscopy is used to record the repetitive turnover of substrates by individual G6pDH enzymes over time; coupling with a PMS/resazurin reaction allowed us to detect stochastic fluctuations of enzyme turnover rates via transient spikes in intensity from the generation of the fluorescent product resorufin (FIGS. 5C-5D and FIGS. 58, 59A-59D, and 60). Such fluctuations have been observed for various enzymes before and are thought to be induced by the conformational switching between more and less active sub-states.

Compared to a control without substrate, more frequent fluorescent spikes were observed with the addition of glucose-6-phosphate substrate (FIGS. 5C and 5D). The average spike frequency was increased from 0.016±0.001 s−1 for unencapsulated enzymes, to 0.019±0.001 s−1 for the half-cage and 0.026±0.002 s−1 for the full-cage (FIG. 5E). Further analysis suggested that the fraction of active enzyme molecules was increased from 20.3% for unencapsulated enzymes to 26.6% for the half-cage and 30.5% for the full-cage (FIG. 5F). Taken together, the 1.6-fold higher spike frequency and the 1.5-fold increase in the fraction of active enzymes yield a 2.5-fold increase in G6pDH activity for the encapsulated compared to the unencapsulated enzyme (FIG. 5G), comparable to the 4-fold enhancement observed in the bulk assay. Conversely, a similar analysis of β-Gal activity showed a 3-fold lower activity of the full-cage enzyme (2.3±0.5 fold lower in spike frequency compared to free enzyme whereas the fractions of active enzymes (65%) were similar) compared to unencapsulated enzyme (FIGS. 59A-59D), also consistent with the bulk measurement.

The activity enhancement for DNA cage-encapsulated enzymes is consistent with recent reports of enhanced enzyme activity upon attachment to a long double-stranded DNA molecule (λDNA), a 2D rectangular DNA origami, or a DNA scaffold that bound to enzyme substrates, and further suggests that it may be a widespread effect of enzyme-DNA interactions. Several mechanisms have been previously proposed to explain these observed enhancements, including micro-environment composed of giant and ordered DNA molecules, molecular crowding and the substrates affinity to DNA scaffolds. We further suggested that the negatively charged phosphate backbones of DNA might also contribute to the activity enhancement. DNA is a negatively charged biopolymer due to its closely spaced backbone phosphates (leading to a linear negative charge density of 0.6 e/Å). Thus, upon encapsulation within a DNA nanocage, an enzyme is exposed to an environment full of negative charges that may resemble the relative abundance of poly-anionic molecules and surfaces (including RNA and phospholipid membranes) within the cell. Phosphate is a known kosmotropic anion that increases the extent of hydrogen-bonded water structures (termed high-density or structured water). A DNA nanocage is thus expected to attract a strongly bound hydration layer of hydrogen-bonded water molecules inside its cavity. Multiple studies have described that proteins are more stable and active in a highly ordered, hydrogen-bonded water environment, possibly due to stabilization of the hydrophobic interactions of a folded protein through an increase in the solvent entropy penalty upon unfolding.

Figure 4B:
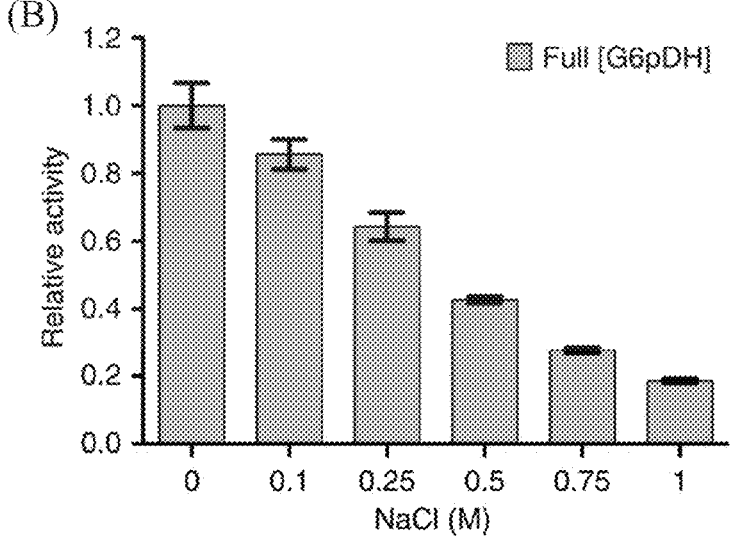

Consistent with this model, polyphosphate has been shown to act as a generic chaperone stabilizing a variety of enzymes. To further test whether this mechanism is at work in our nanocages, we titrated the concentration of NaCl (known to consist of chaotropic ions) for the purpose of interrupting hydrogen-bonded water molecules. Consistent with our hypothesis, the activity of encapsulated enzymes significantly decreased with increasing NaCl concentration (reduced to 25% activity with 1 M NaCl as shown in FIG. 4B. A high concentration of Na+ can shield the negative charge on the DNA surface, thus disrupting the surface-bound hydration layer. As a control, we observed that the bulky kosmotropic cation, triethylammonium, had a much less pronounced effect on enzymatic activity (FIGS. 61A-61D). This model also allowed us to rationalize why we observed smaller enzymes to be more activated than larger enzymes: namely, because their higher surface-to-volume ratio predicts a stronger impact of the hydration layer.

Figure 4C:
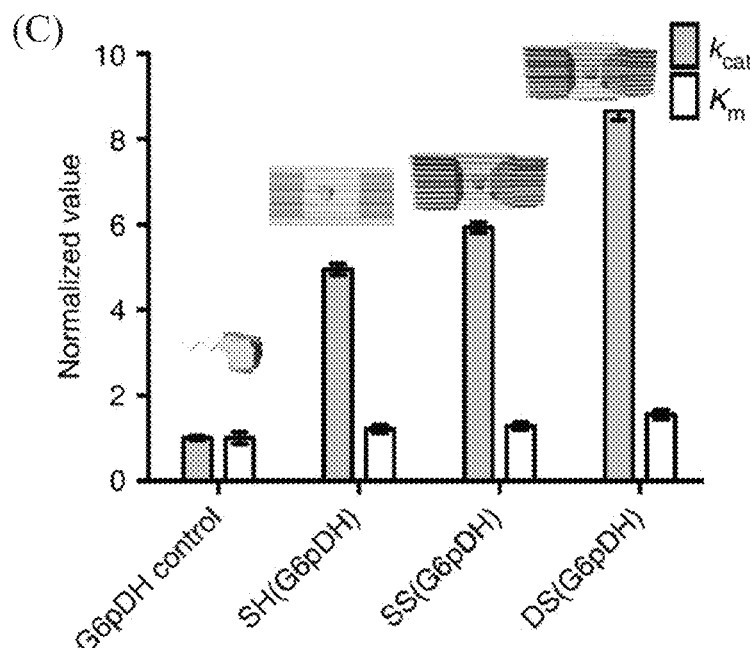

To further test this model, we investigated the effect of DNA helix density on the encapsulated enzyme activity. As shown in FIG. 4C, we designed three nanocages with walls that systematically increase the density of DNA helices, including: 1) a single-layer honeycomb pattern (SH) with 2-3 nm pores between helices; 2) a single-layer square pattern (SS) with smaller 0.5-1 nm pores between helices, and 3) a double-layer square pattern (DS). The helix density at the top and bottom surfaces thus increased from 0.12 helices per nm2 for SH to 0.16 helices per nm2 for the SS and DS designs. The $k_{cat}$ of G6pDH encapsulated in the SH-cage was 4.7-fold higher than that of the free enzyme. As the density of DNA helices was increased, the $k_{cat}$ of encapsulated G6pDH raised to 6-fold for the SS-cage and 8-fold for the DS-cage compared to the free enzyme control. A slight increase in $K_M$ values was also observed from the SH-cage to the SS- and DS-cages, possibly due to a decrease in substrate diffusion through the DNA walls of these more tightly packed structures. For example, the $K_M$ value of G6pDH increased from 411 μM in the SH-cage to 436 μM in the SS-cage and 527 μM in the DS-cage (FIG. 62 and FIG. 4C). Additional studies showed that activities of attached enzymes were enhanced by increasing the helix packing density for various 1D, 2D and 3D DNA scaffolds (FIG. 63). These observations suggest that encapsulated enzymes exhibit higher activity within densely packed DNA cages, consistent with our model that the highly ordered, hydrogen-bonded water environment near closely spaced phosphate groups are responsible for this effect.

Figure 6A:
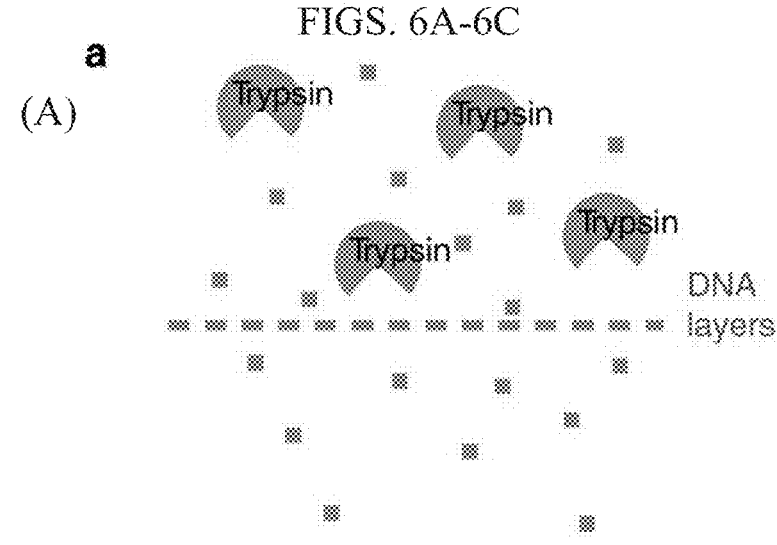
FIGS. 6A-6C show protection of nanocaged enzymes against protease-mediated degradation and aggregation. (A) Schematic representation illustrating how a DNA cage may block access of big proteins such as a protease to the interior of the cage, but still allow the penetration of small molecules. (B) Relative enzyme activity of encapsulated GOx/HRP pairs (Full [GOx/HRP]) and free GOx/HRP pairs (free GOx/HRP) before and after the addition of trypsin. Trypsin digestion conditions: enzyme or enzyme-DNA cage was incubated with 1,000× excess trypsin for 24 h at 37° C. Assay conditions: 0.5 nM enzyme or 0.5 nM enzyme-DNA cage, incubation with 1 mM glucose and 2 mM ABTS in 1×TBS buffer (pH 7.5), and monitoring absorbance at 410 nm. (C) Relative activity data for free G6pDH and Full [G6pDH] (0.5 nM) with trypsin digestion for 0, 1, 4, 8 and 24 h. Digestion by incubation sample with 1,000 times amount of trypsin at 37° C. in 1×TBS buffer (pH 7.5). Error bars were generated as the standard deviation of at least three replicates.
Figure 6B:
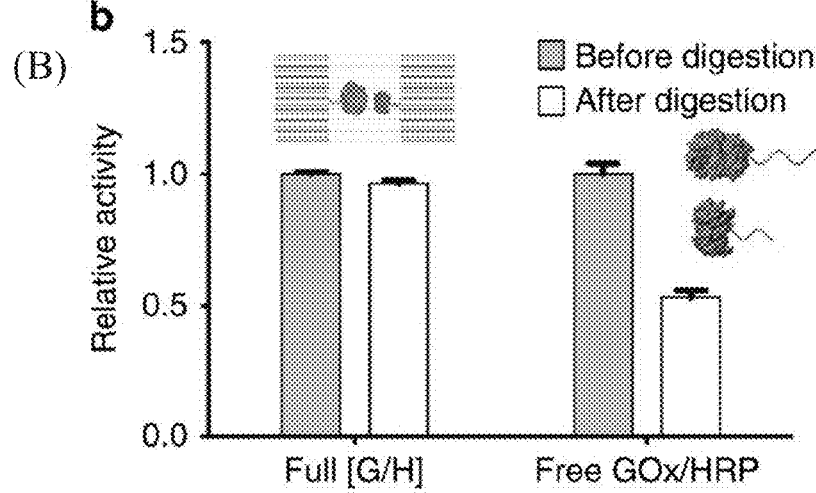
Figure 6C:
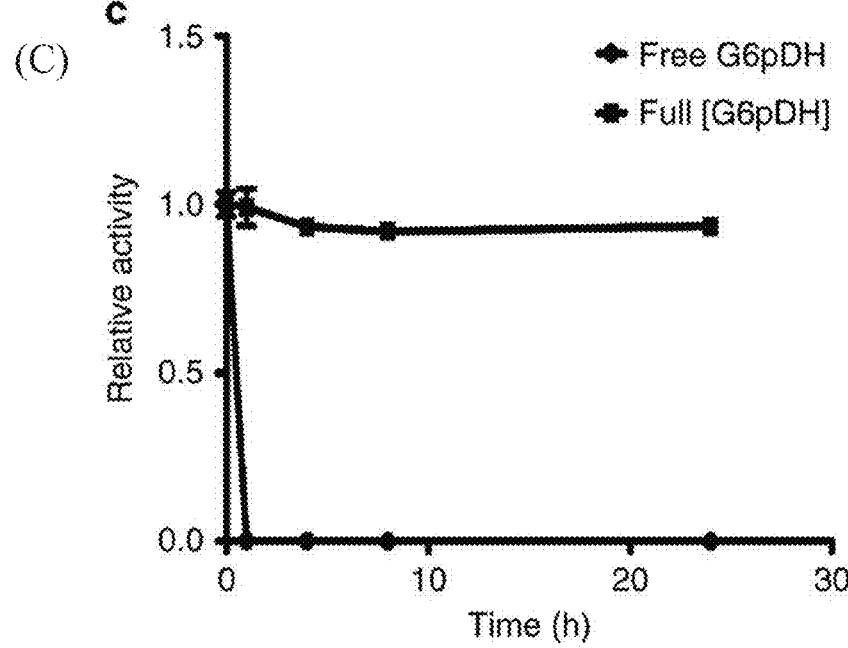

Nanocaged enzymes are protected from proteolysis. Self-assembled DNA nanostructures previously were found to be more resistant against nuclease degradation than single- or double-stranded DNA molecules. Similarly, DNA nanocages should protect encapsulated enzymes from deactivation and aggregation under challenging biological conditions. As shown in FIG. 6, encapsulated GOx/HRP was highly resistant to digestion by trypsin (FIG. 6B), and retained more than 95% of its initial activity after incubation with trypsin for 24 h (FIG. 6C). A time-course experiment was also performed to demonstrate the stability of caged enzymes against Trypsin digestion (FIG. 6C and FIGS. 64-67). In contrast, free GOx/HRP only retained 50% of its initial activity after a similar incubation with trypsin. This result demonstrated the potential utility of DNA nanocages for protecting encapsulated proteins from biological degradation.

TABLE 1

Enzyme kinetic data (values of $K_M$ and $k_{cat}$) for each individual enzyme encapsulated inside a DNA full-cage in comparison with the values for the free enzymes in solution.

| Enzyme | pI | Molecular weight | Substrate | Free enzyme $K_M$ (μM) | Free enzyme $k_{cat}$ (s−1) | Encapsulated enzyme $K_M$ (μM) | Encapsulated enzyme $k_{cat}$ (s−1) |
|---|---|---|---|---|---|---|---|
| GOx | 4.2 | 160 kDa | Glucose | 6,200 ± 900 | 240 ± 10 | 3,000 ± 600 | 1,300 ± 50 |
| HRP | 8.8 | 44 kDa | $H_2O_2$ | 2.3 ± 0.5 | 32 ± 1 | 4.3 ± 0.6 | 290 ± 5 |
| | | | ABTS | 2,600 ± 400 | 59 ± 5 | 2,500 ± 200 | 560 ± 20 |
| G6pDH | 4.3 | 100 kDa | Glucose-6-phosphate | 220 ± 20 | 130 ± 3 | 310 ± 30 | 460 ± 10 |
| | | | NAD+ | 510 ± 50 | 100 ± 3 | 590 ± 40 | 480 ± 10 |
| MDH | 10.0 | 70 kDa | NADH | 180 ± 50 | 51 ± 5 | 270 ± 50 | 460 ± 30 |
| LDH | 5.0 | 140 kDa | NADH | 7.2 ± 1.3 | 46 ± 2 | 17.0 ± 1.5 | 190 ± 5 |
| β-Gal | 4.1 | 465 kDa | RBG | 58.7 ± 16.0 | 8.5 ± 0.6* | 95.5 ± 18.9 | 1.6 ± 0.1* |

ABTS, 2,2'-azino-bis(3-ethylbenzothiazoline-6-sulphonic acid); GOx, glucose oxidase; HRP, horseradish peroxidase; LDH, lactic acid dehydrogenase; MDH, malic dehydrogenase; pI isoelectric point.
The pI values of the enzymes were obtained from brenda-enzymes.org
*$k_{cat}$ values for β-Gal groups were not calibrated

TABLE 2

Estimation of the concentration and DNA labeling ratio of the purified DNA-conjugated enzymes by measuring absorbance at 260 and 280 nm. Concentration of HRP-P1-Cy3 was estimated by the unique absorbance at 405 nm.

| DNA | A260/ A280 | ε260 ($M^{-1}$ $cm^{-1}$) | ε260 ($M^{-1}$ $cm^{-1}$) | Protein | A260/ A280 | ε260 ($M^{-1}$ $cm^{-1}$) | ε260 ($M^{-1}$ $cm^{-1}$) | Sample | A260/ A280 | A260 | A280 | DNA-to-Protein Ratio | Protein Conc. (μM) | Dye (μM) |
|---|---|---|---|---|---|---|---|---|---|---|---|---|---|---|
| P1-Cy3 | 1.27 | 115200 | 90709 | GOx | 0.63 | 168336 | 267200 | GOx-P1-Cy3 | 1.18 | 13.50 | 14.10 | 3.09 | 25.77 | 37.00 |

TABLE 2-continued

Estimation of the concentration and DNA labeling ratio of the purified DNA-conjugated enzymes by measuring absorbance at 260 and 280 nm. Concentration of HRP-P1-Cy3 was estimated by the unique absorbance at 405 nm.

| DNA | A260/ A280 | ε260 (M⁻¹ cm⁻¹) | ε260 (M⁻¹ cm⁻¹) | Protein | A260/ A280 | ε260 (M⁻¹ cm⁻¹) | ε260 (M⁻¹ cm⁻¹) | Sample | A260/ A280 | A260 | A280 | DNA-to-Protein Ratio | Protein Conc. (μM) | Dye (μM) |
|---|---|---|---|---|---|---|---|---|---|---|---|---|---|---|
| P1-Cy3 | 1.27 | 115200 | 90709 | β-Gal | 0.59 | 573534.9 | 972093 | β-Gal-P1-Cy3 | 0.63 | 1.34 | 2.11 | 0.74 | 2.03 | 1.10 |
| P1-Cy3 | 1.27 | 115200 | 90709 | G6pDH | 0.52 | 61594 | 118450 | G6pDH-P1-Gy3 | 1.00 | 11.15 | 11.17 | 2.30 | 34.17 | 53 |
| P2-AF647 | 1.60 | 130100 | 81313 | MDH | 0.72 | 14112 | 19600 | MDH-P2-AF647 | 1.49 | 1.47 | 0.99 | 1.63 | 6.49 | 8 |
| P2-AF647 | 1.60 | 130100 | 81313 | LDH | 0.57 | 115504.8 | 202640 | LDH-P2-AF647 | 0.83 | 2.83 | 3.41 | 0.84 | 12.59 | 22 |

$A_{260}$ (DNA-protein) = $\varepsilon_{260}$ (protein) * Conc. (protein) + $\varepsilon_{260}$ (DNA) * Conc. (DNA)

$A_{280}$ (DNA-protein) = $\varepsilon_{280}$ (protein) * Conc. (protein) + $\varepsilon_{280}$ (DNA) * Conc. (DNA)

$$\text{Ratio} \left( \frac{DNA}{\text{protein}} \right) = \frac{\text{Conc. } (DNA)}{\text{Conc. (protein)}}$$

TABLE 3

Enzyme encapsulation efficiency calculation. Enzyme encapsulation was calculated by taking the ratio of the number of colocalized molecules (i.e., both enzyme and right half-cage) to the total number of molecules containing the right half-cage. N is the number of particles analyzes, $N_{coloc}$ is the number of particles containing both fluorophores, and $N_{right}$ is the number of particles showing evidence of the right half-cage.

| | N | $N_{coloc}$ | $N_{right}$ | $N_{coloc}/N_{right}$ |
|---|---|---|---|---|
| HRP | 176 | 156 | 165 | 0.94 |
| GOx | 205 | 197 | 201 | 0.98 |
| G6pDH | 218 | 209 | 214 | 0.98 |
| LDH | 1229 | 826 | 1008 | 0.82 |
| MDH | 363 | 335 | 348 | 0.96 |
| β-Gal | 284 | 115 | 179 | 0.64 |

TABLE 4

Calculation of enzyme copies per DNA nanocage. The percentage of molecules exhibiting a given number Cy3 photobleaching steps "Cy3 Steps" for both the encapsulated and unencapsulated enzymes are provided. The mean number of enzymes per cage ($N_{enz}$) was calculated by taking the ratio of $\mu_{Cy3\_Encap}$ to $\mu_{Cy3\_Unencap}$. N is the total number of particles analyzed.

| | N | Cy3 Steps (% molecules) | | | $\mu_{Cy3\_Encap}$ | Cy3 Steps (% molecules) | | | $\mu_{Cy3\_Unencap}$ | $N_{enz}$ |
|---|---|---|---|---|---|---|---|---|---|---|
| | | One | Two | Three | | One | Two | Three | | |
| HRP | 176 | 86 | 13 | 1 | 1.15 | 92 | 8 | 0 | 1.08 | 1.0 |
| G6pDH | 218 | 87 | 10 | 3 | 1.16 | 93 | 7 | 0 | 1.07 | 1.1 |
| β-Gal | 284 | 93 | 6 | 1 | 1.08 | 88 | 9 | 3 | 1.15 | 0.9 |

TABLE 5

Conditions for the single-molecule enzyme activity assay

| Solution | Concentration |
|---|---|
| 10X TBS, pH 7.5 | 1X |
| Resazurin Glucose-6-phosphate | 50 nM |
| (G6p) | 1 nM |
| Phenazine Methosulfate (PMS) | 12.5 μM |
| $Mg^{2+}$ ($MgCl_2$) | 1 mM |
| $NAD^+$ | 1 mM |
| PEG 8000 | 10% (w/v) |

Discussion

In summary, we have developed a method for using a DNA nanocage to efficiently encapsulate enzymes with high yield. Using single-molecule characterization, we were able to quantify the copies of encapsulated enzymes per cage with demonstrated one enzyme per cage. Upon encapsulation, five of six tested metabolic enzymes exhibit turnover numbers 4- to 10-fold higher than that of the free enzyme. Conversely, the $K_M$ values remain similar between encapsulated enzymes and free enzymes, indicating an uninterrupted diffusion of small-molecule substrates and products through the nanopores in the DNA cage. Application of a novel single-molecule enzyme assay showed that both the fraction of active enzyme molecules and their individual turnover numbers increase as a consequence of encapsulation.

It is therefore proposed, without being bound to any particular theory or mechanism of action, that the unique local environment created within a DNA nanocage, particularly the high density of negatively charged phosphate groups, enhances the activity of encapsulated enzymes, where the tightly bound, highly structured water layers on DNA surface may stabilize the active enzyme conformations. This effect appears consistent with recent independent evidence that many conserved metabolic enzymes are stabilized by polyphosphate and associate non-specifically with nucleic acids through cryptic binding sites thus taking advantage of the high polyanionic DNA and RNA contents of the cell. DNA nanocages therefore may serve as a molecular tool to precisely sculpt the properties of the local environment of enzymes in smart-material and biotechnological application. DNA nanocages also demonstrated their value in protecting encapsulated enzymes from biological degradation through proteases.

REFERENCES

1. Chen, A. H. & Silver, P. A. Designing biological compartmentalization. *Trends. Cell. Biol.* 12, 662-670 (2012).
2. Hurtley, S. Location, Location, Location. *Science* 326, 1205 (2009).
3. Kertelf, C. A., Heinhorst, S. & Cannon, G. C. Bacterial microcompartments. *Annu. Rev. Microbiol.* 64, 391-408 (2010).
4. Kerfelf, C. A., Sawaya, M. R., Tanaka, S., Nguyen, C. V., Phillips, M., Beeby, M. & Yeates, T. O. Protein structures forming the shell of primitive bacterial organelles. *Science* 309, 936-938 (2005).
5. Graff, A., Winterhalter, M. & Meier, W. Nanoreactors from polymer-stabilized liposomes. *Langmuir* 17, 919-923 (2001).
6. Hartl, F. U. Molecular chaperones in cellular protein folding *Nature* 381, 571-580 (1996).
7. Comellas-Aragones, M. et al. A virus-based single-enzyme nanoreactor. *Nature Nanotech.* 2, 635-639 (2007).
8. Liu, Y. et al. Biomimetic enzyme nanocomplexes and their use as antidotes and preventive measures for alcohol intoxication. *Nature Nanotech.* 8, 187-192 (2013).
9. Sang, L. & Coppens, M. Effects of surface curvature and surface chemistry on the structure and activity of protein adsorbed in nanopores. *Phys. Chem. Chem. Phys.* 13, 6689-6698 (2011).
10. Vriezema, D. M., Aragones, M. C., Elemans, J., Cornelissen, J., Rowan, A. E. & Nolte, R. J. M. Self-assembled nanoreactors. *Chem. Rev.* 105, 1445-1490 (2005).
11. Bruns, N. & Tiller, J. C. Amphiphilic network as nanoreactor for enzymes in organic solvents. *Nano Lett.* 5, 45-48 (2005).
12. Betancor, L., and Luckarift, H. R. Bioinspired enzyme encapsulation for biocatalysis. *Trends. Biotechnol.* 26, 566-572 (2008).
13. Fiedler, J. D., Brown. S. D., Lau. J. & Finn. M. G. RNA-directed packaging of enzymes within virus-like particles. *Angew. Chem. Int. Ed.* 49, 9648-9651 (2010).
14. Douglas, S. M., Dietz, H., Liedl, T., Hogberg, B., Graf, F. & Shih, W. M. Self-assembly of DNA into nanoscale three-dimensional shapes. *Nature* 459, 414-418 (2009).
15. Han, D., Pal, S., Nangreave, J., Deng, Z., Liu, Y. & Yan, H. DNA origami with complex curvatures in three-dimensional space. *Science* 332, 342-346 (2011).
16. Ke, Y., Ong, L. L., Shih, W. M. & Yin, P. Three-dimensional structures self-assembled from DNA bricks. *Science,* 338, 1177-1183 (2012).
17. Kuzyk, A. et al. DNA-based self-assembly of chiral plasmonic nanostructures with tailored optical response. *Nature* 483, 311-314 (2012).
18. Langecker, M., Arnaut, V., Martin, T., List, J., Renner, S., Mayer, M., Dietz, H., & Simmel, F. Synthetic lipid membrane channels by designed DNA nanostructures. *Science* 338, 932-936 (2012).
19. Fu, J., Liu, M., Liu, Y., Woodbury, N. W. & Yan, H. Interenzyme substrate diffusion for an enzyme cascade organized on spatially addressable DNA nanostructure. *J. Am. Chem. Soc.* 134, 5516-5519 (2012).
20. Fu, J., Liu, M., Liu, Y. & Yan, H. Spatially-Interactive Biomolecular Networks Organized by Nucleic Acid Nanostructures, *Acc. Chem. Res.* 45, 1215-1226 (2012).
21. Wilner, O. I., Weizmann, Y., Gill, R., Lioubashevski, O., Freeman, R. & Willner, I. Enzyme cascades activated on topologically programmed DNA scaffolds. *Nature Nanotechnol.* 4, 249-254 (2009).
22. Andersen. E. S. et al. Self-assembly of a nanoscale DNA box with a controllable lid. *Nature* 459, 73-76 (2009).
23. Douglas, S. M., Bachelet, I., Church, G. M. A logic-gated nanorobot for targeted transport of molecular payloads. *Science* 335, 831-834 (2012).
24. Juul, S., et al. Temperature-Controlled Encapsulation and Release of an Active Enzyme in the Cavity of a Self-Assembled DNA Nanocage. *ACS Nano* 7, 9724-9734 (2013).
25. Fu, Y., et al. Single-Step Rapid Assembly of DNA Origami Nanostructures for Addressable Nanoscale Bioreactors. *J. Am. Chem. Soc.* 135, 696-702 (2013).
26. Linko, V., Eerikainen, M. & Kostiainen, M. A modular DNA origami-based enzyme cascade nanoreactor. *Chem. Commun.* 51, 5351-5354 (2015).
27. Gray M. J., et al. Polyphosphate is a primordial chaperone. *Mol. Cell.* 53, 689-699 (2014).
28. Cie§ la, J. Metabolic enzymes that bind RNA: yet another level of cellular regulatory network? *Acta Biochim Pol.* 53, 11-32 (2006).
29. Bellot, G., McClintock, M. A., Lin, C. X., Shih, W. M. Recovery of intact DNA nanostructures after agarose gel-based separation. *Nat. Methods.* 8, 192-194 (2011).
30. Liu, M., Fu, J., Hejesen, C., Yang, Y., Woodbury, N. W., Gothelf, K., Liu, Y., and Yan, H. A DNA Tweezer-Actuated Enzyme Nanoreactors, *Nat. Commun.* 6, 712-719 (2013).
31. Fu, J., Yang, Y. R., Johnson-Buck, A., Liu, Y., Walter, N. G., Woodbury, N. W., and Yan, H. Multi-enzyme complexes on DNA scaffolds capable of substrate channeling with an artificial swinging arm, *Nature Nanotechnol.* 9, 531-536 (2014).
32. Hecht, H. J., Kalisz, K., Hendle, J., Schmid, R. D., Schomburg, D. Crystal structure of glucose oxidase from *Aspergillus niger* refined at 2-3 Å resolution. *J. Mol. Biol.* 229, 153-172 (1993).
33. Henriksen, A., Schuller, D. J., Gajhede, M. Structural interactions between horseradish peroxidase C and the substrate benzhydroxamic acid determined by X-ray crystallography. *Biochemistry* 37, 8054-8060 (1998).
34. Widom, J. R., Dhakal, S., Heinicke, L. A. & Walter, N. G. Single-molecule tools for enzymology, structural biology, systems biology and nanotechnology: an update. *Arch. Toxicol.* 88, 1965-1985 (2014).
35. Veitch, N. C. Horseradish peroxidase: a modern view of a classic enzyme. *Phytochemistry* 65, 249-259 (2004).
36. Chapman, A. D., Cortes, A., Dafforn, T. R., Clarke, A. R. & Brady, R. L. Structural basis of substrate specificity in malate dehydrogenases: crystal structure of a ternary complex of porcine cytoplasmic malate dehydrogenase, alpha-ketomalonate and tetrahydoNAD. *J Mol Biol.* 285, 703-712 (1999).
37. Rowland, P., Basak, A. K., Gover, S., Levy, H. R. & Adams, M. J. The three-dimensional structure of glucose 6-phosphate dehydrogenase from *Leuconostoc mesenteroides* refined at 2.0 A resolution. *Structure* 15, 1073-1087 (1994).

38. Lovell, S. L. & Winzor, D. J. Effects of phosphate on the dissociation and enzymic stability of rabbit muscle lactate dehydrogenase. *Biochemistry* 13, 3527-3531 (1974).

39. Hecht, H. J., Kalisz, H. M., Hendle, J., Schmid, R. D. & Schomburg D. Crystal structure of glucose oxidase from *Aspergillus niger* refined at 2.3 A resolution. J Mol Biol. 229, 153-172 (1993).

40. Jacobson, R. H., Zhang, X. J., DuBose, R. F. & Matthews, B. W. Three-dimensional structure of beta-galactosidase from *E. coli. Nature* 369, 761-766 (1994).

41. Erkelenz, M., Kuo, C. H. & Niemeyer, C. M. DNA-Mediated Assembly of Cytochrome P450 BM3 Sub-domains, *J. Am. Chem. Soc.* 133, 16111-16118 (2011).

42. Rudiuk, S., Venancio-Marques, A. & Baigl, D. Enhancement and modulation of enzymatic activity through higher-order structural changes of giant DNA-protein multibranch conjugates. *Angew. Chem. Int. Ed.* 51, 12694-12698 (2012).

43. English, B. P., et al. Ever-fluctuating single enzyme molecules: Michaelis-Menten equation revisited. *Nat. Chem. Bio.* 2, 87-94 (2006).

44. Liu, B., Baskin, R. J. & Kowalczykowski, S. C. NA unwinding heterogeneity by RecBCD results from static molecules able to equilibrate. *Nature* 500, 482-485 (2013).

45. Ramanathan, A., Savol, A., Burger, V., Chennubhotla, C. S. & Agarwal, P. K. Protein Conformational Populations and Functionally Relevant Substates. *Acc. Chem. Res.* 47, 149-156 (2014).

46. Hammes, G. G., Benkovic, S. J. & Hammes-Schiffer, S. Flexibility, Diversity, and Cooperativity: Pillars of Enzyme Catalysis. *Biochemistry* 50, 10422-10430 (2011).

47. Ramanathan, A. & Agarwal P. K. Evolutionarily Conserved Linkage between Enzyme Fold, Flexibility, and Catalysis. *PLoS Biol.* 9, 1-17 (2011).

48. Timm, C. & Niemeyer, C. M. Assembly and Purification of Enzyme-Functionalized DNA Origami Structures. *Angew. Chem. Int. Ed.* 54, 6745-6750 (2015).

49. Lin, J. & Wheeldon, I. Kinetic Enhancements in DNA—Enzyme Nanostructures Mimic the Sabatier Principle *ACS Catal.* 3, 560-564 (2013).

50. Gao, Y., Roberts, C. C., Zhu, J., Lin, J., Chang, C. A. & Wheeldon, I. Tuning Enzyme Kinetics through Designed Intermolecular Interactions Far from the Active Site. *ACS Catal.* 5, 2149-2153 (2015).

51. Zhao, H. Effects of ions and other compatible solutes on enzyme activity, and its implication for biocatalysis using ionic liquids. *J. Mol. Catal. B-Enzym.* 37, 16-25 (2005).

52. Moelberta, S., Normandb, B. & Rios, P. D. L. Kos-motropes and chaotropes: modelling preferential exclusion, binding and aggregate stability. *Biophys. Chem.* 112, 45-57 (2004).

53. N Leberman, R. & Soper, A. K. Effect of high salt concentrations on water structure. *Nature* 378, 364-366 (1995).

54. N Jana, B., Pal, S., Maiti. P. K., Lin. S., Hynes, J. T. & Bagchi, B. Entropy of Water in the Hydration Layer of Major and Minor Grooves of DNA. *J. Phys. Chem. B* 110, 19611-19618 (2006).

55. N Chuprina, V. P., Heinemann, U., Nurislamov, A. A., Zielenkiewicz, P., Dickerson, R. E. & Saenger W. Molecular dynamics simulation ofthe hydration shell ofa B-DNA decamer reveals two main types of minor-groove hydration depending on groove width. *Proc. Nati. Acad. Sci. USA* 88, 593-597 (1991).

56. Zhao, H., Olubajo, O., Song, Z., Sims, A. L., Person, T. E., Lawal, R. A. & Holley, L. A. Effect of kosmo-tropicity of ionic liquids on the enzyme stability in aqueous solutions. *Bioorg. Chem.* 34, 15-25 (2006).

57. Timasheff, S. N. Protein—solvent preferential inter-actions, protein hydration, and the modulation of bio-chemical reactions by solvent components. *Proc. Natl. Acad. Sci.* 99, 9721-9726 (2002).

58. N Levy, Y. & Onuchic, J. N. Water and proteins: A love—hate relationship. *Proc. Natl. Acad. Sci. USA* 101, 3325-3326 (2004)

59. N Grey, M. J. et al. Polyphosphate is a Primordial Chaperone. *Mol. Cell.* 53, 689-699 (2014).

60. Marcus, Y. Effects of ions on the structure of water: structure making and breaking. *Chem. Rev.* 109, 1346-1370 (2009).

61. Mei, Q., Wei, X., Su, F., Liu, Y., Yongbull, C., Johnson, R., Lindsay, S., Yan, H., Meidrum, D. Stability of DNA origami nanoarrays in cell lysate. *Nano Lett.* 11, 1477-1482 (2011).

62. Jiang, Q., Song, C., Nangreave, J., Liu, X., Lin, L., Qiu, Z., Wang, Z., Zou, G., Liang, X., Yan, H., Ding, B. DNA origami as a carrier for circumvention of drug resistance. *J. Am. Chem. Soc.* 134, 13396-13403 (2012).

63. Castello, A. et al. Insights into RNA Biology from an Atlas of Mammalian mRNA-Binding Proteins. *Cell* 149, 1393-1406 (2012)

64. Wong, C. M., Wong, K. H. and Chen, X. D. Glucose oxidase: natural occurrence, function, properties and industrial application. *Appl. Microbiol. Biotechnol.* 78, 927-38 (2008).

65. Guo, S., Cao, R., Lu, A., Zhou, Q., Lu, T., Ding, X., Li, C. and Huang, X. One of the possible mechanisms for the inhibition effect of Tb(III) on peroxidase activity in horseradish (Armoracia rusticana) treated with Tb(III). *J. Biol. Inorg. Chem.* 13, 587-597 (2008).

66. Sung, J. Y. & Lee, Y. N. Isoforms of glucose 6-phosphate dehydrogenase in Deinococcus radiophilus. *J. Microbiol.* 45, 318-325 (2007).

67. Horikiri, S., Aizawa, Y., Kai, T., Amachi, S., Shinoyama, H. and Fujii, T. Electron acquisition system constructed from an NAD-independent D-lactate dehydrogenase and cytochrome c2 in Rhodopseudomonas palustris No. 7. *Biosci. Biotechnol. Biochem.* 68, 516-522 (2004).

68. Eanes, R. Z., and Kun, E. Separation and characterization of aconitate hydratase isoenzymes from pig tissues. *Biochim. Biophys. Acta* 227, 204-210 (1971).

69. Fu, J., Liu, M., Liu, Y., Woodbury, N. W. & Yan, H. Interenzyme Substrate Diffusion for an Enzyme Cascade Organized on Spatially Addressable DNA Nano-structures. J. Am. Chem. Soc. 134, 5516-5519 (2012).

70. Liu, M., Fu, J., Hejesen, C., Yang, Y., Woodbury, N. W., Gothelf, K., Liu, Y. & Yan, H. A DNA Tweezer-Actuated Enzyme Nanoreactor. Nature Commun. 4, 1-5 (2013).

71. Abelson, J. et al. Conformational dynamics of single pre-mRNA molecules during in vitro splicing Nat. Struct. Mal. Biol. 17, 504-512 (2010).

72. Michelotti, N. et al. A bird's eye view tracking slow nanometer-scale movements of single molecular nano-assemblies. Methods Enzymol. 475, 121-148 (2010).

73. Blanco, M. & Walter, N. G. Analysis of Complex Single-Molecule FRET Time Trajectories. Method. Enzymol. 472, 153-178 (2010).

74. Gourevitch, B. & Eggermont, J. J. A nonparametric approach for detection of bursts in spike trains. Journal of Neuroscience Methods 160, 349-358 (2007).

75. Rinaldi, A. J., Lund, P. E., Blanco, M. R. & Walter, N. G. The Shine-Dalgamo sequence of riboswitch-regulated single mRNAs shows ligand-dependent accessibility bursts. Nat. Commun., 8976 (2015).

We claim:

1. A method of increasing the activity of an enzyme or antibody, the method comprising:

trapping an enzyme or antibody in a first open half cage comprising M13 viral DNA;

presenting a second open half cage which does not comprise an enzyme or antibody;

assembling the first and second open half cages into a closed nanocage having an inner cavity and nanopores;

wherein the inner cavity comprises the enzyme or antibody as a trapped enzyme or antibody respectively, and wherein the enzyme or antibody is less than 465 kDa in size.

2. The method of claim 1, wherein the activity is selected from increased catalytic activity, increased potency, or increased resistance to proteolytic digestion.

3. The method of claim 2, wherein the activity is increased resistance to proteolytic digestion by trypsin.

4. The method of claim 2, wherein the increased resistance to proteolytic digestion is more than 95% of the initial activity of the enzyme or antibody after incubation with trypsin for 24 h relative to that of respective free enzyme or antibody.

5. The method of claim 2, wherein the increased catalytic activity is more than six-fold higher for the trapped enzyme or antibody relative to that of the respective free enzyme or antibody.

6. The method of claim 1, wherein the trapped enzyme or antibody has a mean average cross-sectional size which is less than half the longest width of the inner cavity.

7. The method of claim 1, wherein the closed nanocage comprises a plurality of structural members, each of which independently comprises all or a portion of M13 viral DNA, in a three-dimensional lattice, wherein internal surfaces of the plurality of structural members form an inner cavity which is defined by at least three pairs of opposite walls, wherein a first structural member of the plurality of structural members is linked to a second structural member of the plurality of structural members by short bridge DNA strands, wherein the at least three pairs of opposite walls comprises a first pair, a second pair, and a third pair of opposite walls, and wherein each of the first pair of opposite walls comprises a thickness which is different from the other pairs of opposite walls.

8. The method of claim 1, wherein the nanocage comprises:

a plurality of structural members comprising a single-stranded circular DNA sequence selected from p7308, p7560, p7704, p8064, p8634, and pEGFP, wherein internal surfaces of the plurality of structural members form an inner cavity which is defined by at least three pairs of opposite walls, wherein architectural arrangement of the structural members in the three dimensional body forms an arrangement selected from the group consisting of a honeycomb lattice, a single-walled square lattice, and a double-walled square lattice, and wherein the at least three pairs of opposite walls comprises a first pair, a second pair, and a third pair of opposite walls, and wherein each of the first pair of opposite walls comprises a thickness which is different from the other pairs of opposite walls. 5

9. The method of claim 7, wherein the dimensions of the three dimensional body is less than 100 nm×100 nm×100 nm.

10. The method of claim 7, wherein the dimensions of the three dimensional body is less than 75 nm×50 nm×50 nm in size. 10

11. The method of claim 7, wherein the dimensions of the inner cavity of the three dimensional body is less than 50 nm×50 nm×50 nm. 15

12. The method of claim 7, wherein the three dimensional body further comprises at least one nanopore.

13. The method of claim 7, wherein the at least one nanopore has a diameter of about 1 nm to about 5 nm.

14. The method of claim 7, wherein the three dimensional 20 body comprises between 0.10 to 0.30 DNA helices per nm$^2$.

15. The method of claim 7, wherein the three dimensional body comprises between 0.11 to 0.17 DNA helices per nm$^2$.

\* \* \* \* \*

SEQUENCE LISTING

```
Sequence total quantity: 1395
SEQ ID NO: 1              moltype = DNA  length = 23
FEATURE                   Location/Qualifiers
source                    1..23
                          mol_type = other DNA
                          organism = synthetic construct
SEQUENCE: 1
ggtggagagg cggtttgcgt ttt                                          23

SEQ ID NO: 2              moltype = DNA  length = 23
FEATURE                   Location/Qualifiers
source                    1..23
                          mol_type = other DNA
                          organism = synthetic construct
SEQUENCE: 2
cgagttgggt aacgccaggt ttt                                          23

SEQ ID NO: 3              moltype = DNA  length = 16
FEATURE                   Location/Qualifiers
source                    1..16
                          mol_type = other DNA
                          organism = synthetic construct
SEQUENCE: 3
tttttcgcca ttcagg                                                  16

SEQ ID NO: 4              moltype = DNA  length = 26
FEATURE                   Location/Qualifiers
source                    1..26
                          mol_type = other DNA
                          organism = synthetic construct
SEQUENCE: 4
ttttgccagc tttcatcaac attcgt                                       26

SEQ ID NO: 5              moltype = DNA  length = 34
FEATURE                   Location/Qualifiers
source                    1..34
                          mol_type = other DNA
                          organism = synthetic construct
SEQUENCE: 5
tttttggagc aaacaagaga atcggaagat tagc                              34

SEQ ID NO: 6              moltype = DNA  length = 34
FEATURE                   Location/Qualifiers
source                    1..34
                          mol_type = other DNA
                          organism = synthetic construct
SEQUENCE: 6
ttttgggaga agcctttatt tcaaaaaggg acag                              34

SEQ ID NO: 7              moltype = DNA  length = 46
FEATURE                   Location/Qualifiers
source                    1..46
                          mol_type = other DNA
                          organism = synthetic construct
SEQUENCE: 7
ggtggcatca attcatgggc gcgacctgtt tgtataagca aatttt                 46

SEQ ID NO: 8              moltype = DNA  length = 26
FEATURE                   Location/Qualifiers
source                    1..26
                          mol_type = other DNA
                          organism = synthetic construct
SEQUENCE: 8
atataaagta gtagatgggc gctttt                                       26

SEQ ID NO: 9              moltype = DNA  length = 26
FEATURE                   Location/Qualifiers
source                    1..26
```

-continued

```
                          mol_type = other DNA
                          organism = synthetic construct
SEQUENCE: 9
aatcatacta atagtagtag catttt                                            26

SEQ ID NO: 10             moltype = DNA   length = 31
FEATURE                   Location/Qualifiers
source                    1..31
                          mol_type = other DNA
                          organism = synthetic construct
SEQUENCE: 10
gctgtcatag caccgagctc gaattcgttt t                                      31

SEQ ID NO: 11             moltype = DNA   length = 32
FEATURE                   Location/Qualifiers
source                    1..32
                          mol_type = other DNA
                          organism = synthetic construct
SEQUENCE: 11
tttttgagga ctaaagactt tcaacactaa gg                                     32

SEQ ID NO: 12             moltype = DNA   length = 37
FEATURE                   Location/Qualifiers
source                    1..37
                          mol_type = other DNA
                          organism = synthetic construct
SEQUENCE: 12
cggttttgct ttgcgctagt gagctaactc acatttt                                37

SEQ ID NO: 13             moltype = DNA   length = 34
FEATURE                   Location/Qualifiers
source                    1..34
                          mol_type = other DNA
                          organism = synthetic construct
SEQUENCE: 13
ttttgaagga ttaggattag cggtagcaac gcga                                   34

SEQ ID NO: 14             moltype = DNA   length = 27
FEATURE                   Location/Qualifiers
source                    1..27
                          mol_type = other DNA
                          organism = synthetic construct
SEQUENCE: 14
ttttaaaagg gcgacattca accaggc                                           27

SEQ ID NO: 15             moltype = DNA   length = 37
FEATURE                   Location/Qualifiers
source                    1..37
                          mol_type = other DNA
                          organism = synthetic construct
SEQUENCE: 15
tgactaatat gtttgatgtt tgccccagca ggctttt                                37

SEQ ID NO: 16             moltype = DNA   length = 27
FEATURE                   Location/Qualifiers
source                    1..27
                          mol_type = other DNA
                          organism = synthetic construct
SEQUENCE: 16
ttttaggctt atccggtatt ctagttt                                           27

SEQ ID NO: 17             moltype = DNA   length = 48
FEATURE                   Location/Qualifiers
source                    1..48
                          mol_type = other DNA
                          organism = synthetic construct
SEQUENCE: 17
ctcaacaagt atcacataat ttattaaagt tccagtttgg aacatttt                    48

SEQ ID NO: 18             moltype = DNA   length = 24
FEATURE                   Location/Qualifiers
source                    1..24
                          mol_type = other DNA
                          organism = synthetic construct
SEQUENCE: 18
ttttagagtc cacactagaa aatt                                              24

SEQ ID NO: 19             moltype = DNA   length = 25
FEATURE                   Location/Qualifiers
```

-continued

```
source                  1..25
                        mol_type = other DNA
                        organism = synthetic construct
SEQUENCE: 19
ttttgaaaat cctcagagag atttt                                              25

SEQ ID NO: 20           moltype = DNA   length = 25
FEATURE                 Location/Qualifiers
source                  1..25
                        mol_type = other DNA
                        organism = synthetic construct
SEQUENCE: 20
ttttattggg cggagccacc atttt                                              25

SEQ ID NO: 21           moltype = DNA   length = 22
FEATURE                 Location/Qualifiers
source                  1..22
                        mol_type = other DNA
                        organism = synthetic construct
SEQUENCE: 21
ttttaattgc gaaacaactt tt                                                 22

SEQ ID NO: 22           moltype = DNA   length = 25
FEATURE                 Location/Qualifiers
source                  1..25
                        mol_type = other DNA
                        organism = synthetic construct
SEQUENCE: 22
ttttaatcat ggctcattca gtttt                                              25

SEQ ID NO: 23           moltype = DNA   length = 22
FEATURE                 Location/Qualifiers
source                  1..22
                        mol_type = other DNA
                        organism = synthetic construct
SEQUENCE: 23
ttttgttttc ccagtcattt tt                                                 22

SEQ ID NO: 24           moltype = DNA   length = 31
FEATURE                 Location/Qualifiers
source                  1..31
                        mol_type = other DNA
                        organism = synthetic construct
SEQUENCE: 24
ttttatcgta accgtggcaa agcgccattt t                                       31

SEQ ID NO: 25           moltype = DNA   length = 31
FEATURE                 Location/Qualifiers
source                  1..31
                        mol_type = other DNA
                        organism = synthetic construct
SEQUENCE: 25
ttttatttaa attgtggcct tcctgtattt t                                       31

SEQ ID NO: 26           moltype = DNA   length = 32
FEATURE                 Location/Qualifiers
source                  1..32
                        mol_type = other DNA
                        organism = synthetic construct
SEQUENCE: 26
ttttgagaca gtcaaatgcc tgagagtctt tt                                      32

SEQ ID NO: 27           moltype = DNA   length = 39
FEATURE                 Location/Qualifiers
source                  1..39
                        mol_type = other DNA
                        organism = synthetic construct
SEQUENCE: 27
ttttagcctc agagcataaa gcttaatact tttgctttt                               39

SEQ ID NO: 28           moltype = DNA   length = 30
FEATURE                 Location/Qualifiers
source                  1..30
                        mol_type = other DNA
                        organism = synthetic construct
SEQUENCE: 28
ttttaacatc caatattaag caataatttt                                         30

SEQ ID NO: 29           moltype = DNA   length = 29
```

-continued

```
FEATURE            Location/Qualifiers
source             1..29
                   mol_type = other DNA
                   organism = synthetic construct
SEQUENCE: 29
ttttaaatgg tcaataagct gaaaatttt                                    29

SEQ ID NO: 30      moltype = DNA   length = 29
FEATURE            Location/Qualifiers
source             1..29
                   mol_type = other DNA
                   organism = synthetic construct
SEQUENCE: 30
ttttattccc aatgatacat ttcgctttt                                    29

SEQ ID NO: 31      moltype = DNA   length = 28
FEATURE            Location/Qualifiers
source             1..28
                   mol_type = other DNA
                   organism = synthetic construct
SEQUENCE: 31
ttttaaatat gcaactaaca gttgtttt                                     28

SEQ ID NO: 32      moltype = DNA   length = 26
FEATURE            Location/Qualifiers
source             1..26
                   mol_type = other DNA
                   organism = synthetic construct
SEQUENCE: 32
ttttgcggat ggcctcaaca tgtttt                                       26

SEQ ID NO: 33      moltype = DNA   length = 53
FEATURE            Location/Qualifiers
source             1..53
                   mol_type = other DNA
                   organism = synthetic construct
SEQUENCE: 33
ttttgtttac cagacgacga taatagcaaa aaatcattga gaaaggccgt ttt         53

SEQ ID NO: 34      moltype = DNA   length = 32
FEATURE            Location/Qualifiers
source             1..32
                   mol_type = other DNA
                   organism = synthetic construct
SEQUENCE: 34
ttttacataa cgccaaatca taaccctctt tt                                32

SEQ ID NO: 35      moltype = DNA   length = 27
FEATURE            Location/Qualifiers
source             1..27
                   mol_type = other DNA
                   organism = synthetic construct
SEQUENCE: 35
ttttagaaag atactaatgc agatttt                                      27

SEQ ID NO: 36      moltype = DNA   length = 29
FEATURE            Location/Qualifiers
source             1..29
                   mol_type = other DNA
                   organism = synthetic construct
SEQUENCE: 36
ttttggaaga aaaatctatt acaggtttt                                    29

SEQ ID NO: 37      moltype = DNA   length = 29
FEATURE            Location/Qualifiers
source             1..29
                   mol_type = other DNA
                   organism = synthetic construct
SEQUENCE: 37
ttttgaatta cctgtcagga cgttgtttt                                    29

SEQ ID NO: 38      moltype = DNA   length = 26
FEATURE            Location/Qualifiers
source             1..26
                   mol_type = other DNA
                   organism = synthetic construct
SEQUENCE: 38
ttttgaataa ggtaaattgg gctttt                                       26
```

-continued

```
SEQ ID NO: 39            moltype = DNA   length = 31
FEATURE                  Location/Qualifiers
source                   1..31
                         mol_type = other DNA
                         organism = synthetic construct
SEQUENCE: 39
ttttcaccct cagcaggcta cagaggcttt t                                31

SEQ ID NO: 40            moltype = DNA   length = 28
FEATURE                  Location/Qualifiers
source                   1..28
                         mol_type = other DNA
                         organism = synthetic construct
SEQUENCE: 40
ttttatattc ggtttgcggg atcgtttt                                    28

SEQ ID NO: 41            moltype = DNA   length = 29
FEATURE                  Location/Qualifiers
source                   1..29
                         mol_type = other DNA
                         organism = synthetic construct
SEQUENCE: 41
ttttgatacc gatagtcata accgatttt                                   29

SEQ ID NO: 42            moltype = DNA   length = 25
FEATURE                  Location/Qualifiers
source                   1..25
                         mol_type = other DNA
                         organism = synthetic construct
SEQUENCE: 42
ttttaattgt acttaaacag ctttt                                       25

SEQ ID NO: 43            moltype = DNA   length = 27
FEATURE                  Location/Qualifiers
source                   1..27
                         mol_type = other DNA
                         organism = synthetic construct
SEQUENCE: 43
ttttaataat tttttaagga gcctttt                                     27

SEQ ID NO: 44            moltype = DNA   length = 26
FEATURE                  Location/Qualifiers
source                   1..26
                         mol_type = other DNA
                         organism = synthetic construct
SEQUENCE: 44
ttttcaacag ttaggaattg cgaatt                                      26

SEQ ID NO: 45            moltype = DNA   length = 30
FEATURE                  Location/Qualifiers
source                   1..30
                         mol_type = other DNA
                         organism = synthetic construct
SEQUENCE: 45
ttttcggaac ctatgactcc tcaagatttt                                  30

SEQ ID NO: 46            moltype = DNA   length = 28
FEATURE                  Location/Qualifiers
source                   1..28
                         mol_type = other DNA
                         organism = synthetic construct
SEQUENCE: 46
ttttgtcagt gccccccctg cctatttt                                    28

SEQ ID NO: 47            moltype = DNA   length = 28
FEATURE                  Location/Qualifiers
source                   1..28
                         mol_type = other DNA
                         organism = synthetic construct
SEQUENCE: 47
ttttcataca tggcttttaa cgggtttt                                    28

SEQ ID NO: 48            moltype = DNA   length = 29
FEATURE                  Location/Qualifiers
source                   1..29
                         mol_type = other DNA
                         organism = synthetic construct
SEQUENCE: 48
ttttcattaa agcttccagt aagcgtttt                                   29
```

-continued

```
SEQ ID NO: 49            moltype = DNA  length = 28
FEATURE                  Location/Qualifiers
source                   1..28
                         mol_type = other DNA
                         organism = synthetic construct
SEQUENCE: 49
ttttaggttg aggcagataa atcctttt                                        28

SEQ ID NO: 50            moltype = DNA  length = 29
FEATURE                  Location/Qualifiers
source                   1..29
                         mol_type = other DNA
                         organism = synthetic construct
SEQUENCE: 50
ttttccctca gagagcattg acaggtttt                                       29

SEQ ID NO: 51            moltype = DNA  length = 30
FEATURE                  Location/Qualifiers
source                   1..30
                         mol_type = other DNA
                         organism = synthetic construct
SEQUENCE: 51
ttaagtttat tttgagcgcc aaagactttt                                      30

SEQ ID NO: 52            moltype = DNA  length = 28
FEATURE                  Location/Qualifiers
source                   1..28
                         mol_type = other DNA
                         organism = synthetic construct
SEQUENCE: 52
ttttatacat acaacaccac ggaatttt                                        28

SEQ ID NO: 53            moltype = DNA  length = 28
FEATURE                  Location/Qualifiers
source                   1..28
                         mol_type = other DNA
                         organism = synthetic construct
SEQUENCE: 53
ttttgaactg gcatgaacgt agaaattt                                        28

SEQ ID NO: 54            moltype = DNA  length = 29
FEATURE                  Location/Qualifiers
source                   1..29
                         mol_type = other DNA
                         organism = synthetic construct
SEQUENCE: 54
ttttcaaagt tacgaatacc caaaatttt                                       29

SEQ ID NO: 55            moltype = DNA  length = 27
FEATURE                  Location/Qualifiers
source                   1..27
                         mol_type = other DNA
                         organism = synthetic construct
SEQUENCE: 55
ttttgcaata gctatcatag ccgaatt                                         27

SEQ ID NO: 56            moltype = DNA  length = 29
FEATURE                  Location/Qualifiers
source                   1..29
                         mol_type = other DNA
                         organism = synthetic construct
SEQUENCE: 56
ttttaaccca caaacaatg aaatatttt                                        29

SEQ ID NO: 57            moltype = DNA  length = 32
FEATURE                  Location/Qualifiers
source                   1..32
                         mol_type = other DNA
                         organism = synthetic construct
SEQUENCE: 57
ttttcgagaa caagcaatca gatatagatt tt                                   32

SEQ ID NO: 58            moltype = DNA  length = 29
FEATURE                  Location/Qualifiers
source                   1..29
                         mol_type = other DNA
                         organism = synthetic construct
SEQUENCE: 58
```

-continued

```
ttttagaaac caataccgca ctcattttt                                        29

SEQ ID NO: 59            moltype = DNA   length = 29
FEATURE                  Location/Qualifiers
source                   1..29
                         mol_type = other DNA
                         organism = synthetic construct
SEQUENCE: 59
ttttacgcgc ctgtttcgag catgtttt                                        29

SEQ ID NO: 60            moltype = DNA   length = 29
FEATURE                  Location/Qualifiers
source                   1..29
                         mol_type = other DNA
                         organism = synthetic construct
SEQUENCE: 60
ttttataaag tacagctaat gcagatttt                                        29

SEQ ID NO: 61            moltype = DNA   length = 29
FEATURE                  Location/Qualifiers
source                   1..29
                         mol_type = other DNA
                         organism = synthetic construct
SEQUENCE: 61
tttttgagaa tcgccataag agaattttt                                       29

SEQ ID NO: 62            moltype = DNA   length = 29
FEATURE                  Location/Qualifiers
source                   1..29
                         mol_type = other DNA
                         organism = synthetic construct
SEQUENCE: 62
ttttagcctg tttgtagggc ttaattttt                                       29

SEQ ID NO: 63            moltype = DNA   length = 49
FEATURE                  Location/Qualifiers
source                   1..49
                         mol_type = other DNA
                         organism = synthetic construct
SEQUENCE: 63
gactccaata aacaccaggg aagcgcataa gtcagcggca aatgcagca               49

SEQ ID NO: 64            moltype = DNA   length = 28
FEATURE                  Location/Qualifiers
source                   1..28
                         mol_type = other DNA
                         organism = synthetic construct
SEQUENCE: 64
gaaccatcgt aaagcactaa acttgacg                                        28

SEQ ID NO: 65            moltype = DNA   length = 28
FEATURE                  Location/Qualifiers
source                   1..28
                         mol_type = other DNA
                         organism = synthetic construct
SEQUENCE: 65
tagggttccg aaatagggta aacaaatc                                        28

SEQ ID NO: 66            moltype = DNA   length = 44
FEATURE                  Location/Qualifiers
source                   1..44
                         mol_type = other DNA
                         organism = synthetic construct
SEQUENCE: 66
ggtcaaaaga atagagggcg aaaaaccgta aataagagaa ttaa                     44

SEQ ID NO: 67            moltype = DNA   length = 23
FEATURE                  Location/Qualifiers
source                   1..23
                         mol_type = other DNA
                         organism = synthetic construct
SEQUENCE: 67
ataaaaggaa cacccaccac cgg                                            23

SEQ ID NO: 68            moltype = DNA   length = 42
FEATURE                  Location/Qualifiers
source                   1..42
                         mol_type = other DNA
                         organism = synthetic construct
```

-continued

```
SEQUENCE: 68
gggaaagggg cgctggcaag tcgctgcgcg taaccttgac ga                            42

SEQ ID NO: 69              moltype = DNA   length = 28
FEATURE                    Location/Qualifiers
source                     1..28
                           mol_type = other DNA
                           organism = synthetic construct
SEQUENCE: 69
agcggtcctt ttcaccctca gatttagc                                           28

SEQ ID NO: 70              moltype = DNA   length = 35
FEATURE                    Location/Qualifiers
source                     1..35
                           mol_type = other DNA
                           organism = synthetic construct
SEQUENCE: 70
gtagctcttt agagtcggaa catggcccac tacgt                                   35

SEQ ID NO: 71              moltype = DNA   length = 28
FEATURE                    Location/Qualifiers
source                     1..28
                           mol_type = other DNA
                           organism = synthetic construct
SEQUENCE: 71
cggccaacgc tttcttttct gaatggct                                           28

SEQ ID NO: 72              moltype = DNA   length = 28
FEATURE                    Location/Qualifiers
source                     1..28
                           mol_type = other DNA
                           organism = synthetic construct
SEQUENCE: 72
ctgcattgac gggcagagag tatccctt                                           28

SEQ ID NO: 73              moltype = DNA   length = 42
FEATURE                    Location/Qualifiers
source                     1..42
                           mol_type = other DNA
                           organism = synthetic construct
SEQUENCE: 73
gcacgtaagc taaacaggag gttttataat cagtggtaaa ag                           42

SEQ ID NO: 74              moltype = DNA   length = 45
FEATURE                    Location/Qualifiers
source                     1..45
                           mol_type = other DNA
                           organism = synthetic construct
SEQUENCE: 74
gcccgcgcgg ggttttttcac gctgggtggt tgagtgttga acgtg                       45

SEQ ID NO: 75              moltype = DNA   length = 23
FEATURE                    Location/Qualifiers
source                     1..23
                           mol_type = other DNA
                           organism = synthetic construct
SEQUENCE: 75
gtcgtttttc cagagtaatc ttg                                                23

SEQ ID NO: 76              moltype = DNA   length = 28
FEATURE                    Location/Qualifiers
source                     1..28
                           mol_type = other DNA
                           organism = synthetic construct
SEQUENCE: 76
tggggtgtgt gtgacaaatc actcgaac                                           28

SEQ ID NO: 77              moltype = DNA   length = 28
FEATURE                    Location/Qualifiers
source                     1..28
                           mol_type = other DNA
                           organism = synthetic construct
SEQUENCE: 77
aggccatgag cgggtaacgt gctggtca                                           28

SEQ ID NO: 78              moltype = DNA   length = 42
FEATURE                    Location/Qualifiers
source                     1..42
                           mol_type = other DNA
```

-continued

```
                            organism = synthetic construct
SEQUENCE: 78
agtctgtcac ttgcctgagt aatccagaac aatatacgct ca                              42

SEQ ID NO: 79              moltype = DNA   length = 35
FEATURE                    Location/Qualifiers
source                     1..35
                           mol_type = other DNA
                           organism = synthetic construct
SEQUENCE: 79
cacgaagtgt ccgattaggt tgctaccaca cggcg                                      35

SEQ ID NO: 80              moltype = DNA   length = 49
FEATURE                    Location/Qualifiers
source                     1..49
                           mol_type = other DNA
                           organism = synthetic construct
SEQUENCE: 80
gaggatcaaa cgacaattgc tcagtttgta ggtcaaaatg tgaataatt                       49

SEQ ID NO: 81              moltype = DNA   length = 28
FEATURE                    Location/Qualifiers
source                     1..28
                           mol_type = other DNA
                           organism = synthetic construct
SEQUENCE: 81
gcaggtcatc cgcttaaagt ggaaacct                                              28

SEQ ID NO: 82              moltype = DNA   length = 42
FEATURE                    Location/Qualifiers
source                     1..42
                           mol_type = other DNA
                           organism = synthetic construct
SEQUENCE: 82
ttgcacgtca ggatgtatcg gggcggatcg tcggaaccaa ta                             42

SEQ ID NO: 83              moltype = DNA   length = 46
FEATURE                    Location/Qualifiers
source                     1..46
                           mol_type = other DNA
                           organism = synthetic construct
SEQUENCE: 83
tgcaaggact gttggtgccg gaaaccagca tctgcccttt tgttaa                         46

SEQ ID NO: 84              moltype = DNA   length = 28
FEATURE                    Location/Qualifiers
source                     1..28
                           mol_type = other DNA
                           organism = synthetic construct
SEQUENCE: 84
gaaatattgg taatgaagaa cacaccga                                              28

SEQ ID NO: 85              moltype = DNA   length = 28
FEATURE                    Location/Qualifiers
source                     1..28
                           mol_type = other DNA
                           organism = synthetic construct
SEQUENCE: 85
atcgtctatt tacacagaga tagcgcac                                             28

SEQ ID NO: 86              moltype = DNA   length = 46
FEATURE                    Location/Qualifiers
source                     1..46
                           mol_type = other DNA
                           organism = synthetic construct
SEQUENCE: 86
ctgcgcacga ttaacgttgt acccgggttg tttcccctaa tgcact                        46

SEQ ID NO: 87              moltype = DNA   length = 21
FEATURE                    Location/Qualifiers
source                     1..21
                           mol_type = other DNA
                           organism = synthetic construct
SEQUENCE: 87
cgatcggaaa gggggccaag c                                                     21

SEQ ID NO: 88              moltype = DNA   length = 32
FEATURE                    Location/Qualifiers
source                     1..32
```

-continued

```
                              mol_type = other DNA
                              organism = synthetic construct
SEQUENCE: 88
attcacccat tttgtaccgc cataacatcc at                                    32

SEQ ID NO: 89          moltype = DNA   length = 18
FEATURE                Location/Qualifiers
source                 1..18
                       mol_type = other DNA
                       organism = synthetic construct
SEQUENCE: 89
cggcaccgac gacataga                                                    18

SEQ ID NO: 90          moltype = DNA   length = 42
FEATURE                Location/Qualifiers
source                 1..42
                       mol_type = other DNA
                       organism = synthetic construct
SEQUENCE: 90
aagataaccc ttctagccct aattaaaaac gctgagagct ca                        42

SEQ ID NO: 91          moltype = DNA   length = 42
FEATURE                Location/Qualifiers
source                 1..42
                       mol_type = other DNA
                       organism = synthetic construct
SEQUENCE: 91
agaatacgtc tttaaccagc aaacaccgcc tgcaaaaatc ta                        42

SEQ ID NO: 92          moltype = DNA   length = 43
FEATURE                Location/Qualifiers
source                 1..43
                       mol_type = other DNA
                       organism = synthetic construct
SEQUENCE: 92
tggtcggtgt catataatag gacagaccag aaaaaatcta aag                       43

SEQ ID NO: 93          moltype = DNA   length = 42
FEATURE                Location/Qualifiers
source                 1..42
                       mol_type = other DNA
                       organism = synthetic construct
SEQUENCE: 93
aaacaggaac aaaccctcag gtccagccct cttcgctgga tt                        42

SEQ ID NO: 94          moltype = DNA   length = 26
FEATURE                Location/Qualifiers
source                 1..26
                       mol_type = other DNA
                       organism = synthetic construct
SEQUENCE: 94
aacaacctga ccgtgacttc aaatat                                          26

SEQ ID NO: 95          moltype = DNA   length = 42
FEATURE                Location/Qualifiers
source                 1..42
                       mol_type = other DNA
                       organism = synthetic construct
SEQUENCE: 95
acgaaccatg cgcgaactga tgacctgatg gccaattggc ag                        42

SEQ ID NO: 96          moltype = DNA   length = 39
FEATURE                Location/Qualifiers
source                 1..39
                       mol_type = other DNA
                       organism = synthetic construct
SEQUENCE: 96
cgcgtctaaa cgttagtttc aacgagtaaa ctttgtttt                            39

SEQ ID NO: 97          moltype = DNA   length = 42
FEATURE                Location/Qualifiers
source                 1..42
                       mol_type = other DNA
                       organism = synthetic construct
SEQUENCE: 97
aatcagccag cagcaatcaa caattgagga tttagaagga ga                        42

SEQ ID NO: 98          moltype = DNA   length = 42
FEATURE                Location/Qualifiers
```

-continued

```
source                  1..42
                        mol_type = other DNA
                        organism = synthetic construct
SEQUENCE: 98
aagcatctca atatatatct ttcaatagat aatacacaat tc                    42

SEQ ID NO: 99           moltype = DNA   length = 42
FEATURE                 Location/Qualifiers
source                  1..42
                        mol_type = other DNA
                        organism = synthetic construct
SEQUENCE: 99
agttgtgtac cccgtttgtt attttttatt ctccgtgtcg cc                    42

SEQ ID NO: 100          moltype = DNA   length = 26
FEATURE                 Location/Qualifiers
source                  1..26
                        mol_type = other DNA
                        organism = synthetic construct
SEQUENCE: 100
gtaaacatc agaacagaaa acgaga                                       26

SEQ ID NO: 101          moltype = DNA   length = 42
FEATURE                 Location/Qualifiers
source                  1..42
                        mol_type = other DNA
                        organism = synthetic construct
SEQUENCE: 101
atctaaactg gtcagttggc aaaatgaaca gtgccatacc ga                    42

SEQ ID NO: 102          moltype = DNA   length = 39
FEATURE                 Location/Qualifiers
source                  1..39
                        mol_type = other DNA
                        organism = synthetic construct
SEQUENCE: 102
aggtcattca ccattcattt gactgcggta acggattga                        39

SEQ ID NO: 103          moltype = DNA   length = 42
FEATURE                 Location/Qualifiers
source                  1..42
                        mol_type = other DNA
                        organism = synthetic construct
SEQUENCE: 103
gagagatacc gttctagctg atgcctgaga acccttggaa gg                    42

SEQ ID NO: 104          moltype = DNA   length = 21
FEATURE                 Location/Qualifiers
source                  1..21
                        mol_type = other DNA
                        organism = synthetic construct
SEQUENCE: 104
atgccgtatt agacatcatt t                                           21

SEQ ID NO: 105          moltype = DNA   length = 49
FEATURE                 Location/Qualifiers
source                  1..49
                        mol_type = other DNA
                        organism = synthetic construct
SEQUENCE: 105
gacaactttt aaaaaattat ccatcaatat aatcctgatt gtaccagaa            49

SEQ ID NO: 106          moltype = DNA   length = 42
FEATURE                 Location/Qualifiers
source                  1..42
                        mol_type = other DNA
                        organism = synthetic construct
SEQUENCE: 106
tgcggtaaat gcaataaatt agggtagctc aatcataaaa gg                    42

SEQ ID NO: 107          moltype = DNA   length = 42
FEATURE                 Location/Qualifiers
source                  1..42
                        mol_type = other DNA
                        organism = synthetic construct
SEQUENCE: 107
ggagcgggtt tgagtaacat ttttacaaat ttgaggaagg tt                    42

SEQ ID NO: 108          moltype = DNA   length = 39
```

-continued

```
FEATURE                    Location/Qualifiers
source                     1..39
                           mol_type = other DNA
                           organism = synthetic construct
SEQUENCE: 108
gaccctgaaa tcggaaagaa taaaccaagt aagagttca                           39

SEQ ID NO: 109             moltype = DNA   length = 40
FEATURE                    Location/Qualifiers
source                     1..40
                           mol_type = other DNA
                           organism = synthetic construct
SEQUENCE: 109
cctacaagat aaaaattttt agtaatgttt tgccagaggg                          40

SEQ ID NO: 110             moltype = DNA   length = 49
FEATURE                    Location/Qualifiers
source                     1..49
                           mol_type = other DNA
                           organism = synthetic construct
SEQUENCE: 110
gttagaacaa aattgtagat tttcagaggc tttgcttgta ccaacatat               49

SEQ ID NO: 111             moltype = DNA   length = 42
FEATURE                    Location/Qualifiers
source                     1..42
                           mol_type = other DNA
                           organism = synthetic construct
SEQUENCE: 111
tgaataacat atatttaaca aagaaacctt ggattatact tc                      42

SEQ ID NO: 112             moltype = DNA   length = 42
FEATURE                    Location/Qualifiers
source                     1..42
                           mol_type = other DNA
                           organism = synthetic construct
SEQUENCE: 112
gcatagcgtc tacgagggaa taccacagca tagttaaaaa ac                      42

SEQ ID NO: 113             moltype = DNA   length = 35
FEATURE                    Location/Qualifiers
source                     1..35
                           mol_type = other DNA
                           organism = synthetic construct
SEQUENCE: 113
aagaagtgta ggtaatattc actacaaagg taatc                              35

SEQ ID NO: 114             moltype = DNA   length = 24
FEATURE                    Location/Qualifiers
source                     1..24
                           mol_type = other DNA
                           organism = synthetic construct
SEQUENCE: 114
ggtaatagta aaccaaccta aaac                                          24

SEQ ID NO: 115             moltype = DNA   length = 47
FEATURE                    Location/Qualifiers
source                     1..47
                           mol_type = other DNA
                           organism = synthetic construct
SEQUENCE: 115
tgaatccccc tcaaatgttc aatatgaaga ttcacgcaag acattat                 47

SEQ ID NO: 116             moltype = DNA   length = 42
FEATURE                    Location/Qualifiers
source                     1..42
                           mol_type = other DNA
                           organism = synthetic construct
SEQUENCE: 116
tattagtttg ataaaacggc tcatacaatg attcgaggat ac                      42

SEQ ID NO: 117             moltype = DNA   length = 49
FEATURE                    Location/Qualifiers
source                     1..49
                           mol_type = other DNA
                           organism = synthetic construct
SEQUENCE: 117
caggtttatc tttaaacagt taagcccctg ttaaacatca aaagcgagt              49
```

-continued

```
SEQ ID NO: 118            moltype = DNA   length = 49
FEATURE                   Location/Qualifiers
source                    1..49
                          mol_type = other DNA
                          organism = synthetic construct
SEQUENCE: 118
ccctgacaaa agattaagag aaatatttaa aaacagatga acggctatc              49

SEQ ID NO: 119            moltype = DNA   length = 37
FEATURE                   Location/Qualifiers
source                    1..37
                          mol_type = other DNA
                          organism = synthetic construct
SEQUENCE: 119
aaagcggatt taaattgttg atatagcatg tattttt                          37

SEQ ID NO: 120            moltype = DNA   length = 35
FEATURE                   Location/Qualifiers
source                    1..35
                          mol_type = other DNA
                          organism = synthetic construct
SEQUENCE: 120
cccgaaaaat gggaagggga cgcttctggg aaggg                            35

SEQ ID NO: 121            moltype = DNA   length = 14
FEATURE                   Location/Qualifiers
source                    1..14
                          mol_type = other DNA
                          organism = synthetic construct
SEQUENCE: 121
cgcgttttaa ttga                                                   14

SEQ ID NO: 122            moltype = DNA   length = 42
FEATURE                   Location/Qualifiers
source                    1..42
                          mol_type = other DNA
                          organism = synthetic construct
SEQUENCE: 122
ttgacgtaac tgacgagtat gggaagtgag aaaccgccca ga                    42

SEQ ID NO: 123            moltype = DNA   length = 28
FEATURE                   Location/Qualifiers
source                    1..28
                          mol_type = other DNA
                          organism = synthetic construct
SEQUENCE: 123
cagaccgtac ctttggccag tgatgtgc                                    28

SEQ ID NO: 124            moltype = DNA   length = 42
FEATURE                   Location/Qualifiers
source                    1..42
                          mol_type = other DNA
                          organism = synthetic construct
SEQUENCE: 124
gaggaagcaa ggatattatc aagacgttag ttctaaagcc tc                    42

SEQ ID NO: 125            moltype = DNA   length = 37
FEATURE                   Location/Qualifiers
source                    1..37
                          mol_type = other DNA
                          organism = synthetic construct
SEQUENCE: 125
gggccttgct acgccagctg gcgtgcgggc agctttc                          37

SEQ ID NO: 126            moltype = DNA   length = 26
FEATURE                   Location/Qualifiers
source                    1..26
                          mol_type = other DNA
                          organism = synthetic construct
SEQUENCE: 126
gaaggcaatg tttaataaat attcat                                      26

SEQ ID NO: 127            moltype = DNA   length = 24
FEATURE                   Location/Qualifiers
source                    1..24
                          mol_type = other DNA
                          organism = synthetic construct
SEQUENCE: 127
gaaagaggca aaagagggtt gata                                        24
```

-continued

```
SEQ ID NO: 128          moltype = DNA   length = 42
FEATURE                 Location/Qualifiers
source                  1..42
                        mol_type = other DNA
                        organism = synthetic construct
SEQUENCE: 128
gataaccatc ggcttgctac tggtacagtg ccagtatggg ca                          42

SEQ ID NO: 129          moltype = DNA   length = 42
FEATURE                 Location/Qualifiers
source                  1..42
                        mol_type = other DNA
                        organism = synthetic construct
SEQUENCE: 129
tcatcttaag tacaacggaa caatcgtcga ctggaagtgc aa                          42

SEQ ID NO: 130          moltype = DNA   length = 32
FEATURE                 Location/Qualifiers
source                  1..32
                        mol_type = other DNA
                        organism = synthetic construct
SEQUENCE: 130
taccaagcgc gaaacatgac ccccagcgat ta                                     32

SEQ ID NO: 131          moltype = DNA   length = 26
FEATURE                 Location/Qualifiers
source                  1..26
                        mol_type = other DNA
                        organism = synthetic construct
SEQUENCE: 131
ccatatgcga aaactttaat cattgt                                            26

SEQ ID NO: 132          moltype = DNA   length = 42
FEATURE                 Location/Qualifiers
source                  1..42
                        mol_type = other DNA
                        organism = synthetic construct
SEQUENCE: 132
aagaaaaaag atcagctata ttcagaaagc gagaaaagaa ac                          42

SEQ ID NO: 133          moltype = DNA   length = 42
FEATURE                 Location/Qualifiers
source                  1..42
                        mol_type = other DNA
                        organism = synthetic construct
SEQUENCE: 133
tacttaggaa ccgagtgtac acgagcttca aaggatggga ag                          42

SEQ ID NO: 134          moltype = DNA   length = 18
FEATURE                 Location/Qualifiers
source                  1..18
                        mol_type = other DNA
                        organism = synthetic construct
SEQUENCE: 134
acggtcaatg tcagaagc                                                     18

SEQ ID NO: 135          moltype = DNA   length = 44
FEATURE                 Location/Qualifiers
source                  1..44
                        mol_type = other DNA
                        organism = synthetic construct
SEQUENCE: 135
gagatggttt aatttcaagg ctgtagttag agcataagag gtca                        44

SEQ ID NO: 136          moltype = DNA   length = 28
FEATURE                 Location/Qualifiers
source                  1..28
                        mol_type = other DNA
                        organism = synthetic construct
SEQUENCE: 136
taggcacatg aacgactgac cgacttta                                          28

SEQ ID NO: 137          moltype = DNA   length = 14
FEATURE                 Location/Qualifiers
source                  1..14
                        mol_type = other DNA
                        organism = synthetic construct
SEQUENCE: 137
```

-continued

```
ccacaacgcc tgta                                              14

SEQ ID NO: 138          moltype = DNA   length = 28
FEATURE                 Location/Qualifiers
source                  1..28
                        mol_type = other DNA
                        organism = synthetic construct
SEQUENCE: 138
gaccttccat taccaattgt tgactcta                               28

SEQ ID NO: 139          moltype = DNA   length = 23
FEATURE                 Location/Qualifiers
source                  1..23
                        mol_type = other DNA
                        organism = synthetic construct
SEQUENCE: 139
acccacacat caaactattg cct                                    23

SEQ ID NO: 140          moltype = DNA   length = 49
FEATURE                 Location/Qualifiers
source                  1..49
                        mol_type = other DNA
                        organism = synthetic construct
SEQUENCE: 140
tgaacgaggg ggttttgtat taaggattga gtcatatgag aacgcccaa        49

SEQ ID NO: 141          moltype = DNA   length = 49
FEATURE                 Location/Qualifiers
source                  1..49
                        mol_type = other DNA
                        organism = synthetic construct
SEQUENCE: 141
tccattaata cgtaatgcct aaatagcgag gtttaacgtc aggggtaaa        49

SEQ ID NO: 142          moltype = DNA   length = 35
FEATURE                 Location/Qualifiers
source                  1..35
                        mol_type = other DNA
                        organism = synthetic construct
SEQUENCE: 142
aacggagtac caagttacaa ggcggagagg aagtt                       35

SEQ ID NO: 143          moltype = DNA   length = 49
FEATURE                 Location/Qualifiers
source                  1..49
                        mol_type = other DNA
                        organism = synthetic construct
SEQUENCE: 143
aagacattca tcatcagaca acattacgtt aaccattatc tgcgattcc        49

SEQ ID NO: 144          moltype = DNA   length = 28
FEATURE                 Location/Qualifiers
source                  1..28
                        mol_type = other DNA
                        organism = synthetic construct
SEQUENCE: 144
gccgtcgaga atacactaaa gcaactac                               28

SEQ ID NO: 145          moltype = DNA   length = 24
FEATURE                 Location/Qualifiers
source                  1..24
                        mol_type = other DNA
                        organism = synthetic construct
SEQUENCE: 145
taagtatagc cccaccgtca ccga                                   24

SEQ ID NO: 146          moltype = DNA   length = 26
FEATURE                 Location/Qualifiers
source                  1..26
                        mol_type = other DNA
                        organism = synthetic construct
SEQUENCE: 146
tttagtaccg ccaccctact taacac                                 26

SEQ ID NO: 147          moltype = DNA   length = 42
FEATURE                 Location/Qualifiers
source                  1..42
                        mol_type = other DNA
                        organism = synthetic construct
```

-continued

```
SEQUENCE: 147
ccgccaccgc gacctgctcc tgagatttgt atcatcaaaa at            42

SEQ ID NO: 148          moltype = DNA   length = 41
FEATURE                 Location/Qualifiers
source                  1..41
                        mol_type = other DNA
                        organism = synthetic construct
SEQUENCE: 148
ttttcggttt gctccaacac gttgcgagta gcttgcccaa a             41

SEQ ID NO: 149          moltype = DNA   length = 28
FEATURE                 Location/Qualifiers
source                  1..28
                        mol_type = other DNA
                        organism = synthetic construct
SEQUENCE: 149
gggatagtga gtttcgtcaa aaacatgt                            28

SEQ ID NO: 150          moltype = DNA   length = 45
FEATURE                 Location/Qualifiers
source                  1..45
                        mol_type = other DNA
                        organism = synthetic construct
SEQUENCE: 150
gaagattggc ccagagcagc cctttaataa gcaacgccgc caacg         45

SEQ ID NO: 151          moltype = DNA   length = 14
FEATURE                 Location/Qualifiers
source                  1..14
                        mol_type = other DNA
                        organism = synthetic construct
SEQUENCE: 151
gcattccaca gaca                                           14

SEQ ID NO: 152          moltype = DNA   length = 28
FEATURE                 Location/Qualifiers
source                  1..28
                        mol_type = other DNA
                        organism = synthetic construct
SEQUENCE: 152
gtaacgaaaa tgaacagtcg gtaaagcc                            28

SEQ ID NO: 153          moltype = DNA   length = 46
FEATURE                 Location/Qualifiers
source                  1..46
                        mol_type = other DNA
                        organism = synthetic construct
SEQUENCE: 153
ctagaatcaa cgagccggaa gcacacaatt aagaaccact ccaaca        46

SEQ ID NO: 154          moltype = DNA   length = 42
FEATURE                 Location/Qualifiers
source                  1..42
                        mol_type = other DNA
                        organism = synthetic construct
SEQUENCE: 154
tgatattctg ggccgcttcg ctgagcccac gtgcgccgta ta            42

SEQ ID NO: 155          moltype = DNA   length = 35
FEATURE                 Location/Qualifiers
source                  1..35
                        mol_type = other DNA
                        organism = synthetic construct
SEQUENCE: 155
cattaagctc agtaccaaat cgcgcagaag acgga                    35

SEQ ID NO: 156          moltype = DNA   length = 38
FEATURE                 Location/Qualifiers
source                  1..38
                        mol_type = other DNA
                        organism = synthetic construct
SEQUENCE: 156
atgataaaca caatagaaaa gaaatttatt tggtatta                 38

SEQ ID NO: 157          moltype = DNA   length = 42
FEATURE                 Location/Qualifiers
source                  1..42
                        mol_type = other DNA
```

-continued

```
                        organism = synthetic construct
SEQUENCE: 157
agagcgtaaa aggtgaatta tggaataggt gtaggcgtaa gt                          42

SEQ ID NO: 158          moltype = DNA   length = 24
FEATURE                 Location/Qualifiers
source                  1..24
                        mol_type = other DNA
                        organism = synthetic construct
SEQUENCE: 158
cttgagccat ttcgggaggt tttg                                              24

SEQ ID NO: 159          moltype = DNA   length = 26
FEATURE                 Location/Qualifiers
source                  1..26
                        mol_type = other DNA
                        organism = synthetic construct
SEQUENCE: 159
caatgtgagt caccgtactc aggagg                                            26

SEQ ID NO: 160          moltype = DNA   length = 32
FEATURE                 Location/Qualifiers
source                  1..32
                        mol_type = other DNA
                        organism = synthetic construct
SEQUENCE: 160
attagcaagg ccggaacagt agcaccatta cc                                     32

SEQ ID NO: 161          moltype = DNA   length = 38
FEATURE                 Location/Qualifiers
source                  1..38
                        mol_type = other DNA
                        organism = synthetic construct
SEQUENCE: 161
aggctctgaa tccttatacg caatatagat ataaacaa                               38

SEQ ID NO: 162          moltype = DNA   length = 42
FEATURE                 Location/Qualifiers
source                  1..42
                        mol_type = other DNA
                        organism = synthetic construct
SEQUENCE: 162
gtttggtaga aaccatcgat acaccaccct catctcacag aa                          42

SEQ ID NO: 163          moltype = DNA   length = 24
FEATURE                 Location/Qualifiers
source                  1..24
                        mol_type = other DNA
                        organism = synthetic construct
SEQUENCE: 163
tcagtagcga caacgagcgt cttt                                              24

SEQ ID NO: 164          moltype = DNA   length = 42
FEATURE                 Location/Qualifiers
source                  1..42
                        mol_type = other DNA
                        organism = synthetic construct
SEQUENCE: 164
cgtttgccag ccctcataga gccccagtac aaactaggcg ca                          42

SEQ ID NO: 165          moltype = DNA   length = 14
FEATURE                 Location/Qualifiers
source                  1..14
                        mol_type = other DNA
                        organism = synthetic construct
SEQUENCE: 165
tcaaatagca gcct                                                         14

SEQ ID NO: 166          moltype = DNA   length = 38
FEATURE                 Location/Qualifiers
source                  1..38
                        mol_type = other DNA
                        organism = synthetic construct
SEQUENCE: 166
accttgagcg gttaagcccg gaattatgcg ttatacaa                               38

SEQ ID NO: 167          moltype = DNA   length = 28
FEATURE                 Location/Qualifiers
source                  1..28
```

-continued

```
                              mol_type = other DNA
                              organism = synthetic construct
SEQUENCE: 167
accggaagcc gccaccagtg aaatgaat                                    28

SEQ ID NO: 168          moltype = DNA  length = 38
FEATURE                 Location/Qualifiers
source                  1..38
                        mol_type = other DNA
                        organism = synthetic construct
SEQUENCE: 168
agaccagagc ctgaacatag acggggcgtt atgaccta                         38

SEQ ID NO: 169          moltype = DNA  length = 23
FEATURE                 Location/Qualifiers
source                  1..23
                        mol_type = other DNA
                        organism = synthetic construct
SEQUENCE: 169
aagattgccc tttcctcggc cag                                         23

SEQ ID NO: 170          moltype = DNA  length = 49
FEATURE                 Location/Qualifiers
source                  1..49
                        mol_type = other DNA
                        organism = synthetic construct
SEQUENCE: 170
tattgaaaat tacatttaat agcgaaatgg agggaaggta aaaattatt             49

SEQ ID NO: 171          moltype = DNA  length = 42
FEATURE                 Location/Qualifiers
source                  1..42
                        mol_type = other DNA
                        organism = synthetic construct
SEQUENCE: 171
acctcacaat gttaatgttg agtaaataag ttttgatgtg aa                    42

SEQ ID NO: 172          moltype = DNA  length = 33
FEATURE                 Location/Qualifiers
source                  1..33
                        mol_type = other DNA
                        organism = synthetic construct
SEQUENCE: 172
aagccttaaa tcgagtgaat aattttccat tcc                              33

SEQ ID NO: 173          moltype = DNA  length = 38
FEATURE                 Location/Qualifiers
source                  1..38
                        mol_type = other DNA
                        organism = synthetic construct
SEQUENCE: 173
acacccatcc tcggctgtct ttccttatcc taagaaaa                         38

SEQ ID NO: 174          moltype = DNA  length = 40
FEATURE                 Location/Qualifiers
source                  1..40
                        mol_type = other DNA
                        organism = synthetic construct
SEQUENCE: 174
caattttatc ctgaatccgc ccagcaaaat cacacgtcac                       40

SEQ ID NO: 175          moltype = DNA  length = 42
FEATURE                 Location/Qualifiers
source                  1..42
                        mol_type = other DNA
                        organism = synthetic construct
SEQUENCE: 175
gactttaccg cagaatgcaa acaagtcaga ccaactaatc ag                    42

SEQ ID NO: 176          moltype = DNA  length = 47
FEATURE                 Location/Qualifiers
source                  1..47
                        mol_type = other DNA
                        organism = synthetic construct
SEQUENCE: 176
ccagagccta atgtgaattt taacctccag acgacgacaa agtcctg               47

SEQ ID NO: 177          moltype = DNA  length = 42
FEATURE                 Location/Qualifiers
```

```
source                    1..42
                          mol_type = other DNA
                          organism = synthetic construct
SEQUENCE: 177
aggtaagcag ttaccgacgc cgccccgcca caccctcacc ag                     42

SEQ ID NO: 178            moltype = DNA   length = 38
FEATURE                   Location/Qualifiers
source                    1..38
                          mol_type = other DNA
                          organism = synthetic construct
SEQUENCE: 178
cgatttcgag aggtaaagta attctgtccg gagaggca                          38

SEQ ID NO: 179            moltype = DNA   length = 42
FEATURE                   Location/Qualifiers
source                    1..42
                          mol_type = other DNA
                          organism = synthetic construct
SEQUENCE: 179
tttaatacac ctttagcgtc acatagcccc ctttgtgttt ca                     42

SEQ ID NO: 180            moltype = DNA   length = 32
FEATURE                   Location/Qualifiers
source                    1..32
                          mol_type = other DNA
                          organism = synthetic construct
SEQUENCE: 180
tccaaataag aaacgaatat tatttatccc aa                                32

SEQ ID NO: 181            moltype = DNA   length = 42
FEATURE                   Location/Qualifiers
source                    1..42
                          mol_type = other DNA
                          organism = synthetic construct
SEQUENCE: 181
aaaacaattc gtcaaaaatg attttcataa tcacactatt ag                     42

SEQ ID NO: 182            moltype = DNA   length = 26
FEATURE                   Location/Qualifiers
source                    1..26
                          mol_type = other DNA
                          organism = synthetic construct
SEQUENCE: 182
ttacagagag aaaaagaaca tttcat                                       26

SEQ ID NO: 183            moltype = DNA   length = 46
FEATURE                   Location/Qualifiers
source                    1..46
                          mol_type = other DNA
                          organism = synthetic construct
SEQUENCE: 183
ctcccccgaa ccgcctggcc ctgaacagct ccgcctcttt tgtcgt                 46

SEQ ID NO: 184            moltype = DNA   length = 21
FEATURE                   Location/Qualifiers
source                    1..21
                          mol_type = other DNA
                          organism = synthetic construct
SEQUENCE: 184
tcatttgtca atatattcat t                                            21

SEQ ID NO: 185            moltype = DNA   length = 42
FEATURE                   Location/Qualifiers
source                    1..42
                          mol_type = other DNA
                          organism = synthetic construct
SEQUENCE: 185
tagcaagcaa agccgttcgc aaagtaaagg tttagcaatt aa                     42

SEQ ID NO: 186            moltype = DNA   length = 42
FEATURE                   Location/Qualifiers
source                    1..42
                          mol_type = other DNA
                          organism = synthetic construct
SEQUENCE: 186
aggaagtaag attagttgct aaacctcccg acttggggaa tt                     42

SEQ ID NO: 187            moltype = DNA   length = 39
```

-continued

```
FEATURE            Location/Qualifiers
source             1..39
                   mol_type = other DNA
                   organism = synthetic construct
SEQUENCE: 187
aaccaagtca ataataattt aatcaacaaa taacgcaga                              39

SEQ ID NO: 188     moltype = DNA   length = 35
FEATURE            Location/Qualifiers
source             1..35
                   mol_type = other DNA
                   organism = synthetic construct
SEQUENCE: 188
aagaacgtca tcgtaccgcg cgaggcgttt caatt                                 35

SEQ ID NO: 189     moltype = DNA   length = 26
FEATURE            Location/Qualifiers
source             1..26
                   mol_type = other DNA
                   organism = synthetic construct
SEQUENCE: 189
ataatattat attttgcacc cagcta                                           26

SEQ ID NO: 190     moltype = DNA   length = 42
FEATURE            Location/Qualifiers
source             1..42
                   mol_type = other DNA
                   organism = synthetic construct
SEQUENCE: 190
aacaatattg ccagttacaa atattaccaa cgctagaatc aa                         42

SEQ ID NO: 191     moltype = DNA   length = 39
FEATURE            Location/Qualifiers
source             1..39
                   mol_type = other DNA
                   organism = synthetic construct
SEQUENCE: 191
catgttccga caaaccagta atatttaaag caagagaat                             39

SEQ ID NO: 192     moltype = DNA   length = 28
FEATURE            Location/Qualifiers
source             1..28
                   mol_type = other DNA
                   organism = synthetic construct
SEQUENCE: 192
gaggcatgga aataaacagc cttttttg                                         28

SEQ ID NO: 193     moltype = DNA   length = 35
FEATURE            Location/Qualifiers
source             1..35
                   mol_type = other DNA
                   organism = synthetic construct
SEQUENCE: 193
cttaccagta taaaaacatg taatttacta acata                                 35

SEQ ID NO: 194     moltype = DNA   length = 28
FEATURE            Location/Qualifiers
source             1..28
                   mol_type = other DNA
                   organism = synthetic construct
SEQUENCE: 194
attcttcaat aagaacgtca acccgaga                                         28

SEQ ID NO: 195     moltype = DNA   length = 34
FEATURE            Location/Qualifiers
source             1..34
                   mol_type = other DNA
                   organism = synthetic construct
SEQUENCE: 195
ctaccggcga gaggtgccac ccaaatcaag tttt                                  34

SEQ ID NO: 196     moltype = DNA   length = 49
FEATURE            Location/Qualifiers
source             1..49
                   mol_type = other DNA
                   organism = synthetic construct
SEQUENCE: 196
ttttgctcat ggaaatacct aagtcacata aaagggacat tcaagcgta                  49
```

-continued

```
SEQ ID NO: 197          moltype = DNA   length = 49
FEATURE                 Location/Qualifiers
source                  1..49
                        mol_type = other DNA
                        organism = synthetic construct
SEQUENCE: 197
tataatcgca cttaggttgg gttatacctt ttatcaaaat catagtttt              49

SEQ ID NO: 198          moltype = DNA   length = 32
FEATURE                 Location/Qualifiers
source                  1..32
                        mol_type = other DNA
                        organism = synthetic construct
SEQUENCE: 198
cttgaaatat taattaacct tgcttctgtt tt                                32

SEQ ID NO: 199          moltype = DNA   length = 35
FEATURE                 Location/Qualifiers
source                  1..35
                        mol_type = other DNA
                        organism = synthetic construct
SEQUENCE: 199
tttttagatt aagacgctga gaagagtcta gaatc                            35

SEQ ID NO: 200          moltype = DNA   length = 30
FEATURE                 Location/Qualifiers
source                  1..30
                        mol_type = other DNA
                        organism = synthetic construct
SEQUENCE: 200
ttttaatgct gatgcaaatc cttatcccaa                                  30

SEQ ID NO: 201          moltype = DNA   length = 28
FEATURE                 Location/Qualifiers
source                  1..28
                        mol_type = other DNA
                        organism = synthetic construct
SEQUENCE: 201
aatttaatta gttagcgaga aaactttt                                    28

SEQ ID NO: 202          moltype = DNA   length = 30
FEATURE                 Location/Qualifiers
source                  1..30
                        mol_type = other DNA
                        organism = synthetic construct
SEQUENCE: 202
ttttccgacc gtgtgatcta tcacctaaag                                  30

SEQ ID NO: 203          moltype = DNA   length = 31
FEATURE                 Location/Qualifiers
source                  1..31
                        mol_type = other DNA
                        organism = synthetic construct
SEQUENCE: 203
ttttggggtc acgtggcgag aaaggaattt t                                31

SEQ ID NO: 204          moltype = DNA   length = 42
FEATURE                 Location/Qualifiers
source                  1..42
                        mol_type = other DNA
                        organism = synthetic construct
SEQUENCE: 204
ttttagaaag cgaaaggagc gccgccgcgc ttaatgcgtt tt                    42

SEQ ID NO: 205          moltype = DNA   length = 42
FEATURE                 Location/Qualifiers
source                  1..42
                        mol_type = other DNA
                        organism = synthetic construct
SEQUENCE: 205
tttttacagg gcgcgtacta taagggattt tagacaggtt tt                    42

SEQ ID NO: 206          moltype = DNA   length = 42
FEATURE                 Location/Qualifiers
source                  1..42
                        mol_type = other DNA
                        organism = synthetic construct
SEQUENCE: 206
ttttgtacgc cagaatcctg agcaaattaa ccgttgtatt tt                    42
```

-continued

```
SEQ ID NO: 207            moltype = DNA   length = 43
FEATURE                   Location/Qualifiers
source                    1..43
                          mol_type = other DNA
                          organism = synthetic construct
SEQUENCE: 207
tttttacttc tttgattagt aagccattgc aacaggaaat ttt                     43

SEQ ID NO: 208            moltype = DNA   length = 36
FEATURE                   Location/Qualifiers
source                    1..36
                          mol_type = other DNA
                          organism = synthetic construct
SEQUENCE: 208
tttttacctt ttacatcgat gaatatacag tatttt                             36

SEQ ID NO: 209            moltype = DNA   length = 36
FEATURE                   Location/Qualifiers
source                    1..36
                          mol_type = other DNA
                          organism = synthetic construct
SEQUENCE: 209
ttttattacc tgagcaaagg cgaattattc attttt                             36

SEQ ID NO: 210            moltype = DNA   length = 38
FEATURE                   Location/Qualifiers
source                    1..38
                          mol_type = other DNA
                          organism = synthetic construct
SEQUENCE: 210
ttttaaacag tacataaaaa ttaccttttt taattttt                           38

SEQ ID NO: 211            moltype = DNA   length = 26
FEATURE                   Location/Qualifiers
source                    1..26
                          mol_type = other DNA
                          organism = synthetic construct
SEQUENCE: 211
ttttataaca tcacaatatt actttt                                        26

SEQ ID NO: 212            moltype = DNA   length = 54
FEATURE                   Location/Qualifiers
source                    1..54
                          mol_type = other DNA
                          organism = synthetic construct
SEQUENCE: 212
ttttcgccag ccattgcaac tccagaactt gcctacttct ttgattagta tttt         54

SEQ ID NO: 213            moltype = DNA   length = 26
FEATURE                   Location/Qualifiers
source                    1..26
                          mol_type = other DNA
                          organism = synthetic construct
SEQUENCE: 213
ttttatcgtc tgaggacatt cttttt                                        26

SEQ ID NO: 214            moltype = DNA   length = 54
FEATURE                   Location/Qualifiers
source                    1..54
                          mol_type = other DNA
                          organism = synthetic construct
SEQUENCE: 214
ttttggccaa cagagataga ataaaagaat ggattacatt ttgacgctca tttt         54

SEQ ID NO: 215            moltype = DNA   length = 26
FEATURE                   Location/Qualifiers
source                    1..26
                          mol_type = other DNA
                          organism = synthetic construct
SEQUENCE: 215
ttttaatatt ttttaaaaat actttt                                        26

SEQ ID NO: 216            moltype = DNA   length = 54
FEATURE                   Location/Qualifiers
source                    1..54
                          mol_type = other DNA
                          organism = synthetic construct
SEQUENCE: 216
```

```
ttttcgaacg aaccaccagc tcgccatgaa tggcaatacg tggcacagac tttt        54

SEQ ID NO: 217         moltype = DNA   length = 40
FEATURE                Location/Qualifiers
source                 1..40
                       mol_type = other DNA
                       organism = synthetic construct
SEQUENCE: 217
ttttcctgca acagtgccac gtcagtatta acaccgtttt                        40

SEQ ID NO: 218         moltype = DNA   length = 26
FEATURE                Location/Qualifiers
source                 1..26
                       mol_type = other DNA
                       organism = synthetic construct
SEQUENCE: 218
ttttacctca aatcaaatca actttt                                       26

SEQ ID NO: 219         moltype = DNA   length = 29
FEATURE                Location/Qualifiers
source                 1..29
                       mol_type = other DNA
                       organism = synthetic construct
SEQUENCE: 219
ttttagttga aaggagcact aacaatttt                                    29

SEQ ID NO: 220         moltype = DNA   length = 29
FEATURE                Location/Qualifiers
source                 1..29
                       mol_type = other DNA
                       organism = synthetic construct
SEQUENCE: 220
ttttctaata gattaggaag tattatttt                                    29

SEQ ID NO: 221         moltype = DNA   length = 27
FEATURE                Location/Qualifiers
source                 1..27
                       mol_type = other DNA
                       organism = synthetic construct
SEQUENCE: 221
ttttgacttt acaccgaacg ttatttt                                      27

SEQ ID NO: 222         moltype = DNA   length = 29
FEATURE                Location/Qualifiers
source                 1..29
                       mol_type = other DNA
                       organism = synthetic construct
SEQUENCE: 222
ttttaatttt aaaagtaacc accagtttt                                    29

SEQ ID NO: 223         moltype = DNA   length = 29
FEATURE                Location/Qualifiers
source                 1..29
                       mol_type = other DNA
                       organism = synthetic construct
SEQUENCE: 223
ttttaaggag cggggcaatt catcatttt                                    29

SEQ ID NO: 224         moltype = DNA   length = 31
FEATURE                Location/Qualifiers
source                 1..31
                       mol_type = other DNA
                       organism = synthetic construct
SEQUENCE: 224
ttttatataa tcctgatgtt tttataattt t                                 31

SEQ ID NO: 225         moltype = DNA   length = 25
FEATURE                Location/Qualifiers
source                 1..25
                       mol_type = other DNA
                       organism = synthetic construct
SEQUENCE: 225
ttttaaacat agcatagtga atttt                                        25

SEQ ID NO: 226         moltype = DNA   length = 52
FEATURE                Location/Qualifiers
source                 1..52
                       mol_type = other DNA
                       organism = synthetic construct
```

```
SEQUENCE: 226
ttttatcaaa atcatattag agtcagatag ctcccttaga atccttgatt tt                    52

SEQ ID NO: 227          moltype = DNA   length = 25
FEATURE                 Location/Qualifiers
source                  1..25
                        mol_type = other DNA
                        organism = synthetic construct
SEQUENCE: 227
ttttaacctc cggctgatgc atttt                                                  25

SEQ ID NO: 228          moltype = DNA   length = 28
FEATURE                 Location/Qualifiers
source                  1..28
                        mol_type = other DNA
                        organism = synthetic construct
SEQUENCE: 228
ttttaatcca atcatatatt ttagtttt                                               28

SEQ ID NO: 229          moltype = DNA   length = 29
FEATURE                 Location/Qualifiers
source                  1..29
                        mol_type = other DNA
                        organism = synthetic construct
SEQUENCE: 229
tttttaattt catcttcgtg tgatatttt                                              29

SEQ ID NO: 230          moltype = DNA   length = 29
FEATURE                 Location/Qualifiers
source                  1..29
                        mol_type = other DNA
                        organism = synthetic construct
SEQUENCE: 230
ttttaataag gcgctagaaa aagcctttt                                              29

SEQ ID NO: 231          moltype = DNA   length = 31
FEATURE                 Location/Qualifiers
source                  1..31
                        mol_type = other DNA
                        organism = synthetic construct
SEQUENCE: 231
ttttgtttag tatcagagcg ggagctattt t                                           31

SEQ ID NO: 232          moltype = DNA   length = 25
FEATURE                 Location/Qualifiers
source                  1..25
                        mol_type = other DNA
                        organism = synthetic construct
SEQUENCE: 232
ttttggaatc attaaggctt atttt                                                  25

SEQ ID NO: 233          moltype = DNA   length = 29
FEATURE                 Location/Qualifiers
source                  1..29
                        mol_type = other DNA
                        organism = synthetic construct
SEQUENCE: 233
ttttccggta ttcacttgcg ggaggtttt                                              29

SEQ ID NO: 234          moltype = DNA   length = 21
FEATURE                 Location/Qualifiers
source                  1..21
                        mol_type = other DNA
                        organism = synthetic construct
SEQUENCE: 234
ttttgaagcc tttacaattt t                                                      21

SEQ ID NO: 235          moltype = DNA   length = 29
FEATURE                 Location/Qualifiers
source                  1..29
                        mol_type = other DNA
                        organism = synthetic construct
SEQUENCE: 235
ttttatcctg aatctaattt gccagtttt                                              29

SEQ ID NO: 236          moltype = DNA   length = 23
FEATURE                 Location/Qualifiers
source                  1..23
                        mol_type = other DNA
```

-continued

```
                              organism = synthetic construct
SEQUENCE: 236
ttttacaaaa taaaaacgat ttt                                            23

SEQ ID NO: 237          moltype = DNA   length = 27
FEATURE                 Location/Qualifiers
source                  1..27
                        mol_type = other DNA
                        organism = synthetic construct
SEQUENCE: 237
ttttgtttaa cgaataacat aaatttt                                        27

SEQ ID NO: 238          moltype = DNA   length = 32
FEATURE                 Location/Qualifiers
source                  1..32
                        mol_type = other DNA
                        organism = synthetic construct
SEQUENCE: 238
ttttaacagg gaagcggcgc cgctacagtt tt                                  32

SEQ ID NO: 239          moltype = DNA   length = 26
FEATURE                 Location/Qualifiers
source                  1..26
                        mol_type = other DNA
                        organism = synthetic construct
SEQUENCE: 239
ttttgacatt caaaaattat tctttt                                         26

SEQ ID NO: 240          moltype = DNA   length = 29
FEATURE                 Location/Qualifiers
source                  1..29
                        mol_type = other DNA
                        organism = synthetic construct
SEQUENCE: 240
ttttattaaa ggtggaatta gagcctttt                                      29

SEQ ID NO: 241          moltype = DNA   length = 29
FEATURE                 Location/Qualifiers
source                  1..29
                        mol_type = other DNA
                        organism = synthetic construct
SEQUENCE: 241
ttttagcaaa atcacccgtc accaatttt                                      29

SEQ ID NO: 242          moltype = DNA   length = 27
FEATURE                 Location/Qualifiers
source                  1..27
                        mol_type = other DNA
                        organism = synthetic construct
SEQUENCE: 242
ttttgaaacc attcaagttt gcctttt                                        27

SEQ ID NO: 243          moltype = DNA   length = 25
FEATURE                 Location/Qualifiers
source                  1..25
                        mol_type = other DNA
                        organism = synthetic construct
SEQUENCE: 243
ttttagcgtc agacagcccc ctttt                                          25

SEQ ID NO: 244          moltype = DNA   length = 29
FEATURE                 Location/Qualifiers
source                  1..29
                        mol_type = other DNA
                        organism = synthetic construct
SEQUENCE: 244
ttttattagc gttcagagcc accactttt                                      29

SEQ ID NO: 245          moltype = DNA   length = 32
FEATURE                 Location/Qualifiers
source                  1..32
                        mol_type = other DNA
                        organism = synthetic construct
SEQUENCE: 245
ttttcggaac cgcctcagcg ggcgctagtt tt                                  32

SEQ ID NO: 246          moltype = DNA   length = 26
FEATURE                 Location/Qualifiers
source                  1..26
```

-continued

```
                          mol_type = other DNA
                          organism = synthetic construct
SEQUENCE: 246
ttttaagaga agggcggata agtttt                                              26

SEQ ID NO: 247            moltype = DNA   length = 28
FEATURE                   Location/Qualifiers
source                    1..28
                          mol_type = other DNA
                          organism = synthetic construct
SEQUENCE: 247
ttttgccgtc gagtatcacc gtactttt                                            28

SEQ ID NO: 248            moltype = DNA   length = 28
FEATURE                   Location/Qualifiers
source                    1..28
                          mol_type = other DNA
                          organism = synthetic construct
SEQUENCE: 248
ttttcaggag gtttaaccgc cacctttt                                            28

SEQ ID NO: 249            moltype = DNA   length = 29
FEATURE                   Location/Qualifiers
source                    1..29
                          mol_type = other DNA
                          organism = synthetic construct
SEQUENCE: 249
ttttctcaga gcctaggaac ccatgtttt                                           29

SEQ ID NO: 250            moltype = DNA   length = 28
FEATURE                   Location/Qualifiers
source                    1..28
                          mol_type = other DNA
                          organism = synthetic construct
SEQUENCE: 250
ttttaccgta acactgtagc attctttt                                            28

SEQ ID NO: 251            moltype = DNA   length = 29
FEATURE                   Location/Qualifiers
source                    1..29
                          mol_type = other DNA
                          organism = synthetic construct
SEQUENCE: 251
ttttcacaga caggtcgtct ttccatttt                                           29

SEQ ID NO: 252            moltype = DNA   length = 32
FEATURE                   Location/Qualifiers
source                    1..32
                          mol_type = other DNA
                          organism = synthetic construct
SEQUENCE: 252
ttttgacgtt agtaaagccc ccgatttatt tt                                       32

SEQ ID NO: 253            moltype = DNA   length = 25
FEATURE                   Location/Qualifiers
source                    1..25
                          mol_type = other DNA
                          organism = synthetic construct
SEQUENCE: 253
ttttaaaata cgcagcgatt atttt                                               25

SEQ ID NO: 254            moltype = DNA   length = 28
FEATURE                   Location/Qualifiers
source                    1..28
                          mol_type = other DNA
                          organism = synthetic construct
SEQUENCE: 254
ttttaccaag cggacggtca atcatttt                                            28

SEQ ID NO: 255            moltype = DNA   length = 28
FEATURE                   Location/Qualifiers
source                    1..28
                          mol_type = other DNA
                          organism = synthetic construct
SEQUENCE: 255
ttttaaggga accgagtaat cttgtttt                                            28

SEQ ID NO: 256            moltype = DNA   length = 27
FEATURE                   Location/Qualifiers
```

-continued

```
source                    1..27
                          mol_type = other DNA
                          organism = synthetic construct
SEQUENCE: 256
ttttacaaga acccttgaga tggtttt                                                    27

SEQ ID NO: 257            moltype = DNA   length = 28
FEATURE                   Location/Qualifiers
source                    1..28
                          mol_type = other DNA
                          organism = synthetic construct
SEQUENCE: 257
ttttaatttc aacttctacg ttaatttt                                                   28

SEQ ID NO: 258            moltype = DNA   length = 28
FEATURE                   Location/Qualifiers
source                    1..28
                          mol_type = other DNA
                          organism = synthetic construct
SEQUENCE: 258
ttttaaaacg aagatacata acgctttt                                                   28

SEQ ID NO: 259            moltype = DNA   length = 32
FEATURE                   Location/Qualifiers
source                    1..32
                          mol_type = other DNA
                          organism = synthetic construct
SEQUENCE: 259
ttttcaaaag gaattagaac catcaccctt tt                                              32

SEQ ID NO: 260            moltype = DNA   length = 46
FEATURE                   Location/Qualifiers
source                    1..46
                          mol_type = other DNA
                          organism = synthetic construct
SEQUENCE: 260
actacgtcga ggcaaagttt tccctcataa cgcctgagtt tcgaca                              46

SEQ ID NO: 261            moltype = DNA   length = 35
FEATURE                   Location/Qualifiers
source                    1..35
                          mol_type = other DNA
                          organism = synthetic construct
SEQUENCE: 261
agtgttgagg gcgaaaaacc gctatcattg agaat                                          35

SEQ ID NO: 262            moltype = DNA   length = 49
FEATURE                   Location/Qualifiers
source                    1..49
                          mol_type = other DNA
                          organism = synthetic construct
SEQUENCE: 262
gatagactgc taaagccgcc accagatccc ctcagggaag ggtgcgcgt                           49

SEQ ID NO: 263            moltype = DNA   length = 42
FEATURE                   Location/Qualifiers
source                    1..42
                          mol_type = other DNA
                          organism = synthetic construct
SEQUENCE: 263
aggcctcaga acagagagtc aaaaaataag acagccattt tt                                   42

SEQ ID NO: 264            moltype = DNA   length = 42
FEATURE                   Location/Qualifiers
source                    1..42
                          mol_type = other DNA
                          organism = synthetic construct
SEQUENCE: 264
aagagttgca gcaaatcct gtttgaaaaa ccgccagcgc ta                                    42

SEQ ID NO: 265            moltype = DNA   length = 49
FEATURE                   Location/Qualifiers
source                    1..49
                          mol_type = other DNA
                          organism = synthetic construct
SEQUENCE: 265
tgagaccgaa caccttaatt gagaatacat tcttagtgct ttagacagg                           49

SEQ ID NO: 266            moltype = DNA   length = 45
```

-continued

```
FEATURE                 Location/Qualifiers
source                  1..45
                        mol_type = other DNA
                        organism = synthetic construct
SEQUENCE: 266
cgcgtcacgc aagaaagggc gaacgaaccc tcgaggtgat ggccc                    45

SEQ ID NO: 267          moltype = DNA   length = 35
FEATURE                 Location/Qualifiers
source                  1..35
                        mol_type = other DNA
                        organism = synthetic construct
SEQUENCE: 267
aatcattaga ataattatta aatataccga cctga                              35

SEQ ID NO: 268          moltype = DNA   length = 42
FEATURE                 Location/Qualifiers
source                  1..42
                        mol_type = other DNA
                        organism = synthetic construct
SEQUENCE: 268
aaaatcggcc aacgagggtg gtttttaccc agtataatta tt                      42

SEQ ID NO: 269          moltype = DNA   length = 49
FEATURE                 Location/Qualifiers
source                  1..49
                        mol_type = other DNA
                        organism = synthetic construct
SEQUENCE: 269
attaaagtga gaagttgttt gggtaataag gaaaaaaata cctatttac               49

SEQ ID NO: 270          moltype = DNA   length = 42
FEATURE                 Location/Qualifiers
source                  1..42
                        mol_type = other DNA
                        organism = synthetic construct
SEQUENCE: 270
taatgcgata atggcaattc caatcatgcc ccgggcggcc ag                      42

SEQ ID NO: 271          moltype = DNA   length = 46
FEATURE                 Location/Qualifiers
source                  1..46
                        mol_type = other DNA
                        organism = synthetic construct
SEQUENCE: 271
accgttgaag agtcagaatc cggattttcc tcgttttgac gaccgc                  46

SEQ ID NO: 272          moltype = DNA   length = 26
FEATURE                 Location/Qualifiers
source                  1..26
                        mol_type = other DNA
                        organism = synthetic construct
SEQUENCE: 272
gagccggccg ctcaaagggt tagaac                                        26

SEQ ID NO: 273          moltype = DNA   length = 21
FEATURE                 Location/Qualifiers
source                  1..21
                        mol_type = other DNA
                        organism = synthetic construct
SEQUENCE: 273
agaactcaaa ctaccaaatt a                                             21

SEQ ID NO: 274          moltype = DNA   length = 32
FEATURE                 Location/Qualifiers
source                  1..32
                        mol_type = other DNA
                        organism = synthetic construct
SEQUENCE: 274
ccttgctgat tatagattat ctatacaacg ga                                 32

SEQ ID NO: 275          moltype = DNA   length = 18
FEATURE                 Location/Qualifiers
source                  1..18
                        mol_type = other DNA
                        organism = synthetic construct
SEQUENCE: 275
acgctcgttg cggaatca                                                 18
```

-continued

```
SEQ ID NO: 276          moltype = DNA   length = 26
FEATURE                 Location/Qualifiers
source                  1..26
                        mol_type = other DNA
                        organism = synthetic construct
SEQUENCE: 276
tgccaagcac gacgagatga atatac                                    26

SEQ ID NO: 277          moltype = DNA   length = 46
FEATURE                 Location/Qualifiers
source                  1..46
                        mol_type = other DNA
                        organism = synthetic construct
SEQUENCE: 277
attggcatca cacgacatta tattaaataa atttagaaaa ctatta            46

SEQ ID NO: 278          moltype = DNA   length = 46
FEATURE                 Location/Qualifiers
source                  1..46
                        mol_type = other DNA
                        organism = synthetic construct
SEQUENCE: 278
tgaccatcat ttgacgacaa caactataaa agaacatttt gcacgc            46

SEQ ID NO: 279          moltype = DNA   length = 35
FEATURE                 Location/Qualifiers
source                  1..35
                        mol_type = other DNA
                        organism = synthetic construct
SEQUENCE: 279
aagtattagt ctttaatata gcccaataga ttaaa                        35

SEQ ID NO: 280          moltype = DNA   length = 26
FEATURE                 Location/Qualifiers
source                  1..26
                        mol_type = other DNA
                        organism = synthetic construct
SEQUENCE: 280
ggaagggcgc catttcattt caatta                                   26

SEQ ID NO: 281          moltype = DNA   length = 21
FEATURE                 Location/Qualifiers
source                  1..21
                        mol_type = other DNA
                        organism = synthetic construct
SEQUENCE: 281
gcgcgcagaa agggggtgaa a                                        21

SEQ ID NO: 282          moltype = DNA   length = 49
FEATURE                 Location/Qualifiers
source                  1..49
                        mol_type = other DNA
                        organism = synthetic construct
SEQUENCE: 282
gtgtttcatt aaacaaaatt ccaacaataa tcatacatag tatgtagtt         49

SEQ ID NO: 283          moltype = DNA   length = 46
FEATURE                 Location/Qualifiers
source                  1..46
                        mol_type = other DNA
                        organism = synthetic construct
SEQUENCE: 283
aaaacgcatc tggtggaagg tgctgagata cgagccaaat cagcga            46

SEQ ID NO: 284          moltype = DNA   length = 28
FEATURE                 Location/Qualifiers
source                  1..28
                        mol_type = other DNA
                        organism = synthetic construct
SEQUENCE: 284
gcggctgaga gccagcaaat ctaacctc                                 28

SEQ ID NO: 285          moltype = DNA   length = 35
FEATURE                 Location/Qualifiers
source                  1..35
                        mol_type = other DNA
                        organism = synthetic construct
SEQUENCE: 285
ccagttttgg gcgcagtaca tctgtaaaca aattg                        35
```

-continued

```
SEQ ID NO: 286              moltype = DNA   length = 21
FEATURE                     Location/Qualifiers
source                      1..21
                            mol_type = other DNA
                            organism = synthetic construct
SEQUENCE: 286
gcaaagtctc cagccaagag g                                          21

SEQ ID NO: 287              moltype = DNA   length = 17
FEATURE                     Location/Qualifiers
source                      1..17
                            mol_type = other DNA
                            organism = synthetic construct
SEQUENCE: 287
attctccgtg ggaacaa                                               17

SEQ ID NO: 288              moltype = DNA   length = 39
FEATURE                     Location/Qualifiers
source                      1..39
                            mol_type = other DNA
                            organism = synthetic construct
SEQUENCE: 288
acggcggtaa atgtaaataa tttttgttaa tcagaggta                       39

SEQ ID NO: 289              moltype = DNA   length = 42
FEATURE                     Location/Qualifiers
source                      1..42
                            mol_type = other DNA
                            organism = synthetic construct
SEQUENCE: 289
gataggtgaa gccagctttc atcaacatat tgaccgtaat gg                   42

SEQ ID NO: 290              moltype = DNA   length = 28
FEATURE                     Location/Qualifiers
source                      1..28
                            mol_type = other DNA
                            organism = synthetic construct
SEQUENCE: 290
aattaatttt tagattaaag ccgtccaa                                   28

SEQ ID NO: 291              moltype = DNA   length = 35
FEATURE                     Location/Qualifiers
source                      1..35
                            mol_type = other DNA
                            organism = synthetic construct
SEQUENCE: 291
atcaagatga attaccttta ttttccggcg aactg                           35

SEQ ID NO: 292              moltype = DNA   length = 14
FEATURE                     Location/Qualifiers
source                      1..14
                            mol_type = other DNA
                            organism = synthetic construct
SEQUENCE: 292
cctgagcaaa agaa                                                  14

SEQ ID NO: 293              moltype = DNA   length = 49
FEATURE                     Location/Qualifiers
source                      1..49
                            mol_type = other DNA
                            organism = synthetic construct
SEQUENCE: 293
tgaaatcaag aggcgaatta tcaggctgca ccgctgatcg cagcatctg            49

SEQ ID NO: 294              moltype = DNA   length = 28
FEATURE                     Location/Qualifiers
source                      1..28
                            mol_type = other DNA
                            organism = synthetic construct
SEQUENCE: 294
atattgggtt ccatcctgat tagttagc                                  28

SEQ ID NO: 295              moltype = DNA   length = 42
FEATURE                     Location/Qualifiers
source                      1..42
                            mol_type = other DNA
                            organism = synthetic construct
SEQUENCE: 295
```

-continued

```
gcgcatagtg ctgcacacca ggattcgata ccgagctcat gg                            42

SEQ ID NO: 296          moltype = DNA   length = 24
FEATURE                 Location/Qualifiers
source                  1..24
                        mol_type = other DNA
                        organism = synthetic construct
SEQUENCE: 296
agtaacagta ccaaagtacc gaca                                                24

SEQ ID NO: 297          moltype = DNA   length = 49
FEATURE                 Location/Qualifiers
source                  1..49
                        mol_type = other DNA
                        organism = synthetic construct
SEQUENCE: 297
tcggggtcaa ggtttaacgt cttgtaaaaa ggcgaagctg gcactgttg                     49

SEQ ID NO: 298          moltype = DNA   length = 33
FEATURE                 Location/Qualifiers
source                  1..33
                        mol_type = other DNA
                        organism = synthetic construct
SEQUENCE: 298
aaattgcgta gattttctta attcgtacat cgg                                      33

SEQ ID NO: 299          moltype = DNA   length = 35
FEATURE                 Location/Qualifiers
source                  1..35
                        mol_type = other DNA
                        organism = synthetic construct
SEQUENCE: 299
tattttgaaa agaataacaa tccaatgaaa agcat                                    35

SEQ ID NO: 300          moltype = DNA   length = 24
FEATURE                 Location/Qualifiers
source                  1..24
                        mol_type = other DNA
                        organism = synthetic construct
SEQUENCE: 300
ctaccatatc aaaaagccaa cgct                                                24

SEQ ID NO: 301          moltype = DNA   length = 49
FEATURE                 Location/Qualifiers
source                  1..49
                        mol_type = other DNA
                        organism = synthetic construct
SEQUENCE: 301
tgcacctctt ctgagtacgc ctgtccatca ttgcgctcac tggctgcat                     49

SEQ ID NO: 302          moltype = DNA   length = 41
FEATURE                 Location/Qualifiers
source                  1..41
                        mol_type = other DNA
                        organism = synthetic construct
SEQUENCE: 302
ggccttcctg tgtttgttaa aggaagagta acaagagct t                             41

SEQ ID NO: 303          moltype = DNA   length = 23
FEATURE                 Location/Qualifiers
source                  1..23
                        mol_type = other DNA
                        organism = synthetic construct
SEQUENCE: 303
taaacgtcct tatcattaat tac                                                 23

SEQ ID NO: 304          moltype = DNA   length = 49
FEATURE                 Location/Qualifiers
source                  1..49
                        mol_type = other DNA
                        organism = synthetic construct
SEQUENCE: 304
agtaccgtcg tcgctattaa tcatttaatg gaaacatcgt aacctgaaa                     49

SEQ ID NO: 305          moltype = DNA   length = 14
FEATURE                 Location/Qualifiers
source                  1..14
                        mol_type = other DNA
                        organism = synthetic construct
```

-continued

```
SEQUENCE: 305
cataacggaa tacc                                                                14

SEQ ID NO: 306          moltype = DNA   length = 18
FEATURE                 Location/Qualifiers
source                  1..18
                        mol_type = other DNA
                        organism = synthetic construct
SEQUENCE: 306
atgcagaacc ctgattgc                                                            18

SEQ ID NO: 307          moltype = DNA   length = 28
FEATURE                 Location/Qualifiers
source                  1..28
                        mol_type = other DNA
                        organism = synthetic construct
SEQUENCE: 307
acaatattca gaaacaataa ccaaaatc                                                 28

SEQ ID NO: 308          moltype = DNA   length = 49
FEATURE                 Location/Qualifiers
source                  1..49
                        mol_type = other DNA
                        organism = synthetic construct
SEQUENCE: 308
caagcaagac tgtaaatgct taggtcttta ggaattgaca gttggatca                         49

SEQ ID NO: 309          moltype = DNA   length = 49
FEATURE                 Location/Qualifiers
source                  1..49
                        mol_type = other DNA
                        organism = synthetic construct
SEQUENCE: 309
cctcctttgc aacaattgga tttaagccgt ctaaaacaag aagattgag                         49

SEQ ID NO: 310          moltype = DNA   length = 40
FEATURE                 Location/Qualifiers
source                  1..40
                        mol_type = other DNA
                        organism = synthetic construct
SEQUENCE: 310
tatttaattc gagccagtag gtcgtaaaac agaaataaag                                    40

SEQ ID NO: 311          moltype = DNA   length = 24
FEATURE                 Location/Qualifiers
source                  1..24
                        mol_type = other DNA
                        organism = synthetic construct
SEQUENCE: 311
caacagtagg gcctgaacaa agtc                                                     24

SEQ ID NO: 312          moltype = DNA   length = 35
FEATURE                 Location/Qualifiers
source                  1..35
                        mol_type = other DNA
                        organism = synthetic construct
SEQUENCE: 312
atccgggaga agcctttgcc gccaaaaatc atctg                                         35

SEQ ID NO: 313          moltype = DNA   length = 49
FEATURE                 Location/Qualifiers
source                  1..49
                        mol_type = other DNA
                        organism = synthetic construct
SEQUENCE: 313
cgtagatgat aattatcaca aagattgagt aaccagtaac ccttcgcgt                         49

SEQ ID NO: 314          moltype = DNA   length = 28
FEATURE                 Location/Qualifiers
source                  1..28
                        mol_type = other DNA
                        organism = synthetic construct
SEQUENCE: 314
atttactcgc aaagaataga attaccat                                                 28

SEQ ID NO: 315          moltype = DNA   length = 45
FEATURE                 Location/Qualifiers
source                  1..45
                        mol_type = other DNA
```

-continued

```
                                     organism = synthetic construct
SEQUENCE: 315
atcaggtcat atgccgggta ggtattttta gaatacttga gcata                              45

SEQ ID NO: 316          moltype = DNA   length = 43
FEATURE                 Location/Qualifiers
source                  1..43
                        mol_type = other DNA
                        organism = synthetic construct
SEQUENCE: 316
gatgaacaaa gccccaaaaa caattcgcat taaattcgcg tct                                43

SEQ ID NO: 317          moltype = DNA   length = 46
FEATURE                 Location/Qualifiers
source                  1..46
                        mol_type = other DNA
                        organism = synthetic construct
SEQUENCE: 317
tagaccagcg agggagggta ttaattagcg gtgaggaaac tacgaa                             46

SEQ ID NO: 318          moltype = DNA   length = 23
FEATURE                 Location/Qualifiers
source                  1..23
                        mol_type = other DNA
                        organism = synthetic construct
SEQUENCE: 318
taggaataat tgtataagca aat                                                      23

SEQ ID NO: 319          moltype = DNA   length = 42
FEATURE                 Location/Qualifiers
source                  1..42
                        mol_type = other DNA
                        organism = synthetic construct
SEQUENCE: 319
gcaacagatg tagataatat catagataag tcctgaagat ga                                 42

SEQ ID NO: 320          moltype = DNA   length = 45
FEATURE                 Location/Qualifiers
source                  1..45
                        mol_type = other DNA
                        organism = synthetic construct
SEQUENCE: 320
ggcgtaaata caccgtcttg ctcagatata atcatcttaa gtaca                              45

SEQ ID NO: 321          moltype = DNA   length = 14
FEATURE                 Location/Qualifiers
source                  1..14
                        mol_type = other DNA
                        organism = synthetic construct
SEQUENCE: 321
caaaagaact ggtg                                                                14

SEQ ID NO: 322          moltype = DNA   length = 46
FEATURE                 Location/Qualifiers
source                  1..46
                        mol_type = other DNA
                        organism = synthetic construct
SEQUENCE: 322
gaaccattac acttgagcac cctcagcccg gaactttgcg gaacga                             46

SEQ ID NO: 323          moltype = DNA   length = 42
FEATURE                 Location/Qualifiers
source                  1..42
                        mol_type = other DNA
                        organism = synthetic construct
SEQUENCE: 323
gcaataaaga aaaaaaccaa tgaacgggta ttaactacaa ac                                 42

SEQ ID NO: 324          moltype = DNA   length = 42
FEATURE                 Location/Qualifiers
source                  1..42
                        mol_type = other DNA
                        organism = synthetic construct
SEQUENCE: 324
tttaagaaag gaaaccgagc tgccgacgac aataatttat ca                                 42

SEQ ID NO: 325          moltype = DNA   length = 45
FEATURE                 Location/Qualifiers
source                  1..45
```

-continued

```
                              mol_type = other DNA
                              organism = synthetic construct
SEQUENCE: 325
taaagcaagg agcaccgccg ccactcattt tgaccttcca ttacc                          45

SEQ ID NO: 326          moltype = DNA   length = 24
FEATURE                 Location/Qualifiers
source                  1..24
                        mol_type = other DNA
                        organism = synthetic construct
SEQUENCE: 326
atagcaatag ctcacaaaca aata                                                 24

SEQ ID NO: 327          moltype = DNA   length = 42
FEATURE                 Location/Qualifiers
source                  1..42
                        mol_type = other DNA
                        organism = synthetic construct
SEQUENCE: 327
aagagcaatt ctgtccagag aatataagag aatatttta ca                             42

SEQ ID NO: 328          moltype = DNA   length = 35
FEATURE                 Location/Qualifiers
source                  1..35
                        mol_type = other DNA
                        organism = synthetic construct
SEQUENCE: 328
tttcgtcttt cgttttccag tagcgtcacc agata                                    35

SEQ ID NO: 329          moltype = DNA   length = 26
FEATURE                 Location/Qualifiers
source                  1..26
                        mol_type = other DNA
                        organism = synthetic construct
SEQUENCE: 329
gaattgagtt aagcccacca ccgcca                                              26

SEQ ID NO: 330          moltype = DNA   length = 24
FEATURE                 Location/Qualifiers
source                  1..24
                        mol_type = other DNA
                        organism = synthetic construct
SEQUENCE: 330
agagggtaat tgaccctcag agcc                                                24

SEQ ID NO: 331          moltype = DNA   length = 49
FEATURE                 Location/Qualifiers
source                  1..49
                        mol_type = other DNA
                        organism = synthetic construct
SEQUENCE: 331
atatcgcatt aactaccaca cgcacgtata cttttcacca gtctggccc                     49

SEQ ID NO: 332          moltype = DNA   length = 42
FEATURE                 Location/Qualifiers
source                  1..42
                        mol_type = other DNA
                        organism = synthetic construct
SEQUENCE: 332
atggtttcaa tataaaagaa acatcgagaa caagcagaac ca                            42

SEQ ID NO: 333          moltype = DNA   length = 43
FEATURE                 Location/Qualifiers
source                  1..43
                        mol_type = other DNA
                        organism = synthetic construct
SEQUENCE: 333
accgttctga gaaacattca acgcaaggat aaaaaaagat tca                           43

SEQ ID NO: 334          moltype = DNA   length = 23
FEATURE                 Location/Qualifiers
source                  1..23
                        mol_type = other DNA
                        organism = synthetic construct
SEQUENCE: 334
caatatgtat aaactagcaa acg                                                 23

SEQ ID NO: 335          moltype = DNA   length = 46
FEATURE                 Location/Qualifiers
```

```
source                   1..46
                         mol_type = other DNA
                         organism = synthetic construct
SEQUENCE: 335
cgatattcaa ttttgtcaca atcacaccac gaaaatacgg ctgtct                    46

SEQ ID NO: 336           moltype = DNA   length = 38
FEATURE                  Location/Qualifiers
source                   1..38
                         mol_type = other DNA
                         organism = synthetic construct
SEQUENCE: 336
aatcttgagt tttgcggggc ttgccaaaag acatcgcc                             38

SEQ ID NO: 337           moltype = DNA   length = 42
FEATURE                  Location/Qualifiers
source                   1..42
                         mol_type = other DNA
                         organism = synthetic construct
SEQUENCE: 337
tcagtgcgcc ccctgcctaa ggttccttat tacgcaaagg tg                        42

SEQ ID NO: 338           moltype = DNA   length = 14
FEATURE                  Location/Qualifiers
source                   1..14
                         mol_type = other DNA
                         organism = synthetic construct
SEQUENCE: 338
gtaatgacaa caac                                                       14

SEQ ID NO: 339           moltype = DNA   length = 42
FEATURE                  Location/Qualifiers
source                   1..42
                         mol_type = other DNA
                         organism = synthetic construct
SEQUENCE: 339
tttaacgcaa caggagtgta ccatgattaa gactttggaa ac                        42

SEQ ID NO: 340           moltype = DNA   length = 24
FEATURE                  Location/Qualifiers
source                   1..24
                         mol_type = other DNA
                         organism = synthetic construct
SEQUENCE: 340
aatcctcatt aatctccaaa aaaa                                            24

SEQ ID NO: 341           moltype = DNA   length = 42
FEATURE                  Location/Qualifiers
source                   1..42
                         mol_type = other DNA
                         organism = synthetic construct
SEQUENCE: 341
atggaatatg gccttgatat tatcttaccg aagagatata at                        42

SEQ ID NO: 342           moltype = DNA   length = 49
FEATURE                  Location/Qualifiers
source                   1..49
                         mol_type = other DNA
                         organism = synthetic construct
SEQUENCE: 342
gaacgatagc ccggaaaagt agcacctccc gtaagaacga tatagaccg                 49

SEQ ID NO: 343           moltype = DNA   length = 26
FEATURE                  Location/Qualifiers
source                   1..26
                         mol_type = other DNA
                         organism = synthetic construct
SEQUENCE: 343
cgattcgtaa gagagataac ccacaa                                          26

SEQ ID NO: 344           moltype = DNA   length = 38
FEATURE                  Location/Qualifiers
source                   1..38
                         mol_type = other DNA
                         organism = synthetic construct
SEQUENCE: 344
ttttttttcat aaactacagt tagcttggga aaacaaca                            38

SEQ ID NO: 345           moltype = DNA   length = 24
```

-continued

```
FEATURE            Location/Qualifiers
source             1..24
                   mol_type = other DNA
                   organism = synthetic construct
SEQUENCE: 345
accaccctca gacaactttc aaca                                          24

SEQ ID NO: 346     moltype = DNA   length = 49
FEATURE            Location/Qualifiers
source             1..49
                   mol_type = other DNA
                   organism = synthetic construct
SEQUENCE: 346
aactgccatc cggtcattgt agcgccagag ccttaccaac ccagcaaat              49

SEQ ID NO: 347     moltype = DNA   length = 41
FEATURE            Location/Qualifiers
source             1..41
                   mol_type = other DNA
                   organism = synthetic construct
SEQUENCE: 347
aaagggtagc tgataaatta tgcctgagag tctggagaat c                      41

SEQ ID NO: 348     moltype = DNA   length = 28
FEATURE            Location/Qualifiers
source             1..28
                   mol_type = other DNA
                   organism = synthetic construct
SEQUENCE: 348
aaatcataca gcattgagga caacgaaa                                      28

SEQ ID NO: 349     moltype = DNA   length = 42
FEATURE            Location/Qualifiers
source             1..42
                   mol_type = other DNA
                   organism = synthetic construct
SEQUENCE: 349
gcgaaagtct gaaacatgaa agatttcgga acctaaattc at                     42

SEQ ID NO: 350     moltype = DNA   length = 23
FEATURE            Location/Qualifiers
source             1..23
                   mol_type = other DNA
                   organism = synthetic construct
SEQUENCE: 350
aaagggtagg gccggagaca gtc                                          23

SEQ ID NO: 351     moltype = DNA   length = 26
FEATURE            Location/Qualifiers
source             1..26
                   mol_type = other DNA
                   organism = synthetic construct
SEQUENCE: 351
catcgcccac gcaacggtga cctgct                                       26

SEQ ID NO: 352     moltype = DNA   length = 28
FEATURE            Location/Qualifiers
source             1..28
                   mol_type = other DNA
                   organism = synthetic construct
SEQUENCE: 352
atataataga gttgcgccga caataagt                                     28

SEQ ID NO: 353     moltype = DNA   length = 37
FEATURE            Location/Qualifiers
source             1..37
                   mol_type = other DNA
                   organism = synthetic construct
SEQUENCE: 353
tgaatttctt aaacagcagc ttggaccagg aaagctg                           37

SEQ ID NO: 354     moltype = DNA   length = 42
FEATURE            Location/Qualifiers
source             1..42
                   mol_type = other DNA
                   organism = synthetic construct
SEQUENCE: 354
ccgataataa agcgcagtct cgcttttgat gatttcgccc tt                     42
```

-continued

```
SEQ ID NO: 355          moltype = DNA   length = 42
FEATURE                 Location/Qualifiers
source                  1..42
                        mol_type = other DNA
                        organism = synthetic construct
SEQUENCE: 355
ccccctcaga gtaccgccca tttggaatta tttgacggcc ga                        42

SEQ ID NO: 356          moltype = DNA   length = 26
FEATURE                 Location/Qualifiers
source                  1..26
                        mol_type = other DNA
                        organism = synthetic construct
SEQUENCE: 356
aggctccaaa agttaagaac tgacga                                          26

SEQ ID NO: 357          moltype = DNA   length = 28
FEATURE                 Location/Qualifiers
source                  1..28
                        mol_type = other DNA
                        organism = synthetic construct
SEQUENCE: 357
taattgggtt cacgttgaaa aagccaga                                        28

SEQ ID NO: 358          moltype = DNA   length = 18
FEATURE                 Location/Qualifiers
source                  1..18
                        mol_type = other DNA
                        organism = synthetic construct
SEQUENCE: 358
gcatgtgaat agtagtaa                                                   18

SEQ ID NO: 359          moltype = DNA   length = 40
FEATURE                 Location/Qualifiers
source                  1..40
                        mol_type = other DNA
                        organism = synthetic construct
SEQUENCE: 359
tgcgaataat aatttttaca aaccaccacc agaggtcaga                           40

SEQ ID NO: 360          moltype = DNA   length = 26
FEATURE                 Location/Qualifiers
source                  1..26
                        mol_type = other DNA
                        organism = synthetic construct
SEQUENCE: 360
gtttcagcgg agaaccctcg ttgaga                                          26

SEQ ID NO: 361          moltype = DNA   length = 49
FEATURE                 Location/Qualifiers
source                  1..49
                        mol_type = other DNA
                        organism = synthetic construct
SEQUENCE: 361
agaaaaaggg attttaaatc ggtggcgaga tggtggttcc gaagcccga                 49

SEQ ID NO: 362          moltype = DNA   length = 24
FEATURE                 Location/Qualifiers
source                  1..24
                        mol_type = other DNA
                        organism = synthetic construct
SEQUENCE: 362
tatcgatcta tagtaagatt caac                                            24

SEQ ID NO: 363          moltype = DNA   length = 49
FEATURE                 Location/Qualifiers
source                  1..49
                        mol_type = other DNA
                        organism = synthetic construct
SEQUENCE: 363
agaagccttt atacaaatta agcaataaca tccataaaat caaataacc                 49

SEQ ID NO: 364          moltype = DNA   length = 30
FEATURE                 Location/Qualifiers
source                  1..30
                        mol_type = other DNA
                        organism = synthetic construct
SEQUENCE: 364
gaggcttcgg aacgggccgc taacagtgcc                                      30
```

-continued

```
SEQ ID NO: 365          moltype = DNA   length = 21
FEATURE                 Location/Qualifiers
source                  1..21
                        mol_type = other DNA
                        organism = synthetic construct
SEQUENCE: 365
gaaaagaatt agcaggctac a                                   21

SEQ ID NO: 366          moltype = DNA   length = 48
FEATURE                 Location/Qualifiers
source                  1..48
                        mol_type = other DNA
                        organism = synthetic construct
SEQUENCE: 366
ggcaccaaaa cacgtttcgg tcgctgagat cgtcaccctt taccgggg     48

SEQ ID NO: 367          moltype = DNA   length = 42
FEATURE                 Location/Qualifiers
source                  1..42
                        mol_type = other DNA
                        organism = synthetic construct
SEQUENCE: 367
tgtttagtac atttaagttt cgtagctcaa catgtagaga gt            42

SEQ ID NO: 368          moltype = DNA   length = 30
FEATURE                 Location/Qualifiers
source                  1..30
                        mol_type = other DNA
                        organism = synthetic construct
SEQUENCE: 368
ttgtgtctac aggcaaggcg gagggagtta                          30

SEQ ID NO: 369          moltype = DNA   length = 49
FEATURE                 Location/Qualifiers
source                  1..49
                        mol_type = other DNA
                        organism = synthetic construct
SEQUENCE: 369
tgataaaatc cgcgtaacta aagtacggtg tctggcgcaa atggtcgaa     49

SEQ ID NO: 370          moltype = DNA   length = 49
FEATURE                 Location/Qualifiers
source                  1..49
                        mol_type = other DNA
                        organism = synthetic construct
SEQUENCE: 370
acggagaact tagcaaagag ggctggctca gtatcggttt atcttgata     49

SEQ ID NO: 371          moltype = DNA   length = 49
FEATURE                 Location/Qualifiers
source                  1..49
                        mol_type = other DNA
                        organism = synthetic construct
SEQUENCE: 371
ccatgttttt gtatatacac taacctaata aagacttttt caggcagca     49

SEQ ID NO: 372          moltype = DNA   length = 49
FEATURE                 Location/Qualifiers
source                  1..49
                        mol_type = other DNA
                        organism = synthetic construct
SEQUENCE: 372
ataacaggtt tgaccattag actatattgc attaaagcct cattgcggg     49

SEQ ID NO: 373          moltype = DNA   length = 42
FEATURE                 Location/Qualifiers
source                  1..42
                        mol_type = other DNA
                        organism = synthetic construct
SEQUENCE: 373
acctttactc caacgaagcc ctattatagt cagaacattg aa            42

SEQ ID NO: 374          moltype = DNA   length = 37
FEATURE                 Location/Qualifiers
source                  1..37
                        mol_type = other DNA
                        organism = synthetic construct
SEQUENCE: 374
```

```
ctcattcagt gatttttaaa tatgcacact ttcgagg                              37

SEQ ID NO: 375           moltype = DNA   length = 47
FEATURE                  Location/Qualifiers
source                   1..47
                         mol_type = other DNA
                         organism = synthetic construct
SEQUENCE: 375
caaatcacag aacgtacctt acaggacggt ggaacaacta aaggaat                   47

SEQ ID NO: 376           moltype = DNA   length = 35
FEATURE                  Location/Qualifiers
source                   1..35
                         mol_type = other DNA
                         organism = synthetic construct
SEQUENCE: 376
gaaacacacg taaccgcata gacagatgat aaccg                                35

SEQ ID NO: 377           moltype = DNA   length = 45
FEATURE                  Location/Qualifiers
source                   1..45
                         mol_type = other DNA
                         organism = synthetic construct
SEQUENCE: 377
attgggggat attatcaaga actgaccaat aggtgagggt tgtac                     45

SEQ ID NO: 378           moltype = DNA   length = 42
FEATURE                  Location/Qualifiers
source                   1..42
                         mol_type = other DNA
                         organism = synthetic construct
SEQUENCE: 378
ttcaaataga ccggaagcaa aattgctcta atgctattcc at                       42

SEQ ID NO: 379           moltype = DNA   length = 35
FEATURE                  Location/Qualifiers
source                   1..35
                         mol_type = other DNA
                         organism = synthetic construct
SEQUENCE: 379
ttaagagagg tcaggaataa ggcttgccct gcatc                               35

SEQ ID NO: 380           moltype = DNA   length = 49
FEATURE                  Location/Qualifiers
source                   1..49
                         mol_type = other DNA
                         organism = synthetic construct
SEQUENCE: 380
ggattggctc attaaagatt catgtcataa atattgcaaa gcaaaaaga               49

SEQ ID NO: 381           moltype = DNA   length = 28
FEATURE                  Location/Qualifiers
source                   1..28
                         mol_type = other DNA
                         organism = synthetic construct
SEQUENCE: 381
tccccttgg atagaccaaa atagcgag                                        28

SEQ ID NO: 382           moltype = DNA   length = 42
FEATURE                  Location/Qualifiers
source                   1..42
                         mol_type = other DNA
                         organism = synthetic construct
SEQUENCE: 382
ttattacata ccacagcaac atctatcacc gtaaagcggt tg                       42

SEQ ID NO: 383           moltype = DNA   length = 35
FEATURE                  Location/Qualifiers
source                   1..35
                         mol_type = other DNA
                         organism = synthetic construct
SEQUENCE: 383
tttaggaagg tagataccag ttgcgattga gcctt                               35

SEQ ID NO: 384           moltype = DNA   length = 39
FEATURE                  Location/Qualifiers
source                   1..39
                         mol_type = other DNA
                         organism = synthetic construct
```

-continued

```
SEQUENCE: 384
taatgcacta acgggaaaaa ttaatcatag cccaaacca                              39

SEQ ID NO: 385         moltype = DNA   length = 42
FEATURE                Location/Qualifiers
source                 1..42
                       mol_type = other DNA
                       organism = synthetic construct
SEQUENCE: 385
aggcttttaa aatgtttaga ccaaatgccc ctgacgaaag ac                         42

SEQ ID NO: 386         moltype = DNA   length = 42
FEATURE                Location/Qualifiers
source                 1..42
                       mol_type = other DNA
                       organism = synthetic construct
SEQUENCE: 386
agacgacgat aaaacgtcca atactgcgga atccagttta cc                         42

SEQ ID NO: 387         moltype = DNA   length = 50
FEATURE                Location/Qualifiers
source                 1..50
                       mol_type = other DNA
                       organism = synthetic construct
SEQUENCE: 387
ttttgaacgt ggactccaac gtcaattcca gtttggaaca agagtctttt                 50

SEQ ID NO: 388         moltype = DNA   length = 37
FEATURE                Location/Qualifiers
source                 1..37
                       mol_type = other DNA
                       organism = synthetic construct
SEQUENCE: 388
ttttaaattg ttataagcat aaagtgtaaa gcctttt                               37

SEQ ID NO: 389         moltype = DNA   length = 42
FEATURE                Location/Qualifiers
source                 1..42
                       mol_type = other DNA
                       organism = synthetic construct
SEQUENCE: 389
ttttggtcga ctctagagga tgtcatagct gtttcctgtt tt                         42

SEQ ID NO: 390         moltype = DNA   length = 24
FEATURE                Location/Qualifiers
source                 1..24
                       mol_type = other DNA
                       organism = synthetic construct
SEQUENCE: 390
ttttcccagt cttgcatgcc tttt                                             24

SEQ ID NO: 391         moltype = DNA   length = 28
FEATURE                Location/Qualifiers
source                 1..28
                       mol_type = other DNA
                       organism = synthetic construct
SEQUENCE: 391
ttttaagcgc cattcgatcg gtgctttt                                         28

SEQ ID NO: 392         moltype = DNA   length = 28
FEATURE                Location/Qualifiers
source                 1..28
                       mol_type = other DNA
                       organism = synthetic construct
SEQUENCE: 392
ttttcaagag cgagtaacaa cccgtttt                                         28

SEQ ID NO: 393         moltype = DNA   length = 27
FEATURE                Location/Qualifiers
source                 1..27
                       mol_type = other DNA
                       organism = synthetic construct
SEQUENCE: 393
ttttatgtac cccggttgat aaatttt                                          27

SEQ ID NO: 394         moltype = DNA   length = 28
FEATURE                Location/Qualifiers
source                 1..28
                       mol_type = other DNA
```

-continued

```
                        organism = synthetic construct
SEQUENCE: 394
ttttatcgta aaactagcat gtcatttt                                          28

SEQ ID NO: 395         moltype = DNA   length = 28
FEATURE                Location/Qualifiers
source                 1..28
                       mol_type = other DNA
                       organism = synthetic construct
SEQUENCE: 395
ttttcaatgc ctgagtaatg tagatttt                                          28

SEQ ID NO: 396         moltype = DNA   length = 44
FEATURE                Location/Qualifiers
source                 1..44
                       mol_type = other DNA
                       organism = synthetic construct
SEQUENCE: 396
ttttaaaaac attatgaccc tgtaaccctc atatattta tttt                         44

SEQ ID NO: 397         moltype = DNA   length = 38
FEATURE                Location/Qualifiers
source                 1..38
                       mol_type = other DNA
                       organism = synthetic construct
SEQUENCE: 397
ttttagaggg ggtaatagtg caaaagaagt tttgtttt                               38

SEQ ID NO: 398         moltype = DNA   length = 45
FEATURE                Location/Qualifiers
source                 1..45
                       mol_type = other DNA
                       organism = synthetic construct
SEQUENCE: 398
ttttcctaat gagtgagcta actcacatta attgcgcgaa catac                       45

SEQ ID NO: 399         moltype = DNA   length = 31
FEATURE                Location/Qualifiers
source                 1..31
                       mol_type = other DNA
                       organism = synthetic construct
SEQUENCE: 399
ttttctcttc gctattacgc cttaagttca a                                      31

SEQ ID NO: 400         moltype = DNA   length = 29
FEATURE                Location/Qualifiers
source                 1..29
                       mol_type = other DNA
                       organism = synthetic construct
SEQUENCE: 400
ttttagtatc ggcctcagga atctgtttt                                         29

SEQ ID NO: 401         moltype = DNA   length = 37
FEATURE                Location/Qualifiers
source                 1..37
                       mol_type = other DNA
                       organism = synthetic construct
SEQUENCE: 401
attatatgtc acgttggtgt agagagggga cgatttt                                37

SEQ ID NO: 402         moltype = DNA   length = 23
FEATURE                Location/Qualifiers
source                 1..23
                       mol_type = other DNA
                       organism = synthetic construct
SEQUENCE: 402
tttgaatacg ggtaacgcct ttt                                               23

SEQ ID NO: 403         moltype = DNA   length = 47
FEATURE                Location/Qualifiers
source                 1..47
                       mol_type = other DNA
                       organism = synthetic construct
SEQUENCE: 403
tttaatattg aataaccttg cttaaatcaa ttaacaaccg gaaacca                     47

SEQ ID NO: 404         moltype = DNA   length = 49
FEATURE                Location/Qualifiers
source                 1..49
```

-continued

```
                                mol_type = other DNA
                                organism = synthetic construct
SEQUENCE: 404
aagctaatac taatagtagt attcatttgg ggcgcgagct gaaaatttt                49

SEQ ID NO: 405            moltype = DNA   length = 32
FEATURE                   Location/Qualifiers
source                    1..32
                          mol_type = other DNA
                          organism = synthetic construct
SEQUENCE: 405
ttttaacgag tagatttatt gattcttaat tg                                  32

SEQ ID NO: 406            moltype = DNA   length = 35
FEATURE                   Location/Qualifiers
source                    1..35
                          mol_type = other DNA
                          organism = synthetic construct
SEQUENCE: 406
ctgaatactt ttgataagag gtcatttttg ctttt                              35

SEQ ID NO: 407            moltype = DNA   length = 32
FEATURE                   Location/Qualifiers
source                    1..32
                          mol_type = other DNA
                          organism = synthetic construct
SEQUENCE: 407
ttttcttcaa agcgaaccat cgcgtaaatc ag                                  32

SEQ ID NO: 408            moltype = DNA   length = 35
FEATURE                   Location/Qualifiers
source                    1..35
                          mol_type = other DNA
                          organism = synthetic construct
SEQUENCE: 408
gtctttattt aaacagttca gaaaacgaga atttt                              35

SEQ ID NO: 409            moltype = DNA   length = 41
FEATURE                   Location/Qualifiers
source                    1..41
                          mol_type = other DNA
                          organism = synthetic construct
SEQUENCE: 409
ttttaaatca agttttttgg ggtaaaggga tgaatttccg g                        41

SEQ ID NO: 410            moltype = DNA   length = 27
FEATURE                   Location/Qualifiers
source                    1..27
                          mol_type = other DNA
                          organism = synthetic construct
SEQUENCE: 410
ttttgagctt gacggggaaa gcccgaa                                        27

SEQ ID NO: 411            moltype = DNA   length = 27
FEATURE                   Location/Qualifiers
source                    1..27
                          mol_type = other DNA
                          organism = synthetic construct
SEQUENCE: 411
ttttggcgct ggcaagtgta gcggctt                                        27

SEQ ID NO: 412            moltype = DNA   length = 34
FEATURE                   Location/Qualifiers
source                    1..34
                          mol_type = other DNA
                          organism = synthetic construct
SEQUENCE: 412
ttttggcgcg tactatggtt gctagaatca tatg                                34

SEQ ID NO: 413            moltype = DNA   length = 16
FEATURE                   Location/Qualifiers
source                    1..16
                          mol_type = other DNA
                          organism = synthetic construct
SEQUENCE: 413
ttttaacagg aggccg                                                    16

SEQ ID NO: 414            moltype = DNA   length = 37
FEATURE                   Location/Qualifiers
```

-continued

```
source                    1..37
                          mol_type = other DNA
                          organism = synthetic construct
SEQUENCE: 414
ttttcagtga ggccaccgag taatagcaat gagtaga                              37

SEQ ID NO: 415           moltype = DNA   length = 23
FEATURE                  Location/Qualifiers
source                    1..23
                          mol_type = other DNA
                          organism = synthetic construct
SEQUENCE: 415
aacagcatca ccttgctgat ttt                                             23

SEQ ID NO: 416           moltype = DNA   length = 23
FEATURE                  Location/Qualifiers
source                    1..23
                          mol_type = other DNA
                          organism = synthetic construct
SEQUENCE: 416
cgcttttatt ttcatcgtat ttt                                            23

SEQ ID NO: 417           moltype = DNA   length = 25
FEATURE                  Location/Qualifiers
source                    1..25
                          mol_type = other DNA
                          organism = synthetic construct
SEQUENCE: 417
caaaaggtct gagagactac ctttt                                          25

SEQ ID NO: 418           moltype = DNA   length = 23
FEATURE                  Location/Qualifiers
source                    1..23
                          mol_type = other DNA
                          organism = synthetic construct
SEQUENCE: 418
ttgccaaaga caaaagggct ttt                                             23

SEQ ID NO: 419           moltype = DNA   length = 30
FEATURE                  Location/Qualifiers
source                    1..30
                          mol_type = other DNA
                          organism = synthetic construct
SEQUENCE: 419
cagattagga gaggctgaga ctcctctttt                                     30

SEQ ID NO: 420           moltype = DNA   length = 47
FEATURE                  Location/Qualifiers
source                    1..47
                          mol_type = other DNA
                          organism = synthetic construct
SEQUENCE: 420
ggcgcacgaa acatgacccc taatgccgtt tccattaaac gggtttt                  47

SEQ ID NO: 421           moltype = DNA   length = 16
FEATURE                  Location/Qualifiers
source                    1..16
                          mol_type = other DNA
                          organism = synthetic construct
SEQUENCE: 421
tttttaaaca ctattt                                                    16

SEQ ID NO: 422           moltype = DNA   length = 36
FEATURE                  Location/Qualifiers
source                    1..36
                          mol_type = other DNA
                          organism = synthetic construct
SEQUENCE: 422
ggtataaatc aaaagaataa tcggcaaaat ccctga                              36

SEQ ID NO: 423           moltype = DNA   length = 36
FEATURE                  Location/Qualifiers
source                    1..36
                          mol_type = other DNA
                          organism = synthetic construct
SEQUENCE: 423
cctgccccag caggcgaagc ggtccacgct ggttgc                              36

SEQ ID NO: 424           moltype = DNA   length = 36
```

-continued

```
FEATURE               Location/Qualifiers
source                1..36
                      mol_type = other DNA
                      organism = synthetic construct
SEQUENCE: 424
aagattgccc ttcaccgcga gacgggcaac agctcg                          36

SEQ ID NO: 425        moltype = DNA   length = 36
FEATURE               Location/Qualifiers
source                1..36
                      mol_type = other DNA
                      organism = synthetic construct
SEQUENCE: 425
gcttgcgtat tgggcgcccg cggggagagg cggtaa                          36

SEQ ID NO: 426        moltype = DNA   length = 35
FEATURE               Location/Qualifiers
source                1..35
                      mol_type = other DNA
                      organism = synthetic construct
SEQUENCE: 426
agaaacctgt cgtgccaccc gctttccagt cggac                           35

SEQ ID NO: 427        moltype = DNA   length = 16
FEATURE               Location/Qualifiers
source                1..16
                      mol_type = other DNA
                      organism = synthetic construct
SEQUENCE: 427
gggagtaacg accgtg                                                16

SEQ ID NO: 428        moltype = DNA   length = 36
FEATURE               Location/Qualifiers
source                1..36
                      mol_type = other DNA
                      organism = synthetic construct
SEQUENCE: 428
tgttttgaat ggctattagt ggcacagaca atattg                          36

SEQ ID NO: 429        moltype = DNA   length = 36
FEATURE               Location/Qualifiers
source                1..36
                      mol_type = other DNA
                      organism = synthetic construct
SEQUENCE: 429
tgtgaggcgg tcagtattga agataaaaca gaggca                          36

SEQ ID NO: 430        moltype = DNA   length = 36
FEATURE               Location/Qualifiers
source                1..36
                      mol_type = other DNA
                      organism = synthetic construct
SEQUENCE: 430
agaatatcaa accctcaaac cttgctgaac ctcagg                          36

SEQ ID NO: 431        moltype = DNA   length = 36
FEATURE               Location/Qualifiers
source                1..36
                      mol_type = other DNA
                      organism = synthetic construct
SEQUENCE: 431
ggtaatagat tagagccgta ggagcactaa caacgc                          36

SEQ ID NO: 432        moltype = DNA   length = 36
FEATURE               Location/Qualifiers
source                1..36
                      mol_type = other DNA
                      organism = synthetic construct
SEQUENCE: 432
ggcccgaacg ttattaatcg tattaaatcc tttgca                          36

SEQ ID NO: 433        moltype = DNA   length = 36
FEATURE               Location/Qualifiers
source                1..36
                      mol_type = other DNA
                      organism = synthetic construct
SEQUENCE: 433
cgtcagatga tggcaattat catattcctg attaac                          36
```

```
SEQ ID NO: 434            moltype = DNA   length = 36
FEATURE                   Location/Qualifiers
source                    1..36
                          mol_type = other DNA
                          organism = synthetic construct
SEQUENCE: 434
tcgaaataaa gaaattgcat ttgcacgtaa aacagg                              36

SEQ ID NO: 435            moltype = DNA   length = 34
FEATURE                   Location/Qualifiers
source                    1..34
                          mol_type = other DNA
                          organism = synthetic construct
SEQUENCE: 435
acccaatagg aacgccacag ctcatttttt aaag                                34

SEQ ID NO: 436            moltype = DNA   length = 36
FEATURE                   Location/Qualifiers
source                    1..36
                          mol_type = other DNA
                          organism = synthetic construct
SEQUENCE: 436
atgcctgatt gctttgaaaa acaataacgg attcca                              36

SEQ ID NO: 437            moltype = DNA   length = 36
FEATURE                   Location/Qualifiers
source                    1..36
                          mol_type = other DNA
                          organism = synthetic construct
SEQUENCE: 437
ttgagatcta caaaggctgg gtagctattt ttgaca                              36

SEQ ID NO: 438            moltype = DNA   length = 36
FEATURE                   Location/Qualifiers
source                    1..36
                          mol_type = other DNA
                          organism = synthetic construct
SEQUENCE: 438
aatcaagaaa acaaaattga tgatgaaaca aacatg                              36

SEQ ID NO: 439            moltype = DNA   length = 28
FEATURE                   Location/Qualifiers
source                    1..28
                          mol_type = other DNA
                          organism = synthetic construct
SEQUENCE: 439
tatggcatca attcatcggt tgtaccgg                                       28

SEQ ID NO: 440            moltype = DNA   length = 25
FEATURE                   Location/Qualifiers
source                    1..25
                          mol_type = other DNA
                          organism = synthetic construct
SEQUENCE: 440
ggaatcgtcg cacatagcga tagcg                                          25

SEQ ID NO: 441            moltype = DNA   length = 25
FEATURE                   Location/Qualifiers
source                    1..25
                          mol_type = other DNA
                          organism = synthetic construct
SEQUENCE: 441
gtatggctta gagcccaatt ctgct                                          25

SEQ ID NO: 442            moltype = DNA   length = 25
FEATURE                   Location/Qualifiers
source                    1..25
                          mol_type = other DNA
                          organism = synthetic construct
SEQUENCE: 442
ggctgagaga ctataactat atgag                                          25

SEQ ID NO: 443            moltype = DNA   length = 25
FEATURE                   Location/Qualifiers
source                    1..25
                          mol_type = other DNA
                          organism = synthetic construct
SEQUENCE: 443
tcaccataaa tcaatttaat tcgta                                          25
```

-continued

```
SEQ ID NO: 444          moltype = DNA   length = 25
FEATURE                 Location/Qualifiers
source                  1..25
                        mol_type = other DNA
                        organism = synthetic construct
SEQUENCE: 444
tgaaatatat ttggtttgaa atacc                                                    25

SEQ ID NO: 445          moltype = DNA   length = 34
FEATURE                 Location/Qualifiers
source                  1..34
                        mol_type = other DNA
                        organism = synthetic construct
SEQUENCE: 445
atgaccataa atcgcctgat aaatggaggg aggg                                          34

SEQ ID NO: 446          moltype = DNA   length = 34
FEATURE                 Location/Qualifiers
source                  1..34
                        mol_type = other DNA
                        organism = synthetic construct
SEQUENCE: 446
tgtgtcgaaa tccctcagaa ccgcggaggg aggg                                          34

SEQ ID NO: 447          moltype = DNA   length = 34
FEATURE                 Location/Qualifiers
source                  1..34
                        mol_type = other DNA
                        organism = synthetic construct
SEQUENCE: 447
caccctcaga gcgcagcacc gtaaggaggg aggg                                          34

SEQ ID NO: 448          moltype = DNA   length = 42
FEATURE                 Location/Qualifiers
source                  1..42
                        mol_type = other DNA
                        organism = synthetic construct
SEQUENCE: 448
tttaggcaga ggcattcaac gccaacatgt aaccagccag cc                                 42

SEQ ID NO: 449          moltype = DNA   length = 42
FEATURE                 Location/Qualifiers
source                  1..42
                        mol_type = other DNA
                        organism = synthetic construct
SEQUENCE: 449
cgaacaaagt taccagaaag taagcagata gcccagccag cc                                 42

SEQ ID NO: 450          moltype = DNA   length = 42
FEATURE                 Location/Qualifiers
source                  1..42
                        mol_type = other DNA
                        organism = synthetic construct
SEQUENCE: 450
gtaagcgtca tacatgtgaa tttaccgttc caccagccag cc                                 42

SEQ ID NO: 451          moltype = DNA   length = 19
FEATURE                 Location/Qualifiers
source                  1..19
                        mol_type = other DNA
                        organism = synthetic construct
SEQUENCE: 451
ttgctttgac gagcacgta                                                           19

SEQ ID NO: 452          moltype = DNA   length = 24
FEATURE                 Location/Qualifiers
source                  1..24
                        mol_type = other DNA
                        organism = synthetic construct
SEQUENCE: 452
gccgctacag ggcgcgtggt caat                                                     24

SEQ ID NO: 453          moltype = DNA   length = 35
FEATURE                 Location/Qualifiers
source                  1..35
                        mol_type = other DNA
                        organism = synthetic construct
SEQUENCE: 453
```

-continued

```
taacgtgctt tcaattctac caccgagtaa aagtt                            35

SEQ ID NO: 454        moltype = DNA   length = 32
FEATURE               Location/Qualifiers
source                1..32
                      mol_type = other DNA
                      organism = synthetic construct
SEQUENCE: 454
aacctgttta gctagcttag tttgaccatt ag                               32

SEQ ID NO: 455        moltype = DNA   length = 48
FEATURE               Location/Qualifiers
source                1..48
                      mol_type = other DNA
                      organism = synthetic construct
SEQUENCE: 455
agggcgctga acgtggcgag aaagggagc ccccgattta ggtcgagg               48

SEQ ID NO: 456        moltype = DNA   length = 32
FEATURE               Location/Qualifiers
source                1..32
                      mol_type = other DNA
                      organism = synthetic construct
SEQUENCE: 456
ggtggcatcc tcgttagaat caaatactat gg                               32

SEQ ID NO: 457        moltype = DNA   length = 32
FEATURE               Location/Qualifiers
source                1..32
                      mol_type = other DNA
                      organism = synthetic construct
SEQUENCE: 457
gaaatatttt catttgagta cggtgctgaa ta                               32

SEQ ID NO: 458        moltype = DNA   length = 27
FEATURE               Location/Qualifiers
source                1..27
                      mol_type = other DNA
                      organism = synthetic construct
SEQUENCE: 458
atagtagtag cctaaatcga aactatc                                     27

SEQ ID NO: 459        moltype = DNA   length = 32
FEATURE               Location/Qualifiers
source                1..32
                      mol_type = other DNA
                      organism = synthetic construct
SEQUENCE: 459
gcaaggcaaa gaaggagctt aattgtctgg aa                               32

SEQ ID NO: 460        moltype = DNA   length = 43
FEATURE               Location/Qualifiers
source                1..43
                      mol_type = other DNA
                      organism = synthetic construct
SEQUENCE: 460
gcataaagat taacatcatg agtctgtcca tcagcaaaat cac                   43

SEQ ID NO: 461        moltype = DNA   length = 32
FEATURE               Location/Qualifiers
source                1..32
                      mol_type = other DNA
                      organism = synthetic construct
SEQUENCE: 461
atcttagcaa aattaacagg attaattcga gc                               32

SEQ ID NO: 462        moltype = DNA   length = 48
FEATURE               Location/Qualifiers
source                1..48
                      mol_type = other DNA
                      organism = synthetic construct
SEQUENCE: 462
tgccgtaagt ctatcagtga accattggaa caagagtcca aaagaata             48

SEQ ID NO: 463        moltype = DNA   length = 27
FEATURE               Location/Qualifiers
source                1..27
                      mol_type = other DNA
                      organism = synthetic construct
```

-continued

```
SEQUENCE: 463
gtaccaaaaa caaaatttta ataccta                                                    27

SEQ ID NO: 464          moltype = DNA   length = 32
FEATURE                 Location/Qualifiers
source                  1..32
                        mol_type = other DNA
                        organism = synthetic construct
SEQUENCE: 464
gggaacgtca aagggcgcgt tttagagagt ac                                              32

SEQ ID NO: 465          moltype = DNA   length = 43
FEATURE                 Location/Qualifiers
source                  1..43
                        mol_type = other DNA
                        organism = synthetic construct
SEQUENCE: 465
caaggataat tatgacccgt gctggtaata tcgcgcagtc tct                                  43

SEQ ID NO: 466          moltype = DNA   length = 32
FEATURE                 Location/Qualifiers
source                  1..32
                        mol_type = other DNA
                        organism = synthetic construct
SEQUENCE: 466
gaacgtggac tccagatagt cagacgagaa tg                                              32

SEQ ID NO: 467          moltype = DNA   length = 47
FEATURE                 Location/Qualifiers
source                  1..47
                        mol_type = other DNA
                        organism = synthetic construct
SEQUENCE: 467
aaccctcata taggccggag agggggtgct tttgctattc ggttatt                             47

SEQ ID NO: 468          moltype = DNA   length = 32
FEATURE                 Location/Qualifiers
source                  1..32
                        mol_type = other DNA
                        organism = synthetic construct
SEQUENCE: 468
tgtggcaaaa tccctttcag aaaaagcaaa gc                                              32

SEQ ID NO: 469          moltype = DNA   length = 48
FEATURE                 Location/Qualifiers
source                  1..48
                        mol_type = other DNA
                        organism = synthetic construct
SEQUENCE: 469
gcccgagagc aggcgaaaat cctgagagag ttgcagcaag tttttctt                            48

SEQ ID NO: 470          moltype = DNA   length = 43
FEATURE                 Location/Qualifiers
source                  1..43
                        mol_type = other DNA
                        organism = synthetic construct
SEQUENCE: 470
ggtgagaaat tttaaacagt gacgctcaat cggggatagc aag                                 43

SEQ ID NO: 471          moltype = DNA   length = 24
FEATURE                 Location/Qualifiers
source                  1..24
                        mol_type = other DNA
                        organism = synthetic construct
SEQUENCE: 471
aaatcgtaag cgtccaccag acga                                                       24

SEQ ID NO: 472          moltype = DNA   length = 40
FEATURE                 Location/Qualifiers
source                  1..40
                        mol_type = other DNA
                        organism = synthetic construct
SEQUENCE: 472
agtcaaatca cctattttttt atttttgatg tcaatcatat                                    40

SEQ ID NO: 473          moltype = DNA   length = 32
FEATURE                 Location/Qualifiers
source                  1..32
                        mol_type = other DNA
```

```
                        organism = synthetic construct
SEQUENCE: 473
taggcccttc accgccctcg tttaatactg cg                                    32

SEQ ID NO: 474          moltype = DNA   length = 32
FEATURE                 Location/Qualifiers
source                  1..32
                        mol_type = other DNA
                        organism = synthetic construct
SEQUENCE: 474
gagggtagca tcaataagcg agagaatagt aa                                    32

SEQ ID NO: 475          moltype = DNA   length = 48
FEATURE                 Location/Qualifiers
source                  1..48
                        mol_type = other DNA
                        organism = synthetic construct
SEQUENCE: 475
tgattctgct aatgcagaga atcggaagat tgtattaact cacattaa                  48

SEQ ID NO: 476          moltype = DNA   length = 40
FEATURE                 Location/Qualifiers
source                  1..40
                        mol_type = other DNA
                        organism = synthetic construct
SEQUENCE: 476
ttcaccaggc ggggagaggc ggtttgcgta tttccagtcg                           40

SEQ ID NO: 477          moltype = DNA   length = 35
FEATURE                 Location/Qualifiers
source                  1..35
                        mol_type = other DNA
                        organism = synthetic construct
SEQUENCE: 477
agatctacaa aggctatcaa aactagcaat attta                                35

SEQ ID NO: 478          moltype = DNA   length = 40
FEATURE                 Location/Qualifiers
source                  1..40
                        mol_type = other DNA
                        organism = synthetic construct
SEQUENCE: 478
tctggagcaa aaatcggcca acgctgagac gggcaacagc                           40

SEQ ID NO: 479          moltype = DNA   length = 24
FEATURE                 Location/Qualifiers
source                  1..24
                        mol_type = other DNA
                        organism = synthetic construct
SEQUENCE: 479
taatcgtagg tcattgatgc cgga                                            24

SEQ ID NO: 480          moltype = DNA   length = 37
FEATURE                 Location/Qualifiers
source                  1..37
                        mol_type = other DNA
                        organism = synthetic construct
SEQUENCE: 480
gtaccccggt tgataatcag aatattttga gatgcga                             37

SEQ ID NO: 481          moltype = DNA   length = 48
FEATURE                 Location/Qualifiers
source                  1..48
                        mol_type = other DNA
                        organism = synthetic construct
SEQUENCE: 481
ttgcgttggt cgtgccagct gcattaatgc aagatacata acaacatt                 48

SEQ ID NO: 482          moltype = DNA   length = 35
FEATURE                 Location/Qualifiers
source                  1..35
                        mol_type = other DNA
                        organism = synthetic construct
SEQUENCE: 482
aaacgttaaa agccccttca tcagttgagg gccgc                                35

SEQ ID NO: 483          moltype = DNA   length = 32
FEATURE                 Location/Qualifiers
source                  1..32
```

-continued

```
                          mol_type = other DNA
                          organism = synthetic construct
SEQUENCE: 483
ctaatgagtg agcaagagtc aggaggttta at                                        32

SEQ ID NO: 484           moltype = DNA   length = 37
FEATURE                  Location/Qualifiers
source                   1..37
                         mol_type = other DNA
                         organism = synthetic construct
SEQUENCE: 484
taaatttttg ttaaatcagc ttaattcgct tggtaac                                   37

SEQ ID NO: 485           moltype = DNA   length = 32
FEATURE                  Location/Qualifiers
source                   1..32
                         mol_type = other DNA
                         organism = synthetic construct
SEQUENCE: 485
gttatccgca tagctggctt gccctcttga ca                                        32

SEQ ID NO: 486           moltype = DNA   length = 35
FEATURE                  Location/Qualifiers
source                   1..35
                         mol_type = other DNA
                         organism = synthetic construct
SEQUENCE: 486
atcaaaaaca ttttttgtga attaccttaa gaagc                                     35

SEQ ID NO: 487           moltype = DNA   length = 48
FEATURE                  Location/Qualifiers
source                   1..48
                         mol_type = other DNA
                         organism = synthetic construct
SEQUENCE: 487
gtagccagct ttcatcaaca ttccgtgggc cgaactgcgc agacgacg                       48

SEQ ID NO: 488           moltype = DNA   length = 32
FEATURE                  Location/Qualifiers
source                   1..32
                         mol_type = other DNA
                         organism = synthetic construct
SEQUENCE: 488
tgccaagcac gacgttaacg gtgtgacctg ct                                        32

SEQ ID NO: 489           moltype = DNA   length = 48
FEATURE                  Location/Qualifiers
source                   1..48
                         mol_type = other DNA
                         organism = synthetic construct
SEQUENCE: 489
ctgcaggtaa ttcgtaatca tggtctcaca attccacaca tggggtgc                       48

SEQ ID NO: 490           moltype = DNA   length = 35
FEATURE                  Location/Qualifiers
source                   1..35
                         mol_type = other DNA
                         organism = synthetic construct
SEQUENCE: 490
tcggattcta aatgtgtacc caaatcaacc tgcgg                                     35

SEQ ID NO: 491           moltype = DNA   length = 37
FEATURE                  Location/Qualifiers
source                   1..37
                         mol_type = other DNA
                         organism = synthetic construct
SEQUENCE: 491
ttgaccgtaa tgggataggt ccatctgccg accccca                                   37

SEQ ID NO: 492           moltype = DNA   length = 32
FEATURE                  Location/Qualifiers
source                   1..32
                         mol_type = other DNA
                         organism = synthetic construct
SEQUENCE: 492
taaccgtgac gttggtgaac gaggaccaac tt                                        32

SEQ ID NO: 493           moltype = DNA   length = 48
FEATURE                  Location/Qualifiers
```

-continued

```
source                    1..48
                          mol_type = other DNA
                          organism = synthetic construct
SEQUENCE: 493
tgggaaggag ctggcgaaag ggggcagggt tttcccagtc ttgcatgc                48

SEQ ID NO: 494           moltype = DNA   length = 45
FEATURE                  Location/Qualifiers
source                   1..45
                          mol_type = other DNA
                          organism = synthetic construct
SEQUENCE: 494
gacgacagta tcggcctcag gaagatcgca ctccagcgcg catcg                45

SEQ ID NO: 495           moltype = DNA   length = 24
FEATURE                  Location/Qualifiers
source                   1..24
                          mol_type = other DNA
                          organism = synthetic construct
SEQUENCE: 495
cttctggtgc cggaaagcaa ctgt                                       24

SEQ ID NO: 496           moltype = DNA   length = 32
FEATURE                  Location/Qualifiers
source                   1..32
                          mol_type = other DNA
                          organism = synthetic construct
SEQUENCE: 496
atacatttgc aactaagggc gcgatcatac ag                              32

SEQ ID NO: 497           moltype = DNA   length = 40
FEATURE                  Location/Qualifiers
source                   1..40
                          mol_type = other DNA
                          organism = synthetic construct
SEQUENCE: 497
gtttcattga gtagatgaaa ggagccgccg cgcttaatgc                      40

SEQ ID NO: 498           moltype = DNA   length = 32
FEATURE                  Location/Qualifiers
source                   1..32
                          mol_type = other DNA
                          organism = synthetic construct
SEQUENCE: 498
taatgctgca acaggtgcaa taaaactttt gc                              32

SEQ ID NO: 499           moltype = DNA   length = 40
FEATURE                  Location/Qualifiers
source                   1..40
                          mol_type = other DNA
                          organism = synthetic construct
SEQUENCE: 499
ggcctgaagc aaactctagc tcaaccaata aagctgaaaa                      40

SEQ ID NO: 500           moltype = DNA   length = 32
FEATURE                  Location/Qualifiers
source                   1..32
                          mol_type = other DNA
                          organism = synthetic construct
SEQUENCE: 500
ctttaattgg cttagaaccc taaagaaggg aa                              32

SEQ ID NO: 501           moltype = DNA   length = 48
FEATURE                  Location/Qualifiers
source                   1..48
                          mol_type = other DNA
                          organism = synthetic construct
SEQUENCE: 501
ccagccattc acttgcccat atttaaggct tacaatagca cgaattca             48

SEQ ID NO: 502           moltype = DNA   length = 32
FEATURE                  Location/Qualifiers
source                   1..32
                          mol_type = other DNA
                          organism = synthetic construct
SEQUENCE: 502
ttcaaagcga ctattaagcc tttactgagt aa                              32

SEQ ID NO: 503           moltype = DNA   length = 40
```

-continued

```
FEATURE               Location/Qualifiers
source                1..40
                      mol_type = other DNA
                      organism = synthetic construct
SEQUENCE: 503
catttgtctt taccctgaac cagacctgta atgcctcaga                                40

SEQ ID NO: 504        moltype = DNA   length = 32
FEATURE               Location/Qualifiers
source                1..32
                      mol_type = other DNA
                      organism = synthetic construct
SEQUENCE: 504
ggattgcaca aatatcgaaa aaccagcact aa                                        32

SEQ ID NO: 505        moltype = DNA   length = 48
FEATURE               Location/Qualifiers
source                1..48
                      mol_type = other DNA
                      organism = synthetic construct
SEQUENCE: 505
tacattggtg caacagtaat tttcttaatt gaaaagccaa gaggacga                       48

SEQ ID NO: 506        moltype = DNA   length = 32
FEATURE               Location/Qualifiers
source                1..32
                      mol_type = other DNA
                      organism = synthetic construct
SEQUENCE: 506
accataaaga ctggatggta aagaaaccgt tc                                        32

SEQ ID NO: 507        moltype = DNA   length = 32
FEATURE               Location/Qualifiers
source                1..32
                      mol_type = other DNA
                      organism = synthetic construct
SEQUENCE: 507
aatgtttatc aaaaattgca atgctttcaa cg                                        32

SEQ ID NO: 508        moltype = DNA   length = 32
FEATURE               Location/Qualifiers
source                1..32
                      mol_type = other DNA
                      organism = synthetic construct
SEQUENCE: 508
gaatcgtcta aacagtataa atcactatta aa                                        32

SEQ ID NO: 509        moltype = DNA   length = 48
FEATURE               Location/Qualifiers
source                1..48
                      mol_type = other DNA
                      organism = synthetic construct
SEQUENCE: 509
aacagagaag taataaggat tatatcgtcg ctagtgaata tagccctc                       48

SEQ ID NO: 510        moltype = DNA   length = 32
FEATURE               Location/Qualifiers
source                1..32
                      mol_type = other DNA
                      organism = synthetic construct
SEQUENCE: 510
cgataaaaac attcaaataa attacctgag ag                                        32

SEQ ID NO: 511        moltype = DNA   length = 32
FEATURE               Location/Qualifiers
source                1..32
                      mol_type = other DNA
                      organism = synthetic construct
SEQUENCE: 511
ggataccac caaaattgat attcttcaaa ag                                         32

SEQ ID NO: 512        moltype = DNA   length = 36
FEATURE               Location/Qualifiers
source                1..36
                      mol_type = other DNA
                      organism = synthetic construct
SEQUENCE: 512
caaatcataa cctggccctg tttgatggtg gttccg                                    36
```

-continued

```
SEQ ID NO: 513          moltype = DNA   length = 28
FEATURE                 Location/Qualifiers
source                  1..28
                        mol_type = other DNA
                        organism = synthetic construct
SEQUENCE: 513
ccctaatcct gacagatgat ctattgat                                          28

SEQ ID NO: 514          moltype = DNA   length = 24
FEATURE                 Location/Qualifiers
source                  1..24
                        mol_type = other DNA
                        organism = synthetic construct
SEQUENCE: 514
gcgaactgta cgtggcttct ggcc                                              24

SEQ ID NO: 515          moltype = DNA   length = 25
FEATURE                 Location/Qualifiers
source                  1..25
                        mol_type = other DNA
                        organism = synthetic construct
SEQUENCE: 515
agtcccacca gcttaaaatt cgcat                                             25

SEQ ID NO: 516          moltype = DNA   length = 32
FEATURE                 Location/Qualifiers
source                  1..32
                        mol_type = other DNA
                        organism = synthetic construct
SEQUENCE: 516
attacaggat tatacccaaa tattgtgaaa tt                                     32

SEQ ID NO: 517          moltype = DNA   length = 40
FEATURE                 Location/Qualifiers
source                  1..40
                        mol_type = other DNA
                        organism = synthetic construct
SEQUENCE: 517
ttttaagaac tggctctaga aagaaaaaac agatgaacgg                             40

SEQ ID NO: 518          moltype = DNA   length = 32
FEATURE                 Location/Qualifiers
source                  1..32
                        mol_type = other DNA
                        organism = synthetic construct
SEQUENCE: 518
cggtcagtaa aaatacaagg ccgcttgcgc at                                     32

SEQ ID NO: 519          moltype = DNA   length = 32
FEATURE                 Location/Qualifiers
source                  1..32
                        mol_type = other DNA
                        organism = synthetic construct
SEQUENCE: 519
ttcaactttg aataagtttc ctgtacggcc ag                                     32

SEQ ID NO: 520          moltype = DNA   length = 40
FEATURE                 Location/Qualifiers
source                  1..40
                        mol_type = other DNA
                        organism = synthetic construct
SEQUENCE: 520
aaagctgctc attcagtaat cattaaccaa tataaattgt                             40

SEQ ID NO: 521          moltype = DNA   length = 28
FEATURE                 Location/Qualifiers
source                  1..28
                        mol_type = other DNA
                        organism = synthetic construct
SEQUENCE: 521
atctatcatt ttaattttaa taaaaatc                                          28

SEQ ID NO: 522          moltype = DNA   length = 40
FEATURE                 Location/Qualifiers
source                  1..40
                        mol_type = other DNA
                        organism = synthetic construct
SEQUENCE: 522
ccctcaataa atgaaaccac cagattttgc ggtttcttaa                             40
```

-continued

```
SEQ ID NO: 523              moltype = DNA   length = 32
FEATURE                     Location/Qualifiers
source                      1..32
                            mol_type = other DNA
                            organism = synthetic construct
SEQUENCE: 523
agaaccggga cagatggtaa aacgtcttcg ct                                       32

SEQ ID NO: 524              moltype = DNA   length = 32
FEATURE                     Location/Qualifiers
source                      1..32
                            mol_type = other DNA
                            organism = synthetic construct
SEQUENCE: 524
tgaaagagat attcatagcg agtaggaacg cc                                       32

SEQ ID NO: 525              moltype = DNA   length = 40
FEATURE                     Location/Qualifiers
source                      1..40
                            mol_type = other DNA
                            organism = synthetic construct
SEQUENCE: 525
aggttatctc aacagttaaa gactgcggaa cagtatgcgt                               40

SEQ ID NO: 526              moltype = DNA   length = 40
FEATURE                     Location/Qualifiers
source                      1..40
                            mol_type = other DNA
                            organism = synthetic construct
SEQUENCE: 526
ccatgttacg aaacaatgcg ggcccagctt tccggcaccg                               40

SEQ ID NO: 527              moltype = DNA   length = 32
FEATURE                     Location/Qualifiers
source                      1..32
                            mol_type = other DNA
                            organism = synthetic construct
SEQUENCE: 527
gtcaacacct acgaagtttt catgtttttc ac                                       32

SEQ ID NO: 528              moltype = DNA   length = 40
FEATURE                     Location/Qualifiers
source                      1..40
                            mol_type = other DNA
                            organism = synthetic construct
SEQUENCE: 528
gcgattatac caagcgctta gccggtagat ggacaacccg                               40

SEQ ID NO: 529              moltype = DNA   length = 48
FEATURE                     Location/Qualifiers
source                      1..48
                            mol_type = other DNA
                            organism = synthetic construct
SEQUENCE: 529
aatacattat tcgacagcac caacaagatt gctttgaata tcatttca                      48

SEQ ID NO: 530              moltype = DNA   length = 17
FEATURE                     Location/Qualifiers
source                      1..17
                            mol_type = other DNA
                            organism = synthetic construct
SEQUENCE: 530
ggcaaaagaa tatagat                                                        17

SEQ ID NO: 531              moltype = DNA   length = 15
FEATURE                     Location/Qualifiers
source                      1..15
                            mol_type = other DNA
                            organism = synthetic construct
SEQUENCE: 531
ttggtaaaat acgtt                                                          15

SEQ ID NO: 532              moltype = DNA   length = 48
FEATURE                     Location/Qualifiers
source                      1..48
                            mol_type = other DNA
                            organism = synthetic construct
SEQUENCE: 532
```

-continued

```
ctacagaggc ttccattaag tcaatcatca tctttagttt gaggggac              48

SEQ ID NO: 533         moltype = DNA   length = 15
FEATURE                Location/Qualifiers
source                 1..15
                       mol_type = other DNA
                       organism = synthetic construct
SEQUENCE: 533
ttgtaacatt ggttt                                                  15

SEQ ID NO: 534         moltype = DNA   length = 37
FEATURE                Location/Qualifiers
source                 1..37
                       mol_type = other DNA
                       organism = synthetic construct
SEQUENCE: 534
ggtagcaaaa cctcaataag ggaaaacaaa cggcgga                          37

SEQ ID NO: 535         moltype = DNA   length = 35
FEATURE                Location/Qualifiers
source                 1..35
                       mol_type = other DNA
                       organism = synthetic construct
SEQUENCE: 535
gaaagacagc atcggaaaaa atctaaaagg tgagg                            35

SEQ ID NO: 536         moltype = DNA   length = 48
FEATURE                Location/Qualifiers
source                 1..48
                       mol_type = other DNA
                       organism = synthetic construct
SEQUENCE: 536
tgaggcttgc accctcagct aaaacaggca tcaccgtctg gccttcct              48

SEQ ID NO: 537         moltype = DNA   length = 27
FEATURE                Location/Qualifiers
source                 1..27
                       mol_type = other DNA
                       organism = synthetic construct
SEQUENCE: 537
aaccgataaa aagaagacag acaagag                                     27

SEQ ID NO: 538         moltype = DNA   length = 37
FEATURE                Location/Qualifiers
source                 1..37
                       mol_type = other DNA
                       organism = synthetic construct
SEQUENCE: 538
gacaacaacc atcgcccatt taagggacag gattatt                          37

SEQ ID NO: 539         moltype = DNA   length = 24
FEATURE                Location/Qualifiers
source                 1..24
                       mol_type = other DNA
                       organism = synthetic construct
SEQUENCE: 539
accgatagcc gtaacaatta ccct                                        24

SEQ ID NO: 540         moltype = DNA   length = 32
FEATURE                Location/Qualifiers
source                 1..32
                       mol_type = other DNA
                       organism = synthetic construct
SEQUENCE: 540
acagcccata tatgtgtaat ggaaagtgaa tt                               32

SEQ ID NO: 541         moltype = DNA   length = 45
FEATURE                Location/Qualifiers
source                 1..45
                       mol_type = other DNA
                       organism = synthetic construct
SEQUENCE: 541
ctttcgaggt gaagatcgtc agggagttac gaacgaattt aatgc                 45

SEQ ID NO: 542         moltype = DNA   length = 32
FEATURE                Location/Qualifiers
source                 1..32
                       mol_type = other DNA
                       organism = synthetic construct
```

```
SEQUENCE: 542
gaaattcgac ctttttctga gttttttagt ac                                          32

SEQ ID NO: 543          moltype = DNA   length = 32
FEATURE                 Location/Qualifiers
source                  1..32
                        mol_type = other DNA
                        organism = synthetic construct
SEQUENCE: 543
agattttcat ttaacacatc aagattaggc gg                                          32

SEQ ID NO: 544          moltype = DNA   length = 21
FEATURE                 Location/Qualifiers
source                  1..21
                        mol_type = other DNA
                        organism = synthetic construct
SEQUENCE: 544
ggagccttta attaagacga g                                                      21

SEQ ID NO: 545          moltype = DNA   length = 32
FEATURE                 Location/Qualifiers
source                  1..32
                        mol_type = other DNA
                        organism = synthetic construct
SEQUENCE: 545
tccaaaaaag ttttgtattt cattcccaaa tc                                          32

SEQ ID NO: 546          moltype = DNA   length = 32
FEATURE                 Location/Qualifiers
source                  1..32
                        mol_type = other DNA
                        organism = synthetic construct
SEQUENCE: 546
gttgacagga aacaaaatta cctgtgatgc aa                                          32

SEQ ID NO: 547          moltype = DNA   length = 45
FEATURE                 Location/Qualifiers
source                  1..45
                        mol_type = other DNA
                        organism = synthetic construct
SEQUENCE: 547
tgcgaataat aataggaagt tttgaggact gaaaggaata tcaaa                            45

SEQ ID NO: 548          moltype = DNA   length = 32
FEATURE                 Location/Qualifiers
source                  1..32
                        mol_type = other DNA
                        organism = synthetic construct
SEQUENCE: 548
gcctggaata aacaaccgtc tttcttgctc ag                                          32

SEQ ID NO: 549          moltype = DNA   length = 48
FEATURE                 Location/Qualifiers
source                  1..48
                        mol_type = other DNA
                        organism = synthetic construct
SEQUENCE: 549
tttcaacatc catcgcaaga caaagttaat tttgaaacat ccaagtcc                         48

SEQ ID NO: 550          moltype = DNA   length = 15
FEATURE                 Location/Qualifiers
source                  1..15
                        mol_type = other DNA
                        organism = synthetic construct
SEQUENCE: 550
tttctgtatg gtttt                                                             15

SEQ ID NO: 551          moltype = DNA   length = 22
FEATURE                 Location/Qualifiers
source                  1..22
                        mol_type = other DNA
                        organism = synthetic construct
SEQUENCE: 551
agttagcgta aagtaaatga at                                                     22

SEQ ID NO: 552          moltype = DNA   length = 32
FEATURE                 Location/Qualifiers
source                  1..32
                        mol_type = other DNA
```

-continued

```
                             organism = synthetic construct
SEQUENCE: 552
aacgcctgta gcattcattg tttatcagct tg                                    32

SEQ ID NO: 553           moltype = DNA   length = 27
FEATURE                  Location/Qualifiers
source                   1..27
                         mol_type = other DNA
                         organism = synthetic construct
SEQUENCE: 553
cattttcatc tgaaattttt gccagac                                          27

SEQ ID NO: 554           moltype = DNA   length = 37
FEATURE                  Location/Qualifiers
source                   1..37
                         mol_type = other DNA
                         organism = synthetic construct
SEQUENCE: 554
gccaccctca gagccaccaa tgaaaaacgt attaccg                               37

SEQ ID NO: 555           moltype = DNA   length = 24
FEATURE                  Location/Qualifiers
source                   1..24
                         mol_type = other DNA
                         organism = synthetic construct
SEQUENCE: 555
agaaccgcac cagtatgaag ccag                                             24

SEQ ID NO: 556           moltype = DNA   length = 32
FEATURE                  Location/Qualifiers
source                   1..32
                         mol_type = other DNA
                         organism = synthetic construct
SEQUENCE: 556
cgccacttca tatgcgtact agaaaaagta cc                                    32

SEQ ID NO: 557           moltype = DNA   length = 42
FEATURE                  Location/Qualifiers
source                   1..42
                         mol_type = other DNA
                         organism = synthetic construct
SEQUENCE: 557
cgtactcagg aggcgtcacc acccatgtat tgcgccgaca at                         42

SEQ ID NO: 558           moltype = DNA   length = 32
FEATURE                  Location/Qualifiers
source                   1..32
                         mol_type = other DNA
                         organism = synthetic construct
SEQUENCE: 558
tatcaggagt actggtttat acaattgagg ca                                    32

SEQ ID NO: 559           moltype = DNA   length = 32
FEATURE                  Location/Qualifiers
source                   1..32
                         mol_type = other DNA
                         organism = synthetic construct
SEQUENCE: 559
ataggtctat cataatcgtt aaatcatccc tc                                    32

SEQ ID NO: 560           moltype = DNA   length = 32
FEATURE                  Location/Qualifiers
source                   1..32
                         mol_type = other DNA
                         organism = synthetic construct
SEQUENCE: 560
ataagtgcaa ataaggaata agttccaaag gt                                    32

SEQ ID NO: 561           moltype = DNA   length = 32
FEATURE                  Location/Qualifiers
source                   1..32
                         mol_type = other DNA
                         organism = synthetic construct
SEQUENCE: 561
taccaggttt tgaaatcatc ttcttcaaca at                                    32

SEQ ID NO: 562           moltype = DNA   length = 42
FEATURE                  Location/Qualifiers
source                   1..42
```

-continued

```
                              mol_type = other DNA
                              organism = synthetic construct
SEQUENCE: 562
gattagcggg gttcagacgt tcgatctaaa aaggctccaa aa                          42

SEQ ID NO: 563              moltype = DNA   length = 32
FEATURE                    Location/Qualifiers
source                     1..32
                           mol_type = other DNA
                           organism = synthetic construct
SEQUENCE: 563
atccatcata ttattcaccg accgctcaga ac                                    32

SEQ ID NO: 564              moltype = DNA   length = 15
FEATURE                    Location/Qualifiers
source                     1..15
                           mol_type = other DNA
                           organism = synthetic construct
SEQUENCE: 564
tttccctgcc tattt                                                       15

SEQ ID NO: 565              moltype = DNA   length = 32
FEATURE                    Location/Qualifiers
source                     1..32
                           mol_type = other DNA
                           organism = synthetic construct
SEQUENCE: 565
gagtaacagt gcccgtgatc gtcgagaggg tt                                    32

SEQ ID NO: 566              moltype = DNA   length = 32
FEATURE                    Location/Qualifiers
source                     1..32
                           mol_type = other DNA
                           organism = synthetic construct
SEQUENCE: 566
gaatttaccg ttccagcttc accctcagaa cc                                    32

SEQ ID NO: 567              moltype = DNA   length = 27
FEATURE                    Location/Qualifiers
source                     1..27
                           mol_type = other DNA
                           organism = synthetic construct
SEQUENCE: 567
aatggaaaca gaacaactca tggatag                                          27

SEQ ID NO: 568              moltype = DNA   length = 37
FEATURE                    Location/Qualifiers
source                     1..37
                           mol_type = other DNA
                           organism = synthetic construct
SEQUENCE: 568
aaataaatcc tcattaaatc gctgagtagt aaccgtt                               37

SEQ ID NO: 569              moltype = DNA   length = 24
FEATURE                    Location/Qualifiers
source                     1..24
                           mol_type = other DNA
                           organism = synthetic construct
SEQUENCE: 569
ttggccttag caaggctccg ggaa                                             24

SEQ ID NO: 570              moltype = DNA   length = 32
FEATURE                    Location/Qualifiers
source                     1..32
                           mol_type = other DNA
                           organism = synthetic construct
SEQUENCE: 570
ggtcagcaac cgcgccttta ttttagatta gt                                    32

SEQ ID NO: 571              moltype = DNA   length = 32
FEATURE                    Location/Qualifiers
source                     1..32
                           mol_type = other DNA
                           organism = synthetic construct
SEQUENCE: 571
gacaaccaaa gccgttcgga aacgattgac gg                                    32

SEQ ID NO: 572              moltype = DNA   length = 32
FEATURE                    Location/Qualifiers
```

-continued

```
source                    1..32
                          mol_type = other DNA
                          organism = synthetic construct
SEQUENCE: 572
aaagtaatac cgcactccaa gaaccgcaaa tt                                          32

SEQ ID NO: 573            moltype = DNA   length = 32
FEATURE                   Location/Qualifiers
source                    1..32
                          mol_type = other DNA
                          organism = synthetic construct
SEQUENCE: 573
agagccacac tgtagccatc gagaacattt tg                                          32

SEQ ID NO: 574            moltype = DNA   length = 32
FEATURE                   Location/Qualifiers
source                    1..32
                          mol_type = other DNA
                          organism = synthetic construct
SEQUENCE: 574
cgccagtttt atcattcaat caatccagtt ac                                          32

SEQ ID NO: 575            moltype = DNA   length = 32
FEATURE                   Location/Qualifiers
source                    1..32
                          mol_type = other DNA
                          organism = synthetic construct
SEQUENCE: 575
cagagccgcc acctgtataa acagttaatg cc                                          32

SEQ ID NO: 576            moltype = DNA   length = 32
FEATURE                   Location/Qualifiers
source                    1..32
                          mol_type = other DNA
                          organism = synthetic construct
SEQUENCE: 576
agataccgcc atctttgcgt tttccacaat ca                                          32

SEQ ID NO: 577            moltype = DNA   length = 32
FEATURE                   Location/Qualifiers
source                    1..32
                          mol_type = other DNA
                          organism = synthetic construct
SEQUENCE: 577
tgaacaaggt agaaactcat aatccgcaaa ca                                          32

SEQ ID NO: 578            moltype = DNA   length = 15
FEATURE                   Location/Qualifiers
source                    1..15
                          mol_type = other DNA
                          organism = synthetic construct
SEQUENCE: 578
tttgccccct tattt                                                             15

SEQ ID NO: 579            moltype = DNA   length = 22
FEATURE                   Location/Qualifiers
source                    1..22
                          mol_type = other DNA
                          organism = synthetic construct
SEQUENCE: 579
agtttgcctt ttttcggtca ta                                                     22

SEQ ID NO: 580            moltype = DNA   length = 32
FEATURE                   Location/Qualifiers
source                    1..32
                          mol_type = other DNA
                          organism = synthetic construct
SEQUENCE: 580
tagcagcacc gtaatcagcg agccgccgcc ag                                          32

SEQ ID NO: 581            moltype = DNA   length = 22
FEATURE                   Location/Qualifiers
source                    1..22
                          mol_type = other DNA
                          organism = synthetic construct
SEQUENCE: 581
cagtagcacc agaaaccatc ga                                                     22

SEQ ID NO: 582            moltype = DNA   length = 27
```

-continued

```
FEATURE                Location/Qualifiers
source                 1..27
                       mol_type = other DNA
                       organism = synthetic construct
SEQUENCE: 582
ttagagccac gcaaataaga actcgtt                                          27

SEQ ID NO: 583         moltype = DNA   length = 37
FEATURE                Location/Qualifiers
source                 1..37
                       mol_type = other DNA
                       organism = synthetic construct
SEQUENCE: 583
caccgacttg agccatttgg ttttataata agggatt                               37

SEQ ID NO: 584         moltype = DNA   length = 24
FEATURE                Location/Qualifiers
source                 1..24
                       mol_type = other DNA
                       organism = synthetic construct
SEQUENCE: 584
ttaaaggtat aataagtacc gaag                                             24

SEQ ID NO: 585         moltype = DNA   length = 42
FEATURE                Location/Qualifiers
source                 1..42
                       mol_type = other DNA
                       organism = synthetic construct
SEQUENCE: 585
agggaaggta aattcaccaa tttaccattg atattcacaa ac                        42

SEQ ID NO: 586         moltype = DNA   length = 32
FEATURE                Location/Qualifiers
source                 1..32
                       mol_type = other DNA
                       organism = synthetic construct
SEQUENCE: 586
agacaaaagg gcgacaagta gcgacagaat ca                                   32

SEQ ID NO: 587         moltype = DNA   length = 25
FEATURE                Location/Qualifiers
source                 1..25
                       mol_type = other DNA
                       organism = synthetic construct
SEQUENCE: 587
atagataata cagagagtca aaaat                                            25

SEQ ID NO: 588         moltype = DNA   length = 42
FEATURE                Location/Qualifiers
source                 1..42
                       mol_type = other DNA
                       organism = synthetic construct
SEQUENCE: 588
aagtttattt tgtatcggca tagcgtcagc accctcagag cc                        42

SEQ ID NO: 589         moltype = DNA   length = 24
FEATURE                Location/Qualifiers
source                 1..24
                       mol_type = other DNA
                       organism = synthetic construct
SEQUENCE: 589
gccatatttg tttaacatac ataa                                            24

SEQ ID NO: 590         moltype = DNA   length = 29
FEATURE                Location/Qualifiers
source                 1..29
                       mol_type = other DNA
                       organism = synthetic construct
SEQUENCE: 590
aggtggcaca aacgtagaca ccacggaat                                       29

SEQ ID NO: 591         moltype = DNA   length = 48
FEATURE                Location/Qualifiers
source                 1..48
                       mol_type = other DNA
                       organism = synthetic construct
SEQUENCE: 591
ttttcagaat cctgaacttc tttagatata gaacaacgcc aacatttt                  48
```

-continued

```
SEQ ID NO: 592          moltype = DNA   length = 29
FEATURE                 Location/Qualifiers
source                  1..29
                        mol_type = other DNA
                        organism = synthetic construct
SEQUENCE: 592
tttttttgccc gactttagga gcacttttt                                         29

SEQ ID NO: 593          moltype = DNA   length = 29
FEATURE                 Location/Qualifiers
source                  1..29
                        mol_type = other DNA
                        organism = synthetic construct
SEQUENCE: 593
tttttcatat tccgcctgca acagttttt                                          29

SEQ ID NO: 594          moltype = DNA   length = 29
FEATURE                 Location/Qualifiers
source                  1..29
                        mol_type = other DNA
                        organism = synthetic construct
SEQUENCE: 594
ttttgaaggg ttagaacggc aattctttt                                          29

SEQ ID NO: 595          moltype = DNA   length = 29
FEATURE                 Location/Qualifiers
source                  1..29
                        mol_type = other DNA
                        organism = synthetic construct
SEQUENCE: 595
tttttgcacg taaaacaaat tatcatttt                                          29

SEQ ID NO: 596          moltype = DNA   length = 29
FEATURE                 Location/Qualifiers
source                  1..29
                        mol_type = other DNA
                        organism = synthetic construct
SEQUENCE: 596
ttttgatgaa tatacagaag tttgatttt                                          29

SEQ ID NO: 597          moltype = DNA   length = 53
FEATURE                 Location/Qualifiers
source                  1..53
                        mol_type = other DNA
                        organism = synthetic construct
SEQUENCE: 597
ttttgggaga aacaatataa atccttacaa acatgaggat ttagaagtat ttt              53

SEQ ID NO: 598          moltype = DNA   length = 29
FEATURE                 Location/Qualifiers
source                  1..29
                        mol_type = other DNA
                        organism = synthetic construct
SEQUENCE: 598
ttttaagatg attacctttt acatctttt                                          29

SEQ ID NO: 599          moltype = DNA   length = 25
FEATURE                 Location/Qualifiers
source                  1..25
                        mol_type = other DNA
                        organism = synthetic construct
SEQUENCE: 599
ttaattacag gtttaacgtc atttt                                              25

SEQ ID NO: 600          moltype = DNA   length = 25
FEATURE                 Location/Qualifiers
source                  1..25
                        mol_type = other DNA
                        organism = synthetic construct
SEQUENCE: 600
tttttaaatc aatatcaaaa ttatt                                              25

SEQ ID NO: 601          moltype = DNA   length = 29
FEATURE                 Location/Qualifiers
source                  1..29
                        mol_type = other DNA
                        organism = synthetic construct
SEQUENCE: 601
ttttgaaaac atagcgaacc ttgcttttt                                          29
```

```
SEQ ID NO: 602            moltype = DNA   length = 25
FEATURE                   Location/Qualifiers
source                    1..25
                          mol_type = other DNA
                          organism = synthetic construct
SEQUENCE: 602
ttttgagaag agtcaataca gtaca                                        25

SEQ ID NO: 603            moltype = DNA   length = 25
FEATURE                   Location/Qualifiers
source                    1..25
                          mol_type = other DNA
                          organism = synthetic construct
SEQUENCE: 603
tttaacctcc ggcaaacaaa atttt                                        25

SEQ ID NO: 604            moltype = DNA   length = 52
FEATURE                   Location/Qualifiers
source                    1..52
                          mol_type = other DNA
                          organism = synthetic construct
SEQUENCE: 604
ttttatatgt aaatgcagca aaagcgaatt atccaagtta caaaatcgtt tt          52

SEQ ID NO: 605            moltype = DNA   length = 26
FEATURE                   Location/Qualifiers
source                    1..26
                          mol_type = other DNA
                          organism = synthetic construct
SEQUENCE: 605
ttttaatggt gggttatata actttt                                       26

SEQ ID NO: 606            moltype = DNA   length = 29
FEATURE                   Location/Qualifiers
source                    1..29
                          mol_type = other DNA
                          organism = synthetic construct
SEQUENCE: 606
ttttacaccg gagagagact acctttttt                                    29

SEQ ID NO: 607            moltype = DNA   length = 28
FEATURE                   Location/Qualifiers
source                    1..28
                          mol_type = other DNA
                          organism = synthetic construct
SEQUENCE: 607
tttttttagt atagattaag acgctttt                                     28

SEQ ID NO: 608            moltype = DNA   length = 29
FEATURE                   Location/Qualifiers
source                    1..29
                          mol_type = other DNA
                          organism = synthetic construct
SEQUENCE: 608
ttttagtagg gcccttagaa tcctttttt                                    29

SEQ ID NO: 609            moltype = DNA   length = 29
FEATURE                   Location/Qualifiers
source                    1..29
                          mol_type = other DNA
                          organism = synthetic construct
SEQUENCE: 609
tttttgtaat ttaggcacgc tcaactttt                                    29

SEQ ID NO: 610            moltype = DNA   length = 29
FEATURE                   Location/Qualifiers
source                    1..29
                          mol_type = other DNA
                          organism = synthetic construct
SEQUENCE: 610
ttttaataag agaatataaa gcctgtttt                                    29

SEQ ID NO: 611            moltype = DNA   length = 29
FEATURE                   Location/Qualifiers
source                    1..29
                          mol_type = other DNA
                          organism = synthetic construct
SEQUENCE: 611
```

```
ttttcgacaa taaacaaaag aataatttt                                          29

SEQ ID NO: 612           moltype = DNA   length = 53
FEATURE                  Location/Qualifiers
source                   1..53
                         mol_type = other DNA
                         organism = synthetic construct
SEQUENCE: 612
ttttacgcgc ctgtttagac ctaaatatt ttagaacgcg agaaaacttt ttt              53

SEQ ID NO: 613           moltype = DNA   length = 29
FEATURE                  Location/Qualifiers
source                   1..29
                         mol_type = other DNA
                         organism = synthetic construct
SEQUENCE: 613
ttttgtcttt cccagctaat gcagatttt                                         29

SEQ ID NO: 614           moltype = DNA   length = 29
FEATURE                  Location/Qualifiers
source                   1..29
                         mol_type = other DNA
                         organism = synthetic construct
SEQUENCE: 614
ttttaaccaa gttctgtcca gacgatttt                                         29

SEQ ID NO: 615           moltype = DNA   length = 29
FEATURE                  Location/Qualifiers
source                   1..29
                         mol_type = other DNA
                         organism = synthetic construct
SEQUENCE: 615
ttttgaatca ttttttcgag ccagttttt                                         29

SEQ ID NO: 616           moltype = DNA   length = 29
FEATURE                  Location/Qualifiers
source                   1..29
                         mol_type = other DNA
                         organism = synthetic construct
SEQUENCE: 616
tttttttagcg aacctccagc aaatctttt                                        29

SEQ ID NO: 617           moltype = DNA   length = 29
FEATURE                  Location/Qualifiers
source                   1..29
                         mol_type = other DNA
                         organism = synthetic construct
SEQUENCE: 617
ttttaagcct taaatcacat cgtagtttt                                         29

SEQ ID NO: 618           moltype = DNA   length = 29
FEATURE                  Location/Qualifiers
source                   1..29
                         mol_type = other DNA
                         organism = synthetic construct
SEQUENCE: 618
tttttgaatc ttaccaaggg tattatttt                                         29

SEQ ID NO: 619           moltype = DNA   length = 53
FEATURE                  Location/Qualifiers
source                   1..53
                         mol_type = other DNA
                         organism = synthetic construct
SEQUENCE: 619
ttttagagcc taatttgaat cggctacgag cataaaaata atatcccatt ttt              53

SEQ ID NO: 620           moltype = DNA   length = 29
FEATURE                  Location/Qualifiers
source                   1..29
                         mol_type = other DNA
                         organism = synthetic construct
SEQUENCE: 620
ttttgcagcc ttcgagcgtc tttcctttt                                         29

SEQ ID NO: 621           moltype = DNA   length = 29
FEATURE                  Location/Qualifiers
source                   1..29
                         mol_type = other DNA
                         organism = synthetic construct
```

```
SEQUENCE: 621
ttttattaac tgtacaattt tatcctttt                                          29

SEQ ID NO: 622          moltype = DNA   length = 29
FEATURE                 Location/Qualifiers
source                  1..29
                        mol_type = other DNA
                        organism = synthetic construct
SEQUENCE: 622
ttttagataa ccgcgggagg ttttgtttt                                          29

SEQ ID NO: 623          moltype = DNA   length = 35
FEATURE                 Location/Qualifiers
source                  1..35
                        mol_type = other DNA
                        organism = synthetic construct
SEQUENCE: 623
ttttcccttt ttgccgatta cagtgaggct atttt                                   35

SEQ ID NO: 624          moltype = DNA   length = 41
FEATURE                 Location/Qualifiers
source                  1..41
                        mol_type = other DNA
                        organism = synthetic construct
SEQUENCE: 624
ttagacagga acggtaatag caataacgcg aggcgttttt t                            41

SEQ ID NO: 625          moltype = DNA   length = 52
FEATURE                 Location/Qualifiers
source                  1..52
                        mol_type = other DNA
                        organism = synthetic construct
SEQUENCE: 625
gtagcaatga agtgttattc taagagctat ctagcaagaa acaatgaatt tt               52

SEQ ID NO: 626          moltype = DNA   length = 15
FEATURE                 Location/Qualifiers
source                  1..15
                        mol_type = other DNA
                        organism = synthetic construct
SEQUENCE: 626
tttttagtaa taaca                                                         15

SEQ ID NO: 627          moltype = DNA   length = 33
FEATURE                 Location/Qualifiers
source                  1..33
                        mol_type = other DNA
                        organism = synthetic construct
SEQUENCE: 627
cagattcatc tgtaaacttc tgaataatgt ttt                                     33

SEQ ID NO: 628          moltype = DNA   length = 34
FEATURE                 Location/Qualifiers
source                  1..34
                        mol_type = other DNA
                        organism = synthetic construct
SEQUENCE: 628
ttttgtcaca cgacctagaa cccatcaata taaa                                    34

SEQ ID NO: 629          moltype = DNA   length = 27
FEATURE                 Location/Qualifiers
source                  1..27
                        mol_type = other DNA
                        organism = synthetic construct
SEQUENCE: 629
tttttgacct gaaagcgtaa gaaatag                                            27

SEQ ID NO: 630          moltype = DNA   length = 47
FEATURE                 Location/Qualifiers
source                  1..47
                        mol_type = other DNA
                        organism = synthetic construct
SEQUENCE: 630
ttttacatcg ccattattaa cacctgatta taggagcggg aaataaa                     47

SEQ ID NO: 631          moltype = DNA   length = 29
FEATURE                 Location/Qualifiers
source                  1..29
                        mol_type = other DNA
```

-continued

```
                              organism = synthetic construct
SEQUENCE: 631
ttttgccacg ctgagagcca gcagccaat                                             29

SEQ ID NO: 632          moltype = DNA   length = 47
FEATURE                 Location/Qualifiers
source                  1..47
                        mol_type = other DNA
                        organism = synthetic construct
SEQUENCE: 632
ttttcagttg gcaaataaaa tatacgttat tactcgtata cggattc                        47

SEQ ID NO: 633          moltype = DNA   length = 25
FEATURE                 Location/Qualifiers
source                  1..25
                        mol_type = other DNA
                        organism = synthetic construct
SEQUENCE: 633
ttttaacaac taatagatta gagcc                                                 25

SEQ ID NO: 634          moltype = DNA   length = 12
FEATURE                 Location/Qualifiers
source                  1..12
                        mol_type = other DNA
                        organism = synthetic construct
SEQUENCE: 634
tttttttagac tt                                                              12

SEQ ID NO: 635          moltype = DNA   length = 12
FEATURE                 Location/Qualifiers
source                  1..12
                        mol_type = other DNA
                        organism = synthetic construct
SEQUENCE: 635
ttttcgcaga gg                                                               12

SEQ ID NO: 636          moltype = DNA   length = 12
FEATURE                 Location/Qualifiers
source                  1..12
                        mol_type = other DNA
                        organism = synthetic construct
SEQUENCE: 636
tttttttcaa at                                                               12

SEQ ID NO: 637          moltype = DNA   length = 12
FEATURE                 Location/Qualifiers
source                  1..12
                        mol_type = other DNA
                        organism = synthetic construct
SEQUENCE: 637
ttttcctaat tt                                                               12

SEQ ID NO: 638          moltype = DNA   length = 36
FEATURE                 Location/Qualifiers
source                  1..36
                        mol_type = other DNA
                        organism = synthetic construct
SEQUENCE: 638
aaattcttca caagaaagcg ctaatatcag agtttt                                     36

SEQ ID NO: 639          moltype = DNA   length = 36
FEATURE                 Location/Qualifiers
source                  1..36
                        mol_type = other DNA
                        organism = synthetic construct
SEQUENCE: 639
cacccagcaa caccctcgca ttagacggga gatttt                                     36

SEQ ID NO: 640          moltype = DNA   length = 12
FEATURE                 Location/Qualifiers
source                  1..12
                        mol_type = other DNA
                        organism = synthetic construct
SEQUENCE: 640
ttttataaga aa                                                               12

SEQ ID NO: 641          moltype = DNA   length = 35
FEATURE                 Location/Qualifiers
source                  1..35
```

```
                              mol_type = other DNA
                              organism = synthetic construct
SEQUENCE: 641
gaaaatacga tttttatta tcccaatcca atttt                                          35

SEQ ID NO: 642           moltype = DNA   length = 30
FEATURE                  Location/Qualifiers
source                   1..30
                         mol_type = other DNA
                         organism = synthetic construct
SEQUENCE: 642
ttttggaaag ccggcggcaa gtgtagtttt                                               30

SEQ ID NO: 643           moltype = DNA   length = 30
FEATURE                  Location/Qualifiers
source                   1..30
                         mol_type = other DNA
                         organism = synthetic construct
SEQUENCE: 643
ttttaagttt tttgggagct tgacggtttt                                               30

SEQ ID NO: 644           moltype = DNA   length = 30
FEATURE                  Location/Qualifiers
source                   1..30
                         mol_type = other DNA
                         organism = synthetic construct
SEQUENCE: 644
ttttgttgtt ccagttcacc caaatctttt                                               30

SEQ ID NO: 645           moltype = DNA   length = 30
FEATURE                  Location/Qualifiers
source                   1..30
                         mol_type = other DNA
                         organism = synthetic construct
SEQUENCE: 645
ttttggtttg ccccataggg ttgagttttt                                               30

SEQ ID NO: 646           moltype = DNA   length = 30
FEATURE                  Location/Qualifiers
source                   1..30
                         mol_type = other DNA
                         organism = synthetic construct
SEQUENCE: 646
ttttcgccag ggtggcggtc cacgcttttt                                               30

SEQ ID NO: 647           moltype = DNA   length = 40
FEATURE                  Location/Qualifiers
source                   1..40
                         mol_type = other DNA
                         organism = synthetic construct
SEQUENCE: 647
ttttcataaa gtgtaaagcc acatacgagc cggaagtttt                                    40

SEQ ID NO: 648           moltype = DNA   length = 40
FEATURE                  Location/Qualifiers
source                   1..40
                         mol_type = other DNA
                         organism = synthetic construct
SEQUENCE: 648
ttttccgggt accgagctcg cgactctaga ggatcctttt                                    40

SEQ ID NO: 649           moltype = DNA   length = 40
FEATURE                  Location/Qualifiers
source                   1..40
                         mol_type = other DNA
                         organism = synthetic construct
SEQUENCE: 649
tttttttaagt tgggtaacgc atgtgctgca aggcgatttt                                   40

SEQ ID NO: 650           moltype = DNA   length = 40
FEATURE                  Location/Qualifiers
source                   1..40
                         mol_type = other DNA
                         organism = synthetic construct
SEQUENCE: 650
tttttcgcca ttcaggctgc ccaggcaaag cgccattttt                                    40

SEQ ID NO: 651           moltype = DNA   length = 19
FEATURE                  Location/Qualifiers
```

-continued

```
source                    1..19
                          mol_type = other DNA
                          organism = synthetic construct
SEQUENCE: 651
ttttgagatc gttggtttt                                              19

SEQ ID NO: 652            moltype = DNA   length = 19
FEATURE                   Location/Qualifiers
source                    1..19
                          mol_type = other DNA
                          organism = synthetic construct
SEQUENCE: 652
ttttgagtaa tgacgtttt                                              19

SEQ ID NO: 653            moltype = DNA   length = 19
FEATURE                   Location/Qualifiers
source                    1..19
                          mol_type = other DNA
                          organism = synthetic construct
SEQUENCE: 653
tttttccgca cagactttt                                              19

SEQ ID NO: 654            moltype = DNA   length = 39
FEATURE                   Location/Qualifiers
source                    1..39
                          mol_type = other DNA
                          organism = synthetic construct
SEQUENCE: 654
ttttcggtca cgctgcgcgt aaccaccaca ccgggcgct                        39

SEQ ID NO: 655            moltype = DNA   length = 28
FEATURE                   Location/Qualifiers
source                    1..28
                          mol_type = other DNA
                          organism = synthetic construct
SEQUENCE: 655
ggaaacctcg ctcactgccc gctttttt                                    28

SEQ ID NO: 656            moltype = DNA   length = 33
FEATURE                   Location/Qualifiers
source                    1..33
                          mol_type = other DNA
                          organism = synthetic construct
SEQUENCE: 656
attacgccgc gatcggagta caacggagat ttt                              33

SEQ ID NO: 657            moltype = DNA   length = 44
FEATURE                   Location/Qualifiers
source                    1..44
                          mol_type = other DNA
                          organism = synthetic construct
SEQUENCE: 657
ttaaatatcg cagagcggga gctaaacagg agaagaaaag tttt                  44

SEQ ID NO: 658            moltype = DNA   length = 14
FEATURE                   Location/Qualifiers
source                    1..14
                          mol_type = other DNA
                          organism = synthetic construct
SEQUENCE: 658
ttttaacgga acgc                                                   14

SEQ ID NO: 659            moltype = DNA   length = 45
FEATURE                   Location/Qualifiers
source                    1..45
                          mol_type = other DNA
                          organism = synthetic construct
SEQUENCE: 659
ttttgagaat agactaaaac gtaatgccat aaaacacatt gagga                 45

SEQ ID NO: 660            moltype = DNA   length = 42
FEATURE                   Location/Qualifiers
source                    1..42
                          mol_type = other DNA
                          organism = synthetic construct
SEQUENCE: 660
ttttggctga gacgtttcag cgattttgcc aactaaagga at                    42

SEQ ID NO: 661            moltype = DNA   length = 42
```

-continued

```
FEATURE            Location/Qualifiers
source             1..42
                   mol_type = other DNA
                   organism = synthetic construct
SEQUENCE: 661
ttttccagag ccagaaagta ttcggaacca gagaaggatt ag                    42

SEQ ID NO: 662     moltype = DNA   length = 44
FEATURE            Location/Qualifiers
source             1..44
                   mol_type = other DNA
                   organism = synthetic construct
SEQUENCE: 662
tgctattcgg taattgttga gttaagcagt taccagaagg tttt                  44

SEQ ID NO: 663     moltype = DNA   length = 44
FEATURE            Location/Qualifiers
source             1..44
                   mol_type = other DNA
                   organism = synthetic construct
SEQUENCE: 663
ttttcatatg gtcagggaag gaacaaagtc aataacggaa tacc                  44

SEQ ID NO: 664     moltype = DNA   length = 44
FEATURE            Location/Qualifiers
source             1..44
                   mol_type = other DNA
                   organism = synthetic construct
SEQUENCE: 664
aaaataaaga aaatacgaat aacataaaag actccttatt tttt                  44

SEQ ID NO: 665     moltype = DNA   length = 42
FEATURE            Location/Qualifiers
source             1..42
                   mol_type = other DNA
                   organism = synthetic construct
SEQUENCE: 665
tttttaaaag aaaaaaatca cagcgtttgg aaccgcctcc ct                    42

SEQ ID NO: 666     moltype = DNA   length = 13
FEATURE            Location/Qualifiers
source             1..13
                   mol_type = other DNA
                   organism = synthetic construct
SEQUENCE: 666
ttttgtatgt tag                                                    13

SEQ ID NO: 667     moltype = DNA   length = 34
FEATURE            Location/Qualifiers
source             1..34
                   mol_type = other DNA
                   organism = synthetic construct
SEQUENCE: 667
ttttgaactg gcatgattaa attaccagcg ccaa                            34

SEQ ID NO: 668     moltype = DNA   length = 34
FEATURE            Location/Qualifiers
source             1..34
                   mol_type = other DNA
                   organism = synthetic construct
SEQUENCE: 668
ttttgaggaa acgcaataga gaaccgattg aggg                            34

SEQ ID NO: 669     moltype = DNA   length = 34
FEATURE            Location/Qualifiers
source             1..34
                   mol_type = other DNA
                   organism = synthetic construct
SEQUENCE: 669
ttttagatag ccgaacaacc agaattatca ccgt                            34

SEQ ID NO: 670     moltype = DNA   length = 45
FEATURE            Location/Qualifiers
source             1..45
                   mol_type = other DNA
                   organism = synthetic construct
SEQUENCE: 670
gcgtattggg cgccagggtg gtttttcttt tcaccagctt gcttc                 45
```

-continued

```
SEQ ID NO: 671              moltype = DNA   length = 32
FEATURE                     Location/Qualifiers
source                      1..32
                            mol_type = other DNA
                            organism = synthetic construct
SEQUENCE: 671
atcggccagg aaacagaatt tatccagacg ac                              32

SEQ ID NO: 672              moltype = DNA   length = 32
FEATURE                     Location/Qualifiers
source                      1..32
                            mol_type = other DNA
                            organism = synthetic construct
SEQUENCE: 672
tgtcgaaaat cctgtttgat ggtgaaagaa ta                              32

SEQ ID NO: 673              moltype = DNA   length = 37
FEATURE                     Location/Qualifiers
source                      1..37
                            mol_type = other DNA
                            organism = synthetic construct
SEQUENCE: 673
atttgaatta ccttttttaa tacgcgcggc cagctgc                         37

SEQ ID NO: 674              moltype = DNA   length = 48
FEATURE                     Location/Qualifiers
source                      1..48
                            mol_type = other DNA
                            organism = synthetic construct
SEQUENCE: 674
gcccgagaag tccactatta aagagtctat cagaaccatc gtaaagca             48

SEQ ID NO: 675              moltype = DNA   length = 32
FEATURE                     Location/Qualifiers
source                      1..32
                            mol_type = other DNA
                            organism = synthetic construct
SEQUENCE: 675
aaacaaaaaa gatgatattt acgatgaaaa ta                              32

SEQ ID NO: 676              moltype = DNA   length = 32
FEATURE                     Location/Qualifiers
source                      1..32
                            mol_type = other DNA
                            organism = synthetic construct
SEQUENCE: 676
ggaacaagta gggttgttca gctaagacgc tg                              32

SEQ ID NO: 677              moltype = DNA   length = 45
FEATURE                     Location/Qualifiers
source                      1..45
                            mol_type = other DNA
                            organism = synthetic construct
SEQUENCE: 677
tttcaattac ctgagcaaaa gttaattaca ttctgtcaaa atcat               45

SEQ ID NO: 678              moltype = DNA   length = 32
FEATURE                     Location/Qualifiers
source                      1..32
                            mol_type = other DNA
                            organism = synthetic construct
SEQUENCE: 678
tacaaaatgc ctgatttgag cgcttcaccg ac                              32

SEQ ID NO: 679              moltype = DNA   length = 48
FEATURE                     Location/Qualifiers
source                      1..48
                            mol_type = other DNA
                            organism = synthetic construct
SEQUENCE: 679
ctaaatcgga cggggaaagc cggcaaggag cgggcgctag taaccacc             48

SEQ ID NO: 680              moltype = DNA   length = 32
FEATURE                     Location/Qualifiers
source                      1..32
                            mol_type = other DNA
                            organism = synthetic construct
SEQUENCE: 680
gaggtgccac ccaaatgaat aacacaagaa aa                              32
```

-continued

```
SEQ ID NO: 681            moltype = DNA   length = 45
FEATURE                   Location/Qualifiers
source                    1..45
                          mol_type = other DNA
                          organism = synthetic construct
SEQUENCE: 681
gggagaaaca ataacggatt ccgcgcagag tcaaaaagca tgtag                    45

SEQ ID NO: 682            moltype = DNA   length = 32
FEATURE                   Location/Qualifiers
source                    1..32
                          mol_type = other DNA
                          organism = synthetic construct
SEQUENCE: 682
gaatatacag attttcagca gcactaagtt tt                                  32

SEQ ID NO: 683            moltype = DNA   length = 32
FEATURE                   Location/Qualifiers
source                    1..32
                          mol_type = other DNA
                          organism = synthetic construct
SEQUENCE: 683
gaaagcgaga acgtggttag agccccctga ac                                  32

SEQ ID NO: 684            moltype = DNA   length = 45
FEATURE                   Location/Qualifiers
source                    1..45
                          mol_type = other DNA
                          organism = synthetic construct
SEQUENCE: 684
acagaaataa agaaattgcg tagtaacagt atcaccgaat atcag                    45

SEQ ID NO: 685            moltype = DNA   length = 40
FEATURE                   Location/Qualifiers
source                    1..40
                          mol_type = other DNA
                          organism = synthetic construct
SEQUENCE: 685
acacccgcat ggttgctttg acgagagcgg gagctaaaca                          40

SEQ ID NO: 686            moltype = DNA   length = 40
FEATURE                   Location/Qualifiers
source                    1..40
                          mol_type = other DNA
                          organism = synthetic construct
SEQUENCE: 686
ctaccatatc tgaataatta agagaggagc ggccgaacgt                          40

SEQ ID NO: 687            moltype = DNA   length = 15
FEATURE                   Location/Qualifiers
source                    1..15
                          mol_type = other DNA
                          organism = synthetic construct
SEQUENCE: 687
tatttgcacg taaat                                                     15

SEQ ID NO: 688            moltype = DNA   length = 32
FEATURE                   Location/Qualifiers
source                    1..32
                          mol_type = other DNA
                          organism = synthetic construct
SEQUENCE: 688
cgcgtactcg cgcttatgag taacaacgtc ac                                  32

SEQ ID NO: 689            moltype = DNA   length = 45
FEATURE                   Location/Qualifiers
source                    1..45
                          mol_type = other DNA
                          organism = synthetic construct
SEQUENCE: 689
cctgattgtt tggattatac ttcaaaatta ctggtaacgt aatca                   45

SEQ ID NO: 690            moltype = DNA   length = 24
FEATURE                   Location/Qualifiers
source                    1..24
                          mol_type = other DNA
                          organism = synthetic construct
SEQUENCE: 690
```

-continued

```
ggaggccgat taatatctac aggg                                          24

SEQ ID NO: 691             moltype = DNA   length = 24
FEATURE                    Location/Qualifiers
source                     1..24
                           mol_type = other DNA
                           organism = synthetic construct
SEQUENCE: 691
atggcaatcc accagagctt atac                                          24

SEQ ID NO: 692             moltype = DNA   length = 29
FEATURE                    Location/Qualifiers
source                     1..29
                           mol_type = other DNA
                           organism = synthetic construct
SEQUENCE: 692
tcaagggatt ttagacccta ttattagcg                                     29

SEQ ID NO: 693             moltype = DNA   length = 34
FEATURE                    Location/Qualifiers
source                     1..34
                           mol_type = other DNA
                           organism = synthetic construct
SEQUENCE: 693
tcattttgcg gaacaaagaa atcatcaata taat                               34

SEQ ID NO: 694             moltype = DNA   length = 48
FEATURE                    Location/Qualifiers
source                     1..48
                           mol_type = other DNA
                           organism = synthetic construct
SEQUENCE: 694
ccaccgagtt gtagcaatac ttctaagaac tcaaactatc cgccagcc                48

SEQ ID NO: 695             moltype = DNA   length = 35
FEATURE                    Location/Qualifiers
source                     1..35
                           mol_type = other DNA
                           organism = synthetic construct
SEQUENCE: 695
tattaattgt attaaagaat catgaggaag ttcag                              35

SEQ ID NO: 696             moltype = DNA   length = 36
FEATURE                    Location/Qualifiers
source                     1..36
                           mol_type = other DNA
                           organism = synthetic construct
SEQUENCE: 696
attaaccgta aaagagatta ggattctgaa accagt                             36

SEQ ID NO: 697             moltype = DNA   length = 37
FEATURE                    Location/Qualifiers
source                     1..37
                           mol_type = other DNA
                           organism = synthetic construct
SEQUENCE: 697
ttacaaacaa ttcgacaact cttaaaagtg accccca                            37

SEQ ID NO: 698             moltype = DNA   length = 35
FEATURE                    Location/Qualifiers
source                     1..35
                           mol_type = other DNA
                           organism = synthetic construct
SEQUENCE: 698
tacatttgta gattagcaga ggccgctttt gcaat                              35

SEQ ID NO: 699             moltype = DNA   length = 48
FEATURE                    Location/Qualifiers
source                     1..48
                           mol_type = other DNA
                           organism = synthetic construct
SEQUENCE: 699
attgcaacga cgctcaatcg tctgtcacac gaccagtaat ccttctga                48

SEQ ID NO: 700             moltype = DNA   length = 32
FEATURE                    Location/Qualifiers
source                     1..32
                           mol_type = other DNA
                           organism = synthetic construct
```

-continued

```
SEQUENCE: 700
aatattacgg ccttgcagga ggttgagggt tg                                    32

SEQ ID NO: 701          moltype = DNA   length = 37
FEATURE                 Location/Qualifiers
source                  1..37
                        mol_type = other DNA
                        organism = synthetic construct
SEQUENCE: 701
tttaggagca ctaacaacta aaggatttaa ctaaaga                               37

SEQ ID NO: 702          moltype = DNA   length = 24
FEATURE                 Location/Qualifiers
source                  1..24
                        mol_type = other DNA
                        organism = synthetic construct
SEQUENCE: 702
aggaattgtc agttggcatt gctt                                             24

SEQ ID NO: 703          moltype = DNA   length = 32
FEATURE                 Location/Qualifiers
source                  1..32
                        mol_type = other DNA
                        organism = synthetic construct
SEQUENCE: 703
ttcaccagaa atggataacc catgcctcag ag                                    32

SEQ ID NO: 704          moltype = DNA   length = 37
FEATURE                 Location/Qualifiers
source                  1..37
                        mol_type = other DNA
                        organism = synthetic construct
SEQUENCE: 704
aaaccctcaa tcaatatctg gaggaaggtt gcaggga                               37

SEQ ID NO: 705          moltype = DNA   length = 48
FEATURE                 Location/Qualifiers
source                  1..48
                        mol_type = other DNA
                        organism = synthetic construct
SEQUENCE: 705
cctgaaagaa tggctattag tcttcattaa aaataccgaa cgaaccac                   48

SEQ ID NO: 706          moltype = DNA   length = 24
FEATURE                 Location/Qualifiers
source                  1..24
                        mol_type = other DNA
                        organism = synthetic construct
SEQUENCE: 706
aagcatcaag ccagcacagc ggag                                             24

SEQ ID NO: 707          moltype = DNA   length = 37
FEATURE                 Location/Qualifiers
source                  1..37
                        mol_type = other DNA
                        organism = synthetic construct
SEQUENCE: 707
ctgcaacagt gccacgctga gccttgctgc ggtttat                               37

SEQ ID NO: 708          moltype = DNA   length = 48
FEATURE                 Location/Qualifiers
source                  1..48
                        mol_type = other DNA
                        organism = synthetic construct
SEQUENCE: 708
cagcagaaac agacaatatt tttgcgtaag aaagttttgt ctgtagca                   48

SEQ ID NO: 709          moltype = DNA   length = 29
FEATURE                 Location/Qualifiers
source                  1..29
                        mol_type = other DNA
                        organism = synthetic construct
SEQUENCE: 709
agaggtgagg cggtcagtat taacaccgc                                        29

SEQ ID NO: 710          moltype = DNA   length = 40
FEATURE                 Location/Qualifiers
source                  1..40
                        mol_type = other DNA
```

-continued

```
                              organism = synthetic construct
SEQUENCE: 710
ccattcgcga ataataaaag ctgcattcat taaacccacc                              40

SEQ ID NO: 711          moltype = DNA   length = 48
FEATURE                 Location/Qualifiers
source                  1..48
                        mol_type = other DNA
                        organism = synthetic construct
SEQUENCE: 711
cgcttctggc actccaagtg aatagccaga ggagaggctt tgcgaata                     48

SEQ ID NO: 712          moltype = DNA   length = 40
FEATURE                 Location/Qualifiers
source                  1..40
                        mol_type = other DNA
                        organism = synthetic construct
SEQUENCE: 712
gggacgcata gtaaaacggt gtcttgtttt aagaaatccg                              40

SEQ ID NO: 713          moltype = DNA   length = 48
FEATURE                 Location/Qualifiers
source                  1..48
                        mol_type = other DNA
                        organism = synthetic construct
SEQUENCE: 713
gcatcgtata ggtcacttca ttccggtaaa gaaatgcaat tcagtttg                     48

SEQ ID NO: 714          moltype = DNA   length = 29
FEATURE                 Location/Qualifiers
source                  1..29
                        mol_type = other DNA
                        organism = synthetic construct
SEQUENCE: 714
gaaattgtca tggtcaaccg tgtgataaa                                          29

SEQ ID NO: 715          moltype = DNA   length = 29
FEATURE                 Location/Qualifiers
source                  1..29
                        mol_type = other DNA
                        organism = synthetic construct
SEQUENCE: 715
ctcacatttg gggtgcaaga caaagaacg                                          29

SEQ ID NO: 716          moltype = DNA   length = 40
FEATURE                 Location/Qualifiers
source                  1..40
                        mol_type = other DNA
                        organism = synthetic construct
SEQUENCE: 716
attaatgatg taaatccaat agtgtacata aacatcaaga                              40

SEQ ID NO: 717          moltype = DNA   length = 32
FEATURE                 Location/Qualifiers
source                  1..32
                        mol_type = other DNA
                        organism = synthetic construct
SEQUENCE: 717
cgggaaacga gactaccttt ttaattagta cc                                      32

SEQ ID NO: 718          moltype = DNA   length = 48
FEATURE                 Location/Qualifiers
source                  1..48
                        mol_type = other DNA
                        organism = synthetic construct
SEQUENCE: 718
agaagagtgt cgctattgaa taactgagac gggcaacagc tgattgcc                     48

SEQ ID NO: 719          moltype = DNA   length = 29
FEATURE                 Location/Qualifiers
source                  1..29
                        mol_type = other DNA
                        organism = synthetic construct
SEQUENCE: 719
aggtctgact gtcgtgggag aggcggttt                                          29

SEQ ID NO: 720          moltype = DNA   length = 24
FEATURE                 Location/Qualifiers
source                  1..24
```

-continued

```
                              mol_type = other DNA
                              organism = synthetic construct
SEQUENCE: 720
acggtccgca gaaaagtgag ctaa                                            24

SEQ ID NO: 721            moltype = DNA   length = 42
FEATURE                   Location/Qualifiers
source                    1..42
                          mol_type = other DNA
                          organism = synthetic construct
SEQUENCE: 721
tatataacta tatgaggcat tcaacgccaa agccgttttt at                        42

SEQ ID NO: 722            moltype = DNA   length = 32
FEATURE                   Location/Qualifiers
source                    1..32
                          mol_type = other DNA
                          organism = synthetic construct
SEQUENCE: 722
cgagaaaact ttttatggct taattgagaa tc                                   32

SEQ ID NO: 723            moltype = DNA   length = 24
FEATURE                   Location/Qualifiers
source                    1..24
                          mol_type = other DNA
                          organism = synthetic construct
SEQUENCE: 723
cggagaattt gttaaatcct gtgt                                            24

SEQ ID NO: 724            moltype = DNA   length = 42
FEATURE                   Location/Qualifiers
source                    1..42
                          mol_type = other DNA
                          organism = synthetic construct
SEQUENCE: 724
tttcatcttc tgaattctta ctttagtata gaacgcgagg cg                        42

SEQ ID NO: 725            moltype = DNA   length = 22
FEATURE                   Location/Qualifiers
source                    1..22
                          mol_type = other DNA
                          organism = synthetic construct
SEQUENCE: 725
gaaaaagcct gcagtataaa gc                                              22

SEQ ID NO: 726            moltype = DNA   length = 32
FEATURE                   Location/Qualifiers
source                    1..32
                          mol_type = other DNA
                          organism = synthetic construct
SEQUENCE: 726
caacgctcaa cagtagttca ccgcgcccaa ta                                   32

SEQ ID NO: 727            moltype = DNA   length = 22
FEATURE                   Location/Qualifiers
source                    1..22
                          mol_type = other DNA
                          organism = synthetic construct
SEQUENCE: 727
gccatattta attcgagcca gt                                              22

SEQ ID NO: 728            moltype = DNA   length = 32
FEATURE                   Location/Qualifiers
source                    1..32
                          mol_type = other DNA
                          organism = synthetic construct
SEQUENCE: 728
aataagagaa tataaaagca tcattccaag aa                                   32

SEQ ID NO: 729            moltype = DNA   length = 32
FEATURE                   Location/Qualifiers
source                    1..32
                          mol_type = other DNA
                          organism = synthetic construct
SEQUENCE: 729
gacaataacc atcctagaaa caaataccaa gt                                   32

SEQ ID NO: 730            moltype = DNA   length = 48
FEATURE                   Location/Qualifiers
```

-continued

```
source                    1..48
                          mol_type = other DNA
                          organism = synthetic construct
SEQUENCE: 730
gacaaaagca ataatcggct gtcttcgaga aacgattttt cccacaag                        48

SEQ ID NO: 731            moltype = DNA   length = 32
FEATURE                   Location/Qualifiers
source                    1..32
                          mol_type = other DNA
                          organism = synthetic construct
SEQUENCE: 731
ataatatcac aacatgagtg ttgttcaata ta                                          32

SEQ ID NO: 732            moltype = DNA   length = 29
FEATURE                   Location/Qualifiers
source                    1..29
                          mol_type = other DNA
                          organism = synthetic construct
SEQUENCE: 732
aaaccaatgt aaagtaattt aacaatttc                                              29

SEQ ID NO: 733            moltype = DNA   length = 32
FEATURE                   Location/Qualifiers
source                    1..32
                          mol_type = other DNA
                          organism = synthetic construct
SEQUENCE: 733
taacacttaa taaagcttta ggcagtaaat gc                                          32

SEQ ID NO: 734            moltype = DNA   length = 32
FEATURE                   Location/Qualifiers
source                    1..32
                          mol_type = other DNA
                          organism = synthetic construct
SEQUENCE: 734
cgggtattaa accgtcaaac agccatatta tt                                          32

SEQ ID NO: 735            moltype = DNA   length = 32
FEATURE                   Location/Qualifiers
source                    1..32
                          mol_type = other DNA
                          organism = synthetic construct
SEQUENCE: 735
cactcgaatg taccaactca gagcatcgat ga                                          32

SEQ ID NO: 736            moltype = DNA   length = 32
FEATURE                   Location/Qualifiers
source                    1..32
                          mol_type = other DNA
                          organism = synthetic construct
SEQUENCE: 736
gaacaagcac atgtaagaag cctttcaagg gt                                          32

SEQ ID NO: 737            moltype = DNA   length = 32
FEATURE                   Location/Qualifiers
source                    1..32
                          mol_type = other DNA
                          organism = synthetic construct
SEQUENCE: 737
aacctgtttt gcgggaaaac attatcacaa at                                          32

SEQ ID NO: 738            moltype = DNA   length = 32
FEATURE                   Location/Qualifiers
source                    1..32
                          mol_type = other DNA
                          organism = synthetic construct
SEQUENCE: 738
aatggattaa cgcaagttat acaacctaaa tt                                          32

SEQ ID NO: 739            moltype = DNA   length = 32
FEATURE                   Location/Qualifiers
source                    1..32
                          mol_type = other DNA
                          organism = synthetic construct
SEQUENCE: 739
ggcttcgaat attttagata aaaaattaat gc                                          32

SEQ ID NO: 740            moltype = DNA   length = 24
```

-continued

```
FEATURE                Location/Qualifiers
source                 1..24
                       mol_type = other DNA
                       organism = synthetic construct
SEQUENCE: 740
gtattctaca tatgcgttct aaac                                             24

SEQ ID NO: 741         moltype = DNA   length = 37
FEATURE                Location/Qualifiers
source                 1..37
                       mol_type = other DNA
                       organism = synthetic construct
SEQUENCE: 741
ttttagcgaa cctcccgaag tgttggtgtt ctccgtg                              37

SEQ ID NO: 742         moltype = DNA   length = 32
FEATURE                Location/Qualifiers
source                 1..32
                       mol_type = other DNA
                       organism = synthetic construct
SEQUENCE: 742
aatcaagatt agttgcgtaa actggcatga tt                                   32

SEQ ID NO: 743         moltype = DNA   length = 32
FEATURE                Location/Qualifiers
source                 1..32
                       mol_type = other DNA
                       organism = synthetic construct
SEQUENCE: 743
ttgccagtta caaaataggc tttttaagaa aa                                   32

SEQ ID NO: 744         moltype = DNA   length = 32
FEATURE                Location/Qualifiers
source                 1..32
                       mol_type = other DNA
                       organism = synthetic construct
SEQUENCE: 744
tatcccaatc caaatacgtc aataataaga gc                                   32

SEQ ID NO: 745         moltype = DNA   length = 32
FEATURE                Location/Qualifiers
source                 1..32
                       mol_type = other DNA
                       organism = synthetic construct
SEQUENCE: 745
gcagccttag ggtaatgctt tgaacgtcag at                                   32

SEQ ID NO: 746         moltype = DNA   length = 32
FEATURE                Location/Qualifiers
source                 1..32
                       mol_type = other DNA
                       organism = synthetic construct
SEQUENCE: 746
aaagtcagta cagagacaag tttttccagt tt                                   32

SEQ ID NO: 747         moltype = DNA   length = 29
FEATURE                Location/Qualifiers
source                 1..29
                       mol_type = other DNA
                       organism = synthetic construct
SEQUENCE: 747
agagataatg tttaacggcg aattattca                                       29

SEQ ID NO: 748         moltype = DNA   length = 32
FEATURE                Location/Qualifiers
source                 1..32
                       mol_type = other DNA
                       organism = synthetic construct
SEQUENCE: 748
aattgagtca taattattca ttaaagaatc aa                                   32

SEQ ID NO: 749         moltype = DNA   length = 32
FEATURE                Location/Qualifiers
source                 1..32
                       mol_type = other DNA
                       organism = synthetic construct
SEQUENCE: 749
attgcgcctt taattctcca acagaagtac cg                                   32
```

```
SEQ ID NO: 750            moltype = DNA   length = 42
FEATURE                   Location/Qualifiers
source                    1..42
                          mol_type = other DNA
                          organism = synthetic construct
SEQUENCE: 750
aagaaacaat gaaaaccgat tgccaaagac gtttgccatc tt                    42

SEQ ID NO: 751            moltype = DNA   length = 32
FEATURE                   Location/Qualifiers
source                    1..32
                          mol_type = other DNA
                          organism = synthetic construct
SEQUENCE: 751
agctagtcaa gcaaacgagc ttcaagtagc at                              32

SEQ ID NO: 752            moltype = DNA   length = 32
FEATURE                   Location/Qualifiers
source                    1..32
                          mol_type = other DNA
                          organism = synthetic construct
SEQUENCE: 752
ccgaagccat tagagactaa cgagatctca at                              32

SEQ ID NO: 753            moltype = DNA   length = 32
FEATURE                   Location/Qualifiers
source                    1..32
                          mol_type = other DNA
                          organism = synthetic construct
SEQUENCE: 753
gttcagaaaa gaggtcgtac ctttgctatc ga                              32

SEQ ID NO: 754            moltype = DNA   length = 32
FEATURE                   Location/Qualifiers
source                    1..32
                          mol_type = other DNA
                          organism = synthetic construct
SEQUENCE: 754
gctttacata ccaacgaata taatatatag aa                              32

SEQ ID NO: 755            moltype = DNA   length = 42
FEATURE                   Location/Qualifiers
source                    1..42
                          mol_type = other DNA
                          organism = synthetic construct
SEQUENCE: 755
gaaaccgagg aaaaagacac cgtggcaacc gccaccctca ga                    42

SEQ ID NO: 756            moltype = DNA   length = 32
FEATURE                   Location/Qualifiers
source                    1..32
                          mol_type = other DNA
                          organism = synthetic construct
SEQUENCE: 756
taacgggaaa ttgctgattt ttgcatttcg ca                              32

SEQ ID NO: 757            moltype = DNA   length = 24
FEATURE                   Location/Qualifiers
source                    1..24
                          mol_type = other DNA
                          organism = synthetic construct
SEQUENCE: 757
cccaaaaggc tcaacaggac ttgc                                       24

SEQ ID NO: 758            moltype = DNA   length = 37
FEATURE                   Location/Qualifiers
source                    1..37
                          mol_type = other DNA
                          organism = synthetic construct
SEQUENCE: 758
aagactcctt attacgcata aaggcgatta gatgggc                         37

SEQ ID NO: 759            moltype = DNA   length = 32
FEATURE                   Location/Qualifiers
source                    1..32
                          mol_type = other DNA
                          organism = synthetic construct
SEQUENCE: 759
ttattttgtc acaatccatg aaccagagcc ac                              32
```

```
SEQ ID NO: 760            moltype = DNA   length = 22
FEATURE                   Location/Qualifiers
source                    1..22
                          mol_type = other DNA
                          organism = synthetic construct
SEQUENCE: 760
ggtttaccag cgagggaggg aa                                             22

SEQ ID NO: 761            moltype = DNA   length = 32
FEATURE                   Location/Qualifiers
source                    1..32
                          mol_type = other DNA
                          organism = synthetic construct
SEQUENCE: 761
ggtaaatatt gacggacagt cagactgtag cg                                  32

SEQ ID NO: 762            moltype = DNA   length = 32
FEATURE                   Location/Qualifiers
source                    1..32
                          mol_type = other DNA
                          organism = synthetic construct
SEQUENCE: 762
ttgagccacc atcgataggt ttaagttaga ac                                  32

SEQ ID NO: 763            moltype = DNA   length = 32
FEATURE                   Location/Qualifiers
source                    1..32
                          mol_type = other DNA
                          organism = synthetic construct
SEQUENCE: 763
caatgaaatt tgggaacgag aaagttgggg tc                                  32

SEQ ID NO: 764            moltype = DNA   length = 29
FEATURE                   Location/Qualifiers
source                    1..29
                          mol_type = other DNA
                          organism = synthetic construct
SEQUENCE: 764
gtagcgacag gtgaattacc ttttacatc                                      29

SEQ ID NO: 765            moltype = DNA   length = 32
FEATURE                   Location/Qualifiers
source                    1..32
                          mol_type = other DNA
                          organism = synthetic construct
SEQUENCE: 765
gtttgcctcc tcttttgatg atacaaacaa ag                                  32

SEQ ID NO: 766            moltype = DNA   length = 32
FEATURE                   Location/Qualifiers
source                    1..32
                          mol_type = other DNA
                          organism = synthetic construct
SEQUENCE: 766
ataaagcgtt gagattcgac attcatagca at                                  32

SEQ ID NO: 767            moltype = DNA   length = 21
FEATURE                   Location/Qualifiers
source                    1..21
                          mol_type = other DNA
                          organism = synthetic construct
SEQUENCE: 767
cgttttcatc ggcccggaat t                                              21

SEQ ID NO: 768            moltype = DNA   length = 32
FEATURE                   Location/Qualifiers
source                    1..32
                          mol_type = other DNA
                          organism = synthetic construct
SEQUENCE: 768
tcataataca gatacatagg aatacaaagc gg                                  32

SEQ ID NO: 769            moltype = DNA   length = 32
FEATURE                   Location/Qualifiers
source                    1..32
                          mol_type = other DNA
                          organism = synthetic construct
SEQUENCE: 769
```

-continued

```
cttattagca aaagggagca acaccgaaaa ca                                    32

SEQ ID NO: 770          moltype = DNA   length = 45
FEATURE                 Location/Qualifiers
source                  1..45
                        mol_type = other DNA
                        organism = synthetic construct
SEQUENCE: 770
ttcataatca aaatcctcat tccttgatat tcggtcgaaa cagct                      45

SEQ ID NO: 771          moltype = DNA   length = 32
FEATURE                 Location/Qualifiers
source                  1..32
                        mol_type = other DNA
                        organism = synthetic construct
SEQUENCE: 771
gtgaattaat agtaagtaac gccacagtct ta                                    32

SEQ ID NO: 772          moltype = DNA   length = 32
FEATURE                 Location/Qualifiers
source                  1..32
                        mol_type = other DNA
                        organism = synthetic construct
SEQUENCE: 772
tttaaccgaa ccctcggaaa cgcacgcaat aa                                    32

SEQ ID NO: 773          moltype = DNA   length = 21
FEATURE                 Location/Qualifiers
source                  1..21
                        mol_type = other DNA
                        organism = synthetic construct
SEQUENCE: 773
caccggaacc gccgacggag g                                                21

SEQ ID NO: 774          moltype = DNA   length = 32
FEATURE                 Location/Qualifiers
source                  1..32
                        mol_type = other DNA
                        organism = synthetic construct
SEQUENCE: 774
agccggagaa atagcgttta ccagcctcaa at                                    32

SEQ ID NO: 775          moltype = DNA   length = 24
FEATURE                 Location/Qualifiers
source                  1..24
                        mol_type = other DNA
                        organism = synthetic construct
SEQUENCE: 775
ctcagaacat ataaaagggg tatg                                             24

SEQ ID NO: 776          moltype = DNA   length = 37
FEATURE                 Location/Qualifiers
source                  1..37
                        mol_type = other DNA
                        organism = synthetic construct
SEQUENCE: 776
gccaccaccc tcagagcctt cgccagcttg gggatgt                               37

SEQ ID NO: 777          moltype = DNA   length = 35
FEATURE                 Location/Qualifiers
source                  1..35
                        mol_type = other DNA
                        organism = synthetic construct
SEQUENCE: 777
gccgccagca ttgacaaagg agcctttcaa ctaaa                                 35

SEQ ID NO: 778          moltype = DNA   length = 37
FEATURE                 Location/Qualifiers
source                  1..37
                        mol_type = other DNA
                        organism = synthetic construct
SEQUENCE: 778
ttgaggcaaa tttcttctga ggcttatcta aaatatc                               37

SEQ ID NO: 779          moltype = DNA   length = 48
FEATURE                 Location/Qualifiers
source                  1..48
                        mol_type = other DNA
                        organism = synthetic construct
```

```
SEQUENCE: 779
cagacgattg gaaagccagg ggatcgtctt tgagggaagt attagact                     48

SEQ ID NO: 780         moltype = DNA   length = 35
FEATURE                Location/Qualifiers
source                 1..35
                       mol_type = other DNA
                       organism = synthetic construct
SEQUENCE: 780
ggaaagcgca gtctctaact acagaggcac cctca                                   35

SEQ ID NO: 781         moltype = DNA   length = 37
FEATURE                Location/Qualifiers
source                 1..37
                       mol_type = other DNA
                       organism = synthetic construct
SEQUENCE: 781
taccgttctc cattaatcat ctttttgagt aacatta                                 37

SEQ ID NO: 782         moltype = DNA   length = 35
FEATURE                Location/Qualifiers
source                 1..35
                       mol_type = other DNA
                       organism = synthetic construct
SEQUENCE: 782
taagcgtcat acatgggctt aaaacacacg ggtaa                                   35

SEQ ID NO: 783         moltype = DNA   length = 20
FEATURE                Location/Qualifiers
source                 1..20
                       mol_type = other DNA
                       organism = synthetic construct
SEQUENCE: 783
gcctatgcgc cggaagggaa                                                    20

SEQ ID NO: 784         moltype = DNA   length = 40
FEATURE                Location/Qualifiers
source                 1..40
                       mol_type = other DNA
                       organism = synthetic construct
SEQUENCE: 784
aacggggtat gaaagtatgg aaggtcctga ttatcagatg                              40

SEQ ID NO: 785         moltype = DNA   length = 16
FEATURE                Location/Qualifiers
source                 1..16
                       mol_type = other DNA
                       organism = synthetic construct
SEQUENCE: 785
caagcgcgag gagtgt                                                        16

SEQ ID NO: 786         moltype = DNA   length = 48
FEATURE                Location/Qualifiers
source                 1..48
                       mol_type = other DNA
                       organism = synthetic construct
SEQUENCE: 786
tacaacggag atttgtgaat acacccatgt tataagggaa attttcgg                     48

SEQ ID NO: 787         moltype = DNA   length = 40
FEATURE                Location/Qualifiers
source                 1..40
                       mol_type = other DNA
                       organism = synthetic construct
SEQUENCE: 787
gcgatgagac tcctcaatag cccgtccttt gcatagataa                              40

SEQ ID NO: 788         moltype = DNA   length = 32
FEATURE                Location/Qualifiers
source                 1..32
                       mol_type = other DNA
                       organism = synthetic construct
SEQUENCE: 788
atataagtag agaaggtctg tccaaattat ca                                      32

SEQ ID NO: 789         moltype = DNA   length = 40
FEATURE                Location/Qualifiers
source                 1..40
                       mol_type = other DNA
```

-continued

```
                       organism = synthetic construct
SEQUENCE: 789
aatacgtagc aacggctgac caaccaaata aatcatcatt                              40

SEQ ID NO: 790         moltype = DNA   length = 40
FEATURE                Location/Qualifiers
source                 1..40
                       mol_type = other DNA
                       organism = synthetic construct
SEQUENCE: 790
cttttaggt gtatcactca ttttagccgt cacagttgaa                               40

SEQ ID NO: 791         moltype = DNA   length = 32
FEATURE                Location/Qualifiers
source                 1..32
                       mol_type = other DNA
                       organism = synthetic construct
SEQUENCE: 791
ccaccacccc gtactctggt aaatatcacgc aa                                     32

SEQ ID NO: 792         moltype = DNA   length = 40
FEATURE                Location/Qualifiers
source                 1..40
                       mol_type = other DNA
                       organism = synthetic construct
SEQUENCE: 792
gcagcgaacc gatatattca caaagtaatc tttccctcag                              40

SEQ ID NO: 793         moltype = DNA   length = 40
FEATURE                Location/Qualifiers
source                 1..40
                       mol_type = other DNA
                       organism = synthetic construct
SEQUENCE: 793
gttaaggata gcaagcacag ccctcaaatc aaaaaatcta                              40

SEQ ID NO: 794         moltype = DNA   length = 40
FEATURE                Location/Qualifiers
source                 1..40
                       mol_type = other DNA
                       organism = synthetic construct
SEQUENCE: 794
acgcataaag acagcagtac agactttgaa agattgcccc                              40

SEQ ID NO: 795         moltype = DNA   length = 32
FEATURE                Location/Qualifiers
source                 1..32
                       mol_type = other DNA
                       organism = synthetic construct
SEQUENCE: 795
ttccacagcc aataggtatt tacatccaga ac                                      32

SEQ ID NO: 796         moltype = DNA   length = 15
FEATURE                Location/Qualifiers
source                 1..15
                       mol_type = other DNA
                       organism = synthetic construct
SEQUENCE: 796
tttcgaggtg ggttt                                                         15

SEQ ID NO: 797         moltype = DNA   length = 32
FEATURE                Location/Qualifiers
source                 1..32
                       mol_type = other DNA
                       organism = synthetic construct
SEQUENCE: 797
tgataccgtc caaagaacc ggattcagcc ac                                       32

SEQ ID NO: 798         moltype = DNA   length = 40
FEATURE                Location/Qualifiers
source                 1..40
                       mol_type = other DNA
                       organism = synthetic construct
SEQUENCE: 798
cagctagtta gcgtaaaaca gtttgcaaat gagataaaac                              40

SEQ ID NO: 799         moltype = DNA   length = 40
FEATURE                Location/Qualifiers
source                 1..40
```

```
                          mol_type = other DNA
                          organism = synthetic construct
SEQUENCE: 799
aaaaaggcat agttgccatc aagacaggcg caatttcaac                    40

SEQ ID NO: 800           moltype = DNA   length = 46
FEATURE                  Location/Qualifiers
source                   1..46
                         mol_type = other DNA
                         organism = synthetic construct
SEQUENCE: 800
gggattttgc taaacaactt tccgatctaa tacgtggctt ggcaga           46

SEQ ID NO: 801           moltype = DNA   length = 15
FEATURE                  Location/Qualifiers
source                   1..15
                         mol_type = other DNA
                         organism = synthetic construct
SEQUENCE: 801
tttgagaata gcctt                                              15

SEQ ID NO: 802           moltype = DNA   length = 24
FEATURE                  Location/Qualifiers
source                   1..24
                         mol_type = other DNA
                         organism = synthetic construct
SEQUENCE: 802
ggaattgcca ttcaggtccg gcac                                    24

SEQ ID NO: 803           moltype = DNA   length = 48
FEATURE                  Location/Qualifiers
source                   1..48
                         mol_type = other DNA
                         organism = synthetic construct
SEQUENCE: 803
tttttcagga agatcgtgcc ggaaacgtaa cattttttca cgtttttt         48

SEQ ID NO: 804           moltype = DNA   length = 48
FEATURE                  Location/Qualifiers
source                   1..48
                         mol_type = other DNA
                         organism = synthetic construct
SEQUENCE: 804
ttttccgtaa tgggaaccgt gcactaaagt atgtttagac tggatttt         48

SEQ ID NO: 805           moltype = DNA   length = 29
FEATURE                  Location/Qualifiers
source                   1..29
                         mol_type = other DNA
                         organism = synthetic construct
SEQUENCE: 805
ttttctggcc ttaaaggccg gagactttt                              29

SEQ ID NO: 806           moltype = DNA   length = 29
FEATURE                  Location/Qualifiers
source                   1..29
                         mol_type = other DNA
                         organism = synthetic construct
SEQUENCE: 806
ttttccaata ggtgatattc aaccgtttt                              29

SEQ ID NO: 807           moltype = DNA   length = 29
FEATURE                  Location/Qualifiers
source                   1..29
                         mol_type = other DNA
                         organism = synthetic construct
SEQUENCE: 807
tttttaatat ttttgagaga tctactttt                              29

SEQ ID NO: 808           moltype = DNA   length = 29
FEATURE                  Location/Qualifiers
source                   1..29
                         mol_type = other DNA
                         organism = synthetic construct
SEQUENCE: 808
ttttattgta tacctgagag tctggtttt                              29

SEQ ID NO: 809           moltype = DNA   length = 29
FEATURE                  Location/Qualifiers
```

-continued

```
source                  1..29
                        mol_type = other DNA
                        organism = synthetic construct
SEQUENCE: 809
ttttagcaaa caagagaata aagcttttt                                          29

SEQ ID NO: 810          moltype = DNA   length = 29
FEATURE                 Location/Qualifiers
source                  1..29
                        mol_type = other DNA
                        organism = synthetic construct
SEQUENCE: 810
ttttaaaggc tatcaggtga ccctgtttt                                          29

SEQ ID NO: 811          moltype = DNA   length = 29
FEATURE                 Location/Qualifiers
source                  1..29
                        mol_type = other DNA
                        organism = synthetic construct
SEQUENCE: 811
tttttttctag ctgataattt ttagatttt                                         29

SEQ ID NO: 812          moltype = DNA   length = 29
FEATURE                 Location/Qualifiers
source                  1..29
                        mol_type = other DNA
                        organism = synthetic construct
SEQUENCE: 812
ttttagtcaa atcaccagcc tgagttttt                                          29

SEQ ID NO: 813          moltype = DNA   length = 29
FEATURE                 Location/Qualifiers
source                  1..29
                        mol_type = other DNA
                        organism = synthetic construct
SEQUENCE: 813
ttttaccctc atgtagattt agttttttt                                          29

SEQ ID NO: 814          moltype = DNA   length = 29
FEATURE                 Location/Qualifiers
source                  1..29
                        mol_type = other DNA
                        organism = synthetic construct
SEQUENCE: 814
tttttaatac tttagctata ttttctttt                                          29

SEQ ID NO: 815          moltype = DNA   length = 29
FEATURE                 Location/Qualifiers
source                  1..29
                        mol_type = other DNA
                        organism = synthetic construct
SEQUENCE: 815
ttttaaatcg gtaaggtggc atcaatttt                                          29

SEQ ID NO: 816          moltype = DNA   length = 50
FEATURE                 Location/Qualifiers
source                  1..50
                        mol_type = other DNA
                        organism = synthetic construct
SEQUENCE: 816
ttttcaaggc aaagaattag caaaacctaa tcgtaaaact agcatgtttt                    50

SEQ ID NO: 817          moltype = DNA   length = 29
FEATURE                 Location/Qualifiers
source                  1..29
                        mol_type = other DNA
                        organism = synthetic construct
SEQUENCE: 817
tttttttctac taatagtaag cgaactttt                                         29

SEQ ID NO: 818          moltype = DNA   length = 29
FEATURE                 Location/Qualifiers
source                  1..29
                        mol_type = other DNA
                        organism = synthetic construct
SEQUENCE: 818
ttttatttgg ggcgcgaaat tgctctttt                                          29

SEQ ID NO: 819          moltype = DNA   length = 29
```

-continued

```
FEATURE                Location/Qualifiers
source                 1..29
                       mol_type = other DNA
                       organism = synthetic construct
SEQUENCE: 819
ttttgaccat tagatacgga tggcttttt                                        29

SEQ ID NO: 820         moltype = DNA   length = 29
FEATURE                Location/Qualifiers
source                 1..29
                       mol_type = other DNA
                       organism = synthetic construct
SEQUENCE: 820
tttttttccca attctgcata tgcaatttt                                       29

SEQ ID NO: 821         moltype = DNA   length = 29
FEATURE                Location/Qualifiers
source                 1..29
                       mol_type = other DNA
                       organism = synthetic construct
SEQUENCE: 821
tttttagagc ttatcgtcat aaatatttt                                        29

SEQ ID NO: 822         moltype = DNA   length = 29
FEATURE                Location/Qualifiers
source                 1..29
                       mol_type = other DNA
                       organism = synthetic construct
SEQUENCE: 822
ttttcttttg ataacgagaa tgacctttt                                        29

SEQ ID NO: 823         moltype = DNA   length = 29
FEATURE                Location/Qualifiers
source                 1..29
                       mol_type = other DNA
                       organism = synthetic construct
SEQUENCE: 823
ttttcagacc ggtttaccct gactatttt                                        29

SEQ ID NO: 824         moltype = DNA   length = 50
FEATURE                Location/Qualifiers
source                 1..50
                       mol_type = other DNA
                       organism = synthetic construct
SEQUENCE: 824
ttttaagccc gaaagacttc aaatattctc caataaatca tacaggtttt                 50

SEQ ID NO: 825         moltype = DNA   length = 29
FEATURE                Location/Qualifiers
source                 1..29
                       mol_type = other DNA
                       organism = synthetic construct
SEQUENCE: 825
tttttttatag tcagaagcca cattctttt                                       29

SEQ ID NO: 826         moltype = DNA   length = 29
FEATURE                Location/Qualifiers
source                 1..29
                       mol_type = other DNA
                       organism = synthetic construct
SEQUENCE: 826
tttttataaat caaaaataaa ggaattttt                                       29

SEQ ID NO: 827         moltype = DNA   length = 29
FEATURE                Location/Qualifiers
source                 1..29
                       mol_type = other DNA
                       organism = synthetic construct
SEQUENCE: 827
tttttttcatt gaatcccacg acgattttt                                       29

SEQ ID NO: 828         moltype = DNA   length = 29
FEATURE                Location/Qualifiers
source                 1..29
                       mol_type = other DNA
                       organism = synthetic construct
SEQUENCE: 828
tttttagcgt ccaatacttg caaaatttt                                        29
```

-continued

```
SEQ ID NO: 829              moltype = DNA   length = 29
FEATURE                     Location/Qualifiers
source                      1..29
                            mol_type = other DNA
                            organism = synthetic construct
SEQUENCE: 829
ttttaaaaac catagtaaat tgggctttt                                              29

SEQ ID NO: 830              moltype = DNA   length = 29
FEATURE                     Location/Qualifiers
source                      1..29
                            mol_type = other DNA
                            organism = synthetic construct
SEQUENCE: 830
tttttacgag gcccttatgc gattttttt                                              29

SEQ ID NO: 831              moltype = DNA   length = 29
FEATURE                     Location/Qualifiers
source                      1..29
                            mol_type = other DNA
                            organism = synthetic construct
SEQUENCE: 831
ttttaactaa tgccagtcag gacgttttt                                              29

SEQ ID NO: 832              moltype = DNA   length = 50
FEATURE                     Location/Qualifiers
source                      1..50
                            mol_type = other DNA
                            organism = synthetic construct
SEQUENCE: 832
ttttattatt acaggtagaa agatttaaat caaaaagatt aagaggtttt                       50

SEQ ID NO: 833              moltype = DNA   length = 29
FEATURE                     Location/Qualifiers
source                      1..29
                            mol_type = other DNA
                            organism = synthetic construct
SEQUENCE: 833
tttttgggaa gaaaaatgaa cgaggtttt                                              29

SEQ ID NO: 834              moltype = DNA   length = 29
FEATURE                     Location/Qualifiers
source                      1..29
                            mol_type = other DNA
                            organism = synthetic construct
SEQUENCE: 834
tttttaagaa ctggctcagg acagatttt                                             29

SEQ ID NO: 835              moltype = DNA   length = 29
FEATURE                     Location/Qualifiers
source                      1..29
                            mol_type = other DNA
                            organism = synthetic construct
SEQUENCE: 835
tttttttgaga tggtttatag gctggtttt                                            29

SEQ ID NO: 836              moltype = DNA   length = 29
FEATURE                     Location/Qualifiers
source                      1..29
                            mol_type = other DNA
                            organism = synthetic construct
SEQUENCE: 836
ttttcgagaa acaccagccc aaatctttt                                             29

SEQ ID NO: 837              moltype = DNA   length = 29
FEATURE                     Location/Qualifiers
source                      1..29
                            mol_type = other DNA
                            organism = synthetic construct
SEQUENCE: 837
ttttctgacc ttgccgacaa tgacatttt                                             29

SEQ ID NO: 838              moltype = DNA   length = 19
FEATURE                     Location/Qualifiers
source                      1..19
                            mol_type = other DNA
                            organism = synthetic construct
SEQUENCE: 838
tttttgaacg gttcgtttt                                                        19
```

-continued

```
SEQ ID NO: 839          moltype = DNA  length = 29
FEATURE                 Location/Qualifiers
source                  1..29
                        mol_type = other DNA
                        organism = synthetic construct
SEQUENCE: 839
ttttcgcaga cgacgaaggc accaatttt                              29

SEQ ID NO: 840          moltype = DNA  length = 50
FEATURE                 Location/Qualifiers
source                  1..50
                        mol_type = other DNA
                        organism = synthetic construct
SEQUENCE: 840
ttttaaattg tgtcgaaatc cgcgattaac gaactaacgg aacaactttt       50

SEQ ID NO: 841          moltype = DNA  length = 42
FEATURE                 Location/Qualifiers
source                  1..42
                        mol_type = other DNA
                        organism = synthetic construct
SEQUENCE: 841
ttttcctaaa acgaaagagg caaaaatcat cgcctgattt tt               42

SEQ ID NO: 842          moltype = DNA  length = 51
FEATURE                 Location/Qualifiers
source                  1..51
                        mol_type = other DNA
                        organism = synthetic construct
SEQUENCE: 842
ttttgaacga gggtaatgcc actgtcaatc acttagccgc tacgttattt t      51

SEQ ID NO: 843          moltype = DNA  length = 15
FEATURE                 Location/Qualifiers
source                  1..15
                        mol_type = other DNA
                        organism = synthetic construct
SEQUENCE: 843
ttttcaggca aagcg                                             15

SEQ ID NO: 844          moltype = DNA  length = 41
FEATURE                 Location/Qualifiers
source                  1..41
                        mol_type = other DNA
                        organism = synthetic construct
SEQUENCE: 844
gctgacgaca gtatcggaag ttttaggctt gccctgattt t                41

SEQ ID NO: 845          moltype = DNA  length = 15
FEATURE                 Location/Qualifiers
source                  1..15
                        mol_type = other DNA
                        organism = synthetic construct
SEQUENCE: 845
ttttgccagt ttgag                                             15

SEQ ID NO: 846          moltype = DNA  length = 52
FEATURE                 Location/Qualifiers
source                  1..52
                        mol_type = other DNA
                        organism = synthetic construct
SEQUENCE: 846
ggaacaaata acaaccaggg tgagcctgta gccaaaaata attcgcgttt tt     52

SEQ ID NO: 847          moltype = DNA  length = 33
FEATURE                 Location/Qualifiers
source                  1..33
                        mol_type = other DNA
                        organism = synthetic construct
SEQUENCE: 847
cggcggataa tgtgtaatat aacagttgat ttt                         33

SEQ ID NO: 848          moltype = DNA  length = 33
FEATURE                 Location/Qualifiers
source                  1..33
                        mol_type = other DNA
                        organism = synthetic construct
SEQUENCE: 848
```

-continued

```
ttttttcaatc atatgtaccc cggttgatcc agt                                          33

SEQ ID NO: 849            moltype = DNA   length = 36
FEATURE                   Location/Qualifiers
source                    1..36
                          mol_type = other DNA
                          organism = synthetic construct
SEQUENCE: 849
tgatgttgag caaataccc aaaaacagga agtttt                                          36

SEQ ID NO: 850            moltype = DNA   length = 36
FEATURE                   Location/Qualifiers
source                    1..36
                          mol_type = other DNA
                          organism = synthetic construct
SEQUENCE: 850
agctattttg ttaaaattta aattgtaaac gttttt                                         36

SEQ ID NO: 851            moltype = DNA   length = 36
FEATURE                   Location/Qualifiers
source                    1..36
                          mol_type = other DNA
                          organism = synthetic construct
SEQUENCE: 851
taatgataaa cgccattcag ctcatttttt aatttt                                         36

SEQ ID NO: 852            moltype = DNA   length = 49
FEATURE                   Location/Qualifiers
source                    1..49
                          mol_type = other DNA
                          organism = synthetic construct
SEQUENCE: 852
taaggcgtta aataagaaaa acgtcggata ttaaatgtga gcgagtttt                           49

SEQ ID NO: 853            moltype = DNA   length = 17
FEATURE                   Location/Qualifiers
source                    1..17
                          mol_type = other DNA
                          organism = synthetic construct
SEQUENCE: 853
ttttacaacc atcgccc                                                              17

SEQ ID NO: 854            moltype = DNA   length = 17
FEATURE                   Location/Qualifiers
source                    1..17
                          mol_type = other DNA
                          organism = synthetic construct
SEQUENCE: 854
ttttgaaaat ctccaaa                                                              17

SEQ ID NO: 855            moltype = DNA   length = 40
FEATURE                   Location/Qualifiers
source                    1..40
                          mol_type = other DNA
                          organism = synthetic construct
SEQUENCE: 855
ttttttgcag caagcggtcc cctggccctg agagagtttt                                     40

SEQ ID NO: 856            moltype = DNA   length = 40
FEATURE                   Location/Qualifiers
source                    1..40
                          mol_type = other DNA
                          organism = synthetic construct
SEQUENCE: 856
ttttaatccc ttataaatca gttccgaaat cggcaatttt                                     40

SEQ ID NO: 857            moltype = DNA   length = 40
FEATURE                   Location/Qualifiers
source                    1..40
                          mol_type = other DNA
                          organism = synthetic construct
SEQUENCE: 857
ttttcaaagg gcgaaaaacc acgtggactc caacgttttt                                     40

SEQ ID NO: 858            moltype = DNA   length = 40
FEATURE                   Location/Qualifiers
source                    1..40
                          mol_type = other DNA
                          organism = synthetic construct
```

-continued

```
SEQUENCE: 858
ttttccccga tttagagctt gaaccctaaa gggagctttt                                    40

SEQ ID NO: 859          moltype = DNA   length = 40
FEATURE                 Location/Qualifiers
source                  1..40
                        mol_type = other DNA
                        organism = synthetic construct
SEQUENCE: 859
ttttgcggtc acgctgcgcg ggcgctggca agtgtatttt                                    40

SEQ ID NO: 860          moltype = DNA   length = 40
FEATURE                 Location/Qualifiers
source                  1..40
                        mol_type = other DNA
                        organism = synthetic construct
SEQUENCE: 860
tttttcactt gcctgagtag ttgattagta ataacatttt                                    40

SEQ ID NO: 861          moltype = DNA   length = 40
FEATURE                 Location/Qualifiers
source                  1..40
                        mol_type = other DNA
                        organism = synthetic construct
SEQUENCE: 861
ttttgaaata cctacatttt aggaaaaacg ctcatgtttt                                    40

SEQ ID NO: 862          moltype = DNA   length = 40
FEATURE                 Location/Qualifiers
source                  1..40
                        mol_type = other DNA
                        organism = synthetic construct
SEQUENCE: 862
ttttccaaca gagatagaac aaaagggaca ttctggtttt                                    40

SEQ ID NO: 863          moltype = DNA   length = 40
FEATURE                 Location/Qualifiers
source                  1..40
                        mol_type = other DNA
                        organism = synthetic construct
SEQUENCE: 863
ttttagccct aaaacatcgc taatgcgcga actgattttt                                    40

SEQ ID NO: 864          moltype = DNA   length = 35
FEATURE                 Location/Qualifiers
source                  1..35
                        mol_type = other DNA
                        organism = synthetic construct
SEQUENCE: 864
tttttctaga ggatcaacgc atgcctgcag gtttt                                         35

SEQ ID NO: 865          moltype = DNA   length = 25
FEATURE                 Location/Qualifiers
source                  1..25
                        mol_type = other DNA
                        organism = synthetic construct
SEQUENCE: 865
ttttattcgt aattatccgc ttttt                                                    25

SEQ ID NO: 866          moltype = DNA   length = 25
FEATURE                 Location/Qualifiers
source                  1..25
                        mol_type = other DNA
                        organism = synthetic construct
SEQUENCE: 866
tttttgtaaa gccaattgcg ttttt                                                    25

SEQ ID NO: 867          moltype = DNA   length = 19
FEATURE                 Location/Qualifiers
source                  1..19
                        mol_type = other DNA
                        organism = synthetic construct
SEQUENCE: 867
ttttagatta atgcatttt                                                           19

SEQ ID NO: 868          moltype = DNA   length = 19
FEATURE                 Location/Qualifiers
source                  1..19
                        mol_type = other DNA
```

-continued

```
SEQUENCE: 868
ttttctgaat aaaaatttt                                                    19

SEQ ID NO: 869            moltype = DNA   length = 19
FEATURE                   Location/Qualifiers
source                    1..19
                          mol_type = other DNA
                          organism = synthetic construct
SEQUENCE: 869
tttttgaaca agcaatttt                                                    19

SEQ ID NO: 870            moltype = DNA   length = 19
FEATURE                   Location/Qualifiers
source                    1..19
                          mol_type = other DNA
                          organism = synthetic construct
SEQUENCE: 870
ttttccggaa gtgcctttt                                                    19

SEQ ID NO: 871            moltype = DNA   length = 30
FEATURE                   Location/Qualifiers
source                    1..30
                          mol_type = other DNA
                          organism = synthetic construct
SEQUENCE: 871
tttttcggaa aggaacggca gtgaggtttt                                        30

SEQ ID NO: 872            moltype = DNA   length = 19
FEATURE                   Location/Qualifiers
source                    1..19
                          mol_type = other DNA
                          organism = synthetic construct
SEQUENCE: 872
ttttgtcgat agtactttt                                                    19

SEQ ID NO: 873            moltype = DNA   length = 19
FEATURE                   Location/Qualifiers
source                    1..19
                          mol_type = other DNA
                          organism = synthetic construct
SEQUENCE: 873
ttttcgccac taccgtttt                                                    19

SEQ ID NO: 874            moltype = DNA   length = 19
FEATURE                   Location/Qualifiers
source                    1..19
                          mol_type = other DNA
                          organism = synthetic construct
SEQUENCE: 874
ttttaacgcc gtctttttt                                                    19

SEQ ID NO: 875            moltype = DNA   length = 50
FEATURE                   Location/Qualifiers
source                    1..50
                          mol_type = other DNA
                          organism = synthetic construct
SEQUENCE: 875
cttcaccgac gctggtttgc cccagcaggg agtaattaat tttccctttt                  50

SEQ ID NO: 876            moltype = DNA   length = 12
FEATURE                   Location/Qualifiers
source                    1..12
                          mol_type = other DNA
                          organism = synthetic construct
SEQUENCE: 876
ttttttcctc gt                                                           12

SEQ ID NO: 877            moltype = DNA   length = 36
FEATURE                   Location/Qualifiers
source                    1..36
                          mol_type = other DNA
                          organism = synthetic construct
SEQUENCE: 877
aatcctgata gaatcagcac gtataacgtg cttttt                                 36

SEQ ID NO: 878            moltype = DNA   length = 28
FEATURE                   Location/Qualifiers
source                    1..28
```

-continued

```
                       mol_type = other DNA
                       organism = synthetic construct
SEQUENCE: 878
ttttgaagtg tttttataat tacgccag                                    28

SEQ ID NO: 879        moltype = DNA   length = 47
FEATURE               Location/Qualifiers
source                1..47
                       mol_type = other DNA
                       organism = synthetic construct
SEQUENCE: 879
gggcgaccac cagagaaagg aaaattgtat aacctcaaat atctttt              47

SEQ ID NO: 880        moltype = DNA   length = 21
FEATURE               Location/Qualifiers
source                1..21
                       mol_type = other DNA
                       organism = synthetic construct
SEQUENCE: 880
ccagctcgta gaaaatattt t                                          21

SEQ ID NO: 881        moltype = DNA   length = 21
FEATURE               Location/Qualifiers
source                1..21
                       mol_type = other DNA
                       organism = synthetic construct
SEQUENCE: 881
gttttcttga agccttattt t                                          21

SEQ ID NO: 882        moltype = DNA   length = 21
FEATURE               Location/Qualifiers
source                1..21
                       mol_type = other DNA
                       organism = synthetic construct
SEQUENCE: 882
ccagtgcata attactattt t                                          21

SEQ ID NO: 883        moltype = DNA   length = 34
FEATURE               Location/Qualifiers
source                1..34
                       mol_type = other DNA
                       organism = synthetic construct
SEQUENCE: 883
tttttttccac acaacatatt tatattttag ttaa                           34

SEQ ID NO: 884        moltype = DNA   length = 34
FEATURE               Location/Qualifiers
source                1..34
                       mol_type = other DNA
                       organism = synthetic construct
SEQUENCE: 884
tttttcactg cccgctttaa tgcttaggtt gggt                            34

SEQ ID NO: 885        moltype = DNA   length = 44
FEATURE               Location/Qualifiers
source                1..44
                       mol_type = other DNA
                       organism = synthetic construct
SEQUENCE: 885
ccaatcgcct aatgagttcg cattaaacga gccggaagca tttt                 44

SEQ ID NO: 886        moltype = DNA   length = 44
FEATURE               Location/Qualifiers
source                1..44
                       mol_type = other DNA
                       organism = synthetic construct
SEQUENCE: 886
aaataccgta gctgttcagc tttcatcccc gggtaccgag tttt                 44

SEQ ID NO: 887        moltype = DNA   length = 33
FEATURE               Location/Qualifiers
source                1..33
                       mol_type = other DNA
                       organism = synthetic construct
SEQUENCE: 887
accggaatcc aagcttgacg ttgtaaaact ttt                             33

SEQ ID NO: 888        moltype = DNA   length = 33
FEATURE               Location/Qualifiers
```

```
source                    1..33
                          mol_type = other DNA
                          organism = synthetic construct
SEQUENCE: 888
gggaggttcc agtcacaagt tgggtaacgt ttt                                          33

SEQ ID NO: 889            moltype = DNA   length = 33
FEATURE                   Location/Qualifiers
source                    1..33
                          mol_type = other DNA
                          organism = synthetic construct
SEQUENCE: 889
ttagcaaagg cgaaagggcc tcttcgctat ttt                                          33

SEQ ID NO: 890            moltype = DNA   length = 33
FEATURE                   Location/Qualifiers
source                    1..33
                          mol_type = other DNA
                          organism = synthetic construct
SEQUENCE: 890
cagaaccatc ggtgcgctgc gcaactgttt ttt                                          33

SEQ ID NO: 891            moltype = DNA   length = 37
FEATURE                   Location/Qualifiers
source                    1..37
                          mol_type = other DNA
                          organism = synthetic construct
SEQUENCE: 891
gggtcccaat tctgcgaacc catataacag ttgataa                                      37

SEQ ID NO: 892            moltype = DNA   length = 37
FEATURE                   Location/Qualifiers
source                    1..37
                          mol_type = other DNA
                          organism = synthetic construct
SEQUENCE: 892
ttaggtcatt tttgcggatg ctccttttga taagacg                                      37

SEQ ID NO: 893            moltype = DNA   length = 37
FEATURE                   Location/Qualifiers
source                    1..37
                          mol_type = other DNA
                          organism = synthetic construct
SEQUENCE: 893
ccagaagccc gaaagacttt caaaaagatt aagaggg                                      37

SEQ ID NO: 894            moltype = DNA   length = 37
FEATURE                   Location/Qualifiers
source                    1..37
                          mol_type = other DNA
                          organism = synthetic construct
SEQUENCE: 894
gactcccect caaatgctta taaatattca ttgaagg                                      37

SEQ ID NO: 895            moltype = DNA   length = 37
FEATURE                   Location/Qualifiers
source                    1..37
                          mol_type = other DNA
                          organism = synthetic construct
SEQUENCE: 895
tcgagtaaga gcaacactaa ggaattacga ggcatac                                      37

SEQ ID NO: 896            moltype = DNA   length = 35
FEATURE                   Location/Qualifiers
source                    1..35
                          mol_type = other DNA
                          organism = synthetic construct
SEQUENCE: 896
ctcttaataa aacgaactga agaaaaatct acgga                                        35

SEQ ID NO: 897            moltype = DNA   length = 37
FEATURE                   Location/Qualifiers
source                    1..37
                          mol_type = other DNA
                          organism = synthetic construct
SEQUENCE: 897
cacgtagtaa attgggctta gaaacaccag aacgaaa                                      37

SEQ ID NO: 898            moltype = DNA   length = 35
```

-continued

```
FEATURE            Location/Qualifiers
source             1..35
                   mol_type = other DNA
                   organism = synthetic construct
SEQUENCE: 898
taagctgacc ttcatcaaca ggcgcatagg ctgag                              35

SEQ ID NO: 899     moltype = DNA   length = 37
FEATURE            Location/Qualifiers
source             1..37
                   mol_type = other DNA
                   organism = synthetic construct
SEQUENCE: 899
tgcataaatt gtgtcgaaat ttgtatcatc gcctggc                            37

SEQ ID NO: 900     moltype = DNA   length = 35
FEATURE            Location/Qualifiers
source             1..35
                   mol_type = other DNA
                   organism = synthetic construct
SEQUENCE: 900
aaaacatagc gatagctttt agaatccttg aaaga                              35

SEQ ID NO: 901     moltype = DNA   length = 37
FEATURE            Location/Qualifiers
source             1..37
                   mol_type = other DNA
                   organism = synthetic construct
SEQUENCE: 901
ggacaacaat agataagtcg aacgcgcctg tttatgt                            37

SEQ ID NO: 902     moltype = DNA   length = 35
FEATURE            Location/Qualifiers
source             1..35
                   mol_type = other DNA
                   organism = synthetic construct
SEQUENCE: 902
taagacggga gaattaacca gggaagcgca ttaga                              35

SEQ ID NO: 903     moltype = DNA   length = 37
FEATURE            Location/Qualifiers
source             1..37
                   mol_type = other DNA
                   organism = synthetic construct
SEQUENCE: 903
cggattacca ttagcaagga atcaccagta gcaccaa                            37

SEQ ID NO: 904     moltype = DNA   length = 35
FEATURE            Location/Qualifiers
source             1..35
                   mol_type = other DNA
                   organism = synthetic construct
SEQUENCE: 904
acatgccccc tgcctattcg tataaacagt taata                              35

SEQ ID NO: 905     moltype = DNA   length = 37
FEATURE            Location/Qualifiers
source             1..37
                   mol_type = other DNA
                   organism = synthetic construct
SEQUENCE: 905
acgcaggcgg ataagtgccg ggttttgctc agtacca                            37

SEQ ID NO: 906     moltype = DNA   length = 35
FEATURE            Location/Qualifiers
source             1..35
                   mol_type = other DNA
                   organism = synthetic construct
SEQUENCE: 906
caacgccacc ctcagaaccg ccaccctcag aacaa                              35

SEQ ID NO: 907     moltype = DNA   length = 37
FEATURE            Location/Qualifiers
source             1..37
                   mol_type = other DNA
                   organism = synthetic construct
SEQUENCE: 907
aaacaccagt acaaactact aacactgagt ttcgtcc                            37
```

-continued

```
SEQ ID NO: 908           moltype = DNA   length = 35
FEATURE                  Location/Qualifiers
source                   1..35
                         mol_type = other DNA
                         organism = synthetic construct
SEQUENCE: 908
taaatgaatt ttctgtattc cagacgttag taagc                              35

SEQ ID NO: 909           moltype = DNA   length = 42
FEATURE                  Location/Qualifiers
source                   1..42
                         mol_type = other DNA
                         organism = synthetic construct
SEQUENCE: 909
gatataagta tagtgacaca gacagccctc atggagggag gg                      42

SEQ ID NO: 910           moltype = DNA   length = 32
FEATURE                  Location/Qualifiers
source                   1..32
                         mol_type = other DNA
                         organism = synthetic construct
SEQUENCE: 910
cttttgatga tgtcagtgcc ttggagggag gg                                 32

SEQ ID NO: 911           moltype = DNA   length = 42
FEATURE                  Location/Qualifiers
source                   1..42
                         mol_type = other DNA
                         organism = synthetic construct
SEQUENCE: 911
cattgacagg aggatttaag cgtcatacat ggggagggag gg                      42

SEQ ID NO: 912           moltype = DNA   length = 42
FEATURE                  Location/Qualifiers
source                   1..42
                         mol_type = other DNA
                         organism = synthetic construct
SEQUENCE: 912
gcaagcaaat caggcttatt ttgcacccag ctccagccag cc                      42

SEQ ID NO: 913           moltype = DNA   length = 32
FEATURE                  Location/Qualifiers
source                   1..32
                         mol_type = other DNA
                         organism = synthetic construct
SEQUENCE: 913
acaattttat ccagagccta atccagccag cc                                 32

SEQ ID NO: 914           moltype = DNA   length = 42
FEATURE                  Location/Qualifiers
source                   1..42
                         mol_type = other DNA
                         organism = synthetic construct
SEQUENCE: 914
gtaagcagat agctataata gaaaattcat atccagccag cc                      42

SEQ ID NO: 915           moltype = DNA   length = 40
FEATURE                  Location/Qualifiers
source                   1..40
                         mol_type = other DNA
                         organism = synthetic construct
SEQUENCE: 915
ttttcagtac aaactacaac cactgagttt cgtcactttt                         40

SEQ ID NO: 916           moltype = DNA   length = 29
FEATURE                  Location/Qualifiers
source                   1..29
                         mol_type = other DNA
                         organism = synthetic construct
SEQUENCE: 916
ttttaatttt ctcagctttc cggcatttt                                     29

SEQ ID NO: 917           moltype = DNA   length = 23
FEATURE                  Location/Qualifiers
source                   1..23
                         mol_type = other DNA
                         organism = synthetic construct
SEQUENCE: 917
tttttcacgt tggagatctt ttt                                           23
```

-continued

```
SEQ ID NO: 918          moltype = DNA   length = 40
FEATURE                 Location/Qualifiers
source                  1..40
                        mol_type = other DNA
                        organism = synthetic construct
SEQUENCE: 918
ttttataccg atagttgcgc tttcttaaac agcttgtttt                        40

SEQ ID NO: 919          moltype = DNA   length = 30
FEATURE                 Location/Qualifiers
source                  1..30
                        mol_type = other DNA
                        organism = synthetic construct
SEQUENCE: 919
ttttccatta aacggcaagc gcgaaatttt                                   30

SEQ ID NO: 920          moltype = DNA   length = 52
FEATURE                 Location/Qualifiers
source                  1..52
                        mol_type = other DNA
                        organism = synthetic construct
SEQUENCE: 920
gattatacgt aaaatatgtt tagagtcacc ctgttaaagg ccgctttttt tt          52

SEQ ID NO: 921          moltype = DNA   length = 30
FEATURE                 Location/Qualifiers
source                  1..30
                        mol_type = other DNA
                        organism = synthetic construct
SEQUENCE: 921
ttttcaaagt acaacaaccg aactgatttt                                   30

SEQ ID NO: 922          moltype = DNA   length = 33
FEATURE                 Location/Qualifiers
source                  1..33
                        mol_type = other DNA
                        organism = synthetic construct
SEQUENCE: 922
cataaggggg agatttaaga agtttttgcct ttt                              33

SEQ ID NO: 923          moltype = DNA   length = 30
FEATURE                 Location/Qualifiers
source                  1..30
                        mol_type = other DNA
                        organism = synthetic construct
SEQUENCE: 923
ttttccaact ttgaaaacgt aacaaatttt                                   30

SEQ ID NO: 924          moltype = DNA   length = 33
FEATURE                 Location/Qualifiers
source                  1..33
                        mol_type = other DNA
                        organism = synthetic construct
SEQUENCE: 924
cccaaatcag aggacaccct cgtttaccat ttt                               33

SEQ ID NO: 925          moltype = DNA   length = 30
FEATURE                 Location/Qualifiers
source                  1..30
                        mol_type = other DNA
                        organism = synthetic construct
SEQUENCE: 925
ttttgctgct cattcatgcg attttatttt                                   30

SEQ ID NO: 926          moltype = DNA   length = 33
FEATURE                 Location/Qualifiers
source                  1..33
                        mol_type = other DNA
                        organism = synthetic construct
SEQUENCE: 926
attaccttag tgaatatacg aggcatagtt ttt                               33

SEQ ID NO: 927          moltype = DNA   length = 22
FEATURE                 Location/Qualifiers
source                  1..22
                        mol_type = other DNA
                        organism = synthetic construct
SEQUENCE: 927
```

-continued

```
ttttagaact ggctccggtt tt                                          22

SEQ ID NO: 928           moltype = DNA   length = 41
FEATURE                  Location/Qualifiers
source                   1..41
                         mol_type = other DNA
                         organism = synthetic construct
SEQUENCE: 928
taataaaacg aactaaatta taccgattta ggaatacttt t                     41

SEQ ID NO: 929           moltype = DNA   length = 48
FEATURE                  Location/Qualifiers
source                   1..48
                         mol_type = other DNA
                         organism = synthetic construct
SEQUENCE: 929
ttttaacaac attatgcttc aaattcaaat agagagtacc tttatttt              48

SEQ ID NO: 930           moltype = DNA   length = 40
FEATURE                  Location/Qualifiers
source                   1..40
                         mol_type = other DNA
                         organism = synthetic construct
SEQUENCE: 930
ttttcacatt caactaatga aaaagattaa gaggaatttt                       40

SEQ ID NO: 931           moltype = DNA   length = 50
FEATURE                  Location/Qualifiers
source                   1..50
                         mol_type = other DNA
                         organism = synthetic construct
SEQUENCE: 931
ttttaagagc aacactagac tattaaatca aaatcaacat gttttatttt            50

SEQ ID NO: 932           moltype = DNA   length = 40
FEATURE                  Location/Qualifiers
source                   1..40
                         mol_type = other DNA
                         organism = synthetic construct
SEQUENCE: 932
ttttgacgac gataaaaacg acagttcaga aaacgatttt                       40

SEQ ID NO: 933           moltype = DNA   length = 48
FEATURE                  Location/Qualifiers
source                   1..48
                         mol_type = other DNA
                         organism = synthetic construct
SEQUENCE: 933
ttttagaggg ggtaataata aatatagcgt ccagtagatt tagttttt              48

SEQ ID NO: 934           moltype = DNA   length = 22
FEATURE                  Location/Qualifiers
source                   1..22
                         mol_type = other DNA
                         organism = synthetic construct
SEQUENCE: 934
ttttgattca ttgaatcctt tt                                          22

SEQ ID NO: 935           moltype = DNA   length = 40
FEATURE                  Location/Qualifiers
source                   1..40
                         mol_type = other DNA
                         organism = synthetic construct
SEQUENCE: 935
ttttccctca aatgctttaa ggtgtgtctg gaagtttttt                       40

SEQ ID NO: 936           moltype = DNA   length = 30
FEATURE                  Location/Qualifiers
source                   1..30
                         mol_type = other DNA
                         organism = synthetic construct
SEQUENCE: 936
ttttgaatga ccatatagtc agaagctttt                                  30

SEQ ID NO: 937           moltype = DNA   length = 40
FEATURE                  Location/Qualifiers
source                   1..40
                         mol_type = other DNA
                         organism = synthetic construct
```

-continued

```
SEQUENCE: 937
ttttaaagcg gattgcatca acaggtcatt tttgcgtttt                              40

SEQ ID NO: 938          moltype = DNA   length = 22
FEATURE                 Location/Qualifiers
source                  1..22
                        mol_type = other DNA
                        organism = synthetic construct
SEQUENCE: 938
ttttgcccga aagacgcgtt tt                                                 22

SEQ ID NO: 939          moltype = DNA   length = 48
FEATURE                 Location/Qualifiers
source                  1..48
                        mol_type = other DNA
                        organism = synthetic construct
SEQUENCE: 939
ttttaaccag accggacatt atgaaagcta atcaacgcaa ggattttt                     48

SEQ ID NO: 940          moltype = DNA   length = 40
FEATURE                 Location/Qualifiers
source                  1..40
                        mol_type = other DNA
                        organism = synthetic construct
SEQUENCE: 940
ttttattgct cctttttgcat aaattaagca ataaagtttt                             40

SEQ ID NO: 941          moltype = DNA   length = 50
FEATURE                 Location/Qualifiers
source                  1..50
                        mol_type = other DNA
                        organism = synthetic construct
SEQUENCE: 941
ttttgatggc ttagagccca ataaatacta atatgagaaa ggccggtttt                   50

SEQ ID NO: 942          moltype = DNA   length = 40
FEATURE                 Location/Qualifiers
source                  1..40
                        mol_type = other DNA
                        organism = synthetic construct
SEQUENCE: 942
ttttaatatg caactaaaaa cgcgagctga aaaggttttt                              40

SEQ ID NO: 943          moltype = DNA   length = 37
FEATURE                 Location/Qualifiers
source                  1..37
                        mol_type = other DNA
                        organism = synthetic construct
SEQUENCE: 943
tttttcattc catataagtc aataaaccat tagattt                                 37

SEQ ID NO: 944          moltype = DNA   length = 22
FEATURE                 Location/Qualifiers
source                  1..22
                        mol_type = other DNA
                        organism = synthetic construct
SEQUENCE: 944
tttttttgcct gtttagcttt tt                                                22

SEQ ID NO: 945          moltype = DNA   length = 40
FEATURE                 Location/Qualifiers
source                  1..40
                        mol_type = other DNA
                        organism = synthetic construct
SEQUENCE: 945
ttttatattt tcatttgggg tccaatatga tattcatttt                              40

SEQ ID NO: 946          moltype = DNA   length = 30
FEATURE                 Location/Qualifiers
source                  1..30
                        mol_type = other DNA
                        organism = synthetic construct
SEQUENCE: 946
ttttggcatc aattctcata caggcatttt                                         30

SEQ ID NO: 947          moltype = DNA   length = 40
FEATURE                 Location/Qualifiers
source                  1..40
                        mol_type = other DNA
```

-continued

```
                             organism = synthetic construct
SEQUENCE: 947
ttttaggcaa agaattagca agcatatatt ttaaattttt                        40

SEQ ID NO: 948           moltype = DNA   length = 15
FEATURE                  Location/Qualifiers
source                   1..15
                         mol_type = other DNA
                         organism = synthetic construct
SEQUENCE: 948
ttttcctcag agcat                                                   15

SEQ ID NO: 949           moltype = DNA   length = 44
FEATURE                  Location/Qualifiers
source                   1..44
                         mol_type = other DNA
                         organism = synthetic construct
SEQUENCE: 949
ttttccctgt acatttttc attaaatctg gccttcctgt tttt                    44

SEQ ID NO: 950           moltype = DNA   length = 40
FEATURE                  Location/Qualifiers
source                   1..40
                         mol_type = other DNA
                         organism = synthetic construct
SEQUENCE: 950
ttttaaaaat ttttagatcc taaacgttaa tatttttttt                        40

SEQ ID NO: 951           moltype = DNA   length = 50
FEATURE                  Location/Qualifiers
source                   1..50
                         mol_type = other DNA
                         organism = synthetic construct
SEQUENCE: 951
ttttgcaatg cctgagtaaa caggaggttg ataattgacc gtaatgtttt             50

SEQ ID NO: 952           moltype = DNA   length = 29
FEATURE                  Location/Qualifiers
source                   1..29
                         mol_type = other DNA
                         organism = synthetic construct
SEQUENCE: 952
ttttagacag tcaaatctgt acccctttt                                    29

SEQ ID NO: 953           moltype = DNA   length = 37
FEATURE                  Location/Qualifiers
source                   1..37
                         mol_type = other DNA
                         organism = synthetic construct
SEQUENCE: 953
ttttaccgtt ctagctggag caaacatcag gtcactc                           37

SEQ ID NO: 954           moltype = DNA   length = 32
FEATURE                  Location/Qualifiers
source                   1..32
                         mol_type = other DNA
                         organism = synthetic construct
SEQUENCE: 954
ttgaaaaatc tcgcgaataa taattttttt tt                                32

SEQ ID NO: 955           moltype = DNA   length = 26
FEATURE                  Location/Qualifiers
source                   1..26
                         mol_type = other DNA
                         organism = synthetic construct
SEQUENCE: 955
ttttaaaggc taagagaatc gatttt                                       26

SEQ ID NO: 956           moltype = DNA   length = 40
FEATURE                  Location/Qualifiers
source                   1..40
                         mol_type = other DNA
                         organism = synthetic construct
SEQUENCE: 956
tttttgaacg gtaatcgtaa aactgcatct gccagttttt                        40

SEQ ID NO: 957           moltype = DNA   length = 15
FEATURE                  Location/Qualifiers
source                   1..15
```

-continued

```
                              mol_type = other DNA
                              organism = synthetic construct
SEQUENCE: 957
agattgtata atttt                                              15

SEQ ID NO: 958         moltype = DNA   length = 40
FEATURE                Location/Qualifiers
source                 1..40
                       mol_type = other DNA
                       organism = synthetic construct
SEQUENCE: 958
ttttgcaaat atttaaattg tttcccgtcg gattcttttt                  40

SEQ ID NO: 959         moltype = DNA   length = 15
FEATURE                Location/Qualifiers
source                 1..15
                       mol_type = other DNA
                       organism = synthetic construct
SEQUENCE: 959
ttttgttaaa attcg                                             15

SEQ ID NO: 960         moltype = DNA   length = 44
FEATURE                Location/Qualifiers
source                 1..44
                       mol_type = other DNA
                       organism = synthetic construct
SEQUENCE: 960
ttttaccaat agtcgactca gtgccaagaa attgttatcc tttt             44

SEQ ID NO: 961         moltype = DNA   length = 40
FEATURE                Location/Qualifiers
source                 1..40
                       mol_type = other DNA
                       organism = synthetic construct
SEQUENCE: 961
ttttagccag ctttcatata cagtcacgac gttgtatttt                  40

SEQ ID NO: 962         moltype = DNA   length = 50
FEATURE                Location/Qualifiers
source                 1..50
                       mol_type = other DNA
                       organism = synthetic construct
SEQUENCE: 962
ttttccgtgg gaacaaacaa ggcgaagctg gcgaactcac attaattttt       50

SEQ ID NO: 963         moltype = DNA   length = 40
FEATURE                Location/Qualifiers
source                 1..40
                       mol_type = other DNA
                       organism = synthetic construct
SEQUENCE: 963
ttttggatag gtcacgtgct cggtgcgggc ctcttctttt                  40

SEQ ID NO: 964         moltype = DNA   length = 48
FEATURE                Location/Qualifiers
source                 1..48
                       mol_type = other DNA
                       organism = synthetic construct
SEQUENCE: 964
ttttttgagg ggacgacgcc attcacggaa acccgtattg ggcgtttt         48

SEQ ID NO: 965         moltype = DNA   length = 32
FEATURE                Location/Qualifiers
source                 1..32
                       mol_type = other DNA
                       organism = synthetic construct
SEQUENCE: 965
cagcgtatgg gacagacgtt agtaaatgtt tt                          32

SEQ ID NO: 966         moltype = DNA   length = 32
FEATURE                Location/Qualifiers
source                 1..32
                       mol_type = other DNA
                       organism = synthetic construct
SEQUENCE: 966
ttttccgctt ctggtgcggc tgcgcaactt tt                          32

SEQ ID NO: 967         moltype = DNA   length = 40
FEATURE                Location/Qualifiers
```

-continued

```
source                     1..40
                           mol_type = other DNA
                           organism = synthetic construct
SEQUENCE: 967
tttttgttgg gaagggcgat attgtcgtgc cagctgtttt                              40

SEQ ID NO: 968             moltype = DNA   length = 30
FEATURE                    Location/Qualifiers
source                     1..30
                           mol_type = other DNA
                           organism = synthetic construct
SEQUENCE: 968
ttttgctatt acgccttaag ttgggttttt                                        30

SEQ ID NO: 969             moltype = DNA   length = 40
FEATURE                    Location/Qualifiers
source                     1..40
                           mol_type = other DNA
                           organism = synthetic construct
SEQUENCE: 969
ttttaacgcc agggttttcc aaagtgtaaa gcctggtttt                             40

SEQ ID NO: 970             moltype = DNA   length = 32
FEATURE                    Location/Qualifiers
source                     1..32
                           mol_type = other DNA
                           organism = synthetic construct
SEQUENCE: 970
ttttaaacga cggcctagag gatccccgtt tt                                     32

SEQ ID NO: 971             moltype = DNA   length = 41
FEATURE                    Location/Qualifiers
source                     1..41
                           mol_type = other DNA
                           organism = synthetic construct
SEQUENCE: 971
ttttggtacc gagctcgaat tcgtacaaag ggcattaaag a                           41

SEQ ID NO: 972             moltype = DNA   length = 33
FEATURE                    Location/Qualifiers
source                     1..33
                           mol_type = other DNA
                           organism = synthetic construct
SEQUENCE: 972
ttttgctcac aattccatgt tgttcagaat agc                                    33

SEQ ID NO: 973             moltype = DNA   length = 33
FEATURE                    Location/Qualifiers
source                     1..33
                           mol_type = other DNA
                           organism = synthetic construct
SEQUENCE: 973
ttttggtgcc taatgagcga aatcggaaaa tcc                                    33

SEQ ID NO: 974             moltype = DNA   length = 33
FEATURE                    Location/Qualifiers
source                     1..33
                           mol_type = other DNA
                           organism = synthetic construct
SEQUENCE: 974
tttttgcgtt gcgctcaagc ggtccctgg ccc                                     33

SEQ ID NO: 975             moltype = DNA   length = 40
FEATURE                    Location/Qualifiers
source                     1..40
                           mol_type = other DNA
                           organism = synthetic construct
SEQUENCE: 975
ttttcattaa tgaatcgaga cgggcaacag ctgatttttt                             40

SEQ ID NO: 976             moltype = DNA   length = 39
FEATURE                    Location/Qualifiers
source                     1..39
                           mol_type = other DNA
                           organism = synthetic construct
SEQUENCE: 976
ttttccaggg tggttttct ttttaccgta agcctgtag                               39

SEQ ID NO: 977             moltype = DNA   length = 30
```

-continued

```
FEATURE               Location/Qualifiers
source                1..30
                      mol_type = other DNA
                      organism = synthetic construct
SEQUENCE: 977
ttttgcccctt caccgacgct ggtttgtttt                                    30

SEQ ID NO: 978        moltype = DNA   length = 30
FEATURE               Location/Qualifiers
source                1..30
                      mol_type = other DNA
                      organism = synthetic construct
SEQUENCE: 978
ttttccccag caggcgcaaa atcccttttt                                     30

SEQ ID NO: 979        moltype = DNA   length = 30
FEATURE               Location/Qualifiers
source                1..30
                      mol_type = other DNA
                      organism = synthetic construct
SEQUENCE: 979
tttttataaa tcaaacagtt tggaactttt                                     30

SEQ ID NO: 980        moltype = DNA   length = 15
FEATURE               Location/Qualifiers
source                1..15
                      mol_type = other DNA
                      organism = synthetic construct
SEQUENCE: 980
ttttaagagt ccact                                                     15

SEQ ID NO: 981        moltype = DNA   length = 35
FEATURE               Location/Qualifiers
source                1..35
                      mol_type = other DNA
                      organism = synthetic construct
SEQUENCE: 981
ttttgaaaaa ccgtctatca tccaacgtat catgg                               35

SEQ ID NO: 982        moltype = DNA   length = 33
FEATURE               Location/Qualifiers
source                1..33
                      mol_type = other DNA
                      organism = synthetic construct
SEQUENCE: 982
ccaataggaa cccatgataa cgtgttagag agg                                 33

SEQ ID NO: 983        moltype = DNA   length = 33
FEATURE               Location/Qualifiers
source                1..33
                      mol_type = other DNA
                      organism = synthetic construct
SEQUENCE: 983
cattccacag ttttgtttaa aaatccatca gga                                 33

SEQ ID NO: 984        moltype = DNA   length = 32
FEATURE               Location/Qualifiers
source                1..32
                      mol_type = other DNA
                      organism = synthetic construct
SEQUENCE: 984
tcgagaggtc agtaccaggc ggattaacag tg                                  32

SEQ ID NO: 985        moltype = DNA   length = 48
FEATURE               Location/Qualifiers
source                1..48
                      mol_type = other DNA
                      organism = synthetic construct
SEQUENCE: 985
aagtatagac cctcagagcc accaccctca ttttcaggga aagtgccg                 48

SEQ ID NO: 986        moltype = DNA   length = 40
FEATURE               Location/Qualifiers
source                1..40
                      mol_type = other DNA
                      organism = synthetic construct
SEQUENCE: 986
cgatctaaag acagccaagg gattctttcc tcgctttgac                          40
```

-continued

```
SEQ ID NO: 987          moltype = DNA   length = 33
FEATURE                 Location/Qualifiers
source                  1..33
                        mol_type = other DNA
                        organism = synthetic construct
SEQUENCE: 987
aacaacttaa caactagaac ctactaagga gag                                33

SEQ ID NO: 988          moltype = DNA   length = 48
FEATURE                 Location/Qualifiers
source                  1..48
                        mol_type = other DNA
                        organism = synthetic construct
SEQUENCE: 988
cccgtatagg gtcagtgcct tgagcacaaa caaataaatc gattggcc                48

SEQ ID NO: 989          moltype = DNA   length = 32
FEATURE                 Location/Qualifiers
source                  1..32
                        mol_type = other DNA
                        organism = synthetic construct
SEQUENCE: 989
tagaaaggtc aacagtttca gcggtagcgt aa                                 32

SEQ ID NO: 990          moltype = DNA   length = 48
FEATURE                 Location/Qualifiers
source                  1..48
                        mol_type = other DNA
                        organism = synthetic construct
SEQUENCE: 990
ttttaacgaa cagttaatgc ccccattagc ggggttttgc gttgatat                48

SEQ ID NO: 991          moltype = DNA   length = 34
FEATURE                 Location/Qualifiers
source                  1..34
                        mol_type = other DNA
                        organism = synthetic construct
SEQUENCE: 991
aggctccatt gctttcattt tagttgaatt ctgc                               34

SEQ ID NO: 992          moltype = DNA   length = 28
FEATURE                 Location/Qualifiers
source                  1..28
                        mol_type = other DNA
                        organism = synthetic construct
SEQUENCE: 992
ttatcagcaa aggagcaaca gaaacata                                      28

SEQ ID NO: 993          moltype = DNA   length = 48
FEATURE                 Location/Qualifiers
source                  1..48
                        mol_type = other DNA
                        organism = synthetic construct
SEQUENCE: 993
ttgatattcg cctccctcag agccgagcca ccaccggaac cagtagcg                48

SEQ ID NO: 994          moltype = DNA   length = 31
FEATURE                 Location/Qualifiers
source                  1..31
                        mol_type = other DNA
                        organism = synthetic construct
SEQUENCE: 994
acaacaacct gaggctcatt accgcttatc c                                  31

SEQ ID NO: 995          moltype = DNA   length = 48
FEATURE                 Location/Qualifiers
source                  1..48
                        mol_type = other DNA
                        organism = synthetic construct
SEQUENCE: 995
cagaaccgtt gaggcaggtc agacctcatt aaagccagaa gtaataag                48

SEQ ID NO: 996          moltype = DNA   length = 28
FEATURE                 Location/Qualifiers
source                  1..28
                        mol_type = other DNA
                        organism = synthetic construct
SEQUENCE: 996
ttcggtcgca tcgccctaat ggtttaat                                      28
```

-continued

```
SEQ ID NO: 997          moltype = DNA   length = 24
FEATURE                 Location/Qualifiers
source                  1..24
                        mol_type = other DNA
                        organism = synthetic construct
SEQUENCE: 997
aaagacagct ttgaggcact acga                                            24

SEQ ID NO: 998          moltype = DNA   length = 40
FEATURE                 Location/Qualifiers
source                  1..40
                        mol_type = other DNA
                        organism = synthetic construct
SEQUENCE: 998
acagaatcat agcagcgtga attatcaccg tcaaattatt                           40

SEQ ID NO: 999          moltype = DNA   length = 24
FEATURE                 Location/Qualifiers
source                  1..24
                        mol_type = other DNA
                        organism = synthetic construct
SEQUENCE: 999
ctttttcatg aggaaggcgg gatc                                            24

SEQ ID NO: 1000         moltype = DNA   length = 36
FEATURE                 Location/Qualifiers
source                  1..36
                        mol_type = other DNA
                        organism = synthetic construct
SEQUENCE: 1000
tacagaggca tcggaaatag aaggcgccca attttt                               36

SEQ ID NO: 1001         moltype = DNA   length = 48
FEATURE                 Location/Qualifiers
source                  1..48
                        mol_type = other DNA
                        organism = synthetic construct
SEQUENCE: 1001
aaccatcgaa gtttgccttt agcgaaaatc accggaacca gccaccct                  48

SEQ ID NO: 1002         moltype = DNA   length = 29
FEATURE                 Location/Qualifiers
source                  1..29
                        mol_type = other DNA
                        organism = synthetic construct
SEQUENCE: 1002
aggcaccaaa acactcgcgt tttagcgaa                                       29

SEQ ID NO: 1003         moltype = DNA   length = 24
FEATURE                 Location/Qualifiers
source                  1..24
                        mol_type = other DNA
                        organism = synthetic construct
SEQUENCE: 1003
cgaaagagac cgtaatgcaa cggc                                            24

SEQ ID NO: 1004         moltype = DNA   length = 40
FEATURE                 Location/Qualifiers
source                  1..40
                        mol_type = other DNA
                        organism = synthetic construct
SEQUENCE: 1004
atacactaac ctaaaaaatc agatcgaggg taccgatata                           40

SEQ ID NO: 1005         moltype = DNA   length = 48
FEATURE                 Location/Qualifiers
source                  1..48
                        mol_type = other DNA
                        organism = synthetic construct
SEQUENCE: 1005
cattaaagtt tattttgtca caatgacacc acgaataag tacccaaa                   48

SEQ ID NO: 1006         moltype = DNA   length = 40
FEATURE                 Location/Qualifiers
source                  1..40
                        mol_type = other DNA
                        organism = synthetic construct
SEQUENCE: 1006
```

```
attgacggac cgacttgagc cattgaaacg tcaccaatga                          40

SEQ ID NO: 1007          moltype = DNA   length = 29
FEATURE                  Location/Qualifiers
source                   1..29
                         mol_type = other DNA
                         organism = synthetic construct
SEQUENCE: 1007
aattgtgtcg gaacgatttt gaagcctta                                     29

SEQ ID NO: 1008          moltype = DNA   length = 29
FEATURE                  Location/Qualifiers
source                   1..29
                         mol_type = other DNA
                         organism = synthetic construct
SEQUENCE: 1008
accaggcgtt gacaagtatc ctgaatctt                                     29

SEQ ID NO: 1009          moltype = DNA   length = 48
FEATURE                  Location/Qualifiers
source                   1..48
                         mol_type = other DNA
                         organism = synthetic construct
SEQUENCE: 1009
ggctgaccct ccatgttact tagccgaaat ccgcgacctg gcaaaaga               48

SEQ ID NO: 1010          moltype = DNA   length = 48
FEATURE                  Location/Qualifiers
source                   1..48
                         mol_type = other DNA
                         organism = synthetic construct
SEQUENCE: 1010
agaactggcg caataataac ggaaagagca agaaacaatg gttaagcc               48

SEQ ID NO: 1011          moltype = DNA   length = 48
FEATURE                  Location/Qualifiers
source                   1..48
                         mol_type = other DNA
                         organism = synthetic construct
SEQUENCE: 1011
agactcctat aaaagaaacg caaacaatag aaaattcata aggtaaat               48

SEQ ID NO: 1012          moltype = DNA   length = 36
FEATURE                  Location/Qualifiers
source                   1..36
                         mol_type = other DNA
                         organism = synthetic construct
SEQUENCE: 1012
gaaacaccta atttcatttc cagatattat ttaacg                            36

SEQ ID NO: 1013          moltype = DNA   length = 48
FEATURE                  Location/Qualifiers
source                   1..48
                         mol_type = other DNA
                         organism = synthetic construct
SEQUENCE: 1013
agatggttag aacgagtagt aaatttcatc aagagtaatc cataggct               48

SEQ ID NO: 1014          moltype = DNA   length = 48
FEATURE                  Location/Qualifiers
source                   1..48
                         mol_type = other DNA
                         organism = synthetic construct
SEQUENCE: 1014
caataataaa aacagggaag cgcattagac gggagaatta aacccaca               48

SEQ ID NO: 1015          moltype = DNA   length = 48
FEATURE                  Location/Qualifiers
source                   1..48
                         mol_type = other DNA
                         organism = synthetic construct
SEQUENCE: 1015
agaattgaaa atagcaatag ctataaggaa accgaggaaa catgatta               48

SEQ ID NO: 1016          moltype = DNA   length = 30
FEATURE                  Location/Qualifiers
source                   1..30
                         mol_type = other DNA
                         organism = synthetic construct
```

```
SEQUENCE: 1016
gagagaaaca gccagcctaa tttgccagtt                                        30

SEQ ID NO: 1017          moltype = DNA   length = 24
FEATURE                  Location/Qualifiers
source                   1..24
                         mol_type = other DNA
                         organism = synthetic construct
SEQUENCE: 1017
tcagttgaag tcaggacatt gtga                                              24

SEQ ID NO: 1018          moltype = DNA   length = 24
FEATURE                  Location/Qualifiers
source                   1..24
                         mol_type = other DNA
                         organism = synthetic construct
SEQUENCE: 1018
acaaaataat aacatatggg cttg                                              24

SEQ ID NO: 1019          moltype = DNA   length = 34
FEATURE                  Location/Qualifiers
source                   1..34
                         mol_type = other DNA
                         organism = synthetic construct
SEQUENCE: 1019
cataagtcac tttaatcgtt gggaagactt taca                                   34

SEQ ID NO: 1020          moltype = DNA   length = 23
FEATURE                  Location/Qualifiers
source                   1..23
                         mol_type = other DNA
                         organism = synthetic construct
SEQUENCE: 1020
aaggaatagg cttgcattca tta                                               23

SEQ ID NO: 1021          moltype = DNA   length = 21
FEATURE                  Location/Qualifiers
source                   1..21
                         mol_type = other DNA
                         organism = synthetic construct
SEQUENCE: 1021
accaacgcta acgatcctaa t                                                 21

SEQ ID NO: 1022          moltype = DNA   length = 23
FEATURE                  Location/Qualifiers
source                   1..23
                         mol_type = other DNA
                         organism = synthetic construct
SEQUENCE: 1022
acaatttaac cggatcctga cga                                               23

SEQ ID NO: 1023          moltype = DNA   length = 26
FEATURE                  Location/Qualifiers
source                   1..26
                         mol_type = other DNA
                         organism = synthetic construct
SEQUENCE: 1023
tttgcactaa gatgaacgcg gtcaat                                            26

SEQ ID NO: 1024          moltype = DNA   length = 21
FEATURE                  Location/Qualifiers
source                   1..21
                         mol_type = other DNA
                         organism = synthetic construct
SEQUENCE: 1024
aatcaagatt agtataatcg g                                                 21

SEQ ID NO: 1025          moltype = DNA   length = 25
FEATURE                  Location/Qualifiers
source                   1..25
                         mol_type = other DNA
                         organism = synthetic construct
SEQUENCE: 1025
tagcgaaggg gcgcagagtg tacag                                             25

SEQ ID NO: 1026          moltype = DNA   length = 22
FEATURE                  Location/Qualifiers
source                   1..22
                         mol_type = other DNA
```

-continued

```
                        organism = synthetic construct
SEQUENCE: 1026
ttgcaagtat catcccccca gc                                          22

SEQ ID NO: 1027         moltype = DNA   length = 42
FEATURE                 Location/Qualifiers
source                  1..42
                        mol_type = other DNA
                        organism = synthetic construct
SEQUENCE: 1027
cctcccgact tgccactcat cctgtctttg tatcatatgc gt                    42

SEQ ID NO: 1028         moltype = DNA   length = 22
FEATURE                 Location/Qualifiers
source                  1..22
                        mol_type = other DNA
                        organism = synthetic construct
SEQUENCE: 1028
cgcgagatct ttgagcctga ta                                          22

SEQ ID NO: 1029         moltype = DNA   length = 25
FEATURE                 Location/Qualifiers
source                  1..25
                        mol_type = other DNA
                        organism = synthetic construct
SEQUENCE: 1029
ggtattaaac gtaatgcact aaaga                                       25

SEQ ID NO: 1030         moltype = DNA   length = 40
FEATURE                 Location/Qualifiers
source                  1..40
                        mol_type = other DNA
                        organism = synthetic construct
SEQUENCE: 1030
catcaccgac cgaccggaat acgcgagaat aactattttt                       40

SEQ ID NO: 1031         moltype = DNA   length = 19
FEATURE                 Location/Qualifiers
source                  1..19
                        mol_type = other DNA
                        organism = synthetic construct
SEQUENCE: 1031
agccgttttt aagcaagca                                              19

SEQ ID NO: 1032         moltype = DNA   length = 32
FEATURE                 Location/Qualifiers
source                  1..32
                        mol_type = other DNA
                        organism = synthetic construct
SEQUENCE: 1032
gagaacaaga ataaactgtg ataaataagg cg                               32

SEQ ID NO: 1033         moltype = DNA   length = 21
FEATURE                 Location/Qualifiers
source                  1..21
                        mol_type = other DNA
                        organism = synthetic construct
SEQUENCE: 1033
ttacgagcat aaagccaacg c                                           21

SEQ ID NO: 1034         moltype = DNA   length = 48
FEATURE                 Location/Qualifiers
source                  1..48
                        mol_type = other DNA
                        organism = synthetic construct
SEQUENCE: 1034
tgtttatcac gccaactaat aagaattaat taaccttgct ctttttta             48

SEQ ID NO: 1035         moltype = DNA   length = 36
FEATURE                 Location/Qualifiers
source                  1..36
                        mol_type = other DNA
                        organism = synthetic construct
SEQUENCE: 1035
cgccaaacaa caaaagtacc gacaaaagag tgaata                           36

SEQ ID NO: 1036         moltype = DNA   length = 32
FEATURE                 Location/Qualifiers
source                  1..32
```

-continued

```
                            mol_type = other DNA
                            organism = synthetic construct
SEQUENCE: 1036
taattcgata caggtagaaa gccaatctac gt                                        32

SEQ ID NO: 1037         moltype = DNA   length = 31
FEATURE                 Location/Qualifiers
source                  1..31
                        mol_type = other DNA
                        organism = synthetic construct
SEQUENCE: 1037
aggattatcg cgtttataag tcctgcagat a                                         31

SEQ ID NO: 1038         moltype = DNA   length = 32
FEATURE                 Location/Qualifiers
source                  1..32
                        mol_type = other DNA
                        organism = synthetic construct
SEQUENCE: 1038
ggcattttcg agccagatgt aatttaggca ga                                        32

SEQ ID NO: 1039         moltype = DNA   length = 31
FEATURE                 Location/Qualifiers
source                  1..31
                        mol_type = other DNA
                        organism = synthetic construct
SEQUENCE: 1039
tttaacaaac aatagtaatg cagatcattc a                                         31

SEQ ID NO: 1040         moltype = DNA   length = 34
FEATURE                 Location/Qualifiers
source                  1..34
                        mol_type = other DNA
                        organism = synthetic construct
SEQUENCE: 1040
agaatcagaa gaaaaatttt acccttcacc agct                                      34

SEQ ID NO: 1041         moltype = DNA   length = 33
FEATURE                 Location/Qualifiers
source                  1..33
                        mol_type = other DNA
                        organism = synthetic construct
SEQUENCE: 1041
tcaacagtag ggcacgctga gattttccca aac                                       33

SEQ ID NO: 1042         moltype = DNA   length = 34
FEATURE                 Location/Qualifiers
source                  1..34
                        mol_type = other DNA
                        organism = synthetic construct
SEQUENCE: 1042
ctgaatagta tgtagaaaat atcccagccg ccaa                                      34

SEQ ID NO: 1043         moltype = DNA   length = 29
FEATURE                 Location/Qualifiers
source                  1..29
                        mol_type = other DNA
                        organism = synthetic construct
SEQUENCE: 1043
tgtagcatca ggtcttccaa gaaccaaaa                                            29

SEQ ID NO: 1044         moltype = DNA   length = 41
FEATURE                 Location/Qualifiers
source                  1..41
                        mol_type = other DNA
                        organism = synthetic construct
SEQUENCE: 1044
tatacaaatt cttctttta aaaatcatt acaaaattga g                                41

SEQ ID NO: 1045         moltype = DNA   length = 29
FEATURE                 Location/Qualifiers
source                  1..29
                        mol_type = other DNA
                        organism = synthetic construct
SEQUENCE: 1045
ctgtttacct tatcaaccaa tcatgctat                                           29

SEQ ID NO: 1046         moltype = DNA   length = 35
FEATURE                 Location/Qualifiers
```

-continued

```
source                    1..35
                          mol_type = other DNA
                          organism = synthetic construct
SEQUENCE: 1046
actagaacga ttaaaccgaa tcgtcgtact aagaa                              35

SEQ ID NO: 1047          moltype = DNA   length = 15
FEATURE                  Location/Qualifiers
source                    1..15
                          mol_type = other DNA
                          organism = synthetic construct
SEQUENCE: 1047
tttttttaaat aagca                                                   15

SEQ ID NO: 1048          moltype = DNA   length = 35
FEATURE                  Location/Qualifiers
source                    1..35
                          mol_type = other DNA
                          organism = synthetic construct
SEQUENCE: 1048
ttcccaaatg taggaataag taccggggga ggctt                              35

SEQ ID NO: 1049          moltype = DNA   length = 30
FEATURE                  Location/Qualifiers
source                    1..30
                          mol_type = other DNA
                          organism = synthetic construct
SEQUENCE: 1049
gaacgaatac tgcgtgcagg gacagcagcg                                    30

SEQ ID NO: 1050          moltype = DNA   length = 24
FEATURE                  Location/Qualifiers
source                    1..24
                          mol_type = other DNA
                          organism = synthetic construct
SEQUENCE: 1050
cctaaattac gcataagtat cggt                                          24

SEQ ID NO: 1051          moltype = DNA   length = 25
FEATURE                  Location/Qualifiers
source                    1..25
                          mol_type = other DNA
                          organism = synthetic construct
SEQUENCE: 1051
ttcaaaactt ttaattgcgt agatt                                         25

SEQ ID NO: 1052          moltype = DNA   length = 15
FEATURE                  Location/Qualifiers
source                    1..15
                          mol_type = other DNA
                          organism = synthetic construct
SEQUENCE: 1052
ttttttttct tctga                                                    15

SEQ ID NO: 1053          moltype = DNA   length = 15
FEATURE                  Location/Qualifiers
source                    1..15
                          mol_type = other DNA
                          organism = synthetic construct
SEQUENCE: 1053
ggttgggtta ttttt                                                    15

SEQ ID NO: 1054          moltype = DNA   length = 15
FEATURE                  Location/Qualifiers
source                    1..15
                          mol_type = other DNA
                          organism = synthetic construct
SEQUENCE: 1054
ttttaagagt caata                                                    15

SEQ ID NO: 1055          moltype = DNA   length = 49
FEATURE                  Location/Qualifiers
source                    1..49
                          mol_type = other DNA
                          organism = synthetic construct
SEQUENCE: 1055
tgcgggtact ctgtaaatac caaaaaagca aactccaata ttgttcagc              49

SEQ ID NO: 1056          moltype = DNA   length = 48
```

-continued

| FEATURE | Location/Qualifiers |
|---|---|
| source | 1..48 |
| | mol_type = other DNA |
| | organism = synthetic construct |

SEQUENCE: 1056
atggaaacct aatagattta gaagaatcaa cacaatcaat atctggtc                48

| SEQ ID NO: 1057 | moltype = DNA   length = 32 |
|---|---|
| FEATURE | Location/Qualifiers |
| source | 1..32 |
| | mol_type = other DNA |
| | organism = synthetic construct |

SEQUENCE: 1057
ctttattatc ggttgcttga aaaatagcca ta                                 32

| SEQ ID NO: 1058 | moltype = DNA   length = 32 |
|---|---|
| FEATURE | Location/Qualifiers |
| source | 1..32 |
| | mol_type = other DNA |
| | organism = synthetic construct |

SEQUENCE: 1058
atcaagatta gaatctcgtc gctgaacagg tc                                 32

| SEQ ID NO: 1059 | moltype = DNA   length = 36 |
|---|---|
| FEATURE | Location/Qualifiers |
| source | 1..36 |
| | mol_type = other DNA |
| | organism = synthetic construct |

SEQUENCE: 1059
aaaattcatt tgtttgagga ttagagccag gaaggt                             36

| SEQ ID NO: 1060 | moltype = DNA   length = 32 |
|---|---|
| FEATURE | Location/Qualifiers |
| source | 1..32 |
| | mol_type = other DNA |
| | organism = synthetic construct |

SEQUENCE: 1060
gatgaactcg atagcttatt aacatttaat tg                                 32

| SEQ ID NO: 1061 | moltype = DNA   length = 32 |
|---|---|
| FEATURE | Location/Qualifiers |
| source | 1..32 |
| | mol_type = other DNA |
| | organism = synthetic construct |

SEQUENCE: 1061
caaattttaa aaacaattc caaaccctgt tg                                  32

| SEQ ID NO: 1062 | moltype = DNA   length = 32 |
|---|---|
| FEATURE | Location/Qualifiers |
| source | 1..32 |
| | mol_type = other DNA |
| | organism = synthetic construct |

SEQUENCE: 1062
aggtaaagta ggtctgaaga ttaagttaat tg                                 32

| SEQ ID NO: 1063 | moltype = DNA   length = 32 |
|---|---|
| FEATURE | Location/Qualifiers |
| source | 1..32 |
| | mol_type = other DNA |
| | organism = synthetic construct |

SEQUENCE: 1063
aaaaggggta gtagcgctga tgcagtaaaa gc                                 32

| SEQ ID NO: 1064 | moltype = DNA   length = 32 |
|---|---|
| FEATURE | Location/Qualifiers |
| source | 1..32 |
| | mol_type = other DNA |
| | organism = synthetic construct |

SEQUENCE: 1064
ggattcgcct gattgccggg agaaattcat ca                                 32

| SEQ ID NO: 1065 | moltype = DNA   length = 32 |
|---|---|
| FEATURE | Location/Qualifiers |
| source | 1..32 |
| | mol_type = other DNA |
| | organism = synthetic construct |

SEQUENCE: 1065
agtaccatgt aaatgagact acaccataat gc                                 32

-continued

```
SEQ ID NO: 1066         moltype = DNA   length = 41
FEATURE                 Location/Qualifiers
source                  1..41
                        mol_type = other DNA
                        organism = synthetic construct
SEQUENCE: 1066
acattttgaa tagagcggaa gcggaacatc taaagcatca c                          41

SEQ ID NO: 1067         moltype = DNA   length = 31
FEATURE                 Location/Qualifiers
source                  1..31
                        mol_type = other DNA
                        organism = synthetic construct
SEQUENCE: 1067
atataatcaa tcgcaacgca aatgcagttg a                                     31

SEQ ID NO: 1068         moltype = DNA   length = 42
FEATURE                 Location/Qualifiers
source                  1..42
                        mol_type = other DNA
                        organism = synthetic construct
SEQUENCE: 1068
ttcaggttta acgtacttct gatataatca ttaacaccgc ct                         42

SEQ ID NO: 1069         moltype = DNA   length = 32
FEATURE                 Location/Qualifiers
source                  1..32
                        mol_type = other DNA
                        organism = synthetic construct
SEQUENCE: 1069
aatgccagat caaatatgac aaagacataa tt                                    32

SEQ ID NO: 1070         moltype = DNA   length = 31
FEATURE                 Location/Qualifiers
source                  1..31
                        mol_type = other DNA
                        organism = synthetic construct
SEQUENCE: 1070
ggtagctata catttgaggt gaacgacaat g                                     31

SEQ ID NO: 1071         moltype = DNA   length = 23
FEATURE                 Location/Qualifiers
source                  1..23
                        mol_type = other DNA
                        organism = synthetic construct
SEQUENCE: 1071
cacgtaactt taattagtga gaa                                              23

SEQ ID NO: 1072         moltype = DNA   length = 25
FEATURE                 Location/Qualifiers
source                  1..25
                        mol_type = other DNA
                        organism = synthetic construct
SEQUENCE: 1072
tcaaataat gggcagaaga taaaa                                             25

SEQ ID NO: 1073         moltype = DNA   length = 15
FEATURE                 Location/Qualifiers
source                  1..15
                        mol_type = other DNA
                        organism = synthetic construct
SEQUENCE: 1073
tttttttaat tattt                                                       15

SEQ ID NO: 1074         moltype = DNA   length = 32
FEATURE                 Location/Qualifiers
source                  1..32
                        mol_type = other DNA
                        organism = synthetic construct
SEQUENCE: 1074
catcaattgg tcaatagaat cagctatact tt                                    32

SEQ ID NO: 1075         moltype = DNA   length = 16
FEATURE                 Location/Qualifiers
source                  1..16
                        mol_type = other DNA
                        organism = synthetic construct
SEQUENCE: 1075
tatctaaatt gacgct                                                      16
```

-continued

```
SEQ ID NO: 1076         moltype = DNA   length = 32
FEATURE                 Location/Qualifiers
source                  1..32
                        mol_type = other DNA
                        organism = synthetic construct
SEQUENCE: 1076
ttcgcgtttt tgttagtatt aaaaccacaa ac                             32

SEQ ID NO: 1077         moltype = DNA   length = 14
FEATURE                 Location/Qualifiers
source                  1..14
                        mol_type = other DNA
                        organism = synthetic construct
SEQUENCE: 1077
agttggcata tttt                                                 14

SEQ ID NO: 1078         moltype = DNA   length = 33
FEATURE                 Location/Qualifiers
source                  1..33
                        mol_type = other DNA
                        organism = synthetic construct
SEQUENCE: 1078
aatgttatga caactcataa tacaaataga agc                            33

SEQ ID NO: 1079         moltype = DNA   length = 30
FEATURE                 Location/Qualifiers
source                  1..30
                        mol_type = other DNA
                        organism = synthetic construct
SEQUENCE: 1079
gtaacaagcc cgaacagccc caaaatgtgt                                30

SEQ ID NO: 1080         moltype = DNA   length = 42
FEATURE                 Location/Qualifiers
source                  1..42
                        mol_type = other DNA
                        organism = synthetic construct
SEQUENCE: 1080
cttgctgaac ctccagagat agattcacct ggtaatatcc ag                  42

SEQ ID NO: 1081         moltype = DNA   length = 29
FEATURE                 Location/Qualifiers
source                  1..29
                        mol_type = other DNA
                        organism = synthetic construct
SEQUENCE: 1081
gaaaaaaga aaccgttatt aaagaagat                                  29

SEQ ID NO: 1082         moltype = DNA   length = 34
FEATURE                 Location/Qualifiers
source                  1..34
                        mol_type = other DNA
                        organism = synthetic construct
SEQUENCE: 1082
ccagccggat cagaaacaat cataacccag taac                           34

SEQ ID NO: 1083         moltype = DNA   length = 25
FEATURE                 Location/Qualifiers
source                  1..25
                        mol_type = other DNA
                        organism = synthetic construct
SEQUENCE: 1083
gcaacagtgc cacagaatac ggaac                                     25

SEQ ID NO: 1084         moltype = DNA   length = 34
FEATURE                 Location/Qualifiers
source                  1..34
                        mol_type = other DNA
                        organism = synthetic construct
SEQUENCE: 1084
gatgggagtc tgattgtacc agaagccaag attc                           34

SEQ ID NO: 1085         moltype = DNA   length = 29
FEATURE                 Location/Qualifiers
source                  1..29
                        mol_type = other DNA
                        organism = synthetic construct
SEQUENCE: 1085
```

-continued

```
taaccgtagc atgtagagtc tgataaatt                                                          29

SEQ ID NO: 1086          moltype = DNA   length = 42
FEATURE                  Location/Qualifiers
source                   1..42
                         mol_type = other DNA
                         organism = synthetic construct
SEQUENCE: 1086
cagaggtgag gcgactgata gtggcacaga gtaaaagagt ct                                           42

SEQ ID NO: 1087          moltype = DNA   length = 33
FEATURE                  Location/Qualifiers
source                   1..33
                         mol_type = other DNA
                         organism = synthetic construct
SEQUENCE: 1087
tcggccccaa agggttattg gattatcaga tga                                                     33

SEQ ID NO: 1088          moltype = DNA   length = 31
FEATURE                  Location/Qualifiers
source                   1..31
                         mol_type = other DNA
                         organism = synthetic construct
SEQUENCE: 1088
agatcgcatt gcctgaagga attcaaaaaa a                                                       31

SEQ ID NO: 1089          moltype = DNA   length = 16
FEATURE                  Location/Qualifiers
source                   1..16
                         mol_type = other DNA
                         organism = synthetic construct
SEQUENCE: 1089
tttacgaaac cgattt                                                                        16

SEQ ID NO: 1090          moltype = DNA   length = 40
FEATURE                  Location/Qualifiers
source                   1..40
                         mol_type = other DNA
                         organism = synthetic construct
SEQUENCE: 1090
ccctaaaaag gaacggcagt gaggatgcgc cgtaaccacc                                              40

SEQ ID NO: 1091          moltype = DNA   length = 36
FEATURE                  Location/Qualifiers
source                   1..36
                         mol_type = other DNA
                         organism = synthetic construct
SEQUENCE: 1091
ccttgattag taactatcgg cggcgaacga tttaga                                                  36

SEQ ID NO: 1092          moltype = DNA   length = 32
FEATURE                  Location/Qualifiers
source                   1..32
                         mol_type = other DNA
                         organism = synthetic construct
SEQUENCE: 1092
tcataggcct gaaatgggcc tgcagggaac gc                                                      32

SEQ ID NO: 1093          moltype = DNA   length = 30
FEATURE                  Location/Qualifiers
source                   1..30
                         mol_type = other DNA
                         organism = synthetic construct
SEQUENCE: 1093
ctgtgtgctt gcatgaccag tacaacatta                                                         30

SEQ ID NO: 1094          moltype = DNA   length = 29
FEATURE                  Location/Qualifiers
source                   1..29
                         mol_type = other DNA
                         organism = synthetic construct
SEQUENCE: 1094
aacaatatta ccgcactaaa tttttgggg                                                          29

SEQ ID NO: 1095          moltype = DNA   length = 34
FEATURE                  Location/Qualifiers
source                   1..34
                         mol_type = other DNA
                         organism = synthetic construct
```

-continued

```
SEQUENCE: 1095
tacgagtgca gtcacacatt atttagaaaa ataa                                    34

SEQ ID NO: 1096          moltype = DNA   length = 33
FEATURE                  Location/Qualifiers
source                   1..33
                         mol_type = other DNA
                         organism = synthetic construct
SEQUENCE: 1096
gcataaaggg acattatgtg ctgcggagca aat                                     33

SEQ ID NO: 1097          moltype = DNA   length = 31
FEATURE                  Location/Qualifiers
source                   1..31
                         mol_type = other DNA
                         organism = synthetic construct
SEQUENCE: 1097
ttctttctga cctgctggcc aaaaagagcg a                                       31

SEQ ID NO: 1098          moltype = DNA   length = 15
FEATURE                  Location/Qualifiers
source                   1..15
                         mol_type = other DNA
                         organism = synthetic construct
SEQUENCE: 1098
tttttttact tgcct                                                         15

SEQ ID NO: 1099          moltype = DNA   length = 31
FEATURE                  Location/Qualifiers
source                   1..31
                         mol_type = other DNA
                         organism = synthetic construct
SEQUENCE: 1099
ttgtagctaa agggggtttg aatgtggtgt a                                       31

SEQ ID NO: 1100          moltype = DNA   length = 29
FEATURE                  Location/Qualifiers
source                   1..29
                         mol_type = other DNA
                         organism = synthetic construct
SEQUENCE: 1100
gtccatcacg caacgctggc aaagcgaaa                                          29

SEQ ID NO: 1101          moltype = DNA   length = 33
FEATURE                  Location/Qualifiers
source                   1..33
                         mol_type = other DNA
                         organism = synthetic construct
SEQUENCE: 1101
ctttccccga caatattaaa gcgtagctga gag                                     33

SEQ ID NO: 1102          moltype = DNA   length = 30
FEATURE                  Location/Qualifiers
source                   1..30
                         mol_type = other DNA
                         organism = synthetic construct
SEQUENCE: 1102
gaaacctagt ctttacgcca ttcgacagta                                         30

SEQ ID NO: 1103          moltype = DNA   length = 35
FEATURE                  Location/Qualifiers
source                   1..35
                         mol_type = other DNA
                         organism = synthetic construct
SEQUENCE: 1103
cgcggggacc atcgccaatg cgcgagtccg catcg                                   35

SEQ ID NO: 1104          moltype = DNA   length = 15
FEATURE                  Location/Qualifiers
source                   1..15
                         mol_type = other DNA
                         organism = synthetic construct
SEQUENCE: 1104
tttttttaat cctga                                                         15

SEQ ID NO: 1105          moltype = DNA   length = 31
FEATURE                  Location/Qualifiers
source                   1..31
                         mol_type = other DNA
```

```
                            organism = synthetic construct
SEQUENCE: 1105
cggtttgagg caaagcgtct ttctttttgct a                          31

SEQ ID NO: 1106          moltype = DNA   length = 25
FEATURE                  Location/Qualifiers
source                   1..25
                         mol_type = other DNA
                         organism = synthetic construct
SEQUENCE: 1106
gagcacgtcg cgcttaccaa gtcgg                                  25

SEQ ID NO: 1107          moltype = DNA   length = 23
FEATURE                  Location/Qualifiers
source                   1..23
                         mol_type = other DNA
                         organism = synthetic construct
SEQUENCE: 1107
tgagagagca ccagtggcca acg                                    23

SEQ ID NO: 1108          moltype = DNA   length = 24
FEATURE                  Location/Qualifiers
source                   1..24
                         mol_type = other DNA
                         organism = synthetic construct
SEQUENCE: 1108
acacccgccg ctagggatta accg                                   24

SEQ ID NO: 1109          moltype = DNA   length = 23
FEATURE                  Location/Qualifiers
source                   1..23
                         mol_type = other DNA
                         organism = synthetic construct
SEQUENCE: 1109
tgtttgattt gcagcactgc ccg                                    23

SEQ ID NO: 1110          moltype = DNA   length = 25
FEATURE                  Location/Qualifiers
source                   1..25
                         mol_type = other DNA
                         organism = synthetic construct
SEQUENCE: 1110
ggagcggggg gaaagccctc cggaa                                  25

SEQ ID NO: 1111          moltype = DNA   length = 26
FEATURE                  Location/Qualifiers
source                   1..26
                         mol_type = other DNA
                         organism = synthetic construct
SEQUENCE: 1111
ccgagatagg tggttctgag caatac                                 26

SEQ ID NO: 1112          moltype = DNA   length = 26
FEATURE                  Location/Qualifiers
source                   1..26
                         mol_type = other DNA
                         organism = synthetic construct
SEQUENCE: 1112
gcttgacgcc gtaaagccac tgtttc                                 26

SEQ ID NO: 1113          moltype = DNA   length = 23
FEATURE                  Location/Qualifiers
source                   1..23
                         mol_type = other DNA
                         organism = synthetic construct
SEQUENCE: 1113
acgtggacgg gttgagcaca aca                                    23

SEQ ID NO: 1114          moltype = DNA   length = 40
FEATURE                  Location/Qualifiers
source                   1..40
                         mol_type = other DNA
                         organism = synthetic construct
SEQUENCE: 1114
ttttcaccct cagaaccgcc cccggaatag gtgtattttt                  40

SEQ ID NO: 1115          moltype = DNA   length = 40
FEATURE                  Location/Qualifiers
source                   1..40
```

-continued

```
                             mol_type = other DNA
                             organism = synthetic construct
SEQUENCE: 1115
ttttcaagag aaggattagg tgcctatttc ggaacctttt                          40

SEQ ID NO: 1116          moltype = DNA   length = 40
FEATURE                  Location/Qualifiers
source                   1..40
                         mol_type = other DNA
                         organism = synthetic construct
SEQUENCE: 1116
ttttatacag gagtgtactg tggaaagcgc agtctctttt                          40

SEQ ID NO: 1117          moltype = DNA   length = 40
FEATURE                  Location/Qualifiers
source                   1..40
                         mol_type = other DNA
                         organism = synthetic construct
SEQUENCE: 1117
ttttcagcat tgacaggagg ccaccctcag agccactttt                          40

SEQ ID NO: 1118          moltype = DNA   length = 40
FEATURE                  Location/Qualifiers
source                   1..40
                         mol_type = other DNA
                         organism = synthetic construct
SEQUENCE: 1118
ttttccatct tttcataatc tcagactgta gcgcgttttt                          40

SEQ ID NO: 1119          moltype = DNA   length = 32
FEATURE                  Location/Qualifiers
source                   1..32
                         mol_type = other DNA
                         organism = synthetic construct
SEQUENCE: 1119
ttttcaaggc cgtgggaatt agagccagtt tt                                  32

SEQ ID NO: 1120          moltype = DNA   length = 40
FEATURE                  Location/Qualifiers
source                   1..40
                         mol_type = other DNA
                         organism = synthetic construct
SEQUENCE: 1120
ttttccgatt gagggaggga tggtttacca gcgccatttt                          40

SEQ ID NO: 1121          moltype = DNA   length = 40
FEATURE                  Location/Qualifiers
source                   1..40
                         mol_type = other DNA
                         organism = synthetic construct
SEQUENCE: 1121
ttttataaag gtggcaacat tattacgcag tatgtttttt                          40

SEQ ID NO: 1122          moltype = DNA   length = 40
FEATURE                  Location/Qualifiers
source                   1..40
                         mol_type = other DNA
                         organism = synthetic construct
SEQUENCE: 1122
ttttcgaaca aagttaccag cttaccgaag cccttttttt                          40

SEQ ID NO: 1123          moltype = DNA   length = 40
FEATURE                  Location/Qualifiers
source                   1..40
                         mol_type = other DNA
                         organism = synthetic construct
SEQUENCE: 1123
ttttctaata tcagagagat actgaacacc ctgaactttt                          40

SEQ ID NO: 1124          moltype = DNA   length = 47
FEATURE                  Location/Qualifiers
source                   1..47
                         mol_type = other DNA
                         organism = synthetic construct
SEQUENCE: 1124
ttttgaaaat agcagcaaaa tccaaataag aaacgacgac aattttt                  47

SEQ ID NO: 1125          moltype = DNA   length = 24
FEATURE                  Location/Qualifiers
```

-continued

```
source                    1..24
                          mol_type = other DNA
                          organism = synthetic construct
SEQUENCE: 1125
tttttccaga cgatttttg tttt                                          24

SEQ ID NO: 1126           moltype = DNA   length = 24
FEATURE                   Location/Qualifiers
source                    1..24
                          mol_type = other DNA
                          organism = synthetic construct
SEQUENCE: 1126
ttttactaac aaagtacata tttt                                         24

SEQ ID NO: 1127           moltype = DNA   length = 44
FEATURE                   Location/Qualifiers
source                    1..44
                          mol_type = other DNA
                          organism = synthetic construct
SEQUENCE: 1127
ttttaaagca ttggcacaat cgtcattgca acaggaaaaa tttt                   44

SEQ ID NO: 1128           moltype = DNA   length = 48
FEATURE                   Location/Qualifiers
source                    1..48
                          mol_type = other DNA
                          organism = synthetic construct
SEQUENCE: 1128
ttttgagtag aagaactcaa ataacatcag ggaagaagtg tagctttt              48

SEQ ID NO: 1129           moltype = DNA   length = 52
FEATURE                   Location/Qualifiers
source                    1..52
                          mol_type = other DNA
                          organism = synthetic construct
SEQUENCE: 1129
gaagtgtttt tataattacg ccagctatgg ttgttagaat cagagcggtt tt         52

SEQ ID NO: 1130           moltype = DNA   length = 40
FEATURE                   Location/Qualifiers
source                    1..40
                          mol_type = other DNA
                          organism = synthetic construct
SEQUENCE: 1130
ttttaacagg aggccgatta ctcatagtta gcaagctttt                       40

SEQ ID NO: 1131           moltype = DNA   length = 24
FEATURE                   Location/Qualifiers
source                    1..24
                          mol_type = other DNA
                          organism = synthetic construct
SEQUENCE: 1131
ttttgctgcg cgctacaggg tttt                                         24

SEQ ID NO: 1132           moltype = DNA   length = 24
FEATURE                   Location/Qualifiers
source                    1..24
                          mol_type = other DNA
                          organism = synthetic construct
SEQUENCE: 1132
ttttgagccc ccgtggcgag tttt                                         24

SEQ ID NO: 1133           moltype = DNA   length = 28
FEATURE                   Location/Qualifiers
source                    1..28
                          mol_type = other DNA
                          organism = synthetic construct
SEQUENCE: 1133
tcgaggtgcg atggcccact acgttttt                                     28

SEQ ID NO: 1134           moltype = DNA   length = 24
FEATURE                   Location/Qualifiers
source                    1..24
                          mol_type = other DNA
                          organism = synthetic construct
SEQUENCE: 1134
ttttatcaag ttcggaaccc tttt                                         24

SEQ ID NO: 1135           moltype = DNA   length = 24
```

-continued

```
FEATURE                 Location/Qualifiers
source                  1..24
                        mol_type = other DNA
                        organism = synthetic construct
SEQUENCE: 1135
ttttattgac ggaccgactt tttt                                          24

SEQ ID NO: 1136         moltype = DNA   length = 24
FEATURE                 Location/Qualifiers
source                  1..24
                        mol_type = other DNA
                        organism = synthetic construct
SEQUENCE: 1136
tttttttggg aaaccattag tttt                                          24

SEQ ID NO: 1137         moltype = DNA   length = 24
FEATURE                 Location/Qualifiers
source                  1..24
                        mol_type = other DNA
                        organism = synthetic construct
SEQUENCE: 1137
ttttcggaaa cgatcagtag tttt                                          24

SEQ ID NO: 1138         moltype = DNA   length = 24
FEATURE                 Location/Qualifiers
source                  1..24
                        mol_type = other DNA
                        organism = synthetic construct
SEQUENCE: 1138
ttttaatcaa gtatcggcat tttt                                          24

SEQ ID NO: 1139         moltype = DNA   length = 25
FEATURE                 Location/Qualifiers
source                  1..25
                        mol_type = other DNA
                        organism = synthetic construct
SEQUENCE: 1139
tttttcatag ccaaaatcac ctttt                                         25

SEQ ID NO: 1140         moltype = DNA   length = 53
FEATURE                 Location/Qualifiers
source                  1..53
                        mol_type = other DNA
                        organism = synthetic construct
SEQUENCE: 1140
ttttgagcca ccaccggaac cgagccgcca ccgtaacagc aagccccaga cgt          53

SEQ ID NO: 1141         moltype = DNA   length = 44
FEATURE                 Location/Qualifiers
source                  1..44
                        mol_type = other DNA
                        organism = synthetic construct
SEQUENCE: 1141
ttttcctcag agccaccacc ctaccagaac caccaccaga tttt                    44

SEQ ID NO: 1142         moltype = DNA   length = 43
FEATURE                 Location/Qualifiers
source                  1..43
                        mol_type = other DNA
                        organism = synthetic construct
SEQUENCE: 1142
ttttgccagc attgacagga ggttgagaga tcagaaccgc cac                     43

SEQ ID NO: 1143         moltype = DNA   length = 44
FEATURE                 Location/Qualifiers
source                  1..44
                        mol_type = other DNA
                        organism = synthetic construct
SEQUENCE: 1143
ttttcaaaca aataaatcct caaatggaaa gcgcagtctc tttt                    44

SEQ ID NO: 1144         moltype = DNA   length = 43
FEATURE                 Location/Qualifiers
source                  1..43
                        mol_type = other DNA
                        organism = synthetic construct
SEQUENCE: 1144
tttttaccgt tccagtaagc gtcatacagc ggggttttgc tca                     43
```

-continued

```
SEQ ID NO: 1145         moltype = DNA   length = 36
FEATURE                 Location/Qualifiers
source                  1..36
                        mol_type = other DNA
                        organism = synthetic construct
SEQUENCE: 1145
ttttttttaa cgaaacatga aagtattatt tcgagg                              36

SEQ ID NO: 1146         moltype = DNA   length = 28
FEATURE                 Location/Qualifiers
source                  1..28
                        mol_type = other DNA
                        organism = synthetic construct
SEQUENCE: 1146
ttttggaacc tattattctg gggtcagt                                       28

SEQ ID NO: 1147         moltype = DNA   length = 22
FEATURE                 Location/Qualifiers
source                  1..22
                        mol_type = other DNA
                        organism = synthetic construct
SEQUENCE: 1147
ccgtactctt ggccttgatt tt                                             22

SEQ ID NO: 1148         moltype = DNA   length = 22
FEATURE                 Location/Qualifiers
source                  1..22
                        mol_type = other DNA
                        organism = synthetic construct
SEQUENCE: 1148
cccatgtacc ctcagaactt tt                                             22

SEQ ID NO: 1149         moltype = DNA   length = 38
FEATURE                 Location/Qualifiers
source                  1..38
                        mol_type = other DNA
                        organism = synthetic construct
SEQUENCE: 1149
cagcttgcag aggctgagac tcctatacag gagttttt                            38

SEQ ID NO: 1150         moltype = DNA   length = 42
FEATURE                 Location/Qualifiers
source                  1..42
                        mol_type = other DNA
                        organism = synthetic construct
SEQUENCE: 1150
ttttaaccat cgcccacgca tttttaagaa ctggctcatt tt                       42

SEQ ID NO: 1151         moltype = DNA   length = 28
FEATURE                 Location/Qualifiers
source                  1..28
                        mol_type = other DNA
                        organism = synthetic construct
SEQUENCE: 1151
tattcggttt aaacagcttg atactttt                                       28

SEQ ID NO: 1152         moltype = DNA   length = 44
FEATURE                 Location/Qualifiers
source                  1..44
                        mol_type = other DNA
                        organism = synthetic construct
SEQUENCE: 1152
ttttaaaaat ctacgttaat gaattacctt atgcgaaacc gata                     44

SEQ ID NO: 1153         moltype = DNA   length = 44
FEATURE                 Location/Qualifiers
source                  1..44
                        mol_type = other DNA
                        organism = synthetic construct
SEQUENCE: 1153
ttttgaacga gtagatttag ttttgtaaac gttaatattt tttt                     44

SEQ ID NO: 1154         moltype = DNA   length = 28
FEATURE                 Location/Qualifiers
source                  1..28
                        mol_type = other DNA
                        organism = synthetic construct
SEQUENCE: 1154
agatacatgg aagtttcatt ccattttt                                       28
```

-continued

```
SEQ ID NO: 1155          moltype = DNA   length = 32
FEATURE                  Location/Qualifiers
source                   1..32
                         mol_type = other DNA
                         organism = synthetic construct
SEQUENCE: 1155
tttttcgca ttaaattttt ctattaaatt tt                             32

SEQ ID NO: 1156          moltype = DNA   length = 40
FEATURE                  Location/Qualifiers
source                   1..40
                         mol_type = other DNA
                         organism = synthetic construct
SEQUENCE: 1156
gcaacattaa agattcaacc gattgaggga gggaagtttt                    40

SEQ ID NO: 1157          moltype = DNA   length = 56
FEATURE                  Location/Qualifiers
source                   1..56
                         mol_type = other DNA
                         organism = synthetic construct
SEQUENCE: 1157
ttttgtgctg caaggcgatt aagttggggc gatcggtgcg ggcctcttcg cttttt   56

SEQ ID NO: 1158          moltype = DNA   length = 40
FEATURE                  Location/Qualifiers
source                   1..40
                         mol_type = other DNA
                         organism = synthetic construct
SEQUENCE: 1158
tttttggtca tagctgtttc gcatgcctgc aggtcgtttt                    40

SEQ ID NO: 1159          moltype = DNA   length = 40
FEATURE                  Location/Qualifiers
source                   1..40
                         mol_type = other DNA
                         organism = synthetic construct
SEQUENCE: 1159
ttttgctttc cagtcgggaa agcctggggt gcctaatttt                    40

SEQ ID NO: 1160          moltype = DNA   length = 40
FEATURE                  Location/Qualifiers
source                   1..40
                         mol_type = other DNA
                         organism = synthetic construct
SEQUENCE: 1160
ttttcgcctg ccctgagag gcgccagggt ggtttttttt                     40

SEQ ID NO: 1161          moltype = DNA   length = 40
FEATURE                  Location/Qualifiers
source                   1..40
                         mol_type = other DNA
                         organism = synthetic construct
SEQUENCE: 1161
ttttgttcca gtttggaaca cgaaatcggc aaaatctttt                    40

SEQ ID NO: 1162          moltype = DNA   length = 54
FEATURE                  Location/Qualifiers
source                   1..54
                         mol_type = other DNA
                         organism = synthetic construct
SEQUENCE: 1162
ttttgcgaaa aaccgtctat caatggccca ctacgtgaag agtccagtta aatc     54

SEQ ID NO: 1163          moltype = DNA   length = 30
FEATURE                  Location/Qualifiers
source                   1..30
                         mol_type = other DNA
                         organism = synthetic construct
SEQUENCE: 1163
gccttgagta acagtgcccg tataaatttt                               30

SEQ ID NO: 1164          moltype = DNA   length = 31
FEATURE                  Location/Qualifiers
source                   1..31
                         mol_type = other DNA
                         organism = synthetic construct
SEQUENCE: 1164
```

-continued atagaaaaaa taagttctgg tcagaggtta t                                          31

SEQ ID NO: 1165        moltype = DNA   length = 40
FEATURE                Location/Qualifiers
source                 1..40
                       mol_type = other DNA
                       organism = synthetic construct
SEQUENCE: 1165
tcaccgtcaa attattagcg ccataagaac tctaataaca                                40

SEQ ID NO: 1166        moltype = DNA   length = 34
FEATURE                Location/Qualifiers
source                 1..34
                       mol_type = other DNA
                       organism = synthetic construct
SEQUENCE: 1166
acatataaga aaatacttgc tttgttaatc cccc                                      34

SEQ ID NO: 1167        moltype = DNA   length = 19
FEATURE                Location/Qualifiers
source                 1..19
                       mol_type = other DNA
                       organism = synthetic construct
SEQUENCE: 1167
gcaccatttt agagccgcc                                                       19

SEQ ID NO: 1168        moltype = DNA   length = 31
FEATURE                Location/Qualifiers
source                 1..31
                       mol_type = other DNA
                       organism = synthetic construct
SEQUENCE: 1168
tccttattca aaagaaaaat atatatggtt t                                         31

SEQ ID NO: 1169        moltype = DNA   length = 29
FEATURE                Location/Qualifiers
source                 1..29
                       mol_type = other DNA
                       organism = synthetic construct
SEQUENCE: 1169
gcaccgtatc accaatcagt tcagaaaac                                            29

SEQ ID NO: 1170        moltype = DNA   length = 31
FEATURE                Location/Qualifiers
source                 1..31
                       mol_type = other DNA
                       organism = synthetic construct
SEQUENCE: 1170
accgaggagc cgaacaccaa gaacacaagc a                                         31

SEQ ID NO: 1171        moltype = DNA   length = 29
FEATURE                Location/Qualifiers
source                 1..29
                       mol_type = other DNA
                       organism = synthetic construct
SEQUENCE: 1171
gcgttttctt gcctttcatc gcctgataa                                            29

SEQ ID NO: 1172        moltype = DNA   length = 19
FEATURE                Location/Qualifiers
source                 1..19
                       mol_type = other DNA
                       organism = synthetic construct
SEQUENCE: 1172
tcataatccc cttattact                                                       19

SEQ ID NO: 1173        moltype = DNA   length = 41
FEATURE                Location/Qualifiers
source                 1..41
                       mol_type = other DNA
                       organism = synthetic construct
SEQUENCE: 1173
aagactcagc ctccattcag tacaaagcgt ttgactgtag c                              41

SEQ ID NO: 1174        moltype = DNA   length = 47
FEATURE                Location/Qualifiers
source                 1..47
                       mol_type = other DNA
                       organism = synthetic construct

```
SEQUENCE: 1174
acacccccgc ccagagtgac agggatactg agtttccctc ataacgc                          47

SEQ ID NO: 1175          moltype = DNA   length = 41
FEATURE                  Location/Qualifiers
source                   1..41
                         mol_type = other DNA
                         organism = synthetic construct
SEQUENCE: 1175
cagaggcagg tcagacgaag gaggttcgga atagattttt t                                41

SEQ ID NO: 1176          moltype = DNA   length = 46
FEATURE                  Location/Qualifiers
source                   1..46
                         mol_type = other DNA
                         organism = synthetic construct
SEQUENCE: 1176
ccaaagccag ttaaataagt atagcctagt accgagtgag aaaaca                           46

SEQ ID NO: 1177          moltype = DNA   length = 34
FEATURE                  Location/Qualifiers
source                   1..34
                         mol_type = other DNA
                         organism = synthetic construct
SEQUENCE: 1177
ttttgatgca agagaaggat taggatacct ttaa                                        34

SEQ ID NO: 1178          moltype = DNA   length = 23
FEATURE                  Location/Qualifiers
source                   1..23
                         mol_type = other DNA
                         organism = synthetic construct
SEQUENCE: 1178
ctacaaagcc taatttgccc aat                                                    23

SEQ ID NO: 1179          moltype = DNA   length = 23
FEATURE                  Location/Qualifiers
source                   1..23
                         mol_type = other DNA
                         organism = synthetic construct
SEQUENCE: 1179
gtaccaggcg gataacgaaa atc                                                    23

SEQ ID NO: 1180          moltype = DNA   length = 20
FEATURE                  Location/Qualifiers
source                   1..20
                         mol_type = other DNA
                         organism = synthetic construct
SEQUENCE: 1180
atataagaaa cgatccttta                                                        20

SEQ ID NO: 1181          moltype = DNA   length = 21
FEATURE                  Location/Qualifiers
source                   1..21
                         mol_type = other DNA
                         organism = synthetic construct
SEQUENCE: 1181
aacgccccat aacataactg a                                                      21

SEQ ID NO: 1182          moltype = DNA   length = 23
FEATURE                  Location/Qualifiers
source                   1..23
                         mol_type = other DNA
                         organism = synthetic construct
SEQUENCE: 1182
cctcagaacc gccgagatga att                                                    23

SEQ ID NO: 1183          moltype = DNA   length = 21
FEATURE                  Location/Qualifiers
source                   1..21
                         mol_type = other DNA
                         organism = synthetic construct
SEQUENCE: 1183
cattttacaa agtcaaccca c                                                      21

SEQ ID NO: 1184          moltype = DNA   length = 33
FEATURE                  Location/Qualifiers
source                   1..33
                         mol_type = other DNA
```

```
                              organism = synthetic construct
SEQUENCE: 1184
agccgtcacg agttaagcaa tagctccatc ttt                                    33

SEQ ID NO: 1185          moltype = DNA   length = 24
FEATURE                  Location/Qualifiers
source                   1..24
                         mol_type = other DNA
                         organism = synthetic construct
SEQUENCE: 1185
acagttagcg taacgatcta aagt                                              24

SEQ ID NO: 1186          moltype = DNA   length = 28
FEATURE                  Location/Qualifiers
source                   1..28
                         mol_type = other DNA
                         organism = synthetic construct
SEQUENCE: 1186
ctgtatttgt atagcgtcag cgatagca                                          28

SEQ ID NO: 1187          moltype = DNA   length = 21
FEATURE                  Location/Qualifiers
source                   1..21
                         mol_type = other DNA
                         organism = synthetic construct
SEQUENCE: 1187
tttgtcgtct ttcaatagga a                                                 21

SEQ ID NO: 1188          moltype = DNA   length = 22
FEATURE                  Location/Qualifiers
source                   1..22
                         mol_type = other DNA
                         organism = synthetic construct
SEQUENCE: 1188
tagtaacatt tataccaagc gc                                                22

SEQ ID NO: 1189          moltype = DNA   length = 32
FEATURE                  Location/Qualifiers
source                   1..32
                         mol_type = other DNA
                         organism = synthetic construct
SEQUENCE: 1189
ggattttgct atagaaagga acaactaaag ga                                     32

SEQ ID NO: 1190          moltype = DNA   length = 49
FEATURE                  Location/Qualifiers
source                   1..49
                         mol_type = other DNA
                         organism = synthetic construct
SEQUENCE: 1190
acttcactac gaatacacta aaagaggaag ggaaccagcg tccaatact                   49

SEQ ID NO: 1191          moltype = DNA   length = 21
FEATURE                  Location/Qualifiers
source                   1..21
                         mol_type = other DNA
                         organism = synthetic construct
SEQUENCE: 1191
attgcgaata atagtgtatc a                                                 21

SEQ ID NO: 1192          moltype = DNA   length = 22
FEATURE                  Location/Qualifiers
source                   1..22
                         mol_type = other DNA
                         organism = synthetic construct
SEQUENCE: 1192
cacgttatga gtttccatta aa                                                22

SEQ ID NO: 1193          moltype = DNA   length = 29
FEATURE                  Location/Qualifiers
source                   1..29
                         mol_type = other DNA
                         organism = synthetic construct
SEQUENCE: 1193
tccaaacggc tacaacagca tccaccaga                                         29

SEQ ID NO: 1194          moltype = DNA   length = 23
FEATURE                  Location/Qualifiers
source                   1..23
```

-continued

```
                        mol_type = other DNA
                        organism = synthetic construct
SEQUENCE: 1194
aaggctccaa aaggagtaaa gcg                                       23

SEQ ID NO: 1195         moltype = DNA   length = 32
FEATURE                 Location/Qualifiers
source                  1..32
                        mol_type = other DNA
                        organism = synthetic construct
SEQUENCE: 1195
tgaatttccg ctgaggcttg caggcaactt ta                            32

SEQ ID NO: 1196         moltype = DNA   length = 46
FEATURE                 Location/Qualifiers
source                  1..46
                        mol_type = other DNA
                        organism = synthetic construct
SEQUENCE: 1196
ttgtatttgc gggatcgtca ccgatagtaa attgggctta gaaaga            46

SEQ ID NO: 1197         moltype = DNA   length = 41
FEATURE                 Location/Qualifiers
source                  1..41
                        mol_type = other DNA
                        organism = synthetic construct
SEQUENCE: 1197
aaaggaggct tttaaggctt taacaaagta tcataaccct c                 41

SEQ ID NO: 1198         moltype = DNA   length = 32
FEATURE                 Location/Qualifiers
source                  1..32
                        mol_type = other DNA
                        organism = synthetic construct
SEQUENCE: 1198
aacatgagca gtaccgacaa taaacaagtg cc                            32

SEQ ID NO: 1199         moltype = DNA   length = 15
FEATURE                 Location/Qualifiers
source                  1..15
                        mol_type = other DNA
                        organism = synthetic construct
SEQUENCE: 1199
ttttggtagc aaaaa                                               15

SEQ ID NO: 1200         moltype = DNA   length = 32
FEATURE                 Location/Qualifiers
source                  1..32
                        mol_type = other DNA
                        organism = synthetic construct
SEQUENCE: 1200
aaagacaggg acgacgacaa aaggtcaccc ag                            32

SEQ ID NO: 1201         moltype = DNA   length = 32
FEATURE                 Location/Qualifiers
source                  1..32
                        mol_type = other DNA
                        organism = synthetic construct
SEQUENCE: 1201
tgaggattca gctattcagc ggccagaggc gt                            32

SEQ ID NO: 1202         moltype = DNA   length = 65
FEATURE                 Location/Qualifiers
source                  1..65
                        mol_type = other DNA
                        organism = synthetic construct
SEQUENCE: 1202
cgggtaaaat acgttacaag attcatggta aaccaaacag aggggtaaga aagagcccca  60
ggaag                                                             65

SEQ ID NO: 1203         moltype = DNA   length = 32
FEATURE                 Location/Qualifiers
source                  1..32
                        mol_type = other DNA
                        organism = synthetic construct
SEQUENCE: 1203
aaattccaat agatatgcag aagaaagggt tg                            32

SEQ ID NO: 1204         moltype = DNA   length = 31
```

-continued

```
FEATURE               Location/Qualifiers
source                1..31
                      mol_type = other DNA
                      organism = synthetic construct
SEQUENCE: 1204
tatgctgctc aacagttaat ttacaccctc a                              31

SEQ ID NO: 1205       moltype = DNA   length = 15
FEATURE               Location/Qualifiers
source                1..15
                      mol_type = other DNA
                      organism = synthetic construct
SEQUENCE: 1205
ttttcgaaag agatg                                                15

SEQ ID NO: 1206       moltype = DNA   length = 33
FEATURE               Location/Qualifiers
source                1..33
                      mol_type = other DNA
                      organism = synthetic construct
SEQUENCE: 1206
catcttggat cccatccaag tcctgattct aag                            33

SEQ ID NO: 1207       moltype = DNA   length = 32
FEATURE               Location/Qualifiers
source                1..32
                      mol_type = other DNA
                      organism = synthetic construct
SEQUENCE: 1207
cagcgagtag aaacacagac agcgttttta tt                             32

SEQ ID NO: 1208       moltype = DNA   length = 33
FEATURE               Location/Qualifiers
source                1..33
                      mol_type = other DNA
                      organism = synthetic construct
SEQUENCE: 1208
gaaacaaagt acagccggaa cccgcgaccg ctt                            33

SEQ ID NO: 1209       moltype = DNA   length = 32
FEATURE               Location/Qualifiers
source                1..32
                      mol_type = other DNA
                      organism = synthetic construct
SEQUENCE: 1209
tgtgatttat cattcaatca atcaaccacc ct                             32

SEQ ID NO: 1210       moltype = DNA   length = 33
FEATURE               Location/Qualifiers
source                1..33
                      mol_type = other DNA
                      organism = synthetic construct
SEQUENCE: 1210
gaaatagaga gcattccaag ttaccatctt acc                            33

SEQ ID NO: 1211       moltype = DNA   length = 24
FEATURE               Location/Qualifiers
source                1..24
                      mol_type = other DNA
                      organism = synthetic construct
SEQUENCE: 1211
attgtgtcga aatgaggcgc agac                                      24

SEQ ID NO: 1212       moltype = DNA   length = 42
FEATURE               Location/Qualifiers
source                1..42
                      mol_type = other DNA
                      organism = synthetic construct
SEQUENCE: 1212
ggtcaatcat acagatgaaa gttttgcata gcgaggcgaa cc                  42

SEQ ID NO: 1213       moltype = DNA   length = 21
FEATURE               Location/Qualifiers
source                1..21
                      mol_type = other DNA
                      organism = synthetic construct
SEQUENCE: 1213
aggcgcatag gctacctaaa a                                         21
```

```
SEQ ID NO: 1214           moltype = DNA   length = 33
FEATURE                   Location/Qualifiers
source                    1..33
                          mol_type = other DNA
                          organism = synthetic construct
SEQUENCE: 1214
tattcattac ccaaatcaac ggccctgacc ata                                     33

SEQ ID NO: 1215           moltype = DNA   length = 27
FEATURE                   Location/Qualifiers
source                    1..27
                          mol_type = other DNA
                          organism = synthetic construct
SEQUENCE: 1215
aaaggaacga gggccgcttc ggtttat                                            27

SEQ ID NO: 1216           moltype = DNA   length = 21
FEATURE                   Location/Qualifiers
source                    1..21
                          mol_type = other DNA
                          organism = synthetic construct
SEQUENCE: 1216
acgagtagct ttaggaacaa a                                                  21

SEQ ID NO: 1217           moltype = DNA   length = 48
FEATURE                   Location/Qualifiers
source                    1..48
                          mol_type = other DNA
                          organism = synthetic construct
SEQUENCE: 1217
atcattgtaa aacgaactaa cggactaaag tacggtgtct ttcgcaaa                     48

SEQ ID NO: 1218           moltype = DNA   length = 16
FEATURE                   Location/Qualifiers
source                    1..16
                          mol_type = other DNA
                          organism = synthetic construct
SEQUENCE: 1218
tttaatttga gttaaa                                                        16

SEQ ID NO: 1219           moltype = DNA   length = 37
FEATURE                   Location/Qualifiers
source                    1..37
                          mol_type = other DNA
                          organism = synthetic construct
SEQUENCE: 1219
ttcatcagga tctgtataat gtataaaagg tggcatc                                 37

SEQ ID NO: 1220           moltype = DNA   length = 32
FEATURE                   Location/Qualifiers
source                    1..32
                          mol_type = other DNA
                          organism = synthetic construct
SEQUENCE: 1220
cgtcgcagat tagattatca gtgaagagga ct                                      32

SEQ ID NO: 1221           moltype = DNA   length = 15
FEATURE                   Location/Qualifiers
source                    1..15
                          mol_type = other DNA
                          organism = synthetic construct
SEQUENCE: 1221
tttttgcaga tagag                                                         15

SEQ ID NO: 1222           moltype = DNA   length = 36
FEATURE                   Location/Qualifiers
source                    1..36
                          mol_type = other DNA
                          organism = synthetic construct
SEQUENCE: 1222
acgctaccac atgctgaata gctcaacatt ttcatt                                  36

SEQ ID NO: 1223           moltype = DNA   length = 32
FEATURE                   Location/Qualifiers
source                    1..32
                          mol_type = other DNA
                          organism = synthetic construct
SEQUENCE: 1223
aggatctgat aacttttgaa atacaggcgc ct                                      32
```

```
SEQ ID NO: 1224          moltype = DNA   length = 32
FEATURE                  Location/Qualifiers
source                   1..32
                         mol_type = other DNA
                         organism = synthetic construct
SEQUENCE: 1224
ggcatacaaa atttatcaga cgctgcaacg cc                                    32

SEQ ID NO: 1225          moltype = DNA   length = 32
FEATURE                  Location/Qualifiers
source                   1..32
                         mol_type = other DNA
                         organism = synthetic construct
SEQUENCE: 1225
caacacctgc tcatcctccg gctaagttat ac                                    32

SEQ ID NO: 1226          moltype = DNA   length = 23
FEATURE                  Location/Qualifiers
source                   1..23
                         mol_type = other DNA
                         organism = synthetic construct
SEQUENCE: 1226
gtttaccaga cgacaggaag caa                                              23

SEQ ID NO: 1227          moltype = DNA   length = 32
FEATURE                  Location/Qualifiers
source                   1..32
                         mol_type = other DNA
                         organism = synthetic construct
SEQUENCE: 1227
tgaattcttt ttaaaaaatc atagtttttt ca                                    32

SEQ ID NO: 1228          moltype = DNA   length = 32
FEATURE                  Location/Qualifiers
source                   1..32
                         mol_type = other DNA
                         organism = synthetic construct
SEQUENCE: 1228
taacaataat gggttatcaa ctttgaaaca ct                                    32

SEQ ID NO: 1229          moltype = DNA   length = 33
FEATURE                  Location/Qualifiers
source                   1..33
                         mol_type = other DNA
                         organism = synthetic construct
SEQUENCE: 1229
taaaattgaa aatccaaata actattagta tca                                   33

SEQ ID NO: 1230          moltype = DNA   length = 32
FEATURE                  Location/Qualifiers
source                   1..32
                         mol_type = other DNA
                         organism = synthetic construct
SEQUENCE: 1230
ctggatgaac tgacgttact taacgccgac cg                                    32

SEQ ID NO: 1231          moltype = DNA   length = 33
FEATURE                  Location/Qualifiers
source                   1..33
                         mol_type = other DNA
                         organism = synthetic construct
SEQUENCE: 1231
gcggaatcgt catgactatt aaatcaaaaa atg                                   33

SEQ ID NO: 1232          moltype = DNA   length = 35
FEATURE                  Location/Qualifiers
source                   1..35
                         mol_type = other DNA
                         organism = synthetic construct
SEQUENCE: 1232
cattgattca ctttttctcg caagaacctg acccc                                 35

SEQ ID NO: 1233          moltype = DNA   length = 20
FEATURE                  Location/Qualifiers
source                   1..20
                         mol_type = other DNA
                         organism = synthetic construct
SEQUENCE: 1233
```

-continued

```
taaagaaacc atcaccagta                                          20

SEQ ID NO: 1234        moltype = DNA   length = 30
FEATURE                Location/Qualifiers
source                 1..30
                       mol_type = other DNA
                       organism = synthetic construct
SEQUENCE: 1234
tcaaattgct ccatctggca tgagaaggaa                               30

SEQ ID NO: 1235        moltype = DNA   length = 44
FEATURE                Location/Qualifiers
source                 1..44
                       mol_type = other DNA
                       organism = synthetic construct
SEQUENCE: 1235
gagaatgacc atatagtcag atttagaact atttcaaata ttca               44

SEQ ID NO: 1236        moltype = DNA   length = 22
FEATURE                Location/Qualifiers
source                 1..22
                       mol_type = other DNA
                       organism = synthetic construct
SEQUENCE: 1236
agaccgaaaa gctaaatcgg tt                                       22

SEQ ID NO: 1237        moltype = DNA   length = 29
FEATURE                Location/Qualifiers
source                 1..29
                       mol_type = other DNA
                       organism = synthetic construct
SEQUENCE: 1237
actccagcaa taaaaaggca aagaatcga                                29

SEQ ID NO: 1238        moltype = DNA   length = 42
FEATURE                Location/Qualifiers
source                 1..42
                       mol_type = other DNA
                       organism = synthetic construct
SEQUENCE: 1238
agagagtacc tttaattgct cgaggtcatt tttgcggatg gc                 42

SEQ ID NO: 1239        moltype = DNA   length = 37
FEATURE                Location/Qualifiers
source                 1..37
                       mol_type = other DNA
                       organism = synthetic construct
SEQUENCE: 1239
ttagagctta atttcaacta aattacaggt gagatgg                       37

SEQ ID NO: 1240        moltype = DNA   length = 40
FEATURE                Location/Qualifiers
source                 1..40
                       mol_type = other DNA
                       organism = synthetic construct
SEQUENCE: 1240
tggtcaataa acaggaagat tgtattttaa ccaataggaa                    40

SEQ ID NO: 1241        moltype = DNA   length = 32
FEATURE                Location/Qualifiers
source                 1..32
                       mol_type = other DNA
                       organism = synthetic construct
SEQUENCE: 1241
tagctatatg ttttaaatat gcaaacaaca tt                            32

SEQ ID NO: 1242        moltype = DNA   length = 18
FEATURE                Location/Qualifiers
source                 1..18
                       mol_type = other DNA
                       organism = synthetic construct
SEQUENCE: 1242
tggggcgcgc gaccccgg                                            18

SEQ ID NO: 1243        moltype = DNA   length = 32
FEATURE                Location/Qualifiers
source                 1..32
                       mol_type = other DNA
                       organism = synthetic construct
```

-continued

```
SEQUENCE: 1243
gaacaactgc agatgatatt atactattac ga                                    32

SEQ ID NO: 1244        moltype = DNA   length = 32
FEATURE                Location/Qualifiers
source                 1..32
                       mol_type = other DNA
                       organism = synthetic construct
SEQUENCE: 1244
aattctacta ataagagtaa tcgtaaaact ag                                    32

SEQ ID NO: 1245        moltype = DNA   length = 32
FEATURE                Location/Qualifiers
source                 1..32
                       mol_type = other DNA
                       organism = synthetic construct
SEQUENCE: 1245
cattaataat tgtttggggc aattctgtaa at                                    32

SEQ ID NO: 1246        moltype = DNA   length = 32
FEATURE                Location/Qualifiers
source                 1..32
                       mol_type = other DNA
                       organism = synthetic construct
SEQUENCE: 1246
taaatctaat ggaaacgtaa aacgatttca tt                                    32

SEQ ID NO: 1247        moltype = DNA   length = 33
FEATURE                Location/Qualifiers
source                 1..33
                       mol_type = other DNA
                       organism = synthetic construct
SEQUENCE: 1247
cagaaaggct atgtagctat gcgcatcgta acc                                   33

SEQ ID NO: 1248        moltype = DNA   length = 32
FEATURE                Location/Qualifiers
source                 1..32
                       mol_type = other DNA
                       organism = synthetic construct
SEQUENCE: 1248
gacaacttat ttgcgggtta gaaatgtaag ag                                    32

SEQ ID NO: 1249        moltype = DNA   length = 32
FEATURE                Location/Qualifiers
source                 1..32
                       mol_type = other DNA
                       organism = synthetic construct
SEQUENCE: 1249
ttacaataat aaagaaaata tacaggtaat ag                                    32

SEQ ID NO: 1250        moltype = DNA   length = 32
FEATURE                Location/Qualifiers
source                 1..32
                       mol_type = other DNA
                       organism = synthetic construct
SEQUENCE: 1250
gtaccaaaaa cataagctag ctgataaatt aa                                    32

SEQ ID NO: 1251        moltype = DNA   length = 32
FEATURE                Location/Qualifiers
source                 1..32
                       mol_type = other DNA
                       organism = synthetic construct
SEQUENCE: 1251
ctgtaatagt cagatgattg cgtagttaca tt                                    32

SEQ ID NO: 1252        moltype = DNA   length = 32
FEATURE                Location/Qualifiers
source                 1..32
                       mol_type = other DNA
                       organism = synthetic construct
SEQUENCE: 1252
ccttcctcat atagggtgag gtaatgtgcc ag                                    32

SEQ ID NO: 1253        moltype = DNA   length = 29
FEATURE                Location/Qualifiers
source                 1..29
                       mol_type = other DNA
```

-continued

```
                              organism = synthetic construct
SEQUENCE: 1253
gcgggatacc ttttttttacc ctaaatatt                                29

SEQ ID NO: 1254        moltype = DNA   length = 21
FEATURE                Location/Qualifiers
source                 1..21
                       mol_type = other DNA
                       organism = synthetic construct
SEQUENCE: 1254
taaaaattag caaagcggat t                                         21

SEQ ID NO: 1255        moltype = DNA   length = 32
FEATURE                Location/Qualifiers
source                 1..32
                       mol_type = other DNA
                       organism = synthetic construct
SEQUENCE: 1255
aggagctcgc ctgaacatcg ggtgagttta ga                             32

SEQ ID NO: 1256        moltype = DNA   length = 20
FEATURE                Location/Qualifiers
source                 1..20
                       mol_type = other DNA
                       organism = synthetic construct
SEQUENCE: 1256
caatagcaaa atgtgaatta                                           20

SEQ ID NO: 1257        moltype = DNA   length = 33
FEATURE                Location/Qualifiers
source                 1..33
                       mol_type = other DNA
                       organism = synthetic construct
SEQUENCE: 1257
ctaaaattaa tcaggtcata cataaattaa gac                            33

SEQ ID NO: 1258        moltype = DNA   length = 43
FEATURE                Location/Qualifiers
source                 1..43
                       mol_type = other DNA
                       organism = synthetic construct
SEQUENCE: 1258
tgaaaaggcc ggcaccgctg atcgcaccag tgaggaatcc tga                 43

SEQ ID NO: 1259        moltype = DNA   length = 21
FEATURE                Location/Qualifiers
source                 1..21
                       mol_type = other DNA
                       organism = synthetic construct
SEQUENCE: 1259
caccatcaat atgcgcaagg a                                         21

SEQ ID NO: 1260        moltype = DNA   length = 41
FEATURE                Location/Qualifiers
source                 1..41
                       mol_type = other DNA
                       organism = synthetic construct
SEQUENCE: 1260
accgttcatc tcaggaatct ggtgcttgat tagaaactat c                   41

SEQ ID NO: 1261        moltype = DNA   length = 23
FEATURE                Location/Qualifiers
source                 1..23
                       mol_type = other DNA
                       organism = synthetic construct
SEQUENCE: 1261
tgccggagag gcaggtcatt agg                                       23

SEQ ID NO: 1262        moltype = DNA   length = 21
FEATURE                Location/Qualifiers
source                 1..21
                       mol_type = other DNA
                       organism = synthetic construct
SEQUENCE: 1262
ggagcaaaca agagaattag c                                         21

SEQ ID NO: 1263        moltype = DNA   length = 41
FEATURE                Location/Qualifiers
source                 1..41
```

-continued

```
                          mol_type = other DNA
                          organism = synthetic construct
SEQUENCE: 1263
tgaacgagat gggaacagtt ggtgtggttg cttgaatcag a               41

SEQ ID NO: 1264       moltype = DNA   length = 32
FEATURE               Location/Qualifiers
source                1..32
                      mol_type = other DNA
                      organism = synthetic construct
SEQUENCE: 1264
agctcattta agcaaatatt taaatgacca tt                          32

SEQ ID NO: 1265       moltype = DNA   length = 40
FEATURE               Location/Qualifiers
source                1..40
                      mol_type = other DNA
                      organism = synthetic construct
SEQUENCE: 1265
cgccatcaaa aataatatca gaaaagcccc aaaacctgtt                  40

SEQ ID NO: 1266       moltype = DNA   length = 32
FEATURE               Location/Qualifiers
source                1..32
                      mol_type = other DNA
                      organism = synthetic construct
SEQUENCE: 1266
acgtggagct gatagcccca ccagcgtagt ag                          32

SEQ ID NO: 1267       moltype = DNA   length = 29
FEATURE               Location/Qualifiers
source                1..29
                      mol_type = other DNA
                      organism = synthetic construct
SEQUENCE: 1267
cattaaatgt gagggagcgg gtgcgcgta                              29

SEQ ID NO: 1268       moltype = DNA   length = 32
FEATURE               Location/Qualifiers
source                1..32
                      mol_type = other DNA
                      organism = synthetic construct
SEQUENCE: 1268
caacccagac gaacgaacta aaacattttg cg                          32

SEQ ID NO: 1269       moltype = DNA   length = 32
FEATURE               Location/Qualifiers
source                1..32
                      mol_type = other DNA
                      organism = synthetic construct
SEQUENCE: 1269
tctccgtaaa acaggatcta cagcaacaat tc                          32

SEQ ID NO: 1270       moltype = DNA   length = 21
FEATURE               Location/Qualifiers
source                1..21
                      mol_type = other DNA
                      organism = synthetic construct
SEQUENCE: 1270
taatgggatg cctgagagtc t                                      21

SEQ ID NO: 1271       moltype = DNA   length = 28
FEATURE               Location/Qualifiers
source                1..28
                      mol_type = other DNA
                      organism = synthetic construct
SEQUENCE: 1271
tcacaacggc ggggtcacgc cgctaggg                              28

SEQ ID NO: 1272       moltype = DNA   length = 32
FEATURE               Location/Qualifiers
source                1..32
                      mol_type = other DNA
                      organism = synthetic construct
SEQUENCE: 1272
acacgacgcc tgcaaggtga ggtatcatcc aa                          32

SEQ ID NO: 1273       moltype = DNA   length = 32
FEATURE               Location/Qualifiers
```

-continued

```
source                    1..32
                          mol_type = other DNA
                          organism = synthetic construct
SEQUENCE: 1273
agattctggt tttgagaaaa atctatatga cc                                     32

SEQ ID NO: 1274           moltype = DNA   length = 29
FEATURE                   Location/Qualifiers
source                    1..29
                          mol_type = other DNA
                          organism = synthetic construct
SEQUENCE: 1274
gtgcatctgc cagtacgcca gccaccgag                                         29

SEQ ID NO: 1275           moltype = DNA   length = 32
FEATURE                   Location/Qualifiers
source                    1..32
                          mol_type = other DNA
                          organism = synthetic construct
SEQUENCE: 1275
ggacgaacgg caaatgaaca gtgccttaga ct                                     32

SEQ ID NO: 1276           moltype = DNA   length = 32
FEATURE                   Location/Qualifiers
source                    1..32
                          mol_type = other DNA
                          organism = synthetic construct
SEQUENCE: 1276
atcggccacc ttgcgattca aaatttatct tt                                     32

SEQ ID NO: 1277           moltype = DNA   length = 32
FEATURE                   Location/Qualifiers
source                    1..32
                          mol_type = other DNA
                          organism = synthetic construct
SEQUENCE: 1277
acaggaatca atattgaacc tccaatactt tt                                     32

SEQ ID NO: 1278           moltype = DNA   length = 40
FEATURE                   Location/Qualifiers
source                    1..40
                          mol_type = other DNA
                          organism = synthetic construct
SEQUENCE: 1278
tgggaaggta acgccaggcc agtgccaagc ttctgtgtga                             40

SEQ ID NO: 1279           moltype = DNA   length = 16
FEATURE                   Location/Qualifiers
source                    1..16
                          mol_type = other DNA
                          organism = synthetic construct
SEQUENCE: 1279
caggctgcgc aactgt                                                       16

SEQ ID NO: 1280           moltype = DNA   length = 37
FEATURE                   Location/Qualifiers
source                    1..37
                          mol_type = other DNA
                          organism = synthetic construct
SEQUENCE: 1280
ctgagtagtc gccattgctt tccggagaca gtcaaat                                37

SEQ ID NO: 1281           moltype = DNA   length = 24
FEATURE                   Location/Qualifiers
source                    1..24
                          mol_type = other DNA
                          organism = synthetic construct
SEQUENCE: 1281
ggccttgcag ggcgaccaca atca                                              24

SEQ ID NO: 1282           moltype = DNA   length = 24
FEATURE                   Location/Qualifiers
source                    1..24
                          mol_type = other DNA
                          organism = synthetic construct
SEQUENCE: 1282
tcacttgctt tataattcca gcca                                              24

SEQ ID NO: 1283           moltype = DNA   length = 48
```

-continued

```
FEATURE                 Location/Qualifiers
source                  1..48
                        mol_type = other DNA
                        organism = synthetic construct
SEQUENCE: 1283
aattgttaga agcataaagt gtaaacctgt cgtgccagct gcggtttg                    48

SEQ ID NO: 1284         moltype = DNA   length = 48
FEATURE                 Location/Qualifiers
source                  1..48
                        mol_type = other DNA
                        organism = synthetic construct
SEQUENCE: 1284
tccgctcaca attccagacg ttgtaaaacg acgggttttc ccagtcac                    48

SEQ ID NO: 1285         moltype = DNA   length = 26
FEATURE                 Location/Qualifiers
source                  1..26
                        mol_type = other DNA
                        organism = synthetic construct
SEQUENCE: 1285
taaaagagat acttctcggc attgca                                            26

SEQ ID NO: 1286         moltype = DNA   length = 32
FEATURE                 Location/Qualifiers
source                  1..32
                        mol_type = other DNA
                        organism = synthetic construct
SEQUENCE: 1286
gaagtgttcg tgctttcctc gttatgacga gc                                     32

SEQ ID NO: 1287         moltype = DNA   length = 23
FEATURE                 Location/Qualifiers
source                  1..23
                        mol_type = other DNA
                        organism = synthetic construct
SEQUENCE: 1287
gcgggagcag gaacggtttg agg                                               23

SEQ ID NO: 1288         moltype = DNA   length = 48
FEATURE                 Location/Qualifiers
source                  1..48
                        mol_type = other DNA
                        organism = synthetic construct
SEQUENCE: 1288
cgtattggag ttgcagcaag cggttgtttg atggtggttc ggtgccgt                    48

SEQ ID NO: 1289         moltype = DNA   length = 48
FEATURE                 Location/Qualifiers
source                  1..48
                        mol_type = other DNA
                        organism = synthetic construct
SEQUENCE: 1289
caacgcgcgg ggagaggcat taatgaatcg gccacaacat acgagccg                    48

SEQ ID NO: 1290         moltype = DNA   length = 24
FEATURE                 Location/Qualifiers
source                  1..24
                        mol_type = other DNA
                        organism = synthetic construct
SEQUENCE: 1290
acgtataaag tgtagcattg accg                                              24

SEQ ID NO: 1291         moltype = DNA   length = 26
FEATURE                 Location/Qualifiers
source                  1..26
                        mol_type = other DNA
                        organism = synthetic construct
SEQUENCE: 1291
accaccaccg tactatagaa ccagtc                                            26

SEQ ID NO: 1292         moltype = DNA   length = 24
FEATURE                 Location/Qualifiers
source                  1..24
                        mol_type = other DNA
                        organism = synthetic construct
SEQUENCE: 1292
cgctggcagg gagcccccga ttta                                              24
```

-continued

```
SEQ ID NO: 1293          moltype = DNA   length = 40
FEATURE                  Location/Qualifiers
source                   1..40
                         mol_type = other DNA
                         organism = synthetic construct
SEQUENCE: 1293
aaagcactag tttttgggg tcgaaccatc acccaaatca                            40

SEQ ID NO: 1294          moltype = DNA   length = 48
FEATURE                  Location/Qualifiers
source                   1..48
                         mol_type = other DNA
                         organism = synthetic construct
SEQUENCE: 1294
aaatcggaac cctaaacagc aggcgaaaat ccccacgctg gtttgccc                  48

SEQ ID NO: 1295          moltype = DNA   length = 31
FEATURE                  Location/Qualifiers
source                   1..31
                         mol_type = other DNA
                         organism = synthetic construct
SEQUENCE: 1295
gagcttgacg gggaaaaagc gaaacgagta a                                    31

SEQ ID NO: 1296          moltype = DNA   length = 32
FEATURE                  Location/Qualifiers
source                   1..32
                         mol_type = other DNA
                         organism = synthetic construct
SEQUENCE: 1296
catgtcaatc atatgtaacc agctttcatc aa                                   32

SEQ ID NO: 1297          moltype = DNA   length = 40
FEATURE                  Location/Qualifiers
source                   1..40
                         mol_type = other DNA
                         organism = synthetic construct
SEQUENCE: 1297
tttttaccag cgccaaagac aaatggtaat atccagtttt                           40

SEQ ID NO: 1298          moltype = DNA   length = 30
FEATURE                  Location/Qualifiers
source                   1..30
                         mol_type = other DNA
                         organism = synthetic construct
SEQUENCE: 1298
ttttagacac cacggttcat atggttttt                                       30

SEQ ID NO: 1299          moltype = DNA   length = 30
FEATURE                  Location/Qualifiers
source                   1..30
                         mol_type = other DNA
                         organism = synthetic construct
SEQUENCE: 1299
tttttagcaa acgtaaagaa acgcaatttt                                      30

SEQ ID NO: 1300          moltype = DNA   length = 30
FEATURE                  Location/Qualifiers
source                   1..30
                         mol_type = other DNA
                         organism = synthetic construct
SEQUENCE: 1300
ttttaacgga ataccacgca gtatgttttt                                      30

SEQ ID NO: 1301          moltype = DNA   length = 30
FEATURE                  Location/Qualifiers
source                   1..30
                         mol_type = other DNA
                         organism = synthetic construct
SEQUENCE: 1301
ttttgtaagc agataaacgc aataattttt                                      30

SEQ ID NO: 1302          moltype = DNA   length = 36
FEATURE                  Location/Qualifiers
source                   1..36
                         mol_type = other DNA
                         organism = synthetic construct
SEQUENCE: 1302
gaagcccttg aaatagccca ataataagag catttt                               36
```

-continued

```
SEQ ID NO: 1303          moltype = DNA   length = 27
FEATURE                  Location/Qualifiers
source                   1..27
                         mol_type = other DNA
                         organism = synthetic construct
SEQUENCE: 1303
ttttagaaac aattttaaga aaatttt                                    27

SEQ ID NO: 1304          moltype = DNA   length = 29
FEATURE                  Location/Qualifiers
source                   1..29
                         mol_type = other DNA
                         organism = synthetic construct
SEQUENCE: 1304
ttttctaata tcgtaggaat cattatttt                                  29

SEQ ID NO: 1305          moltype = DNA   length = 29
FEATURE                  Location/Qualifiers
source                   1..29
                         mol_type = other DNA
                         organism = synthetic construct
SEQUENCE: 1305
tttttttagac ggaatcagat atagatttt                                 29

SEQ ID NO: 1306          moltype = DNA   length = 29
FEATURE                  Location/Qualifiers
source                   1..29
                         mol_type = other DNA
                         organism = synthetic construct
SEQUENCE: 1306
ttttaaaatg aagaacctcc cgacttttt                                  29

SEQ ID NO: 1307          moltype = DNA   length = 29
FEATURE                  Location/Qualifiers
source                   1..29
                         mol_type = other DNA
                         organism = synthetic construct
SEQUENCE: 1307
ttttcagcca tattaaatca agatttttt                                  29

SEQ ID NO: 1308          moltype = DNA   length = 33
FEATURE                  Location/Qualifiers
source                   1..33
                         mol_type = other DNA
                         organism = synthetic construct
SEQUENCE: 1308
ttttcaacgc taacgagcgt ctttccagat ggc                             33

SEQ ID NO: 1309          moltype = DNA   length = 29
FEATURE                  Location/Qualifiers
source                   1..29
                         mol_type = other DNA
                         organism = synthetic construct
SEQUENCE: 1309
ttttagttgc tattttgaaa gtaattttt                                  29

SEQ ID NO: 1310          moltype = DNA   length = 37
FEATURE                  Location/Qualifiers
source                   1..37
                         mol_type = other DNA
                         organism = synthetic construct
SEQUENCE: 1310
gtcgaggcct tatttatcca gttacaaaat aaatttt                         37

SEQ ID NO: 1311          moltype = DNA   length = 29
FEATURE                  Location/Qualifiers
source                   1..29
                         mol_type = other DNA
                         organism = synthetic construct
SEQUENCE: 1311
tttttgcggg aggttttcgc gcctgtttt                                  29

SEQ ID NO: 1312          moltype = DNA   length = 34
FEATURE                  Location/Qualifiers
source                   1..34
                         mol_type = other DNA
                         organism = synthetic construct
SEQUENCE: 1312
```

-continued

```
tttagcaata gcagtttttg tttaacgtca tttt                          34

SEQ ID NO: 1313         moltype = DNA   length = 29
FEATURE                 Location/Qualifiers
source                  1..29
                        mol_type = other DNA
                        organism = synthetic construct
SEQUENCE: 1313
ttttaggctt atccggtaac aagaatttt                                29

SEQ ID NO: 1314         moltype = DNA   length = 37
FEATURE                 Location/Qualifiers
source                  1..37
                        mol_type = other DNA
                        organism = synthetic construct
SEQUENCE: 1314
gagccagcag agaattaaaa acagggaagc gcatttt                       37

SEQ ID NO: 1315         moltype = DNA   length = 29
FEATURE                 Location/Qualifiers
source                  1..29
                        mol_type = other DNA
                        organism = synthetic construct
SEQUENCE: 1315
ttttccgcgc ccaatagaat cggcttttt                                29

SEQ ID NO: 1316         moltype = DNA   length = 34
FEATURE                 Location/Qualifiers
source                  1..34
                        mol_type = other DNA
                        organism = synthetic construct
SEQUENCE: 1316
ttcatcagag agatagaggg taattgagcg tttt                          34

SEQ ID NO: 1317         moltype = DNA   length = 53
FEATURE                 Location/Qualifiers
source                  1..53
                        mol_type = other DNA
                        organism = synthetic construct
SEQUENCE: 1317
ttttaccgca ctcatcgaga gggtattagt ctttccaaat aaggcgttat ttt     53

SEQ ID NO: 1318         moltype = DNA   length = 16
FEATURE                 Location/Qualifiers
source                  1..16
                        mol_type = other DNA
                        organism = synthetic construct
SEQUENCE: 1318
aaccaagttt tttttt                                              16

SEQ ID NO: 1319         moltype = DNA   length = 29
FEATURE                 Location/Qualifiers
source                  1..29
                        mol_type = other DNA
                        organism = synthetic construct
SEQUENCE: 1319
ttttaaataa taatcataat tactatttt                                29

SEQ ID NO: 1320         moltype = DNA   length = 29
FEATURE                 Location/Qualifiers
source                  1..29
                        mol_type = other DNA
                        organism = synthetic construct
SEQUENCE: 1320
ttttttttatc aattaccagt ataaatttt                               29

SEQ ID NO: 1321         moltype = DNA   length = 29
FEATURE                 Location/Qualifiers
source                  1..29
                        mol_type = other DNA
                        organism = synthetic construct
SEQUENCE: 1321
tttttctgtc cagcttaatt gagaatttt                                29

SEQ ID NO: 1322         moltype = DNA   length = 50
FEATURE                 Location/Qualifiers
source                  1..50
                        mol_type = other DNA
                        organism = synthetic construct
```

-continued

```
SEQUENCE: 1322
ttttttcga gccagtaata agagaatttt ttatcctgaa tcttactttt                    50

SEQ ID NO: 1323          moltype = DNA   length = 29
FEATURE                  Location/Qualifiers
source                   1..29
                         mol_type = other DNA
                         organism = synthetic construct
SEQUENCE: 1323
tttttcgcca tatttaaaga agagttttt                                          29

SEQ ID NO: 1324          moltype = DNA   length = 29
FEATURE                  Location/Qualifiers
source                   1..29
                         mol_type = other DNA
                         organism = synthetic construct
SEQUENCE: 1324
ttttgccaac gctcaacagg tctgatttt                                          29

SEQ ID NO: 1325          moltype = DNA   length = 29
FEATURE                  Location/Qualifiers
source                   1..29
                         mol_type = other DNA
                         organism = synthetic construct
SEQUENCE: 1325
ttttgaaaaa gcctgttatg taaattttt                                          29

SEQ ID NO: 1326          moltype = DNA   length = 29
FEATURE                  Location/Qualifiers
source                   1..29
                         mol_type = other DNA
                         organism = synthetic construct
SEQUENCE: 1326
ttttaataag aataaaccaa agaactttt                                          29

SEQ ID NO: 1327          moltype = DNA   length = 53
FEATURE                  Location/Qualifiers
source                   1..53
                         mol_type = other DNA
                         organism = synthetic construct
SEQUENCE: 1327
ttttttctga cctaaattta tttagttagc gagaaaattt caattacctt ttt              53

SEQ ID NO: 1328          moltype = DNA   length = 16
FEATURE                  Location/Qualifiers
source                   1..16
                         mol_type = other DNA
                         organism = synthetic construct
SEQUENCE: 1328
atttcatctt tttttt                                                        16

SEQ ID NO: 1329          moltype = DNA   length = 29
FEATURE                  Location/Qualifiers
source                   1..29
                         mol_type = other DNA
                         organism = synthetic construct
SEQUENCE: 1329
ttttgctgat gcaacaaaca tcaagtttt                                          29

SEQ ID NO: 1330          moltype = DNA   length = 29
FEATURE                  Location/Qualifiers
source                   1..29
                         mol_type = other DNA
                         organism = synthetic construct
SEQUENCE: 1330
ttttgagact acaccttttt taatgtttt                                          29

SEQ ID NO: 1331          moltype = DNA   length = 29
FEATURE                  Location/Qualifiers
source                   1..29
                         mol_type = other DNA
                         organism = synthetic construct
SEQUENCE: 1331
ttttcaatag tgtatatgtg agtgatttt                                          29

SEQ ID NO: 1332          moltype = DNA   length = 50
FEATURE                  Location/Qualifiers
source                   1..50
                         mol_type = other DNA
```

-continued

```
                              organism = synthetic construct
SEQUENCE: 1332
ttttttagaat ccttgaaaac atagcctcta atttaggcag aggcattttt              50

SEQ ID NO: 1333          moltype = DNA   length = 29
FEATURE                  Location/Qualifiers
source                   1..29
                         mol_type = other DNA
                         organism = synthetic construct
SEQUENCE: 1333
ttttataacc ttgcttcatc aatattttt                                      29

SEQ ID NO: 1334          moltype = DNA   length = 29
FEATURE                  Location/Qualifiers
source                   1..29
                         mol_type = other DNA
                         organism = synthetic construct
SEQUENCE: 1334
ttttgaaaca gtacataacc taccatttt                                      29

SEQ ID NO: 1335          moltype = DNA   length = 29
FEATURE                  Location/Qualifiers
source                   1..29
                         mol_type = other DNA
                         organism = synthetic construct
SEQUENCE: 1335
ttttaaaaca aaattaaatt ttcagtttt                                      29

SEQ ID NO: 1336          moltype = DNA   length = 29
FEATURE                  Location/Qualifiers
source                   1..29
                         mol_type = other DNA
                         organism = synthetic construct
SEQUENCE: 1336
ttttgagcaa aagaagaaga aacaatttt                                      29

SEQ ID NO: 1337          moltype = DNA   length = 53
FEATURE                  Location/Qualifiers
source                   1..53
                         mol_type = other DNA
                         organism = synthetic construct
SEQUENCE: 1337
ttttatcgcg cagaggcgaa aataccaata acggatacta acaactaatt ttt           53

SEQ ID NO: 1338          moltype = DNA   length = 16
FEATURE                  Location/Qualifiers
source                   1..16
                         mol_type = other DNA
                         organism = synthetic construct
SEQUENCE: 1338
gttacaaatt tttttt                                                    16

SEQ ID NO: 1339          moltype = DNA   length = 29
FEATURE                  Location/Qualifiers
source                   1..29
                         mol_type = other DNA
                         organism = synthetic construct
SEQUENCE: 1339
ttttgtttaa cgataataca tttgatttt                                      29

SEQ ID NO: 1340          moltype = DNA   length = 29
FEATURE                  Location/Qualifiers
source                   1..29
                         mol_type = other DNA
                         organism = synthetic construct
SEQUENCE: 1340
tttttatcaa aatcgtatta aatcctttt                                      29

SEQ ID NO: 1341          moltype = DNA   length = 29
FEATURE                  Location/Qualifiers
source                   1..29
                         mol_type = other DNA
                         organism = synthetic construct
SEQUENCE: 1341
ttttaatcct gattttaaaa gtttgtttt                                      29

SEQ ID NO: 1342          moltype = DNA   length = 50
FEATURE                  Location/Qualifiers
source                   1..50
```

-continued

```
                              mol_type = other DNA
                              organism = synthetic construct
SEQUENCE: 1342
ttttcggaat tatcatcata ttcctttgta ttaattaatt ttcccttttt              50

SEQ ID NO: 1343          moltype = DNA   length = 29
FEATURE                  Location/Qualifiers
source                   1..29
                         mol_type = other DNA
                         organism = synthetic construct
SEQUENCE: 1343
ttttagtaac attatcatcg ccatttttt                                     29

SEQ ID NO: 1344          moltype = DNA   length = 29
FEATURE                  Location/Qualifiers
source                   1..29
                         mol_type = other DNA
                         organism = synthetic construct
SEQUENCE: 1344
tttttttgcc cgaacgtcgg tcagttttt                                     29

SEQ ID NO: 1345          moltype = DNA   length = 29
FEATURE                  Location/Qualifiers
source                   1..29
                         mol_type = other DNA
                         organism = synthetic construct
SEQUENCE: 1345
ttttggattt agaagtaacg ctgagtttt                                     29

SEQ ID NO: 1346          moltype = DNA   length = 29
FEATURE                  Location/Qualifiers
source                   1..29
                         mol_type = other DNA
                         organism = synthetic construct
SEQUENCE: 1346
ttttagatta gagccgtaaa tatcatttt                                     29

SEQ ID NO: 1347          moltype = DNA   length = 53
FEATURE                  Location/Qualifiers
source                   1..53
                         mol_type = other DNA
                         organism = synthetic construct
SEQUENCE: 1347
tttttgaaag gaattgagga ttggcaaaaa ccctcaaaaa cgctcatggt ttt          53

SEQ ID NO: 1348          moltype = DNA   length = 16
FEATURE                  Location/Qualifiers
source                   1..16
                         mol_type = other DNA
                         organism = synthetic construct
SEQUENCE: 1348
tcaacagttt tttttt                                                   16

SEQ ID NO: 1349          moltype = DNA   length = 29
FEATURE                  Location/Qualifiers
source                   1..29
                         mol_type = other DNA
                         organism = synthetic construct
SEQUENCE: 1349
ttttagccag cactcaatcg tctgatttt                                     29

SEQ ID NO: 1350          moltype = DNA   length = 29
FEATURE                  Location/Qualifiers
source                   1..29
                         mol_type = other DNA
                         organism = synthetic construct
SEQUENCE: 1350
ttttattaac acccagtaat aaaagtttt                                     29

SEQ ID NO: 1351          moltype = DNA   length = 29
FEATURE                  Location/Qualifiers
source                   1..29
                         mol_type = other DNA
                         organism = synthetic construct
SEQUENCE: 1351
ttttaaaaat acgatagaac ccttctttt                                     29

SEQ ID NO: 1352          moltype = DNA   length = 47
FEATURE                  Location/Qualifiers
```

-continued

```
source                    1..47
                          mol_type = other DNA
                          organism = synthetic construct
SEQUENCE: 1352
ttgatatcgc gtctggcctt cctgtcacag acaatatttt tgatttt                     47

SEQ ID NO: 1353           moltype = DNA   length = 50
FEATURE                   Location/Qualifiers
source                    1..50
                          mol_type = other DNA
                          organism = synthetic construct
SEQUENCE: 1353
ttttatggct attagtcttt aatgcgagag aaaccaccag aaggagtttt                   50

SEQ ID NO: 1354           moltype = DNA   length = 29
FEATURE                   Location/Qualifiers
source                    1..29
                          mol_type = other DNA
                          organism = synthetic construct
SEQUENCE: 1354
tttttgacct gaaagcgacg tggcgtttt                                          29

SEQ ID NO: 1355           moltype = DNA   length = 29
FEATURE                   Location/Qualifiers
source                    1..29
                          mol_type = other DNA
                          organism = synthetic construct
SEQUENCE: 1355
ttttggacat tctggcccgc ttaattttt                                          29

SEQ ID NO: 1356           moltype = DNA   length = 29
FEATURE                   Location/Qualifiers
source                    1..29
                          mol_type = other DNA
                          organism = synthetic construct
SEQUENCE: 1356
ttttaatgga ttatttaagg ccgattttt                                          29

SEQ ID NO: 1357           moltype = DNA   length = 29
FEATURE                   Location/Qualifiers
source                    1..29
                          mol_type = other DNA
                          organism = synthetic construct
SEQUENCE: 1357
ttttaaatac ctacatttca cgcaattttt                                         29

SEQ ID NO: 1358           moltype = DNA   length = 49
FEATURE                   Location/Qualifiers
source                    1..49
                          mol_type = other DNA
                          organism = synthetic construct
SEQUENCE: 1358
ttttaacaat attaccgcca gcaaataggt aaatattttg taggtggca                    49

SEQ ID NO: 1359           moltype = DNA   length = 38
FEATURE                   Location/Qualifiers
source                    1..38
                          mol_type = other DNA
                          organism = synthetic construct
SEQUENCE: 1359
ttttattaac cgttgtagca tctgtccatt gcgacagt                                38

SEQ ID NO: 1360           moltype = DNA   length = 35
FEATURE                   Location/Qualifiers
source                    1..35
                          mol_type = other DNA
                          organism = synthetic construct
SEQUENCE: 1360
tttttaaagg gattttagac taaacaggca ttggc                                   35

SEQ ID NO: 1361           moltype = DNA   length = 38
FEATURE                   Location/Qualifiers
source                    1..38
                          mol_type = other DNA
                          organism = synthetic construct
SEQUENCE: 1361
ttttgcgccg ctacagggcg acccgccgaa cgtcggat                                38

SEQ ID NO: 1362           moltype = DNA   length = 35
```

-continued

| FEATURE | Location/Qualifiers |
|---|---|
| source | 1..35 |
| | mol_type = other DNA |
| | organism = synthetic construct |

SEQUENCE: 1362
ttttagaaag gaagggaaga gccggcgata agaat                                    35

| SEQ ID NO: 1363 | moltype = DNA  length = 24 |
|---|---|
| FEATURE | Location/Qualifiers |
| source | 1..24 |
| | mol_type = other DNA |
| | organism = synthetic construct |

SEQUENCE: 1363
gtataccgcc accctcagaa ccgc                                                24

| SEQ ID NO: 1364 | moltype = DNA  length = 48 |
|---|---|
| FEATURE | Location/Qualifiers |
| source | 1..48 |
| | mol_type = other DNA |
| | organism = synthetic construct |

SEQUENCE: 1364
gagtattaag aggctgagac tcctcaccgt actcaggagg tttagaat                      48

| SEQ ID NO: 1365 | moltype = DNA  length = 48 |
|---|---|
| FEATURE | Location/Qualifiers |
| source | 1..48 |
| | mol_type = other DNA |
| | organism = synthetic construct |

SEQUENCE: 1365
caacgtcata catggctttt gatgtattat tctgaaacat gaaagcca                      48

| SEQ ID NO: 1366 | moltype = DNA  length = 48 |
|---|---|
| FEATURE | Location/Qualifiers |
| source | 1..48 |
| | mol_type = other DNA |
| | organism = synthetic construct |

SEQUENCE: 1366
cgaaccacc accagagccg ccgctgaatt taccgttcca gtaagggc                       48

| SEQ ID NO: 1367 | moltype = DNA  length = 48 |
|---|---|
| FEATURE | Location/Qualifiers |
| source | 1..48 |
| | mol_type = other DNA |
| | organism = synthetic construct |

SEQUENCE: 1367
ttttagcccc cttattagcg tttgcaccct cagagccgcc accagcag                      48

| SEQ ID NO: 1368 | moltype = DNA  length = 47 |
|---|---|
| FEATURE | Location/Qualifiers |
| source | 1..47 |
| | mol_type = other DNA |
| | organism = synthetic construct |

SEQUENCE: 1368
ggaagtagca ccattaccat tagtttcatc ggcattttcg gtcacgg                       47

| SEQ ID NO: 1369 | moltype = DNA  length = 28 |
|---|---|
| FEATURE | Location/Qualifiers |
| source | 1..28 |
| | mol_type = other DNA |
| | organism = synthetic construct |

SEQUENCE: 1369
cgcgcgacat tcaacaaaat caccacca                                            28

| SEQ ID NO: 1370 | moltype = DNA  length = 28 |
|---|---|
| FEATURE | Location/Qualifiers |
| source | 1..28 |
| | mol_type = other DNA |
| | organism = synthetic construct |

SEQUENCE: 1370
gccaaaatac atacaagaca aaaggcac                                            28

| SEQ ID NO: 1371 | moltype = DNA  length = 28 |
|---|---|
| FEATURE | Location/Qualifiers |
| source | 1..28 |
| | mol_type = other DNA |
| | organism = synthetic construct |

SEQUENCE: 1371
tataagcaga tagcagcaaa cgtaggcc                                            28

-continued

```
SEQ ID NO: 1372            moltype = DNA   length = 28
FEATURE                    Location/Qualifiers
source                     1..28
                           mol_type = other DNA
                           organism = synthetic construct
SEQUENCE: 1372
tgagtaattg agcgttaaga aaagttca                                        28

SEQ ID NO: 1373            moltype = DNA   length = 15
FEATURE                    Location/Qualifiers
source                     1..15
                           mol_type = other DNA
                           organism = synthetic construct
SEQUENCE: 1373
cagaacgtca aaaat                                                      15

SEQ ID NO: 1374            moltype = DNA   length = 28
FEATURE                    Location/Qualifiers
source                     1..28
                           mol_type = other DNA
                           organism = synthetic construct
SEQUENCE: 1374
gtactggtaa taagaaagtc agaggatt                                        28

SEQ ID NO: 1375            moltype = DNA   length = 48
FEATURE                    Location/Qualifiers
source                     1..48
                           mol_type = other DNA
                           organism = synthetic construct
SEQUENCE: 1375
tttttaatgc cccctgccta tttccgatag ttgcgccgac aatgactg                 48

SEQ ID NO: 1376            moltype = DNA   length = 30
FEATURE                    Location/Qualifiers
source                     1..30
                           mol_type = other DNA
                           organism = synthetic construct
SEQUENCE: 1376
ttatcaatat atgtggtaaa gtaattcaac                                      30

SEQ ID NO: 1377            moltype = DNA   length = 48
FEATURE                    Location/Qualifiers
source                     1..48
                           mol_type = other DNA
                           organism = synthetic construct
SEQUENCE: 1377
aataccagtc aggacgttgg gaagataaca gttgattccc aattcagc                 48

SEQ ID NO: 1378            moltype = DNA   length = 28
FEATURE                    Location/Qualifiers
source                     1..28
                           mol_type = other DNA
                           organism = synthetic construct
SEQUENCE: 1378
tgtataccta cattatatct ttaggtgc                                        28

SEQ ID NO: 1379            moltype = DNA   length = 16
FEATURE                    Location/Qualifiers
source                     1..16
                           mol_type = other DNA
                           organism = synthetic construct
SEQUENCE: 1379
cgctcatgga ataaaa                                                     16

SEQ ID NO: 1380            moltype = DNA   length = 16
FEATURE                    Location/Qualifiers
source                     1..16
                           mol_type = other DNA
                           organism = synthetic construct
SEQUENCE: 1380
attacgccag ctgcta                                                     16

SEQ ID NO: 1381            moltype = DNA   length = 40
FEATURE                    Location/Qualifiers
source                     1..40
                           mol_type = other DNA
                           organism = synthetic construct
SEQUENCE: 1381
gaggcgaaag ggggatactc tagaggatcc ccgggtagta                          40
```

-continued

```
SEQ ID NO: 1382        moltype = DNA   length = 48
FEATURE                Location/Qualifiers
source                 1..48
                       mol_type = other DNA
                       organism = synthetic construct
SEQUENCE: 1382
cgcccgagct cgaattcgta atcatgagtg agctaactca cattacac                48

SEQ ID NO: 1383        moltype = DNA   length = 48
FEATURE                Location/Qualifiers
source                 1..48
                       mol_type = other DNA
                       organism = synthetic construct
SEQUENCE: 1383
ggtattgcgt tgcgctcact gccctctttt caccagtgag acggggga                48

SEQ ID NO: 1384        moltype = DNA   length = 48
FEATURE                Location/Qualifiers
source                 1..48
                       mol_type = other DNA
                       organism = synthetic construct
SEQUENCE: 1384
aaacaacagc tgattgccct tcacccttat aaatcaaaag aatagagg                48

SEQ ID NO: 1385        moltype = DNA   length = 48
FEATURE                Location/Qualifiers
source                 1..48
                       mol_type = other DNA
                       organism = synthetic construct
SEQUENCE: 1385
taacccgaga tagggttgag tgttgaacgt ggactccaac gtcaacaa                48

SEQ ID NO: 1386        moltype = DNA   length = 15
FEATURE                Location/Qualifiers
source                 1..15
                       mol_type = other DNA
                       organism = synthetic construct
SEQUENCE: 1386
tgaaccatca ccagg                                                   15

SEQ ID NO: 1387        moltype = DNA   length = 46
FEATURE                Location/Qualifiers
source                 1..46
                       mol_type = other DNA
                       organism = synthetic construct
SEQUENCE: 1387
attcatttca attacccgcg cagaggcgaa tttttggag ggaggg                  46

SEQ ID NO: 1388        moltype = DNA   length = 35
FEATURE                Location/Qualifiers
source                 1..35
                       mol_type = other DNA
                       organism = synthetic construct
SEQUENCE: 1388
tcagatgatg gcaacaataa cttttggagg gaggg                             35

SEQ ID NO: 1389        moltype = DNA   length = 46
FEATURE                Location/Qualifiers
source                 1..46
                       mol_type = other DNA
                       organism = synthetic construct
SEQUENCE: 1389
attatcattt tttatcatca tattcctgat tattttggag ggaggg                 46

SEQ ID NO: 1390        moltype = DNA   length = 65
FEATURE                Location/Qualifiers
source                 1..65
                       mol_type = other DNA
                       organism = synthetic construct
SEQUENCE: 1390
ttctgtgcaa aagaaggcac caggctgacc gtaatcttga caagaaccgg attttccagc  60
cagcc                                                              65

SEQ ID NO: 1391        moltype = DNA   length = 35
FEATURE                Location/Qualifiers
source                 1..35
                       mol_type = other DNA
                       organism = synthetic construct
```

-continued

```
SEQUENCE: 1391
gcaaaagacg gtgtacagac cttttccagc cagcc                              35

SEQ ID NO: 1392        moltype = DNA  length = 56
FEATURE                Location/Qualifiers
source                 1..56
                       mol_type = other DNA
                       organism = synthetic construct
SEQUENCE: 1392
gcatcaaaaa gattaagagg aacttcaaat atcgcgtttt aattttccag ccagcc      56

SEQ ID NO: 1393        moltype = DNA  length = 15
FEATURE                Location/Qualifiers
source                 1..15
                       mol_type = other DNA
                       organism = synthetic construct
misc_binding           1
                       bound_moiety = Cy3-HRP, Cy3-GOx, Cy3-G6pDH, Cy3-betaGal, or
                        ThioC6
SEQUENCE: 1393
tttttccctc cctcc                                                    15

SEQ ID NO: 1394        moltype = DNA  length = 15
FEATURE                Location/Qualifiers
source                 1..15
                       mol_type = other DNA
                       organism = synthetic construct
misc_binding           1
                       bound_moiety = Alexa Fluor 647-MDH, Alexa Fluor 647-LDH,
                        ThioC6
SEQUENCE: 1394
tttttggctg gctgg                                                    15

SEQ ID NO: 1395        moltype = DNA  length = 15
FEATURE                Location/Qualifiers
source                 1..15
                       mol_type = other DNA
                       organism = synthetic construct
misc_binding           1
                       bound_moiety = biotin
SEQUENCE: 1395
tttttggagg gaggg                                                    15
```